US006676948B2

(12) United States Patent
St. Geme, III

(10) Patent No.: US 6,676,948 B2
(45) Date of Patent: Jan. 13, 2004

(54) HAEMOPHILUS ADHERENCE AND PENETRATION PROTEINS

(75) Inventor: Joseph W. St. Geme, III, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 10/080,505

(22) Filed: Feb. 22, 2002

(65) Prior Publication Data

US 2003/0073166 A1 Apr. 17, 2003

Related U.S. Application Data

(63) Continuation-in-part of application No. 08/296,791, filed on Aug. 25, 1994, now Pat. No. 6,245,337, and a continuation-in-part of application No. 09/839,996, filed on Apr. 20, 2001.

(51) Int. Cl.$^7$ ............................................. A61K 39/102
(52) U.S. Cl. ................ 424/256.1; 424/185.1; 424/190.1; 530/350
(58) Field of Search ....................... 530/350; 424/256.1, 424/185.1, 190.1

(56) References Cited

FOREIGN PATENT DOCUMENTS

WO  WO 90/11367  10/1990

OTHER PUBLICATIONS

Bakaletz, L.O., et al., "Frequency of Fimbriation of non-typable Haemophilus influenzae and Its Ability to Adhere to Chinchilla and Human Respiratory Epithelium", Infection and Immunity, 56(2):331–335, (1988).

Barenkamp, S.J., et al., "Cloning Expression, and DNA Sequence Analysis of Genes Encoding Nontypeable Haemophilus influenzae High–Molecular–Weight Surface–Exposed Proteins Related to Filamentous Hemagglutinin of Bordetella Pertussis", Infection and Immunity, 60(4):1302–1313, (1992).

Benz, I., et al., "AIDA–I, the adhesin involved in diffuse adherence of the diarrhoeagenic Escherichia coli strain 2787 (0126:H27), is synthesized via a precursor molecule", Molecular Microbiology, 6(11):1539–1546, (1992).

Brennan, M.J., et al., "Identification of a 69–Kilodalton Nonfimbrial Protein As an Agglutinogen of Bordetella pertussis", Infection and Immunity, 56(12):3189–3195, (1988).

Charles, I.G., et al., "Molecular cloning and characterization of protective outer membrane protein p. 69 from Bordetella pertussis", Proc. Natl. Acad. Sci. USA, pp. 86:3554–3558 (1989).

Ewanowich, C.A., et al., "Invasion of HeLa 229 Cells by Virulent Bordetella pertussis", Infection and Immunity, 57(9):2698–2704, (1989).

Forsgren, J., et al., "Haemophilus influenzae Resides and Multiplies Intracellulary in Human Adenoid Tissue as Demonstrated by In Situ Hybridization and Bacterial Viability Assay", Infection and Immunity, 62(2):673–679, (1994).

Gulig et al., "Immunogenic Proteins in Cell–Free Culture Supernatants of Haemophilus influenzae Type b," Infection & Immunity 44:41–48, 1984.

Isberg, R.R., et al. "Identification of Invasin: A Protein That Allows Enteric Bacteria to Penetrate Cultured Mammalian Cells", Cell, 60:769–778, (1987).

Koomey, J.M., et al., "Nucleotide Sequence Homology Between the Immunoglubulin A1 Protease Genes of Neisseria gonorrhoeae, Neisseria meningitidis, and Haemophilus influenzae" Infection and Immunity, 43(1):101–107, (1984).

Krivan, H.C., et al., "Many pulmonary pathogenic bacteria bind specifically to the carbohydrate sequence Ga1NAc.beta.1–4Gal found in some glycolipids", Proc. Natl. Acad. Sci. USA, 85:6157–6161, (1988).

Leininger, E., et al., "Pertactin, an Arg–Gly–Asp–containing Bordetella pertussis surface protein that promotes adherence of mammalian cells", Proc. Natl. Acad. Sci., USA., 88:345–349, (1991).

Leininger, E., et al., "Comparative Roles of the Arg–Gly–Asp Sequence Present in the Bordetella pertussis Adhesins Pertactin and Filamentous Hemagglutinin", Infection and Immunity, 60(6):2380–2385, (1992).

Pichichero, M.E., "Do Pili Play A Role In Pathogenicity of Haemophilus Influenzae Type B", The Lancet, 56(2) 960–962: (1982).

Pohlner, J., et al., "Gene Structure and extracellular secretion of Neisseria gonorrhoeae IgA protease", Nature, 325(29):458–462, (1987).

Poulsen, K., et al., "Cloning and Sequencing of the Immunoglobulin A1 Protease Gene (iga) of Haemophilus influenzae Serotype b", Infection and Immunity, 57(10):3097–3105, (1989).

Poulsen, K., et al., "A Comparative Genetic Study of Serologically Distinct Haemophilus influenzae Type 1 Immunoglobulin A1 Proteases", Journal of Bacteriology, 174(9):2913–2921, (1992).

Provence, D.L., et al., "Isolation and Characterization of a Gene Involved in Hemagglutination by an Avian Pathogenic Escherichia coli Strain", Infection and Immunity, 62(4):1369–1380, (1994).

Simon, D., et al., "Escherichia coli expressing a Neisseria gonorrhoeae opacity–associated outer membrane protein invade human cervical and endometrial epithelial cell lines", Proc. Natl. Acad. Sci. USA, 89:5512–5516, (1992).

(List continued on next page.)

Primary Examiner—Jennifer E. Graser
(74) Attorney, Agent, or Firm—Richard F. Trecartin; Traci H. Ropp; Dorsey & Whitney LLP

(57) ABSTRACT

Haemophilus adhesion and penetration proteins, nucleic acids, vaccines and monoclonal antibodies are provided.

6 Claims, 51 Drawing Sheets

OTHER PUBLICATIONS

St. Geme, et al., "Haemophilus Influenzae Adheres to and Enters Cultured Human Epithelial Cells", Infection and Immunity, 58(12): 4036–4044, (1990).

St. Geme et al., "A Haemophilus influenzae IgA protease–like protein promotes intimate interaction with human epithelial cells," Molecular Microbiology 14(2):217–233 (1994).

St. Geme, J.W., "Surface Structures and Adherence Properties of Diverse Strains of Haemophilus Influenzae Biogroup Aegyptius", Infection and Immunity, 59(10):3366–3371, (1991).

St. Geme, J.W., et al., "High–molecular–weight proteins of nontypable Haemophilus influenzae mediate attachment to human epithelial cells", Proc. Natl. Acad. Sci. USA, 90:2875–2879, (1993).

Thomas, W.R., et al., "Expression in Escherichia coli of a High–Molecular–Weight Protective Surface Antigen Found in Nontypeable and Type b Haemophilus influenzae," Infection and Immunity, 58(6):1909–1913.

Uphoff, T.S., et al., "Nucleotide Sequencing of the Proteus mirabilis Calcium–Independent Homelysin Genes (hpmA and hpmB) Reveals Sequence Similarity with the Serratia marcescens Hemolysin Genes (sh1A and sh1B)", Journal of Bacteriology, 172(3):1206–1216, (1990).

van Ham, S.M., et al., "Cloning and expression in Escherichia coil of Haemophilus influenzae fimbrial genes establishes adherence to oropharyngeal epithelial cells", The EMBO Journal, 8(11):3535–3540, (1989).

Venkatesan, M.M., et al., "Characterization of invasion plasmid antigen genes (ipaBCD) from Shigella flexneri", Proc. Natl. Acad. Sci. USA, 85:9317–9321, (1988).

Houghten et al., "Relative Importance of Position and Individual Amino Acid Residues in Peptide Antigen–Antibody Interactions: Implications in the Mechanism of Antigenic Drift and Antigenic Shift," in Vaccine 86, Brown et al., eds. Cold Spring Harbor Laboratory, pp. 21–25, 1986.

Lewin R. "When does homology mean something else?" Science. Sep. 25, 1987; 237(4822):1570.

Reeck GR, et al. "Homology in proteins and nucleic acids: a terminology muddle and a way out of it." Cell. Aug. 28, 1987; 50(5):667.

Tebbey PW, et al., "Effective mucosal immunization against respiratory syncytial virus using purified F protein and a genetically detoxified cholera holotoxin, CT–E29H." Vaccine. Jun. 1, 2000;18(24):2723–2734.

Sanders JD, et al., "Reconstitution of a porin–deficient mutant of Haemophilus influenzae type b with a porin gene from nontypeable H. influenzae." Infect Immun. Sep. 1993;61(9):3966–3975.

Fleischmann RD, et al. "Whole–genome random sequencing and assembly of Haemophilus influenzae Rd." Science. Jul. 28, 1995;269(5223):496–512.

Herriott RM, et al., "Defined nongrowth media for stage II development of competence in Haemophilus influenzae." J Bacteriol. Feb. 1970;101(2):517–524.

Carlone GM, et al., "Rapid microprocedure for isolating detergent–insoluble outer membrane proteins from Haemophilus species." J Clin Microbiol. Sep. 1986;24(3):330–332.

Hendrixson DR, et al., "Structural determinants of processing and secretion of the Haemophilus influenzae hap protein." Mol Microbiol. Nov. 1997;26(3):505–518.

Hendrixson DR, and St Geme JW 3rd. "The Haemophilus influenzae Hap serine protease promotes adherence and microcolony formation, potentiated by a soluble host protein." Mol Cell. Dec. 1998;2(6):841–850.

FIG._1A
FIG._1B

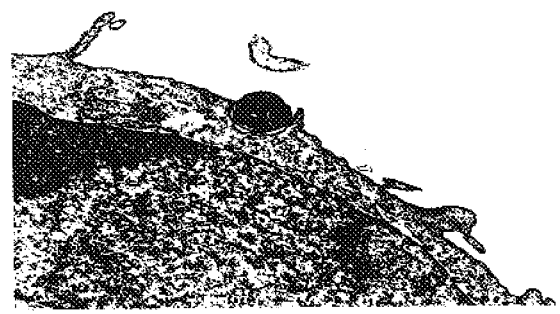
FIG._2A    FIG._2B

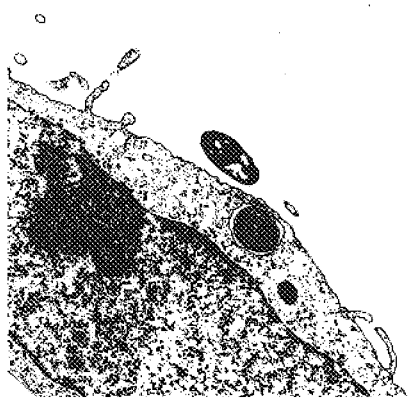 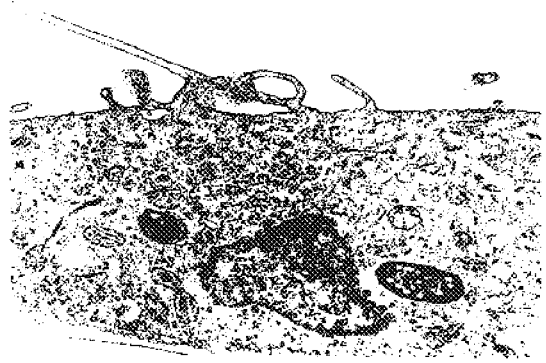
FIG._2C  FIG._2D

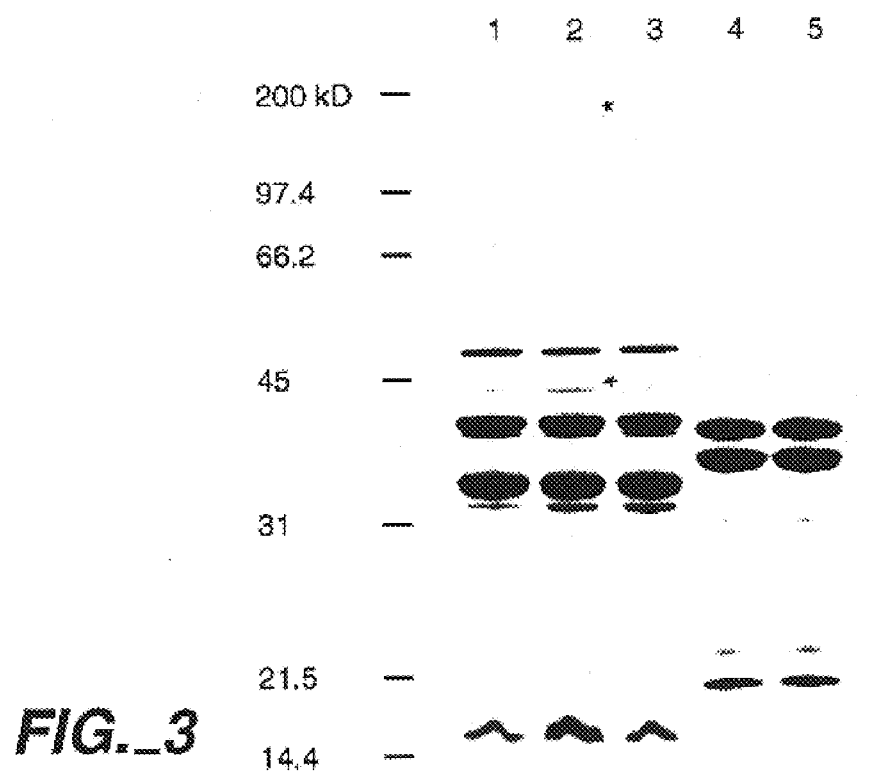
FIG._3
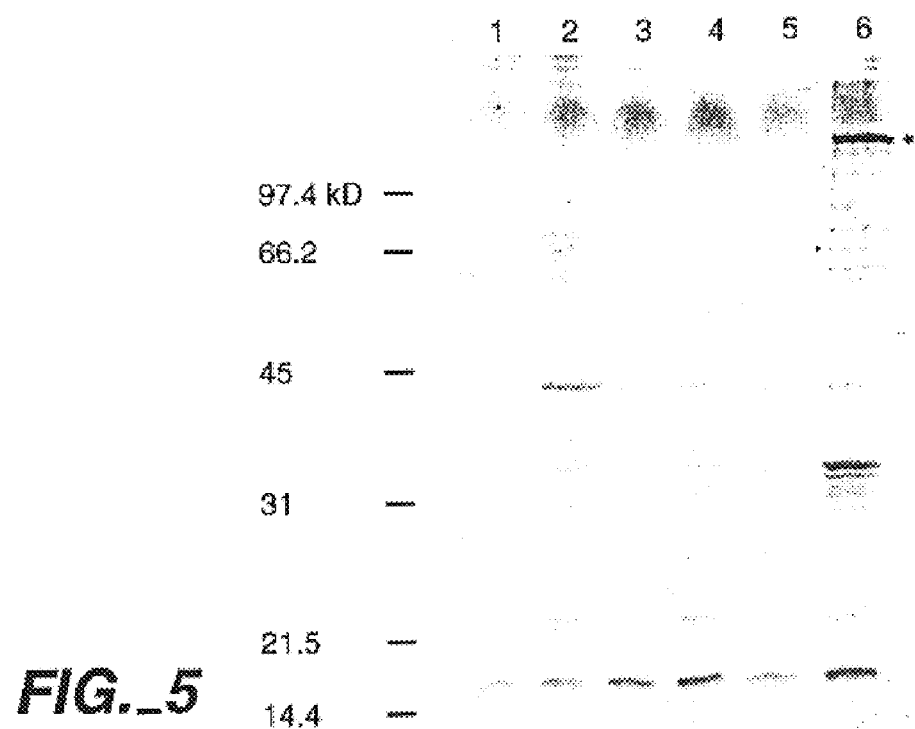
FIG._5

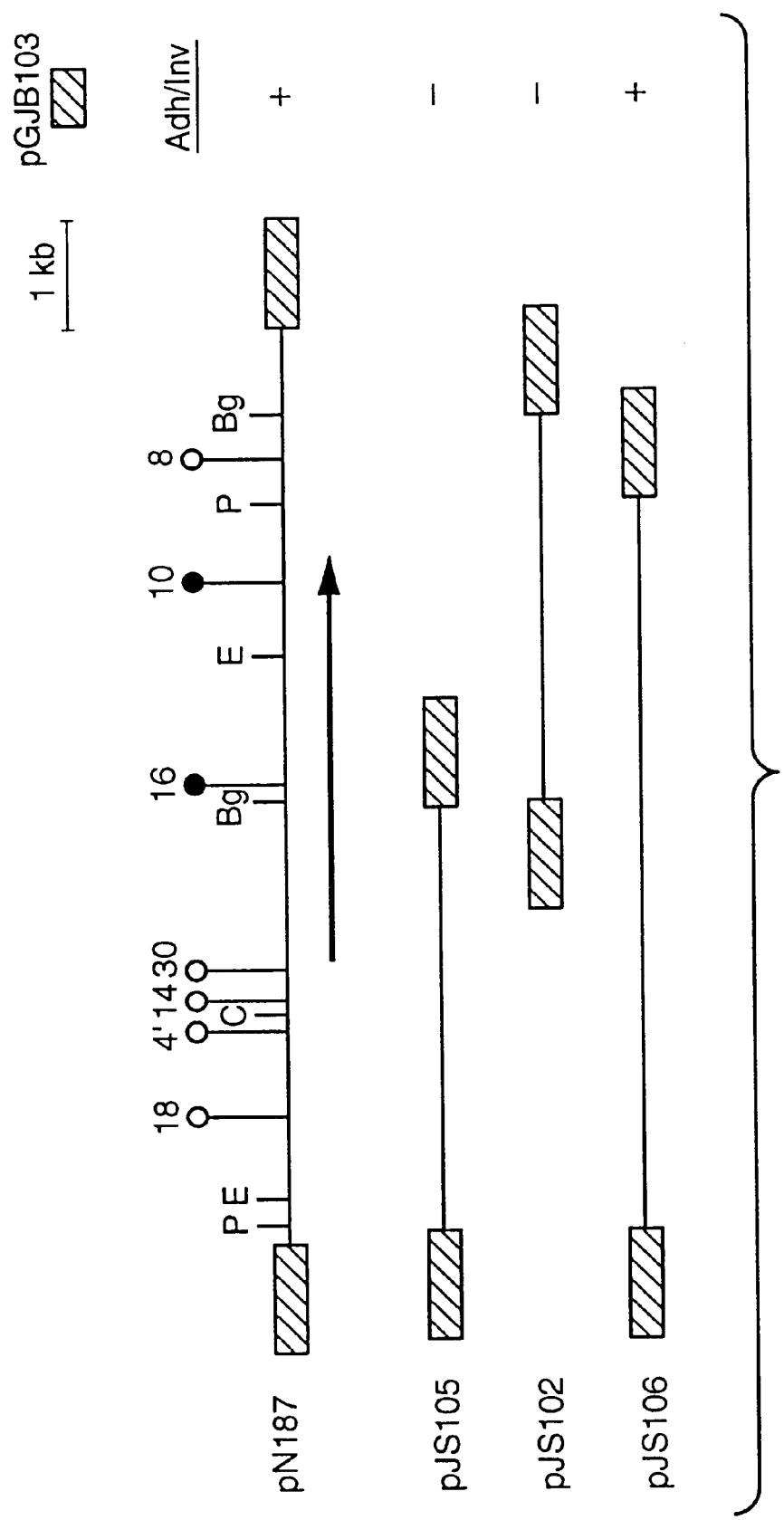
FIG._4

```
         10                  30                  50                            70                        90
TCAATAGTCGTTTAACTAGTATTTTTAATACGAAAAAATTACTTAATTAAACATTATGAAAAAACTGTATTTCGTCTTTAATTTT
     -35                                                         M  K  K  T  V  F  R  L  N  F
                 110                 130                 150                 170
TTAACCGCTTGCATTTCATTAGGGATAGTATCGCAAGCGTGGCTGTCACACTTATTTTGGGATTGATTACCAATATATTCGTGATTTT
L  T  A  C  I  S  L  G  I  V  S  Q  A  W  A  G  H  T  Y  F  G  I  D  Y  Q  Y  Y  R  D  F
           -10
       190                  210                 230                 250                  270
GCCGAGAATAAAGGGAAGTTCACAGTTGGGGCTCAAAATATTAAGGTTTATAACAAACAAGGGCAATTAGTTGGCACATCAATGACAAAA
A  E  N  K  G  K  F  T  V  G  A  Q  N  I  K  V  Y  N  K  Q  G  Q  L  V  G  T  S  M  T  K 290                 310                 330                 350
GCCCCGATGATTGATTTTTCTGTAGTGTCACGTAACGGCGTGGCAGCCCTTGGTTGAAAATCAATATATTGTGAGCGTGGCACATAACGTA
A  P  M  I  D  F  S  V  V  S  R  N  G  V  A  A  L  V  E  N  Q  Y  I  V  S  A  H  N  V 370                 390                 410                 430                 450
GGATATACAGATGTTGATTTGGTGCAGAGGAAACAACCCGATCAACATCGTTTTACTTATATAAGATTGTAAAACGAAATAACTACAAA
G  Y  T  D  V  D  F  G  A  E  G  N  P  D  Q  H  R  F  T  Y  K  I  V  K  R  N  N  Y  K 470                 490                 510                 530
AAAGATAATTTACATCCTTATGAGGACGATTACCATAATCCACGATTACATAAATTCGTTACAGAAGCGGCTCCAATTGATATGACTTCG
K  D  N  L  H  P  Y  E  D  D  Y  H  N  P  R  L  H  K  F  V  T  E  A  A  P  I  D  M  T  S 550                 570                 590                 610                 630
AATATGAATGGCAGTACTTATTCAGATAGAACAAAATATCCAGAACGTGTTCGTATCGGCTCTGGACGGCAGTTTTGGCGAAATGATCAA
N  M  N  G  S  T  Y  S  D  R  T  K  Y  P  E  R  V  R  I  G  S  G  R  Q  F  W  R  N  D  Q 650                 670                 690                 710
GACAAAGGCGACCAAGTTGCCGGTGCATATCATTATCTGACAGCTGGAGCAGGTAATGAAATCAGGGATATATTCGTAT
D  K  G  D  Q  V  A  G  A  Y  H  Y  L  T  A  G  N  T  H  N  Q  R  G  A  G  N  G  Y  S  Y
```

FIG._6A

```
                730                  750                  770                  790                  810
TTGGGAGGCGATGTTCGTAAAGCGGGAGAATATGGTCCATTACCGATTGCAGGCTCAAAGGGGGACAGTGGTTCTCCGATGTTTATTTAT
 L  G  G  D  V  R  K  A  G  E  Y  G  P  L  P  I  A  G  S  K  G  D  S  G  S  P  M  F  I  Y 830                  850                  870                  890
GATGCTGAAAAACAAAAATGGTTAATTAATGGGATATTACGGGAAGGCAACCCTTTTGAAGGCAAAGAAAATGGGTTTCAATTGGTTCGC
 D  A  E  K  Q  K  W  L  I  N  G  I  L  R  E  G  N  P  F  E  G  K  E  N  G  F  Q  L  V  R 910                  930                  950                  970                  990
AAATCTTATTTTGATGAAATTTTCGAAAGAGATTTACATCACTTTACACCCGAGCTGGTAATGGAGTGTACACAATTAGTGGAAAT
 K  S  Y  F  D  E  I  F  E  R  D  L  H  T  S  L  Y  T  R  A  G  N  G  V  T  I  S  G  N 1010                 1030                 1050                 1070
GATAATGGGTCAGGGGTCTATAACTCAGAAATCAGGAATACCATCAGAAATTAAAATTACGTTAGCAAATATGAGTTTACCTTTGAAAGAG
 D  N  G  Q  G  S  I  T  Q  K  S  G  I  P  S  E  I  K  I  T  L  A  N  M  S  L  P  L  K  E 1090                 1110                 1130                 1150                 1170
AAGGATAAAGTTCATAATCCTAGATATGACGGACCTAATATTTATTCCTCCACGTTTAAACAATGGAGAAACGCTATATTTTATGGATCAA
 K  D  K  V  H  N  P  R  Y  D  G  P  N  I  Y  S  P  R  L  N  N  G  E  T  L  Y  F  M  D  Q 1190                 1210                 1230                 1250
AACCAAGGATCATTAATCTTCGCATCTGACATTAACCAGGGCGGTGGTCTTTATTTTGAGGGTAATTTTACAGTATCTCCAAATTCT
 N  Q  G  S  L  I  F  A  S  D  I  N  Q  G  A  G  G  L  Y  F  E  G  N  F  T  V  S  P  N  S 1270                 1290                 1310                 1330                 1350
AACCAAACTTGGCAAGGAGCTGGCATACATGTAAGTGAAAATAGCACCGTTACTTGGAAAGTAAATGGCGTGGAACATGATCGACTTTCT
 N  Q  T  W  Q  G  A  G  I  H  V  S  E  N  S  T  V  T  W  K  V  N  G  V  E  H  D  R  L  S 1370                 1390                 1410                 1430
AAAATTGGTAAAGGAACATTGCACGTTCAAGCCAAAGGGGAAAATAAAGGTTCGATCAGCGTAGGCGATGGTAAAGTCATTTTGGAGCAG
 K  I  G  K  G  T  L  H  V  Q  A  K  G  E  N  K  G  S  I  S  V  G  D  G  K  V  I  L  E  Q
```

FIG._6B

```
                          1470              1490                1510                  1530
CAGGCAGACGATCAAGGCAACAAACAACAAGCCTTTAGTGAAATTGGCTTGGTTAGCGGCAGAGGGACTGTTCAATTAAACGATGATAAACAA
 Q  A  D  D  Q  G  N  K  Q  A  F  S  E  I  G  L  V  S  G  R  G  T  V  Q  L  N  D  D  K  Q
       1550              1570                1590                1610
TTTGATACCGATAAATTTTATTTCGGCTTTCGTGGTGGTCGCTTAGATCTTAACGGCATTCATTAACCTTTAAACGTATCCAAATACG
 F  D  T  D  K  F  Y  F  G  F  R  G  G  R  L  D  L  N  G  H  S  L  T  F  K  R  I  Q  N  T
              1630              1650                1670                1690              1710
GACGAGGGGGCAATGATTGTGAACCATAATACAACTCAAGCCGCTAATGTCACTATTACTGGGAACAGAAAGCATTGTTCTACCTAATGGA
 D  E  G  A  M  I  V  N  H  N  T  T  Q  A  A  N  V  T  I  T  G  N  E  S  I  V  L  P  N  G
              1730              1750                1770                1790
AATAATATTAATAAACTTGATTACAGAAAAGAAATTGCCTACAACGGTTGGTTTGGCGAAACAGATAAAAATAAACACAATGGGCGATTA
 N  N  I  N  K  L  D  Y  R  K  E  I  A  Y  N  G  W  F  G  E  T  D  K  N  K  H  N  G  R  L
              1810              1830                1850                1870              1890
AACCTTATTATAAACCACCAGAAGATCGTACTTTGCTACTTTCAGGTGGTACAAATTTAAAATAAACGTTGTTCAGAAATGGAAGGTATACCAAAGGT
 N  L  I  Y  K  P  T  T  E  D  R  T  L  L  L  S  G  G  T  N  L  K  G  D  I  T  Q  T  K  G
              1910              1930                1950                1970
AAACTATTTTTCAGCGGTAGACCGGGTACACCGCCACACGCCTAATCATTTAAATAACGTTGGTCAGAAATGGAAGGTATACCAAGGCGAA
 K  L  F  F  S  G  R  P  T  P  H  A  Y  N  H  L  N  K  R  W  S  E  M  E  G  I  P  Q  G  E
              1990              2010                2030                2050              2070
ATTGTGGGATCACGATTGGATCAACCGTACATTTAAAGCTGAAAACTTCCAAATTTGAAAATGCAAATGCAAATCAACAAAATACCATTTGCACGCGT
 I  V  W  D  H  D  W  I  N  R  T  F  K  A  E  N  F  Q  I  K  G  G  S  A  V  V  S  R  N  V
              2090              2110                2130                2150
TCTTCAATTGAGGGAAATTGGACAGTCAGCAATAATGCAAATGCAAATAACCATTTGCACGCGT
 S  S  I  E  G  N  W  T  V  S  N  N  A  N  A  T  F  G  V  V  P  N  Q  Q  N  T  I  C  T  R
```

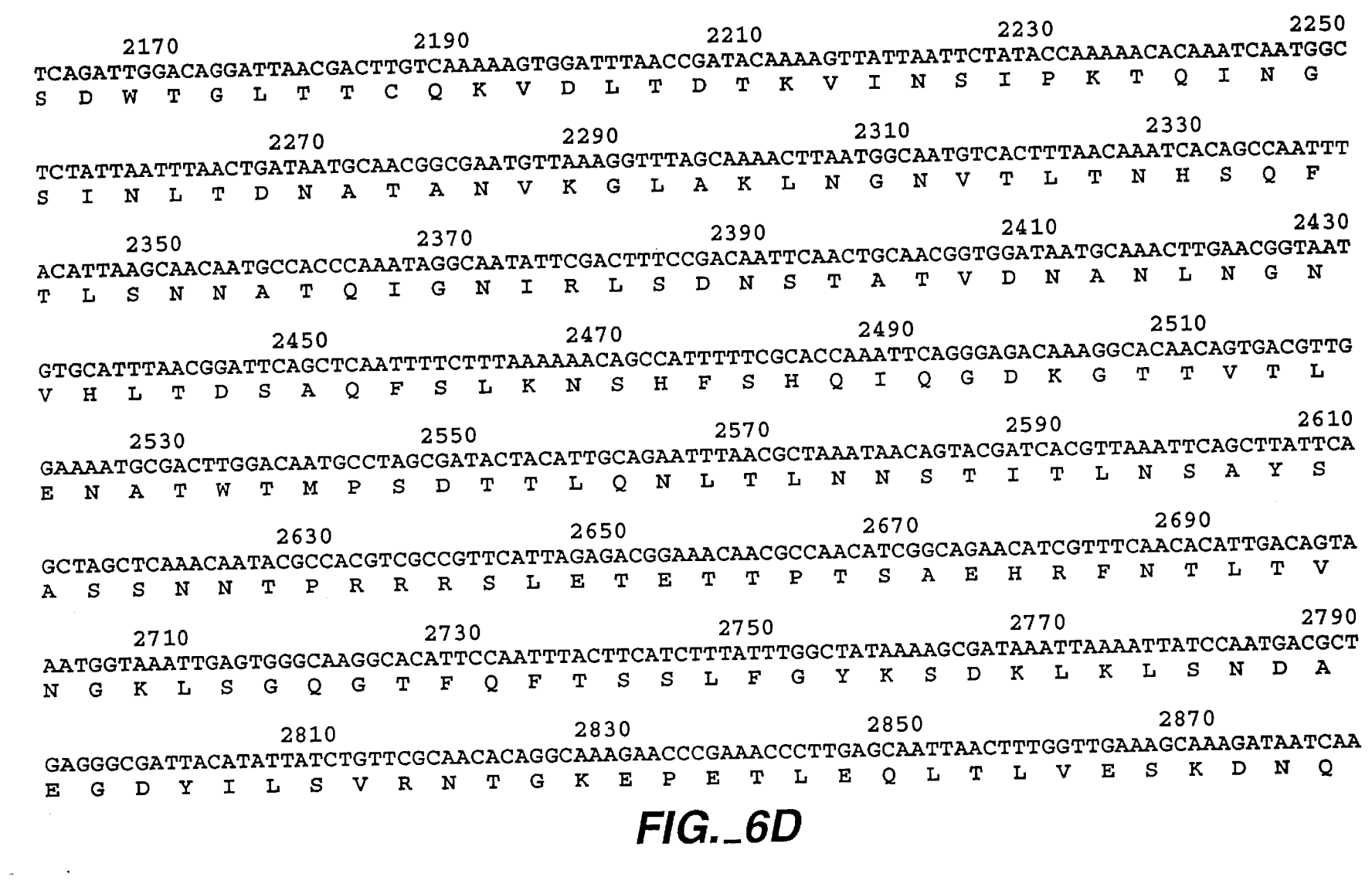

```
                              2910                    2930                   2950                         2970
CCGTTATCAGATAAGCTCAAATTTACTTTAGAAAATGACCACGTTGATGCAGGTGCATTACGTTATAAATTAGTGAAGAATGATGGCGAA
 P  L  S  D  K  L  K  F  T  L  E  N  D  H  V  D  A  G  A  L  R  Y  K  L  V  K  N  D  G  E 2990                   3010                    3030                   3050
TTCCGCTTGCATAACCCAATAAAGAGCAGGAATTGCACAATGATTTAGTAAGAGCAGAGCAAGCAGAGAACGAACATTAGAAGCCAAACAA
 F  R  L  H  N  P  I  K  E  Q  E  L  H  N  D  L  V  R  A  E  Q  A  E  R  T  L  E  A  K  Q 3070                    3090                   3110                    3130                   3150
GTTGAACCGACTGCTAAAACACAAACAAGGTGAGCCAAAAGTGCGGGTCAAGAGAGCAGCGAGAGCAGCGTTTCCTGATACCCTGCCTGAT
 V  E  P  T  A  K  T  Q  T  G  E  P  P  K  V  R  S  R  R  A  A  R  A  A  F  P  D  T  L  P  D 3170                   3190                    3210                   3230
CAAAGCCTGTTAAACGCATTAGAAGCCAAACAAGCTGACTGCTGAAACACAAAAAGTAAGGCAAAAACAAAAAAGTGCGGTCA
 Q  S  L  L  N  A  L  E  A  K  Q  A  E  L  T  A  E  T  Q  K  S  K  A  K  T  K  K  V  R  S 3250                    3270                    3290                    3310                    3330
AAAAAGACAGTGTTTTCTGATCCCCTGCTTGATCAAAGCCTGTTCGCATTAGAAGCCCACTTGAGGTTATTGATGCCCCACAGCAATCG
 K  R  A  V  F  S  D  P  L  L  D  Q  S  L  F  A  L  E  A  A  L  E  V  I  D  A  P  Q  Q  S 3350                    3370                   3390                    3410
GAAAAAGATCGTCTAGCTCAAGAAGAAGCGGAAAAACAAAGACTTGATCAGCCGTTATTCAAATAGTGCTTATCAGAA
 E  K  D  R  L  A  Q  E  E  A  E  K  Q  R  K  Q  K  D  L  I  S  R  Y  S  N  S  A  L  S  E 3430                    3450                    3470                   3490                    3510
TTATCTGCAACAGTAAATAGTATGCTTTCTGTTCAAGATGAATTAGATCGTCTTTTTGTAGATCAAGCACAATCTGCCGTGTGGACAAAT
 L  S  A  T  V  N  S  M  L  S  V  Q  D  E  L  D  R  L  F  V  D  Q  A  Q  S  A  V  W  T  N 3530                    3550                    3570                    3590
ATCGCACAGGATAAAAGACGCTATGATTCTGATGCTTCCGTGCTTATCAGCAGCAGAAAACGAACTTACGTCAAATTGGGGTGCAAAAA
 I  A  Q  D  K  R  R  Y  D  S  D  A  F  R  A  Y  Q  Q  Q  K  T  N  L  R  Q  I  G  V  Q  K
```

*FIG._6E*

```
                3610                      3630                          3650                        3670                             3690
GCCTTAGCTAATGGACGAATTGGGCAGTTTTCTCGCATAGCCGTTCAGATAATACCTTTGATGAACAGGTTAAAAATCACGCGACATTA
 A  L  A  N  G  R  I  G  A  V  F  S  H  S  R  S  D  N  T  F  D  E  Q  V  K  N  H  A  T  L 3710                        3730                         3750                        3770
ACGATGATGTCGGGTTTTGCCCAATATCAATGGGGCGATTTACAATTGGTGTAAAACGTGGGAACGGGAATCAGTGCGAGTAAAATGGCT
 T  M  M  S  G  F  A  Q  Y  Q  W  G  D  L  Q  F  G  V  N  V  G  T  G  I  S  A  S  K  M  A 3790                        3810                         3830                         3850                         3870
GAAGAACAAAGCCGAAAAATTCATCGAAAAGCGATAAATTATGGCGTGAATGCAAGTTATCAGTTCCGTTTAGGGCAATTGGGCATTCAG
 E  E  Q  S  R  K  I  H  R  K  A  I  N  Y  G  V  N  A  S  Y  Q  F  R  L  G  Q  L  G  I  Q 3890                        3910                         3930                        3950
CCTTATTTTGGAGTTAATCGCTATTTTATTGAACGTGAAAATTATCAATCTGAGGAAGTGAGAGTGAAAACGCCTAGCTTGCATTTAAT
 P  Y  F  G  V  N  R  Y  F  I  E  R  E  N  Y  Q  S  E  E  V  R  V  K  T  P  S  L  A  F  N 3970                        3990                         4010                        4030                          4050
CGCTATAAATGCTGGCATTCGAGTTGATTATACATTTACTCCGACAGATAATATCAGCGTTAAGCCTTATTTCTTCGTCAATTATGTTGAT
 R  Y  N  A  G  I  R  V  D  Y  T  F  T  P  T  D  N  I  S  V  K  P  Y  F  F  V  N  Y  V  D 4070                       4090                          4110                       4130
GTTTCAAACGCTAACGTACAAACCGTTGTTAACCTTCAAGGTTCAACAACTCGGCAAGGTTCACAACTCTCAAAATCTCAAAAATGTGGGCGTTATTGGCAAAAAGAAGTGGGATTAAAG
 V  S  N  A  N  V  Q  T  V  N  L  T  V  L  Q  Q  P  F  G  R  Y  W  Q  K  E  V  G  L  K 4150                        4170                         4190                        4210                         4230
GCAGAAATTTTACATTTCCAAATTTCCGCTTTTATCTCAAAATCTCAAGGTTCAAGCTCAAGGTTCAAGTCAAGGCTCAAGTCAGCTGGGCAAACAGCAAAATGTGGGCGTGAAATTG
 A  E  I  L  H  F  Q  I  S  A  F  I  S  K  S  Q  G  S  Q  L  G  K  Q  Q  N  V  G  V  K  L 4250                        4270                         4290                        4310
GGCTATCGTTGGTAAAAATCAACATAATTTTATCGTTTATTGATAAACAAGGTGGGTCAGATCGAGATCCCACCTTTTTTATTCCAATAAT
 G  Y  R  W  *
```

FIG._6F

```
              1
Hap           MKKTVFRLNF  LTACISLGIV  SQAWAGHTYF  GIDYQYYRDF  AENKGKFTVG
HK368IGA      MLNKKFKLNF  IALTVAYALT  PYTEAALVRD  DVDYQIFRDF  AENKGKFSVG
HK393IGA      MLNKKFKLNF  IALTVAYALT  PYTEAALVRD  DVDYQIFRDF  AENKGKFSVG
HK715IGA      MLNKKFKLNF  IALTVAYALT  PYTEAALVRD  DVDYQIFRDF  AENKGKFSVG
HK61IGA       MLNKKFKLNF  IALTVAYALT  PYTEAALVRD  DVDYQIFRDF  AENKGKFSVG
Consensus     M----F-LNF  ---------   ----A----   --DYQ---RDF AENKG-F-VG 51                                                    100
Hap           AQNIKVYNKQ  GQLVGTSMTK  A.PMIDFSVV  SRNG.VAALV  ENQYIVSVAH
HK368IGA      ATNVLVKDKN  NKDLGTALPN  GIPMIDFSVV  DVDKRIATLI  NPQYVVGVKH
HK393IGA      ATNVEVRDKN  NRPLGNVLPN  GIPMIDFSVV  DVDKRIATLV  NPQYVVGVKH
HK715IGA      ATNVEVRDKN  NHSLGNVLPN  GIPMIDFSVV  DVDKRIATLI  NPQYVVGVKH
HK61IGA       ATNVEVRDKK  NQSLGSALPN  GIPMIDFSVV  DVDKRIATLV  NPQYVVGVKH
Consensus     A-N--V--K-  ----G-----  --PMIDFSVV  ------A-L-  --QY-V-V-H 101                                                   150
Hap           .....NVGY   TDVDFGAEGN  NPDQHR....  ..FTYKIVKR  NNY.......
HK368IGA      VSNGVSELHF  GNLNGNMNNG  NAKAHRDVSS  EENRYFSVEK  NEYPTKLNGK
HK393IGA      VSNGVSELHF  GNLNGNMNNG  NAKAHRDVSS  EENRYYTVEK  NEYPTKLNGK
HK715IGA      VSNGVSELHF  GNLNGNMNNG  NDKSHRDVSS  EENRYFSVEK  NEYPTKLNGK
HK61IGA       VSNGVSELHF  GNLNGNMNNG  NAKSHRDVSS  EENRYYTVEK  NNFPTENVTS
Consensus     ----------  ----------  N----HR---  ------Y--V- -N--------

151                                                   200
Hap           ....KKDNLH  PYEDDYHNPR  LHKFVTEAAP  IDM.TSNMNG  STYSDRTKYP
HK368IGA      TVTTEDQ.TQ  KRREDYYMPR  LDKFVTEVAP  IEASTASSDA  GTYNDQNKYP
HK393IGA      AVTTEDQ..AQ KRREDYYMPR  LDKFVTEVAP  IEASTDSSDA  GTYNNKDKYP
HK715IGA      AVTTEDQ.TQ  KRREDYYMPR  LDKFVTEVAP  IEASTASSDA  GTYNDQNKYP
HK61IGA       FTTKEEQDAQ  KRREDYYMPR  LDKFVTEVAP  IEASTANNNK  GEYNNSDKYP
Consensus     ----------  ----DY---PR L-KFVTE-AP  I----T----  --Y----KYP
```

FIG._7A

```
            201
Hap         ERVRLGSGRQ F.........  ..........  ......WRNDQ DKGDQVAGAY
HK368IGA    AFVRLGSGSQ FIYKKGDNYS  LIL.......N NH....EVGG  NNLKLVGDAY
HK393IGA    YFVRLGSGTQ FIYENGTRYE  LWL.......G KEGQKSDAGG  YNLKLVGNAY
HK715IGA    AFVRLGSGSQ FIYKKGDNYS  LIL.......N NH....EVGG  NNLKLVGDAY
HK61IGA     AFVRLGSGSQ FIYKKGSRYQ  LILTEKDKQG  NLLRNWDVGG  DNLELVGNAY
Consensus   --VR-GSG-Q F---------  ----------  ----------  -----V--AY 251                                                  300
Hap         HYLTAGNTHN ORGAGNGYSY  LGG......D  VRKAGEYGPL  PIAGSKGDSG
HK368IGA    TYGIAGTPYK VNHENNGLIG  FGNSKEEHSD  PKGILSQDPL  TNYAVLGDSG
HK393IGA    TYGIAGTPYE VNHENDGLIG  FGNSNNEYIN  PKEILSKKPL  TNYAVLGDSG
HK715IGA    TYGIAGTPYK VNHENNGLIG  FGNSKEEHSD  PKGILSQDPL  TNYAVLGDSG
HK61IGA     TYGIAGTPYK VNHENNGLIG  FGNSKEEHSD  PKGILSQDPL  TNYAVLGDSG
Consensus   -Y--AG----- ------G---  ----------  --------PL  ------GDSG 301                                                  350
Hap         SPMFIYDAEK QKWLINGILR  EGNPFEGKEN  GFQLVRKSYF  D.EIFERDLH
HK368IGA    SPLFVYDREK GKWLFLGSYD  FWAGYN....  ......KKSWQ EWNIYKSQFT
HK393IGA    SPLFVYDREK GKWLFLGSYD  YWAGYN....  ......KKSWQ EWNIYKPEFA
HK715IGA    SPLFVYDREK GKWLFLGSYD  FWAGYN....  ......KKSWQ EWNIYKPEFA
HK61IGA     SPLFVYDREK GKWLFLGSYD  FWAGYN....  ......KKSWQ EWNIYKHEFA
Consensus   SP-F-YD-EK -KWL--G---  ----------  ------KS--  ---I------

351                                                  400
Hap         TSLYTRAGNG VYTISGNDNG  QGSITQKSGI  PSEIKITLAN  MSLPLKEKDK
HK368IGA    KDVLNKDSAG SLIGSKTDYS  WSSNGKTSTI  TGGEK.....S LNVDLAD...
HK393IGA    EKIYEOYSAG SLIGSKTDYS  WSSNGKTSTI  TGGEK.....S LNVDLAD...
HK715IGA    KTVLDKDTAG SLTGSNTQYN  WNPTGKTSVI  SNGSE.....S LNVDLFD...
HK61IGA     EKIYQQYSAG SLTGSNTQYT  WQATGSTSTI  TGGGE.....P LSVDLTD...
Consensus   ---------- ------S---  ----------  -----S--I-  ---L------
```

FIG._7B

```
              401
Hap           VHNPRYDGPN IYSPRLNNGE TLYFMDQKQG SLIFASDINQ GAGGLYFEGN
HK368IGA      ..........GKD. .....KPNHGK SVTFEG..SG TLTLNNNIDQ GAGGLFFEGD
HK393IGA      ..........GKD. .....KPNHGK SVTFEG..SG TLTLNNNIDQ GAGGLFFEGD
HK715IGA      ..........SSQD TDSKKNNHGK SVTLRG..SG TLTLNNNIDQ GAGGLFFEGD
HK61IGA       ..........GKD. .....KPNHGK SITLKG..SG TLTLNNHHDQ GAGGLFFEGD
Consensus     ------------- ------N-G-- ---------- -L-------Q -GAGGL-FEG- 451                                                   500
Hap           FTVSPNSNQ. TWQGAGIHVS ENSTVTWKVN GVEHDRLSKI GKGTLHVQAK
HK368IGA      YEVKGTSDNT TWKGAGVSVA EGKTVTWKVH NPQYDRLAKI GKGTLIVEGT
HK393IGA      YEVKGTSDNT TWKGAGVSVA EGKTVTWKVH NPQYDRLAKI GKGTLIVEGT
HK715IGA      YEVKGTSDST TWKGAGVSVA DGKTVTWKVH NPKSDRLAKI GKGTLIVEGK
HK61IGA       YEVKGTSDST TWKGAGVSVA DGKTVTWKVH NPKYDRLAKI GKGTLVVEGK
Consensus     --V----S--- TW-GAG---- ---TVTWKV- ----DRL-KI GKGTL-V---

501                                                   550
Hap           GENKGSISVG DGKVILEQQA DDQGNKQAFS EIGLVSGRGT VQLNDDKQFD
HK368IGA      GDNKGSLKVG DGTVILKQQT NGSGQ.HAFA SVGIVSGRST LVLNDDKQVD
HK393IGA      GDNKGSLKVG DGTVILKQQT NGSGQ.HAFA SVGIVSGRST LVLNDDKQVD
HK715IGA      GENKGSLKVG DGTVILKQQA DANNKVKAFS QVGIVSGRST VVLNDDKQVD
HK61IGA       GKNEGLLKVG DGTVILKQKA DANNKVQAFS QVGIVSGRST LVLNDDKQVD
Consensus     G-N-G----VG DG-VIL-Q-- ------AF-- --G-VSGR-T --LNDDKQ-D 551                                                   600
Hap           TDKFYFGFRG GRLDLNGHSL TFKRIQNTDE GAMIVNHNTT QAANVTITGN
HK368IGA      PNSIYFGFRG GRLDLNGNSL TFDHIRNIDD GARLVNHNMT NASNITITGE
HK393IGA      PNSIYFGFRG GRLDLNGNSL TFDHIRNIDE GARLVNHSTS KHSTVTITGD
HK715IGA      PNSIYFGFRG GRLDANGNNL TFEHIRNIDD GARLVNHNTS KTSTVTITGE
HK61IGA       PNSIYFGFRG GRLDLNGNSL TFDHIRNIDD GARVVNHNMT NTSNITITGE
Consensus     ----YFGFRG GRLD-NG--L TF---I-N-D- GA---VNH--- -----TITG-
```

FIG._7C

```
          601                                                                650
Hap       ESIVLPNG.. ........  .......... NPYAFRRIKD GGQLYLNLEN YTYYALRKGA
HK368IGA  SLITDPNTIT PYNIDAPDED NPYAFRRIKD GGQLYLNLEN YTYYALRKGA
HK393IGA  NLITDPNNVS IYYVKPLEDD NPYAIRQIKY GYQLYFNEEN RTYYALKKDA
HK715IGA  SLITDPNTIT PYNIDAPDED NPYAFRRIKD GGQLYLNLEN YTYYALRKGA
HK61IGA   SLITNPNTIT SYNIEAQDDD HPLRIRSIPY R.QLYFNQDN RSYYTLKKGA
Consensus --I--PN--- ---------- ---------- ---------- ----------

651                                                                700
Hap       ........ .  ........ . N NINKLDYRKE IAYNGWFGET
HK368IGA  STRSELPKNS GESNENWLYM GKTSDEAKRN VMNHINNERM NGFNGYFGEE
HK393IGA  SIRSEFPQNR GESNNSWLYM GTEKADAQKN AMNHINNERM NGFNGYFGEE
HK715IGA  STRSELPKNS GESNENWLYM GKTSDEAKRN VMNHINNERM NGFNGYFGEE
HK61IGA   STRSELPQNS GESNENWLYM GRTSDEAKRN VMNHINNERM NGFNGYFGEE
Consensus ---------- ---------- ---------N ---N------ ---NG-FGE- 701                                                                750
Hap       D.KNKHNGRL NLIYKPTTED RTLLLSGGTN LKGDITQTKG KLFFSGRPTP
HK368IGA  EGK..NNGNL NVTFKGKSEQ NRFLLTGGTN LNGDLTVEKG TLFLSGRPTP
HK393IGA  EGK..NNGNL NVTFKGKSEQ NRFLLTGGTN LNGDLNVQQG TLFLSGRPTP
HK715IGA  EGK..NNGNL NVTFKGKSEQ NRFLLTGGTN LNGDLKVEKG TLFLSGRPTP
HK61IGA   ETKATQNGKL NVTFNGKSDQ NRFLLTGGTN LNGDLNVEKG TLFLSGRPTP
Consensus --K---NG-L -N-------- ---LL-GGTN L--GD----- -LF-SGRPTP 751                                                                800
Hap       HAYNHLNKRW SEMEG..IPQ GEIVWDHDWI NRTFKAENFQ IKGGSAVVS.
HK368IGA  HARDIAGISS TKKDPHFAEN NEVVVEDDWI NRNFKATTMN VTGNASLYSG
HK393IGA  HARDIAGISS TKKDSHFSEN NEVVVEDDWI NRNFKATNIN VTNNATLYSG
HK715IGA  HARDIAGISS TKKDQHFAEN NEVVVEDDWI NFNERATNIN VTNNATLYSG
HK61IGA   HARDIAGISS TKKDPHFTEN NEVVVEDDWI NRNFKATTMN VTGNASLYSG
Consensus HA-------- ---------- -E-V----DWI NR-FKA---- -------S-
```

FIG._7D

```
           801
Hap        RNVSSIEGNW TVSNNANATF GVVPNQQNTI CTRSDWTGLT TCQKVDLTDT  850
HK368IGA   RNVANITSNI TASNKAQVHI GY..KTGDTV CVRSDYTGYV TCTTDKLSD.
HK393IGA   RNVESITSNI TASNNAKVHI GY..KAGDTV CVRSDYTGYV TCTTDKLSD.
HK715IGA   RNVANITSNI TASDNAKVHI GY..KAGDTV CVRSDYTGYV TCTTDKLSD.
HK61IGA    RNVANITSNI TASNNAQVHI GY..KTGDTV CVRSDYTGYV TCHNSNLSE.
Consensus  RNV--I---N- T-S--A---- G------T-- C-RSD-TG-- TC----L---
                                                         *
           851
Hap        KVINSIPKTQ INGSINLTDN ATANVKGLAK LNGNVTLTNH SQFTLSNNAT  900
HK368IGA   KALNSFNPTN LRGNVNLTES A.................................
HK393IGA   KALNSFNPTN LRGNVNLTES A.................................
HK715IGA   KALNSFNATN VSGNVNLSGN A.................................
HK61IGA    KALNSFNPTN LRGNVNLTEN A.................................
Consensus  K--NS---T- --G--NL--- A-------------------------------
                                 *

901
Hap        QIGNIRLSDN STATVDNANL NGNVHLTDSA QFSLKNSHFS HQIQGDKGTT  950
HK368IGA   .ENSHWHL  TGNSDVHQLD FGTIQSRGNS QVRLT...............
HK393IGA   .ENSHWHL  TGNSDVHQLD FGTIQSRGNS QVRLT...............
HK715IGA   .ENSHMHL  TGDSNVHQLD FGTISGTGNS QVRLT...............
HK61IGA    .ENSHWHL  TGNSNVNQLN FGTIQSIGTS QVNLK...............
Consensus  ------ANL  -G-------- Q--L--------------

951
Hap        VTLENATWTM PSDTTLQNLT LNNSTITLNS AYSASSNNTP RRRSLETETT  1000
HK368IGA   ...ENSHWHL TGNSDVHQLD LANGHIHLNS ADNSNNVTK........
HK393IGA   ...ENSHWHL TGNSDVHQLD LANGHIHLNS ADNSNNVTK........
HK715IGA   ...ENSHMHL TGDSNVHQLD LDKGHIHLNA QNDANKVTT........
HK61IGA    ...ENSHWHL TGNSNVNQLN LTNGHIHLNA QNDANKVTT........
Consensus  ---EN--W-- --------L- L----I--LN- ----------
```

FIG._7E

```
           1001                                                        1050
Hap        PTSAEHRFNT LTVNGKLSGQ GTFQFTSSLF GYKSDKLKLS NDAEGDYILS
HK368IGA   .......YNT LTVNS.LSGN GSFYYLTDLS NKQGDKVVVT KSATGNFTLQ
HK393IGA   .......YNT LTVNS.LSGN GSFYYLTDLS NKQGDKVVVT KSATGNFTLQ
HK715IGA   .......YNT LTVNS.LSGN GSFYYLTDLS NKQGDKVVVT KSATGNFTLQ
HK61IGA    .......YNT LTVNS.LSGN GSFYYWVDFT NNKSNKVVVN KSATGNFTLQ
Consensus  -------NT  LTVN--LSG- G-F------- ------K--- --A-G---L-

1051                                                       1100
Hap        VRNTGKEPET LEQLTLVESK DNQPLSDKLK FTLENDHVDA GALRYKLVKN
HK368IGA   VADKTGEPNH .NELTLFDAS KAQR..DHLN VSLVGNTVDL GAWKYKLRNV
HK393IGA   VADKTGEPNH .NELTLFDAS KAQR..DHLN VSLVGNTVDL GAWKYKLRNV
HK715IGA   VADKTGEPTK .NELTLFDAS NATR..NNLN VSLVGNTVDL GAWKYKLRNV
HK61IGA    VADKTGEPNH .NELTLFDAS NATR..NNLE VTLANGSVDR GAWKYKLRNV
Consensus  V------EP- ---LTL---- ---------L- ----VD---- GA--YKL---

1101                                                       1150
Hap        DGEFRLHNPI KEQELHNDLV .......... .......... NNEEIARVDE
HK368IGA   NGRYDLYNP. .EVEKRNQTV DTTNITTPNN IQADVPSVPS NNEEIARVDE
HK393IGA   NGRYDLYNP. .EVEKRNQTV DTTNITTPNN IQADVPSVPS NNEEIARVDE
HK715IGA   NGRYDLYNP. .EVEKRNQTV DTTNITTPNN IQADVPSVPS NNEEIARV.E
HK61IGA    NGRYDLYNP. .EVEKRNQTV DTTNITTPND IQADAPSAQS NNEEIARV.E
Consensus  -G---L-NP- -E-E---N--V ---------- ---------- ----------

1151                                                       1200
Hap        APVPPPAPAT .......... .......... .......... ..........
HK368IGA   APVPPPAPAT .......... .......... .......... ..........
HK393IGA   TPVPPPAPAT .......... .......... .......... ..........
HK715IGA   TPVPPPAPAT ESAIASEQPE TRPAETAQPA MEETNTANST ETAPKSDTAT
HK61IGA    ---------- ---------- ---------- ---------- ----------
Consensus  ---------- ---------- ---------- ---------- ----------
```

FIG._7F

```
                                                                  1250
Hap         ..........  ..........  RAEQAERTLE  AKQVEPT...  ..........
HK368IGA    ..........  .PSETTETVAE  NSKQESKTVE  KNEQDATETT  AQNREVAKEA
HK393IGA    ..........  .PSETTETVAE  NSKQESKTVE  KNEQDATETT  AQNREVAKEA
HK715IGA    ..........  .PSETTETVAE  NSKQESKTVE  KNEQDATETT  AQNGEVAEEA
HK61IGA     ..........  .PSETTEKVAE  NPPQENETVA  KNEQEATEPT  PQNGEVAKED
Consensus   ----------  ----------  -------Q--  ----T-----  ----------

1251                                                  1300
Hap         ....AKTQT.  GE........  ..........  ..........  ..........
HK368IGA    KSNVKANTQT  NEVAQSGSET  KETQTTETK.  ..........  ....ETATVE
HK393IGA    KSNVKANTQT  NEVAQSGSET  KETQTTETK.  ..........  ....ETATVE
HK715IGA    KPNVKANTQT  NEVAQSGSET  EETQTTEIK.  ..........  ....ETAKVE
HK61IGA     QPTVEANTQT  NEATQSEGKT  EETQTAETKS  EPTESVTVSE  NQPEKTVSQS
Consensus   ----A-TQT   -E--------  ----------  ----------  ----------

1301                                                  1350
Hap         ..........  ..........  ..........  ..........  ..........
HK368IGA    .KEEK.....  ..........  ..........  ..........  ..........
HK393IGA    .KEEK.....  ..........  ..........  ..........  ..........
HK715IGA    KEEKAKVEKE  EKAKVEKDEI  QEAPQMASET  SPKQAKPAPK  EVSTDTKVEE
HK61IGA     TEDKVVVEKE  EKAKVETEET  QKAPQVTSKE  PPKQAEPAPE  EVPTDTNAEE
Consensus   ----------  ----------  ----------  ----------  ----------

1351                                                  1400
Hap         ..........  ..........  ..........  ..........  ..........
HK368IGA    ..........  ..........  ..........  ..........  ..........
HK393IGA    ..........  ..........  ..........  ..........  ..........
HK715IGA    .TQVQAQPQTQ  STTVAAAEAT  SPNSKPAEET  .QPSEKTNAE  PVTPVVSKNQ
HK61IGA     A..QALQQTQ  PTTVAAAETT  SPNSKPAEET  QQPSEKTNAE  PVTPVVS...
Consensus   ----------  ----------  ----------  ----------  ----------
```

*FIG._7G*

```
              1401                                                    1450
Hap           ..........  ..........  ..........  ....PKVRS  RRAARAAFPD  TLP.......
HK368IGA      ..........  ..........  ....AKVETE  KTQEVPKVTS  QVSPKQEQSE  T.........
HK393IGA      ..........  ..........  ....AKVETE  KTQEVPKVTS  QVSPKQEQSE  T.........
HK71SIGA      TENTTDQPTE  REKTAKVETE  KTQEPPQVAS  QASPKQEQSE  T.........
HK61IGA       .ENTATQPTE  TEETAKVEKE  KTQEVPQVAS  QESPKQEQPA  AKPQAQTKPQ
Consensus     ----------  ----------  ----------  ------P-V-S  ----------  ----------

1451                                                    1500
Hap           ..........  ..........  ..........  ..........  ..........  ..........
HK368IGA      ..........  ..........  ..........  ..........  ..........  ........V
HK393IGA      ..........  ..........  ..........  ..........  ..........  ........V
HK71SIGA      ..........  ..........  ..........  ..........  ..........  ........V
HK61IGA       AEPARENVLT  TKNVGEPQPQ  AQPQTQSTAV  PTTGETAANS  KPAAKPQAQA
Consensus     ----------  ----------  ----------  ----------  ----------  ----------

1501                                                    1550
Hap           ..........D  QSLLNALEA.  ......KQAEL  TAETQKSKAK  TKK.......
HK368IGA      QPQAEPAREN  DPTVNIKEP.  ......QSQTNT  TADTEQPAKE  TSSNVE....
HK393IGA      QPQAEPAREN  DPTVNIKEP.  ......QSQTNT  TADTEQPAKE  TSSNVE....
HK71SIGA      QPQAVLESEN  VPTVNNAEEV  QAQLQTQTSA  TVSTKQPAPE  NSINTG....
HK61IGA       KPQTEPAREN  VSTVNTKEP.  ......QSQTSA  TVSTEQPAKE  TSSNVEQPAP
Consensus     ----------  ----N--E--  -------Q---  ----T--T--  ----------

1551                                                    1600
Hap           ..........  ..........  ......V  RSKRAVFSDP  LLDQSL....
HK368IGA      ........SAT  AITETAEKSD  KPQTETAAST  QPVT  ESTTVNTGNS  VVEN......
HK393IGA      ........SAT  AITETAEKSD  KPQTETAAST  QPVT  ESTTVNTGNS  VVEN......
HK71SIGA      ENSINTGSAT  TMTETAEKSD  KPQMET..VT  EDASQHKANT  VADNSVANNS
HK61IGA       ENSINTGSAT  TMTETAEKSD  KPQMET..VT  ENDRQPEANT  VADNSVANNS
Consensus     ----------  ----------  ----------  ----------  ----------
```

FIG._7H

```
                                                                              1650
Hap         .........F  ALEAALEVID  APQQSEKDRL  AQEEAEKQRK
HK368IGA    ..........  ..........  PENTTPATTQ  PTVNSESSN.  .KPK.NRHRR
HK393IGA    ..........  ..........  PENTTPATTQ  PTVNSESSN.  .KPK.NRHRR
HK715IGA    ESSEPKSRRR  RSISQPQETS  AEETTAASTD  ETTIADNSKR  SKPN.RRSRR
HK61IGA     ESSESKSRRR  RSVSQPKETS  AEETTVASTQ  ETTVDNSVST  PKPRSRRTRR
Consensus   ----------  ----------  ----------  ----------  -R--------

1700
Hap         ..........  ..........  ..........  ....QKDLI   SRYSNSALSE
HK368IGA    SVRSVPHNVE  PATTSSND..  ..........  RSTVALCDLT  STNTNAVLSD
HK393IGA    SVRSVPHNVE  PATTSSND..  ..........  RSTVALCDLT  STNTNAVLSD
HK715IGA    SVRS.....E  PTVTNGSD..  ..........  RSTVALRDLT  STNTNAVISD
HK61IGA     SVQTNSYEPV  ELPTENAENA  ENVQSGNNVA  NSQPALRNLT  SKNTNAVLSN
Consensus   ----------  ----------  ----------  -------L--  S---N---S-

1750
Hap         LSA....TV   NSMLSVQDEL  DRL.FVDQAQ  SAVWTNIAQD  KRRYDSDAFR
HK368IGA    ARAKAQFVAL  NVGKAVSQHI  SQLEMNNEGQ  YNVWVSNTSM  NKNYSSSQYR
HK393IGA    ARAKAQFVAL  NVGKAVSQHI  SQLEMNNEGQ  YNVWVSNTSM  NKNYSSSQYR
HK715IGA    AMAKAQFVAL  NVGKAVSQHI  SQLEMNNEGQ  YNVWVSNTSM  NENYSSSQYR
HK61IGA     AMAKAQFVAL  NVGKAVSQHI  SQLEMNNEGQ  YNVWISNTSM  NKNYSSEQYR
Consensus   ----A-----  N-----V---  ----L-----  --VW------  ---Y-S---R 1800
Hap         AYQQQKTNLR  QIGVQKALAN  GRIGAVFSHS  RSDNTFDEQV  KNHATLTMMS
HK368IGA    RFSSKSTQTQ  LGWDQTISNN  VQLGGVFTYV  RNSNNFDKAT  SKN.TLAQVN
HK393IGA    RFSSKSTQTQ  LGWDQTISNN  VQLGGVFTYV  RNSNNFDKAT  SKN.TLAQVN
HK715IGA    RFSSKSTQTQ  LGWDQTISNN  VQLGGVFTYV  RNSNNFDKAS  SKN.TLAQVN
HK61IGA     RFSSKSTQTQ  LGWDQTISNN  VQLGGVFTYV  RNSNNFDKAS  SKN.TLAQVN
Consensus   -----T----  ------Q---  ---G-VF---  R--N-FD---  ------TL--
```

FIG._71

```
              1801                                                          1850
Hap           GFAQYQWGDL QF..GVNVGT GISASKMAEE QSRKIHRKAI NYGVNASYQF
HK368IGA      FYSKY.YADN HWYLGIDLGY GKFQSKLQTN HNAKFARHTA QFGLTAGKAF
HK393IGA      FYSKY.YADN HWYLGIDLGY GKFQSKLQTN HNAKFARHTA QFGLTAGKAF
HK715IGA      FYSKY.YADN HWYLGIDLGY GKFQSNLKTN HNAKFARHTA QFGLTAGKAF
HK61IGA       FYSKY.YADN HWYLGIDLGY GKFQSNLQTN NNAKFARHTA QIGLTAGKAF
Consensus     -----Y---- -----G---G G-----S--- ---K---R-- --G---A---F 1851                                                          1900
Hap           RLGQLGIQPY FGVNRYFIER ENYQSEEVRV KTPSLAFNRY NAGIRVDYTF
HK368IGA      NLGNFGITPI VGVRYSYLSN ADFALDQARI KVNPISVKTA FAQVDLSYTY
HK393IGA      NLGNFGITPI VGVRYSYLSN ADFALDQARI KVNPISVKTA FAQVDLSYTY
HK715IGA      NLGNFGITPI VGVRYSYLSN ANFALAKDRI KVNPISVKTA FAQVDLSYTY
HK61IGA       NLGNFAVKPT VGVRYSYLSN ADFALAQDRI KVNPISVKTA FAQVDLSYTY
Consensus     -LG-----P- -GV------- ------R--- K--------- -A-----YT- 1901                                                          1950
Hap           TPTDNISVKP YFFVNYVDVS NANVQTTVNL TVLQQPFGRY WQKEVGLKAE
HK368IGA      .HLGEFSVTP ILSARY.DAN QGSGKINVNG YDFAYNVENQ QQYNAGLKLK
HK393IGA      .HLGEFSVTP ILSARY.DAN QGSGKINVNG YDFAYNVENQ QQYNAGLKLK
HK715IGA      .HLGEFSVTP ILSARY.DTN QGSGKINVNQ YDFAYNVENQ QQYNAGLKLK
HK61IGA       .HLGEFSITP ILSARY.DAN QGNGKINVSV YDFAYNVENQ QQYNAGLKLK
Consensus     -----S--P ------Y-D-- ----V----- ---------- -Q----GLK--

1951                                1982
Hap           ILHFQISAFI SKSQGSQLGK QQNVGVKLGY RW
HK368IGA      YHNVKLSLIG GLTKAKQAEK QKTAELKLSF SF
HK393IGA      YHNVKLSLIG GLTKAKQAEK QKTAELKLSF SF
HK715IGA      YHNVKLSLIG GLTKAKQAEK QKTAELKLSF SF
HK61IGA       YHNVKLSLIG GLTKAKQAEK QKTAEVKLSF SF
Consensus     -----S---- ------Q--K Q----KL--- --
```

FIG._7J

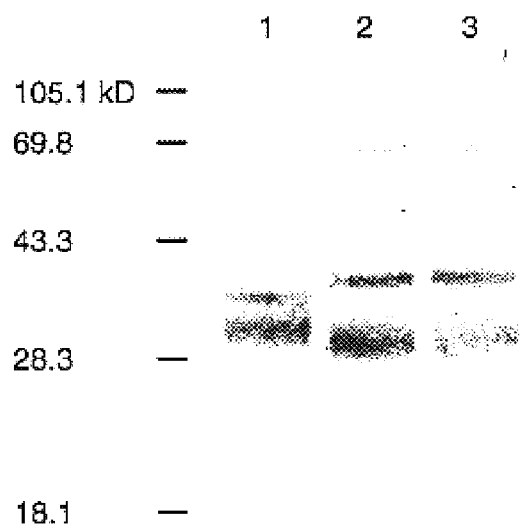
FIG._8
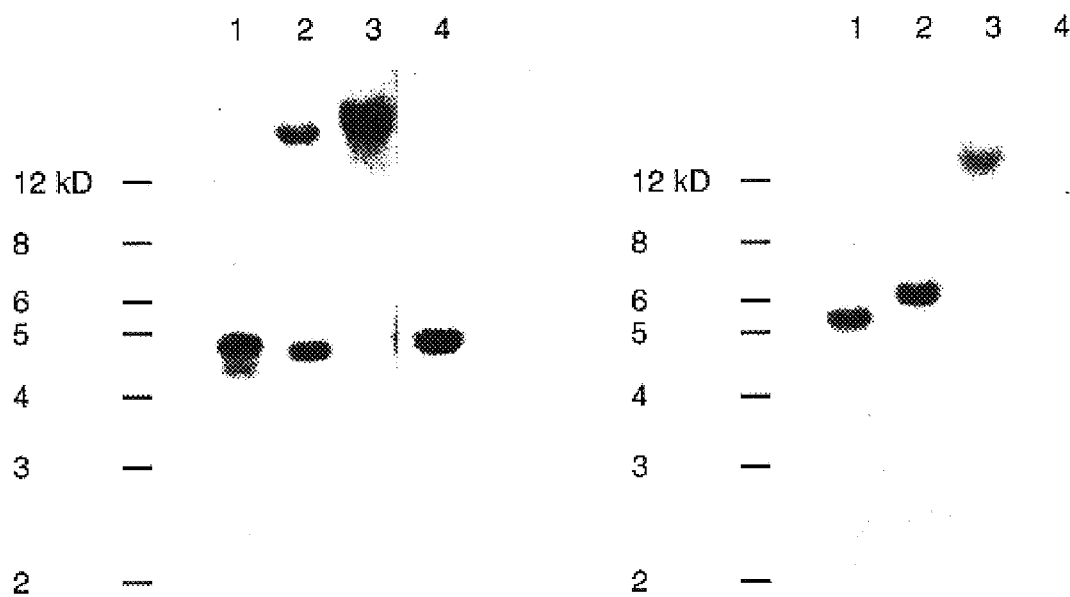
FIG._9A  FIG._9B

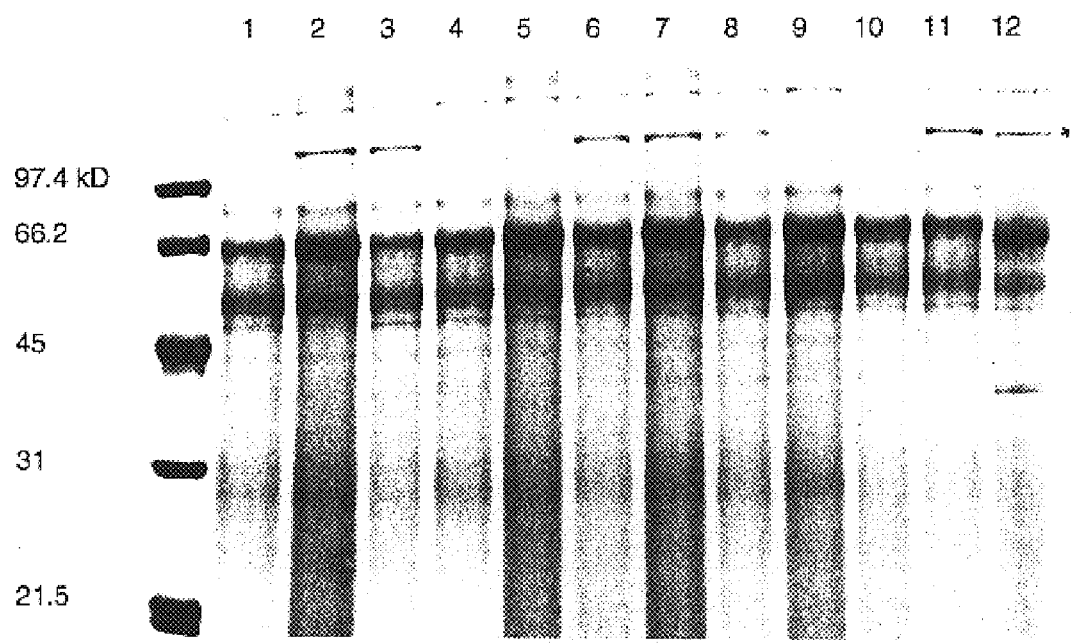
FIG._10

```
              1                                                50
HapN187    (1)  MKKTVFRLNFLTACISLGIVSQAWAGHTYFGIDYQYYRDFAENKGKFTVG
HapTN106   (1)  MKKTVFRLNFLTACISLGIVSQAWAGHTYFGIDYQYYRDFAENKGKFTVG
Hap860295  (1)  MKKTVFRLNFLTACISLGIVSQAWAGHTYFGIDYQYYRDFAENKGKFSVG
Consensus  (1)  MKKTVFRLNFLTACISLGIVSQAWAGHTYFGIDYQYYRDFAENKGKF VG
              51                                              100
HapN187   (51)  AQNIKVYNKQGRVGTSMTKAPMIDESVWSRNGVAALVSENQYTVSVAHNV
HapTN106  (51)  AGDIDINIKGEMIGGMKGVEMPDLSSMVEGGYSTDISEGHLIGVAHNV
Hap860295 (51)  AKNIEVYNKEGTVGTSMKAPMIDESVVSRNGVAELVGGDQYIVSVAHNG
Consensus (51)  A   I YNK G  GT M  PM D S   R G  L     Q SVAHN
              101                                             150
HapN187  (101)  GYTDVDFGAEGNNPDQHRFYKLVKRNNYKDNLHPYEDDYHNPRLHKFV
HapTN106 (101)  GYDVVDFGMEGENDDQHRFKVKVVKRYNYKSS--DRQYNDYQHPRLEKFV
Hap860295(101)  GINSVDFGAEGPNPDQHRFYQIVKRNNIKPGKDNEYHGDYHMPRLHKFV
Consensus(101)  GY  VDFG EG NPDQHRF Y  VKR NYK        DY  PRL KFV
              151                                             200
HapN187  (151)  TETAPIDMISNMNGSTMSDRTKVRERVRIGSGRQFWRNDQDK--GDQ---
HapTN106 (149)  TETAPIEMVRYMDGNHMKNFNQYBLRVEVGSGHQWWKDDNNKTIGD----
Hap860295(151)  IDEEPAKMIDNMNGKNVADLSEDRVFIGTGEQWRTDEEQKQGSKSSW
Consensus(151)  T    P  M   MG Y         YP RVR G  GQW D        G
              201                                            250
HapN187  (196)  VRGAYHYETAGNTHNQRGAGNGYSYTGGDVRKAGEYGELEIAGSKGDSGS
HapTN106 (195)  VAYGGSWITGGNRFEDGPAGNGTLELNGRVONENKVGPLETAGSEGDSGS
Hap860295(201)  EADAYLWRIAGNTHSQSGAGNGTVNLSGDITKPNNYGPLPIGVSEGDSGS
Consensus(201)       A        GNT   AGNG   L G       YGPLP   S GDSGS
              251                                            300
HapN187  (246)  PMFIYDAEKQKWLINGILREGNPEEGKENGEQLVRKSYEDE-TEERQLHT
HapTN106 (245)  PMFIYDKEVKKWLNGVDEEGNBYAAVGNSYQITRKDYEQG-ELNQDITA
Hap860295(251)  PMFIYDAIRQKWLINGVLQTGNEESGAGNGEQLIRKNWEYDNVEVEDLPI
Consensus(251)  PMFIYD   KWL NG L  GNP      N   Q  RK F     D
              301                                            350
HapN187  (295)  SLYTRAGNGVYTESGNDNG-----QGSITQKSGIPSEIKITLANMSEPLK
HapTN106 (294)  NEWDTNAEYRFNEGSDHNGRVATIKSTLPKKAIQEERIVGLYDNSQLHDA
Hap860295(301)  TELEPRSNGHYSFTSNNNG-----TGTVLQTNEKVSMPQFKVRTVQLFNE
Consensus(301)                  NG                                L
              351                                            400
HapN187  (340)  -EKDKVHNPRYDGR--NIYSDRLNNGETLYFMDQKQGSIIFASDINQGAG
HapTN106 (344)  RDKNGDESPSYKGR--NPWSPALHHGKSIYEGDQGTGTLTIENNINQGAG
Hap860295(346)  ALKEKDKERVAAGGVNAYKPRLNNGKNIYEDRGTGTLTIENNINQGAG
Consensus(351)    K         PY      N  PL G   YF D  G L   INQGAG
              401                                            450
HapN187  (387)  GLYFEGNFTVSPNSN-QTWQGAGIHVSENSTVEWKVNGVEHDRLSKIGKG
HapTN106 (392)  GLYFEGNFVVKGNQNNITWQGAGVSVGEESTVEWQVHNPEGDRESKIGLG
Hap860295(396)  GLYFEGNFTVSSENN-ATWQGAGVHVGEDSTVTNKVNGVEHDRLSKIGKG
Consensus(401)  GLYFEGNF V   N   TWQGAG V E STV W V  E DRLSKIG G
```

FIG. 11A

```
            451                                              500
HapN187   (436) TLHVQAKGENKGSILVGDGKVILEQQADDQGNKQAFSEIGLVSGRGIVQL
HapTN106  (442) TLLVNGKGRNICSLSVGNGLVVEDQQADESQKQAFTEVGIVSGRATVQL
Hap860295 (445) TLHIQAKGENLGSISVGDGKVILPQQADENNQKQAFEKVGIVSGRATVQL
Consensus (451) TL   KG N GS SVG G V L QQAD   KQAF E G VSGR TVQL
            501                                              550
HapN187   (486) NDDKQFITDKFYFGFRGGRLDLNGHSLTFKRIQNTDEGAMIVNHNTTQAA
HapTN106  (492) NSADQVDRNDYFGFRGGRLDLNGHSLTFERIQNTDEGAMIVNHNPASQTA
Hap860295 (495) NSADQVDRNDYFGFRGGRLDLNGHSLTFKRIQNTDEGAMIVNHNTTQAVA
Consensus (501) N  Q D    YFGFRGGRLDLNGHSLTF RIQNTDEGAMIVNHN  Q A
            551                                              600
HapN187   (536) NVIITGNESIVLQ-NGNNINKLDYRKEIAYNGWEGETDKNHHNGRLNLIY
HapTN106  (542) NTIITGNATINS-----DSKQLTNKRDIAFNGWFGEQDKAKTNGRLNVNY
Hap860295 (545) NTIITGNESITAHSNKNNINKLDYSKEIAYNGWFGETDENKHNGRLNLIY
Consensus (551) N TITGN  I        L   K  IA NGWFGE D  K NGRLN  Y
            601                                              650
HapN187   (585) KRIIEDRILLLSGGTNIKGDITQTKGKLFFSGRPTPHAYNHLNKRWSEME
HapTN106  (587) QRVNAENHILLSGGTNLNGNITQNGITNFSGRPTPHAYNHLRPDLSNME
Hap860295 (595) KRTTEDRILLLSGGTNLKGNLTQEGITLVFSGRPTPHAYNHLNR--PNEL
Consensus (601) P     LLLSGGTNL G ITQ  G L FSGRPTPHAYNHL
            651                                              700
HapN187   (635) GIPQGEIVWDHDWINRTFKAENFQIKGGSAVVSRNVSSIEGNWTVSNNAN
HapTN106  (637) GIPQGEIVWDHDWINRTFKAENFQIKGGSAVVSRNVSSIEGNWTVSNNAN
Hap860295 (643) GRPQGEVVIDDDWITRTFKAENFQIKGGSAVVSRNVSSIEGNWTVSNNAN
Consensus (651) G PQGE V D DWI RTFKAENFQIKGGSAVVSRNVSSIEGNWTVSNNAN
            701                                              750
HapN187   (685) ATFGVVPNQQNTICTRSDWTGLTTCQKVDLTDTKVINSIPKTQINGSINL
HapTN106  (687) ATFGVVPNQQNTICTRSDWTGLTTCKVDLTDKKVINSIPTTQINGSINL
Hap860295 (693) AAFGVAPNQQNTICTRSDWTGLTTCKTVDLTDRVINSIPTTQINGSINL
Consensus (701) A FGVVPNQQNTICTRSDWTGLTTC  VDLTD KVINSIP TQINGSINL
            751                                              800
HapN187   (735) TDNATANVKGLAKLNGNVTLTNHSQFTLSNNATQIGNIRLSDNSTATVDN
HapTN106  (737) TDNATVNTHGLAKLNGNVTLLDHSQFTLSNNATQGNIKLSNHANATVDN
Hap860295 (743) TDNATVNIHGLAKLNGNVTLINHSQFTLSNNATQIGNIKQLSNHANAEVDN
Consensus (751) TDNAT N  GLAKLNGNVTL  HSQFTLSNNATQ GNI LS    ATVDN
            801                                              850
HapN187   (785) ANLNGNVHLTDSAQFSLKNSHFSHQIQGDKSGTTVLENATWTMPSDTTLQ
HapTN106  (787) ANLNGNVNLMDSAQFSLKNSHFSHQIQGIEDTVVMIENATWTMPSDTTLQ
Hap860295 (793) ANLNGNVHLTDSAQFSLKNSHFSHQIQGDKDTTVVLENATWTMPSDATLQ
Consensus (801) ANLNGNV L DSAQFSLKNSHFSHQIQG    TTV LENATWTMPSD TLQ
            851                                              900
HapN187   (835) NLTLNNSTITLNSAYSASSNNTPRRRRSLETETTPTSAEHRFNTLTVNG
HapTN106  (837) NLTLNNSRVTLNSAYSANISNNAPRRRRSLETETTPTSAEHRFNTLTVNG
Hap860295 (843) NLTLNNSRVTLNSAYSASSNNAPR-HRRSLETETTPTSAEHRFNTLTVNG
Consensus (851) NLTLNNST TLNSAYSA SNN PR  RRSLETETTPTSAEHRFNTLTVNG
```

FIG. 11B

```
                901                                              950
HapN187   (885) KLSGQGTFQFTSSLFGYKSDKLKLSNDAEGDY ILSVRNTGKEPFFEQLT
HapTN106  (887) KLSGQGTFQFTSSLFGKSDKLKLSNDAEGDY TSVRNTGKEP VTFGQLT
Hap860295 (892) KLSGQGTFQFTSSFGYKSDKEKLSNDAEGDY TSVRNTGKEP ALEQLT
Consensus (901) KLSGQGTFQFTSSLFGYKSDKLKLSNDAEGDY LSVRNTGKEP    QLT
                951                                             1000
HapN187   (935) LVESKDNQPLSDKLFTLENDHVDAGALRYKLVKNDGEFRLHNPIKESEL
HapTN106  (937) LVESKDNKPLSDKL TFTLENDHVDAGALRYKLVKNDSEFRLHNPIKEQEL
Hap860295 (942) LVESKDNEPLSEKDKNLLENDHVDAGALRYKLVKN NGEFRLHNPIKEQEL
Consensus (951) LVESKDN PLSDKL FTLENDHVDAGALRYKLVKN GEFRLHNPIKEQEL
                1001                                            1050
HapN187   (985) HNDLVRAEQAERTLEAKQVEPTAKTQTGEPKVRSKRAARAAEPDTLPDQS
HapTN106  (987) RSDLVRAEQARRTLEAKQVEQTAKTQTSKARVRSR---RAVFSDPDPAQS
Hap860295 (992) RNDLVRAEQAERTLEAKQVEQTAETQTSNARVRSK---RAVFSDTLPDQS
Consensus (1001)   DLVRAEQAERTLEAKQVE TA TQT   VRS   RA F D LP QS
                1051                                            1100
HapN187   (1035) ENALEAKQAEETAETQTSKATKKVRSKRAV--FSDPELDQS--------
HapTN106  (1034) TKALEAKQA-LRTETQTS--KAKKVRSKRAAREFSDTLPDQ--------
Hap860295 (1039) QLDVLQAEQVEPTAEKQKN--KAKKVRSKRAV--FSDTLPDQS QLDVLQA
Consensus (1051)    L   LAQ   T EQ   K KKVRSKRA   FSD L DQ
                1101                                            1150
HapN187   (1076) -----------------------------IFALEAALEVIDAPQ
HapTN106  (1073) -----------------------------I LQAALEVIDAQQ
Hap860295 (1085) EQVEPTAEKQKNKAKKVRSKRAAREFSDTPLDLSR QKVLEVKDEVINAQQ
Consensus (1101)                              L    LEVI A Q
                1151                                            1200
HapN187   (1091) QSEKDRLAQEEAEK-QRKQKDELSRYSNSALSELSATVNSMLSVQDELDR
HapTN106  (1086) QVKKEPQTQEEEEKRQRKQKELISRYSNSALSELSATVNSMLSVQDELDR
Hap860295 (1135) QVKKEPQDQ---EK-QRKQKDELISRYSNSALSELSATVNSMLSVQDELDR
Consensus (1151) Q K     Q   EK QRKQK LISRYSNSALSELSATVNSMLSVQDELDR
                1201                                            1250
HapN187   (1140) LFVDQAQSAVWTNIAQDKRRYDSDAFRAYQQKTNLRQIGVQKALANGRIG
HapTN106  (1136) LFVDQAQSAVWTNIAQDKRRYDSDAFRAYQQKTNLRQIGVQKAL DNGRIG
Hap860295 (1181) LFVDQAQSAVWTNIAQDKRRYDSDAFRAYQQKTNLRQIGVQKALANGRIG
Consensus (1201) LFVDQAQSAVWTNIAQDKRRYDSDAFRAYQQKTNLRQIGVQKAL NGRIG
                1251                                            1300
HapN187   (1190) AVFSHSRSDNTFDEQVKNHATLIMMSGFAQYQWGDLQFGVNVGTGISASK
HapTN106  (1186) AVFSHSRSDNTFDEQVKNHATLAMMSGFAQYQWGDLQFGVNVGAGISASK
Hap860295 (1231) AVFSHSRSDNTFDEQVKNHATLIMMSGFAQYQWGDLQFGVNVGTGISASK
Consensus (1251) AVFSHSRSDNTFDEQVKNHATL MMSGFAQYQWGDLQFGVNVG GISASK
                1301                                            1350
HapN187   (1240) MAEEQSRKIHRKAINYGVNASYQFRLGQLGIQPYFGVNRYFIERENYQSE
HapTN106  (1236) MAEEQSRKIHRKAINYGVNASYQFRLGQLGIQPY LGVNRYFIERENYQSE
Hap860295 (1281) MAEEQSRKIHRKAINYGVNASYQFRLGQLGIQPYFGVNRYFIERENYQSE
Consensus (1301) MAEEQSRKIHRKAINYGVNASYQFRLGQLGIQPY GVNRYFIERENYQSE
```

FIG. 11C

```
              1351                                              1400
HapN187   (1290) EVRITTPSLAENRYNAGIRVDYTFTPTDNISVKYFFVNYVDVSNANVQT
HapTN106  (1286) EVKVQTPSDVFNRYNAGTRVDYTFTPTDNISIKPYFFVNYVDVSNANVQT
Hap860295 (1331) EVKVTPSLAENRYNAGIRVDYTFTPTDNISVKPYFFVNYVDVSNANVQT
Consensus (1351) EV V TPSL FNRYNAGIRVDYTFTPTDNIS KPYFFVNYVDVSNANVQT
              1401                                             1450
HapN187   (1340) TVNLEVLQQPFGRYWQKEVGLKAEILHFQIGAFISKSQGSQLGKQQNVGV
HapTN106  (1336) TVNREMLQQSFGRYWQKEVGLKAEILHFQLSAFISKSQGSQLGKQQNVGV
Hap860295 (1381) TVNSEVLQQPFGRYWQKEVGLKAEILHFQLSAFISHSQGSQLGKQQNVGV
Consensus (1401) TVN T LQQ FGRYWQKEVGLKAEILHFQ SAFISKSQGSQLGKQQNVGV
              1451
HapN187   (1390) KLGYRW
HapTN106  (1386) KLGYRW
Hap860295 (1431) KLGYRW
Consensus (1451) KLGYRW
```

FIG. 11D

Nucleotide sequence for NTHi strain 11 hap gene (start codon to stop codon):

```
   1  ATGAAAAAAA CTGTATTTCG TCTTAATTTT TTAACCGCTT GCATTTCATT
  51  AGGGATAGTA TCGCAAGCGT GGGCAGGTCA TACTTATTTT GGGATTGACT
 101  ACCAATATTA TCGTGATTTT GCCGAGAATG AAGGCAAGTT TGCAGTTGGG
 151  GCTAAAAATA TTGATGTTTA TAACAAAGAA GGGCAATTAG TTGGCACATC
 201  AATGACAAAA GCCCCGATGA TTGATTTCTC AGTCGTTTCC AGAAATGGAG
 251  TTGCTGCCTT AGTAGGCGAT CAGTATATTG TGAGTGTGGC ACATAATGTA
 301  GGCTATACCA ATGTGGATTT TGGTGCTGAA GGACAAAATC CTGATCAACA
 351  TCGTTTTACT TATAAAATTG TGAAACGGAA TAATTATAAT CACGATGCGA
 401  AGCACCGCTA TCTAGATGAC TACCATAATC CACGTTTACA TAAATTTGTA
 451  ACGGATGCGG CACCAATTGA TATGACTTCA CATATGGATG CAATAAGTA
 501  TGCAAATAAG GAAAAATATC CTGAACGAGT ACGCGTCGGA TCTGGAGATC
 551  AGTATTGGGA TGACGATCAA ACAACAGAA CTTATTTATC TGACGGATAT
 601  AATTATTTAA CAGGTGGGAA TACATATAAT CAAAGCGGTA GAGGTGATGG
 651  ATATTCATAT GTGAGAGGTG ATATTCGCAA AGTTGGCGAT TATGGTCCAT
 701  TACCGATTGC AAGTTCATTC GGGGACAGTG GATCTCCAAT GTTTATTTAT
 751  GATGCTGAAA CACAAAAATG gcTAATTAAT GGAGTATTGC GGGAGGGGCA
 801  ACCTTATACA GGCGAATTCG ATGGATTTCA ATTAGCCCGT AAATCTTTCC
 851  TTGATGAAAT TATACGCAAA GATCAACCAA ATGGTTTTTT AACCCCTAAG
 901  GGGAATGGCG TTTATACCAT TTCTAAAAGT GACGATGGGA TAGGAGTTGT
 951  TACTTCGAAA ATTGGAAAAC CTCGTGAAAT ACCTTTAGCG AACAACAAAT
1001  TAAAAATAGA AGATAAAGAT ACTGTCTATA ATAACAGATA TAATGGTCCT
1051  AATATTTATT CTCCTCAATT AAACAATGGC AAGAATATTT ATTTTGGAGA
1101  TGAAGAATTA GGATCCATAA CTTTAACGAC TGATATCGAT CAAGGTGCAG
1151  GCGGTTTGTA TTTTGAGGGG GATTTATAG TTTCGCCTAC CAAAAATGAA
1201  ACGTGGAAAG GTGCGGGCAT TCATGTCAGT GAAATTAGTA CCGTTACTTG
1251  GAAAGTAAAC GGCGTGGAAA ATGATCGACT TTCTAAAATC GGTAAAGGAA
1301  CATTACACGT TAAAGCCAAA GGGGAAAATA AAGGTTCGAT CAGCGTAGGC
1351  GATGGTAAAG TCATTTTGGA GCAGCAGGCA GACGATCAAG GCAACAAACA
1401  AGCCTTTAGT GAAATTGGCT TGGTTAGCGG CAGAGGGACT GTTCAATTAA
1451  ACGATGATAA ACAATTTGAT ACCGATAAAT TTTATTTCGG CTTTCGTGGT
1501  GGTCGCTTAG ATCTTAACGG ACATTCATTA ACCTTTAAAC GTATCCAAAA
1551  TACGGACGAG GGGGCGATGA TTGTGAACCA ATATACAACT CAAGTCGCTA
1601  ATATTACTAT TACTGGGAAC GAAAGTATTA CTGCTCCATC TAATAAAAAT
1651  AATATTAATA AACTTGATTA CAGCAAAGAA ATTGCCTACA ACGGCTGGTT
1701  TNGCGAAACA GATAAAAATA AACATAATGG ACGATTAAAC CTTATTTATA
1751  AACCAACCAC AGAAGATCGT ACTTTGCTAC TTTCAGGCGG CACAAACTTA
1801  AAAGGCGATA TTACTCAAAC AAAAGGTAAA CTATTTTTCA GCGGTAGACC
1851  GACACCCCAC GCCTACAATC ATTTAGACAA ACGTTGGTCA GAAATGGAAG
1901  GTATCCCACA AGGCGAAATT GTGTGGATT ACGATTGGAT TAACCGCACA
1951  TTTAAAGCTG AAAACTTCCA AATTAAAGGC GGAAGTGCGG TGGTTTCTCG
2001  CAATGTTTCT TCAATTGAGG GAAATTGGAC AGTCAGCAAT AATGCAAATG
```

Fig. 16A

```
2051  CCACATTTGG TGTTGTGCCA AATCAGCAAA ATACCATTTG CACGCGTTCA
2101  GATTGGACAG GATTAACGAC TTGTAAAACA GTTAATTTAA CCGATAAAAA
2151  AGTTATTGAT TCCATACCGA CAACACAAAT TAATGGTTCT ATTAATTTAA
2201  CTGATAATGC AACAGTGAAT ATTAATGGTT TAGCAAAACT TAATGGTAAT
2251  GTCACTTTAA TAAATCATAG CCAATTTACA TTGAGCAACA ATGCCACCCA
2301  AATAGGCAAT ATCAAACTTT CAAATCACGC AAATGCAAGG GTAAATAATG
2351  CCACTTTAAT GGGCGATGTG AATTTAGCGG ATACTAGCCG TTTTACATTA
2401  AGCAATCAAG CAACACAGAT TGGCACAATC AGTCTTCATC AGCAAGCTCA
2451  AGCAACAGTG GATAATGCAA ACTTGAACGG TAATGTGCAT TTAACGGATT
2501  CTGCCAGATT TTCTTTAAAA AACAGTCATT TTTCGCACCA AATTCAGGGC
2551  GACAAAGACA CAACAGTGAC GTTGGAAAAT GCGACTTGGA CAATGCCTAG
2601  CGATACTACA TTGCAGAATT TAACGCTAAA TAATAGTACT GTTACGTTAA
2651  ATTCAGCTTA TTCAGCTAGC TCAAATAATG CGCCACGTCG CCgCCGTTCA
2701  TTAGAGACGG AAACAACGCC AACATCGGCA GAACATCGTT TCAACACATT
2751  GACAGTAAAT GGTAAATTGA GCGGGCAAGG CACATTCCAA TTTACTCCAT
2801  CTTTATTTGG CTATGAAAGC GATAAATTAA AATTATCCAA TGACGCTGAG
2851  GGCGATTACA CATTATCTGT TCGCAACACA GGCAAAGAAC CCGTGACCCT
2901  TGAGCAATTA ACTTTGGTTG AAAGCAAAGA TAATAAACCG TTATCAGACA
2951  AACTCAAATT TACTTTAGAA AATGACCACG TTGATGCAGG TGCATTACGT
3001  TATAAATTAG TGAAGAATAA GGGCGAATTC CGCTTGCATA ACCCAATAAA
3051  AGAGCAGGAA TTGCGCTCTG ATTTAGTAAG AGCAGAGCAA GCAGAACGAA
3101  CATTAGAAGC CAAACAAGTT GAACAGACTG CTGAAACACA AACAAGTAAT
3151  GCAAGAGTGC GGTCAAGAAG AGCGGTGTTG TCTGATACCC CGTCTGCTCA
3201  AAGCCTGTTA AACGCATTAG AAGTCAAACA AGCTGAACCG AATGCTAAAA
3251  CACAAAAAAG TAAGGCAAAA ACAAAAAAAG CGCGGTCAAA AAGAGCATTG
3301  AGAGAAGCGT TTTCTGATAC CCCGCCTGAT CTAAGCCAGT TAAACGTATT
3351  AGAAGCCGCA CTTAAGGTTA TTAATGCCCA ACCGCAAACA GAAAAGAAC
3401  GTCAAGCTCA AGAGGAAGAA GCGAAAAGAC AACGCaAACA AAAAGACTTG
3451  ATCAGCCGTT ACTCAAATAG TGCGTTATCG GAGTTGTCTG CAACAGTAAA
3501  TAGTATGCTT TCCGTTCAAG ATGAATTGGA TCGTCTTTTT GTAGATCAAG
3551  CACAATCTGC CCTGTGGACA AATATCGCAC AGGATAAAAG ACGCTATGAT
3601  TCTGATGCGT TCCGTGCTTA TCAGCAGAAA ACGAACTTGC GTCAAATTGG
3651  GGTGCAAAAA GCCTTAGATA ATGGACGAAT TGGGGCGGTT TTCTCGCATA
3701  GCCGTTCAGA TAATACCTTT GACGAACAGG TTAAAAATCA CGCGACATTA
3751  ACGATGATGT CGGGTTTTGC CCAATATCAA TGGGGCGATT TACAATTTGG
3801  TGTAAACGTG GGCGCGGGAA TTAGTGCGAG TAAAATGGCT GAAGAACAAA
3851  GCCGAAAAAT TCATCGAAAA GCGATAAATT ATGGTGTGAA TGCAAGTTAT
3901  CAGTTCCGTT TAGGGCAATT GGGTATTCAG CCTTATTTGG GTGTTAATCG
3951  ATATTTATT GAACGTGAAA ATTATCAATC TGAAGAAGTG AAAGTGCAAA
4001  CACCGAGCCT TGCATTTAAT CGCTATAATG CTGGCATTCG AGTTGATTAT
4051  ACATTTACCC CGACAGATAA TATCAGCGTT AAGCCTTATT CTTTGTCAA
4101  TTATGTTGAT GTTTCAAACG CTAACGTACA AACCACTGTA AATAGCACGA
4151  TGTTGCAACA ATCATTTGGG CGTTATTGGC AAAAAGAAGT GGGATTAAAG
4201  GCAGAAATTT TACATTTCCA ACTTTCCGCT TTTATCTCAA AATCTCAAGG
```

Fig. 16B

```
4251  TTCACAACTC GGTAAACAGC AAAATGTGGG CGTGAAATTG GGCTATCGTT
4301  GGTAA
```

Fig. 16C

Amino acid sequence for NTHi strain 11 Hap protein (first amino acid to last amino acid):

```
   1  MKKTVFRLNF  LTACISLGIV  SQAWAGHTYF  GIDYQYYRDF  AENEGKFAVG
  51  AKNIDVYNKE  GQLVGTSMTK  APMIDFSVVS  RNGVAALVGD  QYIVSVAHNV
 101  GYTNVDFGAE  GQNPDQHRFT  YKIVKRNNYN  HDAKHRYLDD  YHNPRLHKFV
 151  TDAAPIDMTS  HMDGNKYANK  EKYPERVRVG  SGDQYWDDDQ  NNRTYLSDGY
 201  NYLTGGNTYN  QSGRGDGYSY  VRGDIRKVGD  YGPLPIASSF  GDSGSPMFIY
 251  DAETQKWLIN  GVLREGQPYT  GEFDGFQLAR  KSFLDEIIRK  DQPNGFLTPK
 301  GNGVYTISKS  DDGIGVVTSK  IGKPREIPLA  NNKLKIEDKD  TVYNNRYNGP
 351  NIYSPQLNNG  KNIYFGDEEL  GSITLTTDID  QGAGGLYFEG  DFIVSPTKNE
 401  TWKGAGIHVS  EISTVTWKVN  GVENDRLSKI  GKGTLHVKAK  GENKGSISVG
 451  DGKVILEQQA  DDQGNKQAFS  EIGLVSGRGT  VQLNDDKQFD  TDKFYFGFRG
 501  GRLDLNGHSL  TFKRIQNTDE  GAMIVNHNTT  QVANITITGN  ESITAPSNKN
 551  NINKLDYSKE  IAYNGWFXET  DKNKHNGRLN  LIYKPTTEDR  TLLLSGGTNL
 601  KGDITQTKGK  LFFSGRPTPH  AYNHLDKRWS  EMEGIPQGEI  VWDYDWINRT
 651  FKAENFQIKG  GSAVVSRNVS  SIEGNWTVSN  NANATFGVVP  NQQNTICTRS
 701  DWTGLTTCKT  VNLTDKKVID  SIPTTQINGS  INLTDNATVN  INGLAKLNGN
 751  VTLINHSQFT  LSNNATQIGN  IKLSNHANAR  VNNATLMGDV  NLADTSRFTL
 801  SNQATQIGTI  SLHQQAQATV  DNANLNGNVH  LTDSARFSLK  NSHFSHQIQG
 851  DKDTTVTLEN  ATWTMPSDTT  LQNLTLNNST  VTLNSAYSAS  SNNAPRRRRS
 901  LETETTPTSA  EHRFNTLTVN  GKLSGQGTFQ  FTPSLFGYES  DKLKLSNDAE
 951  GDYTLSVRNT  GKEPVTLEQL  TLVESKDNKP  LSDKLKFTLE  NDHVDAGALR
1001   YKLVKNKGEF  RLHNPIKEQE  LRSDLVRAEQ  AERTLEAKQV  EQTAETQTSN
1051   ARVRSRRAVL  SDTPSAQSLL  NALEVKQAEP  NAKTQKSKAK  TKKARSKRAL
1101   REAFSDTPPD  LSQLNVLEAA  LKVINAQPQT  EKERQAQEEE  AKRQRKQKDL
1151   ISRYSNSALS  ELSATVNSML  SVQDELDRLF  VDQAQSALWT  NIAQDKRRYD
1201   SDAFRAYQQK  TNLRQIGVQK  ALDNGRIGAV  FSHSRSDNTF  DEQVKNHATL
1251   TMMSGFAQYQ  WGDLQFGVNV  GAGISASKMA  EEQSRKIHRK  AINYGVNASY
1301   QFRLGQLGIQ  PYLGVNRYFI  ERENYQSEEV  KVQTPSLAFN  RYNAGIRVDY
1351   TFTPTDNISV  KPYFFVNYVD  VSNANVQTTV  NSTMLQQSFG  RYWQKEVGLK
1401    AEILHFQLSA  FISKSQGSQL  GKQQNVGVKL  GYRW
```

Fig. 17

Nucleotide sequence for NTHi strain TN106 *hap* gene (start codon begins at position 422, stop codon begins at position 4595):

```
   1   TGGCGGCGGA CAAATTATTG CGACGGGTAC ACCAGAACAA GTTGCTAAAG
  51   TAAAAAGTTC CCACACCGCT CGCTTCCTTA AACCGATTTT AGAAAAACCT
 101   TAGAAAAAAT GACCGCACTT TCAGAGAAAA CTCACATAAA GTGCGGTTAT
 151   TTTATTAGTG ATATTGTTTT AATTTTAGTT ATCTGTATAA ATTACATACA
 201   ATATTAATCC ATCGCAAGAT TAGATTACCC ACTAAGTATT AAGCAAAAAC
 251   CTAGAAATTT TGGCTTAATT ACTATATAGT TTTACTCATT TATTTTCTTT
 301   TGTGCCTTTT AGTTCATTTT TTTAGCTGAA ATCCCTTAGA AAATCACCGC
 351   ACTTTTATTG TTCAATAGTC GTTTAACCAC GTATTTTTTA ATACGAAAAA
 401   TTACTTAATT AAATAAACAT TATGAAAAAA ACTGTATTTC GTCTGAATTT
 451   TTTAACCGCT TGCATTTCAT TAGGGATAGT ATCGCAAGCG TGGGCAGGTC
 501   ATACTTATTT TGGGATTGAC TACCAATATT ATCGTGATTT TGCCGAGAAT
 551   AAAGGGAAGT TTACAGTTGG GGCTCAAGAT ATTGATATCT ACAATAAAAA
 601   AGGGGAAATG ATAGGTACGA TGATGAAAGG TGTGCCTATG CCTGATTTAT
 651   CTTCCATGGT TCGTGGTGGT TATTCAACAT TGATAAGTGA GCAGCATTTA
 701   ATTAGCGTCG CACATAATGT AGGGTATGAT GTCGTTGATT TTGGTATGGA
 751   GGGGGAAAAT CCAGACCAAC ATCGTTTTAA GTATAAAGTT GTTAAACGAT
 801   ATAATTATAA GAGCGGTGAT AGACAATATA ATGATTATCA ACATCCAAGA
 851   TTAGAGAAAT TTGTAACGGA AACTGCACCT ATTGAAATGG TTTCATATAT
 901   GGATGGTAAT CATTACAAAA ATTTTAATCA ATATCCTTTG CGAGTTAGAG
 951   TTGGAAGTGG GCATCAATGG TGGAAAGACG ATAATAATAA AACCATTGGA
1001   GACTTAGCCT ATGGAGGTTC ATGGTTAATA GGTGGAAATA CCTTTGAAGA
1051   TGGACCAGCT GGTAACGGTA CATTAGAATT AAATGGGCGA GTACAAAATC
1101   CTAATAAATA TGGTCCACTA CCTACGGCAG GTTCATTCGG GGATAGTGGT
1151   TCTCCAATGT TTATTTATGA TAAGGAAGTT AAGAAATGGT TATTAAATGG
1201   CGTGTTACGT GAAGGAAATC CTTATGCTGC AGTAGGAAAC AGCTATCAAA
1251   TTACACGAAA AGATTATTTT CAAGGTATTC TTAATCAAGA CATTACAGCT
1301   AATTTTTGGG ATACTAATGC TGAATATAGA TTTAATATAG GGAGTGACCA
1351   CAATGGAAGA GTGGCAACAA TCAAAGTAC ATTACCTAAA AAAGCTATTC
1401   AGCCTGAACG AATAGTGGGT CTTTATGATA ATAGCCAACT TCATGATGCT
1451   AGAGATAAAA ATGGCGATGA ATCTCCCTCT TATAAAGGTC CTAATCCATG
1501   GTCGCCAGCA TTACATCATG GAAAAGTAT TTACTTTGGC GATCAAGGAA
1551   CAGGAACTTT AACAATTGAA AATAATATAA ATCAAGGTGC AGGTGGATTG
1601   TATTTGAAG GTAATTTTGT TGTAAAAGGC AATCAAAATA ATATAACTTG
1651   GCAAGGTGCA GGCGTTTCTG TTGGAGAAGA AAGTACTGTT GAATGGCAGG
1701   TGCATAATCC AGAAGGCGAT CGCTTATCCA AAATTGGGCT GGGAACCTTA
1751   CTTGTTAATG GTAAAGGGAA AAACTTAGGA AGCCTGAGTG TCGGTAACGG
1801   TTTGGTTGTG TTAGATCAAC AAGCAGATGA ATCAGGTCAA AAACAAGCCT
1851   TAAAGAAGT TGGCATTGTA AGTGGTAGAG CTACCGTTCA ACTAAATAGT
1901   GCAGATCAAG TTGATCCTAA CAATATTTAT TTCGGCTTTC GTGGTGGTCG
1951   CTTAGATCTT AATGGGCATT CATTAACCTT TGAACGTATC CAAAATACGG
2001   ATGAAGGCGC GATGATTGTG AACCACAACG CTTCTCAAAC CGCAAATATT
```

Fig. 18A

```
2051  ACGATTACAG GCAACGCAAC TATTAATTCA GATAGCAAAC AACTTACTAA
2101  TAAAAAAGAT ATTGCATTTA ACGGCTGGTT TGGTGAGCAA GATAAAGCTA
2151  AAACAAATGG TCGTTTAAAT GTGAATTATC AACCAGTTAA TGCAGAAAAT
2201  CATTTGTTGC TTTCTGGGGG GACAAATTTA AACGGCAATA TCACGCAAAA
2251  TGGTGGTACG TTAGTTTTTA GTGGTCGTCC AACGCCTCAT GCTTACAATC
2301  ATTTAAGAAG AGACTTGTCT AACATGGAAG GTATCCCACA AGGCGAAATT
2351  GTGTGGGATC ACGATTGGAT CAACCGCACA TTTAAAGCTG AAAACTTCCA
2401  AATTAAAGGC GGAAGTGCGG TGGTTTCTCG CAATGTTTCT TCAATTGAGG
2451  GAAATTGGAC AGTCAGCAAT AATGCAAATG CCACATTTGG TGTTGTGCCA
2501  AATCAGCAAA ATACCATTTG CACGCGTTCA GATTGGACAG GATTAACGAC
2551  TTGTAAAACA GTTGATTTAA CCGATAAAAA AGTTATTAAT TCCATACCGA
2601  CAACACAAAT TAATGGTTCT ATTAATTTAA CTGATAATGC AACAGTGAAT
2651  ATTCATGGTT TAGCAAAACT TAATGGTAAT GTCACTTTAA TAGATCACAG
2701  CCAATTTACA TTGAGCAACA ATGCCACCCA AACAGGCAAT ATCAAACTTT
2751  CAAATCACGC AAATGCAACG GTGGACAATG CAAATTTGAA CGGTAATGTG
2801  AATTTAATGG ATTCTGCTCA ATTTTCTTTA AAAAACAGCC ATTTTTCGCA
2851  CCAAATCCAA GGTGGGGAAG ACACAACAGT GATGTTGGAA AATGCGACTT
2901  GGACAATGCC TAGCGATACC ACATTGCAGA ATTTAACGCT AAATAATAGT
2951  ACTGTTACGT TAAATTCAGC TTATTCAGCT ATCTCAAATA ATGCGCCACG
3001  CCGTCGCCGC CGTTCATTAG AGACGGAAAC AACGCCAACA TCGGCAGAAC
3051  ATCGTTTCAA CACATTGACA GTAAATGGTA AATTGAGCGG GCAAGGCACA
3101  TTCCAATTTA CTTCATCTTT ATTTGGCTAT AAAAGCGATA AATTAAAATT
3151  ATCCAATGAC GCTGAGGGCG ATTACACATT ATCTGTTCGC AACACAGGCA
3201  AAGAACCCGT GACCTTTGGG CAATTAACTT TGGTTGAAAG CAAAGATAAT
3251  AAACCGTTAT CAGACAAACT CACATTCACG TTAGAAAATG ACCACGTTGA
3301  TGCAGGTGCA TTACGTTATA AATTAGTGAA GAATGATGGC GAATTCCGCT
3351  TACATAACCC AATAAAAGAG CAGGAATTGC GCTCTGATTT AGTAAGAGCA
3401  GAGCAAGCAG AACGAACATT AGAAGCCAAA CAAGTTGAAC AGACTGCTAA
3451  AACACAAACA GTAAGGCAA GAGTGCGGTC AAGAAGAGCG GTGTTTTCTG
3501  ATCCCCTGCC TGCTCAAAGC CTGTTAAAAG CATTAGAAGC CAAACAAGCT
3551  CTGACTACTG AAACACAAAC AAGTAAGGCA AAAAAAGTGC GGTCAAAAAG
3601  AGCTGCGAGA GAGTTTTCTG ATACCCTGCC TGATCAAATA TTACAAGCCG
3651  CACTTGAGGT TATTGATGCC CAACAGCAAG TGAAAAAAGA ACCTCAAACT
3701  CAAGAGGAAG AAGAGAAAAG ACAACGCAAA CAAAAAGAAT TGATCAGCCG
3751  TTACTCAAAT AGTGCGTTAT CGGAGTTGTC TGCGACAGTA AATAGTATGC
3801  TTTCCGTTCA AGATGAATTG GATCGTCTTT TTGTAGATCA AGCACAATCT
3851  GCCGTGTGGA CAAATATCGC ACAGGATAAA AGACGCTATG ATTCTGATGC
3901  GTTCCGTGCT TATCAGCAGA AAACGAACTT GCGTCAAATT GGGGTGCAAA
3951  AAGCCTTAGA TAATGGACGA ATTGGGGCGG TTTTCTCGCA TAGCCGTTCA
4001  GATAATACCT TTGACAACA GGTTAAAAAT CACGCGACAT TAGCGATGAT
4051  GTCGGGTTTT GCCCAATATC AATGGGGCGA TTTACAATTT GGTGTAAACG
4101  TGGGTGCGGG AATTAGTGCG AGTAAAATGG CTGAAGAACA AAGCCGAAAA
4151  ATTCATCGAA AAGCGATAAA TTATGGTGTG AATGCAAGTT ATCAGTTCCG
4201  TTTAGGGCAA TTGGGTATTC AGCCTTATTT GGGTGTTAAT CGATATTTTA
```

Fig. 18B

```
4251  TTGAACGTGA AAATTATCAA TCTGAAGAAG TGAAAGTGCA AACACCGAGC
4301  CTTGTATTTA ATCGCTATAA TGCTGGCATT CGAGTTGATT ATACATTTAC
4351  CCCGACAGAT AATATCAGCA TTAAGCCTTA TTTCTTCGTC AATTATGTTG
4401  ATGTTTCAAA CGCTAACGTA CAAACCACTG TAAATCGCAC GATGTTGCAA
4451  CAATCATTTG GGCGTTATTG GCAAAAAGAA GTGGGATTAA AGGCAGAAAT
4501  TTTACATTTC CAACTTTCCG CTTTTATCTC AAAATCTCAA GGTTCACAAC
4551  TCGGCAAACA GCAAAATGTG GGCGTGAAAT TGGGGTATCG TTGGTAAAAA
4601  TCAAC
```

Fig. 18C

Amino acid sequence for NTHi strain TN106 Hap protein (first amino acid to last amino acid):

```
   1  MKKTVFRLNF  LTACISLGIV  SQAWAGHTYF  GIDYQYYRDF  AENKGKFTVG
  51  AQDIDIYNKK  GEMIGTMMKG  VPMPDLSSMV  RGGYSTLISE  QHLISVAHNV
 101  GYDVVDFGME  GENPDQHRFK  YKVVKRYNYK  SGDRQYNDYQ  HPRLEKFVTE
 151  TAPIEMVSYM  DGNHYKNFNQ  YPLRVRVGSG  HQWWKDDNNK  TIGDLAYGGS
 201  WLIGGNTFED  GPAGNGTLEL  NGRVQNPNKY  GPLPTAGSFG  DSGSPMFIYD
 251  KEVKKWLLNG  VLREGNPYAA  VGNSYQITRK  DYFQGILNQD  ITANFWDTNA
 301  EYRFNIGSDH  NGRVATIKST  LPKKAIQPER  IVGLYDNSQL  HDARDKNGDE
 351  SPSYKGPNPW  SPALHHGKSI  YFGDQGTGTL  TIENNINQGA  GGLYFEGNFV
 401  VKGNQNNITW  QGAGVSVGEE  STVEWQVHNP  EGDRLSKIGL  GTLLVNGKGK
 451  NLGSLSVGNG  LVVLDQQADE  SGQKQAFKEV  GIVSGRATVQ  LNSADQVDPN
 501  NIYFGFRGGR  LDLNGHSLTF  ERIQNTDEGA  MIVNHNASQT  ANITITGNAT
 551  INSDSKQLTN  KKDIAFNGWF  GEQDKAKTNG  RLNVNYQPVN  AENHLLLSGG
 601  TNLNGNITQN  GGTLVFSGRP  TPHAYNHLRR  DLSNMEGIPQ  GEIVWDHDWI
 651  NRTFKAENFQ  IKGGSAVVSR  NVSSIEGNWT  VSNNANATFG  VVPNQQNTIC
 701  TRSDWTGLTT  CKTVDLTDKK  VINSIPTTQI  NGSINLTDNA  TVNIHGLAKL
 751  NGNVTLIDHS  QFTLSNNATQ  TGNIKLSNHA  NATVDNANLN  GNVNLMDSAQ
 801  FSLKNSHFSH  QIQGGEDTTV  MLENATWTMP  SDTTLQNLTL  NNSTVTLNSA
 851  YSAISNNAPR  RRRRSLETET  TPTSAEHRFN  TLTVNGKLSG  QGTFQFTSSL
 901  FGYKSDKLKL  SNDAEGDYTL  SVRNTGKEPV  TFGQLTLVES  KDNKPLSDKL
 951  TFTLENDHVD  AGALRYKLVK  NDGEFRLHNP  IKEQELRSDL  VRAEQAERTL
1001   EAKQVEQTAK  TQTSKARVRS  RRAVFSDPLP  AQSLLKALEA  KQALTTETQT
1051   SKAKKVRSKR  AAREFSDTLP  DQILQAALEV  IDAQQQVKKE  PQTQEEEEKR
1101   QRKQKELISR  YSNSALSELS  ATVNSMLSVQ  DELDRLFVDQ  AQSAVWTNIA
1151   QDKRRYDSDA  FRAYQQKTNL  RQIGVQKALD  NGRIGAVFSH  SRSDNTFDEQ
1201   VKNHATLAMM  SGFAQYQWGD  LQFGVNVGAG  ISASKMAEEQ  SRKIHRKAIN
1251   YGVNASYQFR  LGQLGIQPYL  GVNRYFIERE  NYQSEEVKVQ  TPSLVFNRYN
1301   AGIRVDYTFT  PTDNISIKPY  FFVNYVDVSN  ANVQTTVNRT  MLQQSFGRYW
1351   QKEVGLKAEI  LHFQLSAFIS  KSQGSQLGKQ  QNVGVKLGYR  W
```

Fig. 19

Nucleotide sequence for NTHi strain 860295 hap gene (start codon begins at position 430, stop codon begins at position 4738):

```
   1  GGAGGCAGTG GTGGCGGACA AATTATTGCG ACGGGTACGC CAGAACAAGT
  51  TGCCAAAGTA GAAAGTTCCC ACACCGCCCG CTTCCTTAAA CCGATTTTAG
 101  AAAAACCTTA GAAAAATGA CCGCACTTTC AGAGAAAACT CACATAAAGT
 151  GCGGTTATTT TATTAGTGAT ATTGTTTTAA TTTTAGTTAT CTGTATAAAT
 201  TACATATAAT ATTAATCCAT CGCAAGATAA GATTACCCAC TAAGTATTAA
 251  GCAAAAACCT AGAAATTTTG GCTTAATTAC TATATAGTTT TACTGCTTTA
 301  TTTTCTTTTG TGCCTTTTAG TTCGTTTTTT TAGCTGAAAT CCCTTAGAAA
 351  ATCACCGCAC TTTTATTGTT CAATAGTCGT TTAACCACGT ATTTTTAAT
 401  ACGAAAAATT ACTTAATTAA ATAAACATTA TGAAAAAAC TGTATTTCGT
 451  CTGAACTTTT TAACCGCTTG CATTTCATTA GGGATAGTAT CGCAAGCGTG
 501  GGCAGGTCAC ACTTATTTTG GGATTGACTA CCAATATTAT CGTGATTTTG
 551  CTGAGAATAA AGGGAAGTTT TCAGTTGGGG CTAAAAATAT TGAGGTTTAT
 601  AACAAAGAGG GGACTTTAGT TGGCACATCA ATGACAAAAG CCCCGATGAT
 651  TGATTTTTCT GTGGTGTCGC GAAATGGGGT GGCGGCATTA GTAGGCGATC
 701  AGTATATTGT GAGTGTGGCA CATAACGGTG GATATAATAG CGTTGATTTT
 751  GGAGCAGAAG GTCCAAATCC CGATCAGCAT CGTTTTACTT ATCAAATTGT
 801  AAAAGAAAT AATTATAAGC CAGGCAAAGA TAACCCTTAT CATGGTGACT
 851  ATCACATGCC TCGTTTGCAC AAATTTGTCA CTGACGCTGA ACCAGCAAAG
 901  ATGACAGACA ATATGAATGG AAAGAACTAC GCTGATTTAA GTAAATATCC
 951  TGATCGTGTG CGTATTGGTA CAGGTGAACA ATGGTGGAGG ACTGATGAAG
1001  AACAAAAGCA AGGAAGTAAG AGTTCATGGC TTGCTGATGC TTATCTGTGG
1051  AGAATAGCAG GTAACACACA TTCACAAAGT GGAGCGGGCA ACGGCACGGT
1101  AAACTTAAGT GGAGATATCA CAAAACCAAA TAACTATGGA CCTCTTCCTA
1151  CGGGTGTTTC GTTTGGAGAT AGTGGTTCTC CAATGTTTAT TTATGATGCA
1201  ATAAAACAAA AATGGCTTAT TAATGGCGTA TTGCAAACTG GTAACCCTTT
1251  CTCGGGAGCT GGAAATGGAT CCAATTAAT TAGAAAAAAT TGGTTTTATG
1301  ATAATGTCTT TGTAGAAGAT TTGCCTATAA CATTTTTAGA GCCAAGAAGT
1351  AACGGTCATT ATTCATTTAC TTCAAATAAT AATGGAACTG GTACGGTTAC
1401  TCAAACGAAT GAAAAGTGA GTATGCCTCA ATTTAAAGTC AGAACGGTTC
1451  AGTTATTTAA TGAAGCATTA AAAGAAAAAG ATAAAGAACC TGTTTATGCT
1501  GCAGGTGGTG TAAATGCTTA TAAACCAAGA CTAAATAATG GTAAAAATAT
1551  TTACTTTGGC GATCGAGGAA CAGGAACTTT AACAATTGAA AATAATATAA
1601  ATCAAGGTGC TGGTGGTTTG TATTTTGAGG GTAACTTTAC GGTATCTTCA
1651  GAAAATAATG CAACTTGGCA AGGTGCTGGA GTGCATGTAG GTGAAGACAG
1701  TACTGTTACT TGGAAAGTAA ACGGCGTGGA ACATGATCGC CTTTCTAAAA
1751  TTGGTAAAGG AACGTTGCAT ATTCAAGCAA AAGGTGAAAA CTTAGGCTCA
1801  ATTAGCGTAG GTGACGGCAA AGTCATTTTA GATCAACAAG CCGATGAGAA
1851  CAACCAAAAA CAAGCCTTTA AGAAGTTGG CATTGTAAGT GGTAGAGCTA
1901  CCGTTCAACT AAATAGTGCA GATCAAGTTG ATCCTAACAA TATTTATTTC
1951  GGATTTCGTG GTGGTCGCTT AGATCTTAAC GGACATTCAT TAACCTTTAA
2001  ACGTATCCAA AATACGGACG AGGGCGCGAT GATTGTGAAC CATAATACAA
```

Fig. 20A

```
2051 CTCAAGTCGC TAATATTACT ATTACTGGGA ACGAAAGTAT TACTGCTCCA
2101 TCTAATAAAA ATAATATTAA TAAACTTGAT TACAGCAAAG AAATTGCTTA
2151 CAACGGTTGG TTTGGCGAAA CAGATGAAAA TAAACACAAT GGAAGATTAA
2201 ACCTTATTTA TAAACCAACC ACAGAAGATC GTACTTTGCT ACTTTCAGGT
2251 GGAACAAATT TAAAAGGCAA TATTACTCAG GAAGGCGGCA CTTTAGTGTT
2301 TAGTGGTCGC CCAACTCCAC ACGCTTACAA TCATTTAAAT CGCCCAAACG
2351 AGCTTGGGCG ACCTCAAGGC GAAGTGGTTA TTGATGACGA TTGGATCACC
2401 CGCACATTTA AAGCTGAAAA CTTCCAAATT AAAGGCGGAA GTGCGGTGGT
2451 TTCTCGCAAT GTTTCTTCAA TTGAGGGAAA TTGGACAGTC AGCAATAATG
2501 CAAATGCCGC ATTTGGTGTT GTGCCAAATC AGCAAAATAC CATTTGCACG
2551 CGTTCAGATT GGACAGGATT AACGACTTGT AAAACTGTGG ATTTAACCGA
2601 TACAAAAGTT ATTAATTCCA TACCGACAAC ACAAATTAAT GGCTCTATTA
2651 ATTTAACTGA TAATGCAACA GTGAATATTC ATGGTTTAGC AAAACTTAAT
2701 GGTAATGTCA CTTTAATAAA TCATAGCCAA TTTACATTGA GCAACAATGC
2751 CACCCAAACA GGCAATATCC AACTTTCAAA TCACGCAAAT GCAACGGTGG
2801 ACAATGCAAA TTTGAACGGT AATGTGCATT TAACGGATTC TGCTCAATTT
2851 TCTTTAAAAA ACAGCCATTT TTCGCACCAA ATTCAGGGCG ACAAAGACAC
2901 AACAGTGACG TTGGAAAATG CGACTTGGAC AATGCCTAGC GATGCCACAT
2951 TGCAGAATTT AACGCTAAAT AATAGTACTG TTACGTTAAA TTCAGCTTAT
3001 TCAGCTAGCT CAAATAATGC GCCACGTCAC CGCCGTTCAT TAGAGACGGA
3051 AACAACGCCA ACATCGGCAG AACATCGTTT CAACACATTG ACAGTAAATG
3101 GTAAATTGAG CGGGCAAGGC ACATTCCAAT TTACTTCATC TTTATTTGGC
3151 TATAAAAGCG ATAAATTAAA ATTATCCAAT GACGCTGAGG GCGATTACAC
3201 ATTATCTGTT CGCAACACAG GCAAAGAACC CGAAGCCCTT GAGCAATTAA
3251 CTTTGGTTGA AGCAAAGAT AATAAACCGT TATCAGACAA ACTCAAATTT
3301 ACTTTAGAAA ATGACCACGT TGATGCAGGT GCATTACGTT ATAAATTAGT
3351 GAAGAATAAT GGCGAATTCC GCTTGCATAA CCCAATAAAA GAGCAGGAAT
3401 TGCGCAATGA TTTAGTAAGA GCAGAGCAAG CAGAACGAAC ATTAGAAGCC
3451 AAACAAGTTG AACAGACTGC TGAAACACAA ACAAGTAATG CAAGAGTGCG
3501 GTCAAAAGA GCGGTGTTTT CTGATACCCT GCCTGATCAA AGCCAGTTAG
3551 ACGTATTACA AGCCGAACAA GTTGAACCGA CTGCTGAAAA ACAAAAAAAT
3601 AAGGCAAAAA AAGTGCGGTC AAAAGAGCG GTGTTTTCTG ATACCCTGCC
3651 TGATCAAAGC CAGTTAGACG TATTACAAGC CGAACAAGTT GAACCGACTG
3701 CTGAAAAACA AAAAATAAG GCAAAAAAG TGCGGTCAAA AGAGCCGCG
3751 AGAGAGTTTT CTGATACCCC GCTTGATCTA AGCCGGTTAA AGGTATTAGA
3801 AGTCAAACTT GAGGTTATTA ATGCCCAACA GCAAGTGAAA AAAGAACCTC
3851 AAGATCAAGA GAAACAACGC AAACAAAAAG ACTTGATCAG CCGTTATTCA
3901 AATAGTGCGT TATCAGAATT ATCTGCAACA GTAAATAGTA TGCTTTCTGT
3951 TCAAGATGAA TTAGATCGTC TTTTGTAGA TCAAGCACAA TCTGCCGTGT
4001 GGACAAATAT CGCACAGGAT AAAAGACGCT ATGATTCTGA TGCGTTCCGT
4051 GCTTATCAGC AGAAAACGAA CTTACGTCAA ATTGGGGTGC AAAAAGCCTT
4101 AGCTAATGGA CGAATTGGGG CAGTTTCTC GCATAGCCGT TCAGATAATA
4151 CTTTTGATGA ACAGGTTAAA AATCACGCGA CATTAACGAT GATGTCGGGT
4201 TTTGCCCAAT ATCAATGGGG CGATTTACAA TTTGGTGTAA ACGTGGGAAC
```

Fig. 20B

```
4251  GGGAATCAGT GCGAGTAAAA TGGCTGAAGA ACAAAGCCGA AAAATTCATC
4301  GAAAAGCGAT AAATTATGGC GTGAATGCAA GTTATCAGTT CCGTTTAGGG
4351  CAATTGGGCA TTCAGCCTTA TTTTGGAGTT AATCGCTATT TTATTGAACG
4401  TGAAAATTAT CAATCTGAGG AAGTGAAAGT GAAAACGCCT AGCCTTGCAT
4451  TTAATCGCTA TAATGCTGGC ATTCGAGTTG ATTATACATT TACTCCGACA
4501  GATAATATCA GCGTTAAGCC TTATTTCTTC GTCAATTATG TTGATGTTTC
4551  AAACGCTAAC GTACAAACCA CGGTAAATAG CACGGTGTTG CAACAACCAT
4601  TTGGACGTTA TTGGCAAAAA GAAGTGGGAT TAAAAGCGGA AATTTTACAT
4651  TTCCAACTTT CTGCTTTTAT TTCTAAATCT CAAGGTTCGC AACTCGGCAA
4701  ACAGCAAAAT GTGGGCGTGA ATTGGGGTA TCGTTGGTAA AAATCAACAT
4751  AATTGTATCG TTTATTGATA ACAAGGTGG GGCAGATCCC ACCTTTTTA
4801  TTTCAATAAT GGAACTTTAT TTAATTAAGA GCATCTAAGT AGCACCCCAT
4851  ATAGGGGATT AATTAAGAGG ATTTAATAAT GAATTTAACT AAACTTTTAC
4901  CAGCATTTGC TGCTGCAGTC GTATTATCTG CTTGTGCAAA GGATGCACCT
4951  GAAATGACAA AATCATCTGC GCAAATAGCT GAAATGCAAA CACTTCCAAC
5001  AATCACTGAT AAAACAGTTG TATATTCCTG CAATAAACAA ACTGTAACTG
5051  CCGTGTATCA ATTTGAAAAC CAAGAACCAG TTGCTGCAAT GGTAAGTGTG
5101  GGCGATGGCA TTATTGCGAA AGATTTTACT CGTGATAAAT CACAAAATGA
5151  CTTTACAAGT TTCGTTTCTG GGATTATGT TTGGAATGTA GATAGTGGCT
5201  TAACGTTAGA TAAATTTGAT TCTGTTGTGC CTGTCAATTT AATTC
```

Fig. 20C

Amino acid Sequence for NTHi strain 860295 Hap protein (first amino acid to last amino acid):

```
   1  MKKTVFRLNF LTACISLGIV SQAWAGHTYF GIDYQYYRDF AENKGKFSVG
  51  AKNIEVYNKE GTLVGTSMTK APMIDFSVVS RNGVAALVGD QYIVSVAHNG
 101  GYNSVDFGAE GPNPDQHRFT YQIVKRNNYK PGKDNPYHGD YHMPRLHKFV
 151  TDAEPAKMTD NMNGKNYADL SKYPDRVRIG TGEQWWRTDE EQKQGSKSSW
 201  LADAYLWRIA GNTHSQSGAG NGTVNLSGDI TKPNNYGPLP TGVSFGDSGS
 251  PMFIYDAIKQ KWLINGVLQT GNPFSGAGNG FQLIRKNWFY DNVFVEDLPI
 301  TFLEPRSNGH YSFTSNNNGT GTVTQTNEKV SMPQFKVRTV QLFNEALKEK
 351  DKEPVYAAGG VNAYKPRLNN GKNIYFGDRG TGTLTIENNI NQGAGGLYFE
 401  GNFTVSSENN ATWQGAGVHV GEDSTVTWKV NGVEHDRLSK IGKGTLHIQA
 451  KGENLGSISV GDGKVILDQQ ADENNQKQAF KEVGIVSGRA TVQLNSADQV
 501  DPNNIYFGFR GGRLDLNGHS LTFKRIQNTD EGAMIVNHNT TQVANITITG
 551  NESITAPSNK NNINKLDYSK EIAYNGWFGE TDENKHNGRL NLIYKPTTED
 601  RTLLLSGGTN LKGNITQEGG TLVFSGRPTP HAYNHLNRPN ELGRPQGEVV
 651  IDDDWITRTF KAENFQIKGG SAVVSRNVSS IEGNWTVSNN ANAAFGVVPN
 701  QQNTICTRSD WTGLTTCKTV DLTDTKVINS IPTTQINGSI NLTDNATVNI
 751  HGLAKLNGNV TLINHSQFTL SNNATQTGNI QLSNHANATV DNANLNGNVH
 801  LTDSAQFSLK NSHFSHQIQG DKDTTVTLEN ATWTMPSDAT LQNLTLNNST
 851  VTLNSAYSAS SNNAPRHRRS LETETTPTSA EHRFNTLTVN GKLSGQGTFQ
 901  FTSSLFGYKS DKLKLSNDAE GDYTLSVRNT GKEPEALEQL TLVESKDNKP
 951  LSDKLKFTLE NDHVDAGALR YKLVKNNGEF RLHNPIKEQE LRNDLVRAEQ
1001   AERTLEAKQV EQTAETQTSN ARVRSKRAVF SDTLPDQSQL DVLQAEQVEP
1051   TAEKQKNKAK KVRSKRAVFS DTLPDQSQLD VLQAEQVEPT AEKQKNKAKK
1101   VRSKRAAREF SDTPLDLSRL KVLEVKLEVI NAQQQVKKEP QDQEKQRKQK
1151   DLISRYSNSA LSELSATVNS MLSVQDELDR LFVDQAQSAV WTNIAQDKRR
1201   YDSDAFRAYQ QKTNLRQIGV QKALANGRIG AVFSHSRSDN TFDEQVKNHA
1251   TLTMMSGFAQ YQWGDLQFGV NVGTGISASK MAEEQSRKIH RKAINYGVNA
1301   SYQFRLGQLG IQPYFGVNRY FIERENYQSE EVKVKTPSLA FNRYNAGIRV
1351   DYTFTPTDNI SVKPYFFVNY VDVSNANVQT TVNSTVLQQP FGRYWQKEVG
1401   LKAEILHFQL SAFISKSQGS QLGKQQNVGV KLGYRW
```

Fig. 21

Nucleotide sequence for NTHi strain 3219B *hap* gene (start codon begins at position 388, stop codon begins at position 4561):

```
   1   CCTGAAGACG TTGCTCAAGT TAAAGGCTCT CACACAGCCC GATTCCTTAA
  51   ACCGATTTTA GAAAAACCTT AGAAAAAATG ACCGCACTTT CAGAGAAAAC
 101   TCACATAAAG TGCGGTTATT TTATTAGTGA TATTGTTTTA ATTATTTGTA
 151   TAAATTACAT ACAATATTAA TCCATCGAAA AATAAGATTA CCCACTAAGT
 201   ATTAAGCCAA AACCTAGAAA TTTTGGCTTA ATTACTATAT AATTTTACTC
 251   CTTTATTTTC TTTTGTGCCT TTAGTTAGT TCGTTTTTTA GCTGAAATCC
 301   CTCAGAAAAT CACCGCACTT TTATTGTTCA ATAGTCGTTT AACCACGTAT
 351   TTTTAATAC GAAAATTAC TTAATTAAAT AAACATTATG AAAAAAACTG
 401   TATTTCGTCT TAATTTTCTA ACCGCTTGTA TTTCATTAGG GATAGTATCG
 451   CAAGCGTGGG CAGGTCACAC TTATTTTGGG ATTGACTACC AATATTATCG
 501   TGATTTTGCC GAGAATAAAG GGAAGTTTAC AGTTGGGGCT CAAGATATTG
 551   ATATCTACAA TAAAAAGGG GAATGATAG GTACGATGAT GAAAGGTGTG
 601   CCTATGCCTG ATTTATCTTC CATGGTTCGT GGTGGTTATT CAACATTGAT
 651   AAGTGAGCAG CATTTAATTA GCGTCGCACA TAATGTAGGG TATGATGTCG
 701   TTGATTTTGG TATGGAGGGG GAAAATCCAG ACCAACATCG TTTTAAGTAT
 751   AAAGTTGTTA AACGATATAA TTATAAGAGC GGTGATAGAC AATATAATGA
 801   TTATCAACAT CCAAGATTAG AGAAATTTGT AACGGAAACT GCACCTATTG
 851   AAATGGTTTC ATATATGGAT GGTAATCATT ACAAAAATTT TAATCAATAT
 901   CCTTTGCGAG TTAGAGTTGG AAGTGGGCAT CAATGGTGGA AAGACGATAA
 951   TAATAAAACC ATTGGAGACT TAGCCTATGG AGGTTCATGG TTAATAGGTG
1001   GAAATACCTT TGAAGATGGA CCAGCTGGTA ACGGTACATT AGAATTAAAT
1051   GGGCGAGTAC AAAATCCTAA TAAATATGGT CCACTACCTA CGGCAGGTTC
1101   ATTCGGGGAT AGTGGTTCTC CAATGTTTAT TTATGATAAG GAAGTTAAGA
1151   AATGGTTATT AAATGGCGTG TTACGTGAAG GAAATCCTTA TGCTGCAGTA
1201   GGAAACAGCT ATCAAATTAC ACGAAAAGAT TATTTTCAAG GTATTCTTAA
1251   TCAAGACATT ACAGCTAATT TTTGGGATAC TAATGCTGAA TATAGATTTA
1301   ATATAGGGAG TGACCACAAT GGAAGAGTGG CAACAATCAA AAGTACATTA
1351   CCTAAAAAAG CTATTCAGCC TGAACGAATA GTGGGTCTTT ATGATAATAG
1401   CCAACTTCAT GATGCTAGAG ATAAAAATGG CGATGAATCT CCCTCTTATA
1451   AAGGTCCTAA TCCATGGTCG CCAGCATTAC ATCATGGGAA AGTATTTTAC
1501   TTTGGCGATC AAGGAACAGG AACTTTAACA ATTGAAAATA ATATAAATCA
1551   AGGTGCAGGT GGATTGTATT TTGAAGGTAA TTTTGTTGTA AAAGGCAATC
1601   AAAATAATAT AACTTGGCAA GGTGCAGGCG TTTCTGTTGG AGAAGAAAGT
1651   ACTGTTGAAT GGCAGGTGCA TAATCCAGAA GGCGATCGCT TATCCAAAAT
1701   TGGGCTGGGA ACCTTACTTG TTAATGGTAA AGGGAAAAAC TTAGGAAGCC
1751   TGAGTGTCGG TAACGGTTTG GTTGTGTTAG ATCAACAAGC AGATGAATCA
1801   GGTCAAAAAC AAGCCTTTAA AGAAGTTGGC ATTGTAAGTG GTAGAGCTAC
1851   CGTTCAACTA AATAGTGCAG ATCAAGTTGA TCCTAACAAT ATTTATTTCG
1901   GCTTTCGTGG TGGTCGCTTA GATCTTAATG GGCATTCATT AACCTTTGAA
1951   CGTATCCAAA ATACGGATGA AGGCGCGATG ATTGTGAACC ACAACGCTTC
2001   TCAAACCGCA AATATTACGA TTACAGGCAA CGCAACTATT AATTCAGATA
```

Fig. 22A

```
2051    GCAAACAACT TACTAATAAA AAAGATATTG CATTTAACGG CTGGTTTGGT
2101    GAGCAAGATA AAGCTAAAAC AAATGGTCGT TTAAATGTGA ATTATCAACC
2151    AGTTAATGCA GAAAATCATT TGTTGCTTTC TGGGGGGACA AATTTAAACG
2201    GCAATATCAC GCAAAATGGT GGTACGTTAG TTTTTAGTGG TCGTCCAACG
2251    CCTCATGCTT ACAATCATTT AAGAAGAGAC TTGTCTAACA TGGAAGGTAT
2301    CCCACAAGGC GAAATTGTGT GGGATCACGA TTGGATCAAC CGCACATTTA
2351    AAGCTGAAAA CTTCCAAATT AAAGGCGGAA GTGCGGTGGT TTCTCGCAAT
2401    GTTTCTTCAA TTGAGGGAAA TTGGACAGTC AGCAATAATG CAAATGCCAC
2451    ATTTGGTGTT GTGCCAAATC AGCAAAATAC CATTTGCACG CGTTCAGATT
2501    GGACAGGATT AACGACTTGT AAAACAGTTG ATTAACCGA TAAAAAGTT
2551    ATTAATTCCA TACCGACAAC ACAAATTAAT GGTTCTATTA ATTTAACTGA
2601    TAATGCAACA GTGAATATTC ATGGTTTAGC AAAACTTAAT GGTAATGTCA
2651    CTTTAATAGA TCACAGCCAA TTTACATTGA GCAACAATGC CACCCAAGCA
2701    GGCAATATCA AACTTTCAAA TCACGCAAAT GCAACGGTGG ACAATGCAAA
2751    TTTGAACGGT AATGTGAATT TAATGGATTC TGCTCAATTT TCTTTAAAAA
2801    ACAGCCATTT TTCGCACCAA ATCCAAGGTG GGAAGACAC AACAGTGATG
2851    TTGGAAAATG CGACTTGGAC AATGCCTAGC GATACCACAT TGCAGAATTT
2901    AACGCTAAAT AATAGTACTG TTACGTTAAA TTCAGCTTAT TCAGCTATCT
2951    CAAATAATGC GCCACGCCGT CGCCGCCGTT CATTAGAGAC GGAAACAACG
3001    CCAACATCGG CAGAACATCG TTTCAACACA TTGACAGTAA ATGGTAAATT
3051    GAGCGGGCAA GGCACATTCC AATTTACTTC ATCTTTATTT GGCTATAAAA
3101    GCGATAAATT AAAATTATCC AATGACGCTG AGGGCGATTA CACATTATCT
3151    GTTCGCAACA CAGGCAAAGA ACCCGTGACC TTTGGGCAAT TAACTTTGGT
3201    TGAAAGCAAA GATAATAAAC CGTTATCAGA CAAACTCACA TTCACGTTAG
3251    AAAATGACCA CGTTGATGCA GGTGCATTAC GTTATAAATT AGTGAAGAAT
3301    GATGGCGAAT TCCGCTTACA TAACCCAATA AAAGAGCAGG AATTGCGCTC
3351    TGATTTAGTA AGAGCAGAGC AAGCAGAACG AACATTAGAA GCCAAACAAG
3401    TTGAACAGAC TGCTAAAACA CAAACAAGTA AGGCAAGAGT GCGGTCAAGA
3451    AGAGCGGTGT TTTCTGATCC CCTGCCTGCT CAAAGCCTGT TAAACGCATT
3501    AGAAGCCAAA CAAGCTCTGA CTACTGAAAC ACAAACAAGT AAGGCAAAAA
3551    AAGTGCGGTC AAAAAGAGCT GCGAGAGAGT TTTCTGATAC CCTGCCTGAT
3601    CAAATATTAC AAGCCGCACT TGAGGTTATT GATGCCCAAC AGCAAGTGAA
3651    AAAAGAACCT CAAACTCAAG AGGAAGAAGA GAAAAGACAA CGCAAACAAA
3701    AAGAATTGAT CAGCCGTTAC TCAAATAGTG CGTTATCGGA GTTGTCTGCG
3751    ACAGTAAATA GTATGCTTTC CGTTCAAGAT GAATTGGATC GTCTTTTTGT
3801    AGATCAAGCA CAATCTGCCG TGTGGACAAA TATCGCACAG GATAAAAGAC
3851    GCTATGATTC TGATGCGTTC CGTGCTTATC AGCAGAAAAC GAACTTGCGT
3901    CAAATTGGGG TGCAAAAAGC CTTAGATAAT GGACGAATTG GGGCGGTTTT
3951    CTCGCATAGC CGTTCAGATA ATACCTTTGA CGAACAGGTT AAAAATCACG
4001    CGACATTAGC GATGATGTCT GGTTTTGCCC AATATCAATG GGGCGATTTA
4051    CAATTTGGTG TAAACGTGGG TGCGGGAATT AGTGCGAGTA AAATGGCTGA
4101    AGAACAAAGC CGAAAAATTC ATCGAAAAGC GATAAATTAT GGTGTGAATG
4151    CAAGTTATCA GTTCCGTTTA GGGCAATTGG GTATTCAGCC TTATTTGGGT
4201    GTTAATCGAT ATTTATTGA ACGTGAAAAT TATCAATCTG AAGAAGTGAA
```

Fig. 22B

```
4251  AGTGCAAACA CCGAGCCTTG TATTTAATCG CTATAATGCT GGCATTCGAG
4301  TTGATTATAC ATTTACCCCG ACAGATAATA TCAGCATTAA GCCTTATTTC
4351  TTCGTCAATT ATGTTGATGT TCAAACGCT  AACGTACAAA CCACTGTAAA
4401  TCGCACGATG TTGCAACAAT CATTTGGGCG TTATTGGCAA AAAGAAGTGG
4451  GATTAAAGGC AGAAATTTTA CATTTCCAAC TTTCCGCTTT TATCTCAAAA
4501  TCTCAAGGTT CACAACTCGG CAAACAGCAA AATGTGGGCG TGAAATTGGG
4551  GTATCGTTGG TAAAAATCAA CATAATTTTA TCGTTTATTG ATAAACAAGG
4601  TGGGGCAGAT CAAATCCTAC CTTTTTTATT CCAATAATGG AACTTTATTT
4651  TATTAAAGGT ATCTAAGTAG CACCCTATAT AGGGATTAAT TAAGAGGATT
4701  TAATAATGAA TTTAACTAAA ATTTTACCCA CATTTGCTGC TGTAGTCGTA
4751  TTATCTGCTT GTGCAAAGGA TGCACCTGAA ATGACAAAAT CATCTGCGCA
4801  AATAGCTGAA ATGCAAACAC TT
```

Fig. 22C

Amino acid sequence for NTHi strain 3219B Hap protein (first amino acid to last amino acid):

```
   1  MKKTVFRLNF  LTACISLGIV  SQAWAGHTYF  GIDYQYYRDF  AENKGKFTVG
  51  AQDIDIYNKK  GEMIGTMMKG  VPMPDLSSMV  RGGYSTLISE  QHLISVAHNV
 101  GYDVVDFGME  GENPDQHRFK  YKVVKRYNYK  SGDRQYNDYQ  HPRLEKFVTE
 151  TAPIEMVSYM  DGNHYKNFNQ  YPLRVRVGSG  HQWWKDDNNK  TIGDLAYGGS
 201  WLIGGNTFED  GPAGNGTLEL  NGRVQNPNKY  GPLPTAGSFG  DSGSPMFIYD
 251  KEVKKWLLNG  VLREGNPYAA  VGNSYQITRK  DYFQGILNQD  ITANFWDTNA
 301  EYRFNIGSDH  NGRVATIKST  LPKKAIQPER  IVGLYDNSQL  HDARDKNGDE
 351  SPSYKGPNPW  SPALHHGKSI  YFGDQGTGTL  TIENNINQGA  GGLYFEGNFV
 401  VKGNQNNITW  QGAGVSVGEE  STVEWQVHNP  EGDRLSKIGL  GTLLVNGKGK
 451  NLGSLSVGNG  LVVLDQQADE  SGQKQAFKEV  GIVSGRATVQ  LNSADQVDPN
 501  NIYFGFRGGR  LDLNGHSLTF  ERIQNTDEGA  MIVNHNASQT  ANITITGNAT
 551  INSDSKQLTN  KKDIAFNGWF  GEQDKAKTNG  RLNVNYQPVN  AENHLLLSGG
 601  TNLNGNITQN  GGTLVFSGRP  TPHAYNHLRR  DLSNMEGIPQ  GEIVWDHDWI
 651  NRTFKAENFQ  IKGGSAVVSR  NVSSIEGNWT  VSNNANATFG  VVPNQQNTIC
 701  TRSDWTGLTT  CKTVDLTDKK  VINSIPTTQI  NGSINLTDNA  TVNIHGLAKL
 751  NGNVTLIDHS  QFTLSNNATQ  AGNIKLSNHA  NATVDNANLN  GNVNLMDSAQ
 801  FSLKNSHFSH  QIQGGEDTTV  MLENATWTMP  SDTTLQNLTL  NNSTVTLNSA
 851  YSAISNNAPR  RRRRSLETET  TPTSAEHRFN  TLTVNGKLSG  QGTFQFTSSL
 901  FGYKSDKLKL  SNDAEGDYTL  SVRNTGKEPV  TFGQLTLVES  KDNKPLSDKL
 951  TFTLENDHVD  AGALRYKLVK  NDGEFRLHNP  IKEQELRSDL  VRAEQAERTL
1001  EAKQVEQTAK  TQTSKARVRS  RRAVFSDPLP  AQSLLNALEA  KQALTTETQT
1051  SKAKKVRSKR  AAREFSDTLP  DQILQAALEV  IDAQQQVKKE  PQTQEEEEKR
1101  QRKQKELISR  YSNSALSELS  ATVNSMLSVQ  DELDRLFVDQ  AQSAVWTNIA
1151  QDKRRYDSDA  FRAYQQKTNL  RQIGVQKALD  NGRIGAVFSH  SRSDNTFDEQ
1201  VKNHATLAMM  SGFAQYQWGD  LQFGVNVGAG  ISASKMAEEQ  SRKIHRKAIN
1251  YGVNASYQFR  LGQLGIQPYL  GVNRYFIERE  NYQSEEVKVQ  TPSLVFNRYN
1301  AGIRVDYTFT  PTDNISIKPY  FFVNYVDVSN  ANVQTTVNRT  MLQQSFGRYW
1351  QKEVGLKAEI  LHFQLSAFIS  KSQGSQLGKQ  QNVGVKLGYR  W
```

Fig. 23

Nucleotide sequence for NTHi strain 1396B hap gene (start codon begins at position 313, stop codon begins at position 4546):

```
   1  TGACCGCACT TTCAGAGAAA ACTCACATAA AGTGCGGTTA TTTTATTAGT
  51  GATATTGTTT TAATTTTAGT TATCTGTATA AATTACATAC AATATTAATC
 101  CATCGCAAGA TAAGATTACC CACTAAGTAT TAAGCAAAAA CCTAGAAATT
 151  TTGGCTTAAT TACTATATAG TTTTACTCAT TTATTTTCTT TTGTGCCTTT
 201  TAGTTCGTTT TTTTAGCTGA AATCCCTTAG AAAATCACCG CACTTTTATT
 251  GTTCAATAGT CGTTTAACCA CGTATTTTTT AATACGAAAA ATTACTTAAT
 301  TAAATAAACA TTATGAAAAA AACTGTATTT CGTCTGAATT TTTTAACCGC
 351  TTGCATTTCA TTAGGGATAG TATCGCAAGC GTGGGCAGGT CATACTTATT
 401  TTGGGATTGA CTACCAATAT TATCGTGATT TGCCGAGAA TAAAGGGAAG
 451  TTCACAGTTG GGCTAAAAA TATTGAGGTT TACAATAAAA ATGGAAATTT
 501  AGTTGGCACA TCAATGACAA AGCCCCAAT GATTGATTTT TCCGTGGTGT
 551  CGCGAAATGG GGTGGCGGCA TTGGTGGGCG ATCAGTATAT TGTGAGTGTG
 601  GCACATAATG TAGGCTATAC CAATGTGGAT TTTGGTGCTG AAGGACAAAA
 651  TCCTGATCAA CATCGTTTTA CTTATAAAAT TGTGAAACGG AATAATTATA
 701  AAAACGATCA AACGCATCCT TATGAGAAAG ACTACCACAA CCCACGCTTA
 751  CATAAATTTG TTACGGAAGC CACCCCAATC GATATGACTT CTGATATGAA
 801  CGGCAACAAA TATACAGATA GGACGAAATA TCCCGAACGC GTGCGTATCG
 851  GCTCCGGGTG GCAGTTTTGG CGAAACGATC AAAACAACGG CGACCAAGTT
 901  GCCGGCGCAT ATCATTACCT GACAGCAGGC AATACACACA ACCAAGGCGG
 951  AGCAGGGGGC GGCTGGTCAA GTCTGAGCGG CGATGTGCGC CAAGCGGGCA
1001  ATTACGGCCC CATTCCTATT GCAGGCTCAA GCGGCGACAG CGGTTCGCCT
1051  ATGTTTATTT ATGATGCGGA AAAACAAAAA TGGTTGATTA ACGGCGTATT
1101  GAGGACCGGC AACCCTTGGG CGGGGACAGA GAATACATTC CAACTGGTAC
1151  GCAAGTCTTT TTTTGATGAA ATCCTTGAAA AAGATTTGCG TACATCGTTT
1201  TATAGCCCAT CGGGCAATGG TGCATACACC ATTACAGACA AAGGCGACGG
1251  CAGCGGCATT GTCAAACAAC AAACAGGAAG ACCATCTGAA GTCCGCATCG
1301  GTTTAAAAGA CGACAAATTA CCTGCCGAAG GTAAAGACGA TGTTTACCAA
1351  TACCAAGGTC AAATATATA CCTGCCTCGT TTGAATAACG GTGGAAACCT
1401  GTATTTCGGA GATCAAAAAA ACGGCACTGT TACCTTATCA ACCAACATCA
1451  ACCAAGGTGC GGGCGGTTTG TATTTTGAGG GTAACTTTAC GGTATCTTCA
1501  GAAAATAATG CAACTTGGCA AGGTGCTGGA GTGCATGTAG GTGAAGACAG
1551  TACTGTTACT TGGAAAGTAA ATGGTGTTGA AATGATCGC CTTTCTAAAA
1601  TCGGCAAAGG CACATTGCAC GTTAAAGCCA AGGGGAAAA TAAAGGTTCG
1651  ATCAGCGTAG CGATGGTAA AGTCATTTTG GAGCAGCAGG CAGACGATCA
1701  AGGCAACAAA CAAGCCTTTA GTGAAATTGG CTTGGTTAGT GGCAGAGGTA
1751  CGGTTCAGTT AAACGATGAC AAGCAATTTA ATACTGATAA ATTTTATTTC
1801  GGCTTCCGTG GTGGTCGCTT AGATCTTAAT GGGCATTCAT TAACCTTTAA
1851  ACGTATCCAA AATACGGATG AGGGAGCAAC GATTGTTAAT CACAATGCCA
1901  CAACAGAATC TACAGTGACC ATTACTGGCA GCGATACCAT TAATGACAAC
1951  ACTGGCGATT TAACCAATAA ACGTGATATT GCTTTTAATG GTTGGTTTGG
2001  TGATAAAGAT GATACTAAAA ATACTGGACG TTTGAATGTT ACTTACAATC
```

Fig. 24A

```
2051  CGCTTAACAA AGATAATCAC TTCCTTCTAT CAGGTGGAAC AAATTTAAAA
2101  GGCAATATTA CTCAAGACGG TGGCACTTTA GTGTTTAGTG GTCGCCCAAC
2151  ACCACACGCA TACAATCATT TAAATCGCCT AAACGAGCTT GGGCGACCTA
2201  AGGGCGAAGT GGTTATTGAT GACGATTGGA TCAACCGTAC ATTTAAAGCT
2251  GAAAACTTCC AAATTAAAGG CGGAAGTACG GTGGTTTCTC GCAATGTTTC
2301  TTCAATTGAA GGAAATTGGA CAATCAGCAA TAACGCCAAC GCGACATTTG
2351  GTGTTGTGCC AAATCAACAA AATACCATTT GCACGCGTTC AGATTGGACA
2401  GGATTAACGA CTTGTAAAAC AGTTAATTTA ACCGATAAAA AAGTTATTGA
2451  TTCCATACCG ACAACACAAA TTAATGGCTC TATTAATTTA ACTAATAATG
2501  CAACAGTGAA TATTCATGGT TTAGCAAAAC TTAATGGTAA TGTCACTTTA
2551  ATAAATCATA GCCAATTTAC ATTGAGCAAC AATGCCACCC AAACAGGCAA
2601  TATCCAACTT TCAAATCACG CAAATGCAAC GGTGGATAAT GCAAACTTGA
2651  ACGGTAATGT GCATTTAACG GATTCTGCTC AATTTTCTTT AAAAAACAGC
2701  CATTTTCGC ACCAAATTCA GGGCGACAAA GACACAACAG TGACGTTGGA
2751  AAATGCGACT TGGACAATGC CTAGCGATAC TACATTGCAG AATTTAACGC
2801  TAAATAATAG TACTGTTACG TTAAATTCAG CTTATTCAGC TAGCTCAAAT
2851  AATGCGCCAC GTCACCGCCG TTCATTAGAG ACGGAAACAA CGCCAACATC
2901  GGAAGAACAT CGTTTCAACA CATTGACAGT AAATGGTAAA TTGAGCGGGC
2951  AAGGCACATT CCAATTTACT TCATCTTTAT TTGGCTATAA AAGCGATAAA
3001  ATAAAATTAT CTAATGACGC TGAAGGCGAT TACACATTAG CTGTTCGCGA
3051  CACAGGCAAA GAACCTGTGA CCCTTGAGCA ATTAACTTTA ATTGAAGGCT
3101  TGGATAATCA ACCCTTGCCA GATAAGCTAA AAATTACTTT AAAAAATAAA
3151  CACGTTGATG CGGGTGCATG GCGTTATGAA TTAGTGAAGA AAAACGGCGA
3201  ATTCCGCTTG CATAATCCAA TAAAAGAGCA GGAATTGCGC AATGATTTAG
3251  TAAAAGCAGA GCAAGTAGAA CGAGCATTAG AAGCAAAACA AGCTGAACTG
3301  ACTACTAAAA AACAAAAAAC TGAGGCTAAA GTGCGGTCAA AAAGAGCGGC
3351  GTTTTCTGAT ACCCCGCCTG ATCAAAGCCA GTTAAACGCA TTACAAGCCG
3401  AACTCGAGAC GATTAATGCC CAACAGCAAG TGGCACAAGC GGTGCAAAAT
3451  CAGAAAGTAA CTGCACTTAA CCAAAAGAAC GAGCAAGTTA AAACCACTCA
3501  AGATAAAGCA AATTTAGTCT TGGCAACTGC ATTGGTGGAA AAAGAAACCG
3551  CTCAGATTGA TTTTGCTAAT GCAAAATTAG CTCAGTTGAA TTTAACACAA
3601  CAACTAGAAA AAGCCTTAGC AGTGGCTGAG CAAGCAGAAA AAGAGCGTAA
3651  AGCTCAAGAG CAAGCGAAAA GACAACGCAA ACAAAAAGAC TTGATCAGCC
3701  GTTATTCAAA TAGTGCGTTA TCAGAATTAT CTGCAACAGT AAATAGTATG
3751  CTTTCCGTTC AAGATGAATT AGATCGTCTT TTTGTAGATC AAGCTCAATC
3801  TGCGGTGTGG ACAAATATCT CACAGGATAA AAGACGTTAT GATTCTGATG
3851  CGTTCCGTGC TTATCAGCAG AAAACGAACT TGCGTCAAAT TGGGGTGCAA
3901  AAAGCCTTAG CTAACGGACG AATTGGGGCA GTTTTCTCGC ATAGCCGTTC
3951  AGATAATACT TTTGATGAAC AGGTTAAAAA TCACGCAACA TTAACGATGA
4001  TGTCGGGTTT TGCCCAATAT CAATGGGGTG ATTTACAATT TGGTGTAAAC
4051  GTGGGAACGG GAATTAGTGC GAGTAAAATG GCTGAAGAAC AAAGCCGAAA
4101  AATTCATCGA AAAGCGATAA ATTATGGCGT GAATGCAAGT TATTCGTTCC
4151  ATTTAGGGCA ATTGGGTATT CAGCCTTATT TTGGAGTTAA TCGCTATTTT
4201  ATTGAACGTA AAAATTATCA ATCTGAGGAA GTGAAAGTGC AAACACCGAG
```

Fig. 24B

```
4251 CCTTGCATTT AATCGCTATA ATGCTGGAGT ACGGGTCGAT TATACGTTTA
4301 CCCCGACAGA GAATATCAGC GTTAAGCCTT ATTTCTTCGT CAATTATGTT
4351 GATGTTTCAA ACGCTAACGT ACAAACCACT GTAAATCGCG CGGTGTTGCA
4401 ACAACCATTT GGACGTTATT GGCAAAAAGA AGTGGGATTA AAAGCGGAAA
4451 TTTTACATTT CCAACTTTCT GCTTTTATTT CTAAATCTCA AGGTTCGCAA
4501 CTCGGTAAAC AGCGAAATAT GGGCGTGAAA TTAGGATATC GTTGGTAAAA
4551 ATCAACATAA TTTTATTCTA ATAATGGAAC TTTATTTAAT TAAAAGTATC
4601 TAAGTAGCAC CCTATAGGGG ATTAATTAAG AGGATTTAAT AATGAATTTA
4651 ACTAAAATTT TACCCGCATT TGCTGCTGCA GTCGTATTAT CTGCTTGTGC
4701 AAAGGATGCA CCTGAAATGA CAAAATCATC TGCGCAAATA GCTGAAATGC
4751 AAACACTTCC AACAATCACT GATAAAACAG TTGTATATTC TTGCAATAAA
4801 CAAACTGTGA CTGCAGTGTA TCAATTTG
```

Fig. 24C

Amino acid sequence for NTHi strain 1396B Hap protein (first amino acid to last amino acid):

```
   1  MKKTVFRLNF LTACISLGIV SQAWAGHTYF GIDYQYYRDF AENKGKFTVG
  51  AKNIEVYNKN GNLVGTSMTK APMIDFSVVS RNGVAALVGD QYIVSVAHNV
 101  GYTNVDFGAE GQNPDQHRFT YKIVKRNNYK NDQTHPYEKD YHNPRLHKFV
 151  TEATPIDMTS DMNGNKYTDR TKYPERVRIG SGWQFWRNDQ NNGDQVAGAY
 201  HYLTAGNTHN QGGAGGGWSS LSGDVRQAGN YGPIPIAGSS GDSGSPMFIY
 251  DAEKQKWLIN GVLRTGNPWA GTENTFQLVR KSFFDEILEK DLRTSFYSPS
 301  GNGAYTITDK GDGSGIVKQQ TGRPSEVRIG LKDDKLPAEG KDDVYQYQGP
 351  NIYLPRLNNG GNLYFGDQKN GTVTLSTNIN QGAGGLYFEG NFTVSSENNA
 401  TWQGAGVHVG EDSTVTWKVN GVENDRLSKI GKGTLHVKAK GENKGSISVG
 451  DGKVILEQQA DDQGNKQAFS EIGLVSGRGT VQLNDDQFN  TDKFYFGFRG
 501  GRLDLNGHSL TFKRIQNTDE GATIVNHNAT TESTVTITGS DTINDNTGDL
 551  TNKRDIAFNG WFGDKDDTKN TGRLNVTYNP LNKDNHFLLS GGTNLKGNIT
 601  QDGGTLVFSG RPTPHAYNHL NRLNELGRPK GEVVIDDDWI NRTFKAENFQ
 651  IKGGSTVVSR NVSSIEGNWT ISNNANATFG VVPNQQNTIC TRSDWTGLTT
 701  CKTVNLTDKK VIDSIPTTQI NGSINLTNNA TVNIHGLAKL NGNVTLINHS
 751  QFTLSNNATQ TGNIQLSNHA NATVDNANLN GNVHLTDSAQ FSLKNSHFSH
 801  QIQGDKDTTV TLENATWTMP SDTTLQNLTL NNSTVTLNSA YSASSNNAPR
 851  HRRSLETETT PTSEEHRFNT LTVNGKLSGQ GTFQFTSSLF GYKSDKIKLS
 901  NDAEGDYTLA VRDTGKEPVT LEQLTLIEGL DNQPLPDKLK ITLKNKHVDA
 951  GAWRYELVKK NGEFRLHNPI KEQELRNDLV KAEQVERALE AKQAELTTKK
1001  QKTEAKVRSK RAAFSDTPPD QSQLNALQAE LETINAQQQV AQAVQNQKVT
1051  ALNQKNEQVK TTQDKANLVL ATALVEKETA QIDFANAKLA QLNLTQQLEK
1101  ALAVAEQAEK ERKAQEQAKR QRKQKDLISR YSNSALSELS ATVNSMLSVQ
1151  DELDRLFVDQ AQSAVWTNIS QDKRRYDSDA FRAYQQKTNL RQIGVQKALA
1201  NGRIGAVFSH SRSDNTFDEQ VKNHATLTMM SGFAQYQWGD LQFGVNVGTG
1251  ISASKMAEEQ SRKIHRKAIN YGVNASYSFH LGQLGIQPYF GVNRYFIERK
1301  NYQSEEVKVQ TPSLAFNRYN AGVRVDYTFT PTENISVKPY FFVNYVDVSN
1351  ANVQTTVNRA VLQQPFGRYW QKEVGLKAEI LHFQLSAFIS KSQGSQLGKQ
1401  RNMGVKLGYR W
```

Fig. 25

SEQUENCE LISTING

```
<160> NUMBER OF SEQ ID NOS: 58

<210> SEQ ID NO 1
<211> LENGTH: 4319
<212> TYPE: DNA
<213> ORGANISM: Haemophilus influenzae
<220> FEATURE:
<221> NAME/KEY: CDS
<222> LOCATION: (60)..(4241)
<223> OTHER INFORMATION:

<400> SEQUENCE: 1
tcaatagtcg tttaactagt attttttaat acgaaaaatt acttaattaa ataaacatt         59 atg aaa aaa act gta ttt cgt ctt aat ttt tta acc gct tgc att tca       107
Met Lys Lys Thr Val Phe Arg Leu Asn Phe Leu Thr Ala Cys Ile Ser
1               5                   10                  15 tta ggg ata gta tcg caa gcg tgg gct ggt cac act tat ttt ggg att       155
Leu Gly Ile Val Ser Gln Ala Trp Ala Gly His Thr Tyr Phe Gly Ile
            20                  25                  30
```

```
gat tac caa tat tat cgt gat ttt gcc gag aat aaa ggg aag ttc aca        203
Asp Tyr Gln Tyr Tyr Arg Asp Phe Ala Glu Asn Lys Gly Lys Phe Thr
        35                  40                  45 gtt ggg gct caa aat att aag gtt tat aac aaa caa ggg caa tta gtt        251
Val Gly Ala Gln Asn Ile Lys Val Tyr Asn Lys Gln Gly Gln Leu Val
50                  55                  60 ggc aca tca atg aca aaa gcc ccg atg att gat ttt tct gta gtg tca        299
Gly Thr Ser Met Thr Lys Ala Pro Met Ile Asp Phe Ser Val Val Ser
65                  70                  75                  80 cgt aac ggc gtg gca gcc ttg gtt gaa aat caa tat att gtg agc gtg        347
Arg Asn Gly Val Ala Ala Leu Val Glu Asn Gln Tyr Ile Val Ser Val
            85                  90                  95 gca cat aac gta gga tat aca gat gtt gat ttt ggt gca gag gga aac        395
Ala His Asn Val Gly Tyr Thr Asp Val Asp Phe Gly Ala Glu Gly Asn
            100                 105                 110 aac ccc gat caa cat cgt ttt act tat aag att gta aaa cga aat aac        443
Asn Pro Asp Gln His Arg Phe Thr Tyr Lys Ile Val Lys Arg Asn Asn
        115                 120                 125 tac aaa aaa gat aat tta cat cct tat gag gac gat tac cat aat cca        491
Tyr Lys Lys Asp Asn Leu His Pro Tyr Glu Asp Asp Tyr His Asn Pro
130                 135                 140 cga tta cat aaa ttc gtt aca gaa gcg gct cca att gat atg act tcg        539
Arg Leu His Lys Phe Val Thr Glu Ala Ala Pro Ile Asp Met Thr Ser
145                 150                 155                 160 aat atg aat ggc agt act tat tca gat aga aca aaa tat cca gaa cgt        587
Asn Met Asn Gly Ser Thr Tyr Ser Asp Arg Thr Lys Tyr Pro Glu Arg
            165                 170                 175 gtt cgt atc ggc tct gga cgg cag ttt tgg cga aat gat caa gac aaa        635
Val Arg Ile Gly Ser Gly Arg Gln Phe Trp Arg Asn Asp Gln Asp Lys
            180                 185                 190 ggc gac caa gtt gcc ggt gca tat cat tat ctg aca gct ggc aat aca        683
Gly Asp Gln Val Ala Gly Ala Tyr His Tyr Leu Thr Ala Gly Asn Thr
        195                 200                 205 cac aat cag cgt gga gca ggt aat gga tat tcg tat ttg gga ggc gat        731
His Asn Gln Arg Gly Ala Gly Asn Gly Tyr Ser Tyr Leu Gly Gly Asp
        210                 215                 220 gtt cgt aaa gcg gga gaa tat ggt cca tta ccg att gca ggc tca aag        779
Val Arg Lys Ala Gly Glu Tyr Gly Pro Leu Pro Ile Ala Gly Ser Lys
225                 230                 235                 240 ggg gac agt ggt tct ccg atg ttt att tat gat gct gaa aaa caa aaa        827
Gly Asp Ser Gly Ser Pro Met Phe Ile Tyr Asp Ala Glu Lys Gln Lys
            245                 250                 255 tgg tta att aat ggg ata tta cgg gaa ggc aac cct ttt gaa ggc aaa        875
Trp Leu Ile Asn Gly Ile Leu Arg Glu Gly Asn Pro Phe Glu Gly Lys
            260                 265                 270 gaa aat ggg ttt caa ttg gtt cgc aaa tct tat ttt gat gaa att ttc        923
Glu Asn Gly Phe Gln Leu Val Arg Lys Ser Tyr Phe Asp Glu Ile Phe
        275                 280                 285 gaa aga gat tta cat aca tca ctt tac acc cga gct ggt aat gga gtg        971
Glu Arg Asp Leu His Thr Ser Leu Tyr Thr Arg Ala Gly Asn Gly Val
        290                 295                 300 tac aca att agt gga aat gat aat ggt cag ggg tct ata act cag aaa       1019
Tyr Thr Ile Ser Gly Asn Asp Asn Gly Gln Gly Ser Ile Thr Gln Lys
305                 310                 315                 320 tca gga ata cca tca gaa att aaa att acg tta gca aat atg agt tta       1067
Ser Gly Ile Pro Ser Glu Ile Lys Ile Thr Leu Ala Asn Met Ser Leu
            325                 330                 335 cct ttg aaa gag aag gat aaa gtt cat aat cct aga tat gac gga cct       1115
Pro Leu Lys Glu Lys Asp Lys Val His Asn Pro Arg Tyr Asp Gly Pro
        340                 345                 350
```

-continued

| | |
|---|---|
| aat att tat tct cca cgt tta aac aat gga gaa acg cta tat ttt atg<br>Asn Ile Tyr Ser Pro Arg Leu Asn Asn Gly Glu Thr Leu Tyr Phe Met<br>355                      360                   365 | 1163 |
| gat caa aaa caa gga tca tta atc ttc gca tct gac att aac caa ggg<br>Asp Gln Lys Gln Gly Ser Leu Ile Phe Ala Ser Asp Ile Asn Gln Gly<br>370                      375                   380 | 1211 |
| gcg ggt ggt ctt tat ttt gag ggt aat ttt aca gta tct cca aat tct<br>Ala Gly Gly Leu Tyr Phe Glu Gly Asn Phe Thr Val Ser Pro Asn Ser<br>385                      390                   395                   400 | 1259 |
| aac caa act tgg caa gga gct ggc ata cat gta agt gaa aat agc acc<br>Asn Gln Thr Trp Gln Gly Ala Gly Ile His Val Ser Glu Asn Ser Thr<br>405                      410                   415 | 1307 |
| gtt act tgg aaa gta aat ggc gtg gaa cat gat cga ctt tct aaa att<br>Val Thr Trp Lys Val Asn Gly Val Glu His Asp Arg Leu Ser Lys Ile<br>420                      425                   430 | 1355 |
| ggt aaa gga aca ttg cac gtt caa gcc aaa ggg gaa aat aaa ggt tcg<br>Gly Lys Gly Thr Leu His Val Gln Ala Lys Gly Glu Asn Lys Gly Ser<br>435                      440                   445 | 1403 |
| atc agc gta ggc gat ggt aaa gtc att ttg gag cag cag gca gac gat<br>Ile Ser Val Gly Asp Gly Lys Val Ile Leu Glu Gln Gln Ala Asp Asp<br>450                      455                   460 | 1451 |
| caa ggc aac aaa caa gcc ttt agt gaa att ggc ttg gtt agc ggc aga<br>Gln Gly Asn Lys Gln Ala Phe Ser Glu Ile Gly Leu Val Ser Gly Arg<br>465                      470                   475                   480 | 1499 |
| ggg act gtt caa tta aac gat gat aaa caa ttt gat acc gat aaa ttt<br>Gly Thr Val Gln Leu Asn Asp Asp Lys Gln Phe Asp Thr Asp Lys Phe<br>485                      490                   495 | 1547 |
| tat ttc ggc ttt cgt ggt ggt cgc tta gat ctt aac ggg cat tca tta<br>Tyr Phe Gly Phe Arg Gly Gly Arg Leu Asp Leu Asn Gly His Ser Leu<br>500                      505                   510 | 1595 |
| acc ttt aaa cgt atc caa aat acg gac gag ggg gca atg att gtg aac<br>Thr Phe Lys Arg Ile Gln Asn Thr Asp Glu Gly Ala Met Ile Val Asn<br>515                      520                   525 | 1643 |
| cat aat aca act caa gcc gct aat gtc act att act ggg aac gaa agc<br>His Asn Thr Thr Gln Ala Ala Asn Val Thr Ile Thr Gly Asn Glu Ser<br>530                      535                   540 | 1691 |
| att gtt cta cct aat gga aat aat att aat aaa ctt gat tac aga aaa<br>Ile Val Leu Pro Asn Gly Asn Asn Ile Asn Lys Leu Asp Tyr Arg Lys<br>545                      550                   555                   560 | 1739 |
| gaa att gcc tac aac ggt tgg ttt ggc gaa aca gat aaa aat aaa cac<br>Glu Ile Ala Tyr Asn Gly Trp Phe Gly Glu Thr Asp Lys Asn Lys His<br>565                      570                   575 | 1787 |
| aat ggg cga tta aac ctt att tat aaa cca acc aca gaa gat cgt act<br>Asn Gly Arg Leu Asn Leu Ile Tyr Lys Pro Thr Thr Glu Asp Arg Thr<br>580                      585                   590 | 1835 |
| ttg cta ctt tca ggt ggt aca aat tta aaa ggc gat att acc caa aca<br>Leu Leu Leu Ser Gly Gly Thr Asn Leu Lys Gly Asp Ile Thr Gln Thr<br>595                      600                   605 | 1883 |
| aaa ggt aaa cta ttt ttc agc ggt aga ccg aca ccg cac gcc tac aat<br>Lys Gly Lys Leu Phe Phe Ser Gly Arg Pro Thr Pro His Ala Tyr Asn<br>610                      615                   620 | 1931 |
| cat tta aat aaa cgt tgg tca gaa atg gaa ggt ata cca caa ggc gaa<br>His Leu Asn Lys Arg Trp Ser Glu Met Glu Gly Ile Pro Gln Gly Glu<br>625                      630                   635                   640 | 1979 |
| att gtg tgg gat cac gat tgg atc aac cgt aca ttt aaa gct gaa aac<br>Ile Val Trp Asp His Asp Trp Ile Asn Arg Thr Phe Lys Ala Glu Asn<br>645                      650                   655 | 2027 |
| ttc caa att aaa ggc gga agt gcg gtg gtt tct cgc aat gtt tct tca<br>Phe Gln Ile Lys Gly Gly Ser Ala Val Val Ser Arg Asn Val Ser Ser<br>660                      665                   670 | 2075 |

```
att gag gga aat tgg aca gtc agc aat aat gca aat gcc aca ttt ggt    2123
Ile Glu Gly Asn Trp Thr Val Ser Asn Asn Ala Asn Ala Thr Phe Gly
        675                 680                 685 gtt gtg cca aat caa caa aat acc att tgc acg cgt tca gat tgg aca    2171
Val Val Pro Asn Gln Gln Asn Thr Ile Cys Thr Arg Ser Asp Trp Thr
690                 695                 700 gga tta acg act tgt caa aaa gtg gat tta acc gat aca aaa gtt att    2219
Gly Leu Thr Thr Cys Gln Lys Val Asp Leu Thr Asp Thr Lys Val Ile
705                 710                 715                 720 aat tct ata cca aaa aca caa atc aat ggc tct att aat tta act gat    2267
Asn Ser Ile Pro Lys Thr Gln Ile Asn Gly Ser Ile Asn Leu Thr Asp
            725                 730                 735 aat gca acg gcg aat gtt aaa ggt tta gca aaa ctt aat ggc aat gtc    2315
Asn Ala Thr Ala Asn Val Lys Gly Leu Ala Lys Leu Asn Gly Asn Val
        740                 745                 750 act tta aca aat cac agc caa ttt aca tta agc aac aat gcc acc caa    2363
Thr Leu Thr Asn His Ser Gln Phe Thr Leu Ser Asn Asn Ala Thr Gln
        755                 760                 765 ata ggc aat att cga ctt tcc gac aat tca act gca acg gtg gat aat    2411
Ile Gly Asn Ile Arg Leu Ser Asp Asn Ser Thr Ala Thr Val Asp Asn
770                 775                 780 gca aac ttg aac ggt aat gtg cat tta acg gat tca gct caa ttt tct    2459
Ala Asn Leu Asn Gly Asn Val His Leu Thr Asp Ser Ala Gln Phe Ser
785                 790                 795                 800 tta aaa aac agc cat ttt tcg cac caa att cag gga gac aaa ggc aca    2507
Leu Lys Asn Ser His Phe Ser His Gln Ile Gln Gly Asp Lys Gly Thr
            805                 810                 815 aca gtg acg ttg gaa aat gcg act tgg aca atg cct agc gat act aca    2555
Thr Val Thr Leu Glu Asn Ala Thr Trp Thr Met Pro Ser Asp Thr Thr
        820                 825                 830 ttg cag aat tta acg cta aat aac agt acg atc acg tta aat tca gct    2603
Leu Gln Asn Leu Thr Leu Asn Asn Ser Thr Ile Thr Leu Asn Ser Ala
        835                 840                 845 tat tca gct agc tca aac aat acg cca cgt cgc cgt tca tta gag acg    2651
Tyr Ser Ala Ser Ser Asn Asn Thr Pro Arg Arg Arg Ser Leu Glu Thr
850                 855                 860 gaa aca acg cca aca tcg gca gaa cat cgt ttc aac aca ttg aca gta    2699
Glu Thr Thr Pro Thr Ser Ala Glu His Arg Phe Asn Thr Leu Thr Val
865                 870                 875                 880 aat ggt aaa ttg agt ggg caa ggc aca ttc caa ttt act tca tct tta    2747
Asn Gly Lys Leu Ser Gly Gln Gly Thr Phe Gln Phe Thr Ser Ser Leu
            885                 890                 895 ttt ggc tat aaa agc gat aaa tta aaa tta tcc aat gac gct gag ggc    2795
Phe Gly Tyr Lys Ser Asp Lys Leu Lys Leu Ser Asn Asp Ala Glu Gly
            900                 905                 910 gat tac ata tta tct gtt cgc aac aca ggc aaa gaa ccc gaa acc ctt    2843
Asp Tyr Ile Leu Ser Val Arg Asn Thr Gly Lys Glu Pro Glu Thr Leu
        915                 920                 925 gag caa tta act ttg gtt gaa agc aaa gat aat caa ccg tta tca gat    2891
Glu Gln Leu Thr Leu Val Glu Ser Lys Asp Asn Gln Pro Leu Ser Asp
930                 935                 940 aag ctc aaa ttt act tta gaa aat gac cac gtt gat gca ggt gca tta    2939
Lys Leu Lys Phe Thr Leu Glu Asn Asp His Val Asp Ala Gly Ala Leu
945                 950                 955                 960 cgt tat aaa tta gtg aag aat gat ggc gaa ttc cgc ttg cat aac cca    2987
Arg Tyr Lys Leu Val Lys Asn Asp Gly Glu Phe Arg Leu His Asn Pro
            965                 970                 975 ata aaa gag cag gaa ttg cac aat gat tta gta aga gca gag caa gca    3035
Ile Lys Glu Gln Glu Leu His Asn Asp Leu Val Arg Ala Glu Gln Ala
            980                 985                 990
```

```
gaa cga aca tta gaa gcc aaa caa gtt gaa ccg act gct aaa aca caa    3083
Glu Arg Thr Leu Glu Ala Lys Gln Val Glu Pro Thr Ala Lys Thr Gln
        995                 1000                1005 aca ggt gag cca aaa gtg cgg tca aga aga gca gcg aga gca gcg        3128
Thr Gly Glu Pro Lys Val Arg Ser Arg Arg Ala Ala Arg Ala Ala
    1010                1015                1020 ttt cct gat acc ctg cct gat caa agc ctg tta aac gca tta gaa        3173
Phe Pro Asp Thr Leu Pro Asp Gln Ser Leu Leu Asn Ala Leu Glu
    1025                1030                1035 gcc aaa caa gct gaa ctg act gct gaa aca caa aaa agt aag gca        3218
Ala Lys Gln Ala Glu Leu Thr Ala Glu Thr Gln Lys Ser Lys Ala
    1040                1045                1050 aaa aca aaa aaa gtg cgg tca aaa aga gca gtg ttt tct gat ccc        3263
Lys Thr Lys Lys Val Arg Ser Lys Arg Ala Val Phe Ser Asp Pro
    1055                1060                1065 ctg ctt gat caa agc ctg ttc gca tta gaa gcc gca ctt gag gtt        3308
Leu Leu Asp Gln Ser Leu Phe Ala Leu Glu Ala Ala Leu Glu Val
    1070                1075                1080 att gat gcc cca cag caa tcg gaa aaa gat cgt cta gct caa gaa        3353
Ile Asp Ala Pro Gln Gln Ser Glu Lys Asp Arg Leu Ala Gln Glu
    1085                1090                1095 gaa gcg gaa aaa caa cgc aaa caa aaa gac ttg atc agc cgt tat        3398
Glu Ala Glu Lys Gln Arg Lys Gln Lys Asp Leu Ile Ser Arg Tyr
    1100                1105                1110 tca aat agt gcg tta tca gaa tta tct gca aca gta aat agt atg        3443
Ser Asn Ser Ala Leu Ser Glu Leu Ser Ala Thr Val Asn Ser Met
    1115                1120                1125 ctt tct gtt caa gat gaa tta gat cgt ctt ttt gta gat caa gca        3488
Leu Ser Val Gln Asp Glu Leu Asp Arg Leu Phe Val Asp Gln Ala
    1130                1135                1140 caa tct gcc gtg tgg aca aat atc gca cag gat aaa aga cgc tat        3533
Gln Ser Ala Val Trp Thr Asn Ile Ala Gln Asp Lys Arg Arg Tyr
    1145                1150                1155 gat tct gat gcg ttc cgt gct tat cag cag cag aaa acg aac tta        3578
Asp Ser Asp Ala Phe Arg Ala Tyr Gln Gln Gln Lys Thr Asn Leu
    1160                1165                1170 cgt caa att ggg gtg caa aaa gcc tta gct aat gga cga att ggg        3623
Arg Gln Ile Gly Val Gln Lys Ala Leu Ala Asn Gly Arg Ile Gly
    1175                1180                1185 gca gtt ttc tcg cat agc cgt tca gat aat acc ttt gat gaa cag        3668
Ala Val Phe Ser His Ser Arg Ser Asp Asn Thr Phe Asp Glu Gln
    1190                1195                1200 gtt aaa aat cac gcg aca tta acg atg atg tcg ggt ttt gcc caa        3713
Val Lys Asn His Ala Thr Leu Thr Met Met Ser Gly Phe Ala Gln
    1205                1210                1215 tat caa tgg ggc gat tta caa ttt ggt gta aac gtg gga acg gga        3758
Tyr Gln Trp Gly Asp Leu Gln Phe Gly Val Asn Val Gly Thr Gly
    1220                1225                1230 atc agt gcg agt aaa atg gct gaa gaa caa agc cga aaa att cat        3803
Ile Ser Ala Ser Lys Met Ala Glu Glu Gln Ser Arg Lys Ile His
    1235                1240                1245 cga aaa gcg ata aat tat ggc gtg aat gca agt tat cag ttc cgt        3848
Arg Lys Ala Ile Asn Tyr Gly Val Asn Ala Ser Tyr Gln Phe Arg
    1250                1255                1260 tta ggg caa ttg ggc att cag cct tat ttt gga gtt aat cgc tat        3893
Leu Gly Gln Leu Gly Ile Gln Pro Tyr Phe Gly Val Asn Arg Tyr
    1265                1270                1275 ttt att gaa cgt gaa aat tat caa tct gag gaa gtg aga gtg aaa        3938
Phe Ile Glu Arg Glu Asn Tyr Gln Ser Glu Glu Val Arg Val Lys
    1280                1285                1290
```

```
                                                        -continued acg cct agc ctt gca ttt aat cgc tat aat gct ggc att cga gtt    3983
Thr Pro Ser Leu Ala Phe Asn Arg Tyr Asn Ala Gly Ile Arg Val
    1295                1300                1305 gat tat aca ttt act ccg aca gat aat atc agc gtt aag cct tat    4028
Asp Tyr Thr Phe Thr Pro Thr Asp Asn Ile Ser Val Lys Pro Tyr
1310                1315                1320 ttc ttc gtc aat tat gtt gat gtt tca aac gct aac gta caa acc    4073
Phe Phe Val Asn Tyr Val Asp Val Ser Asn Ala Asn Val Gln Thr
    1325                1330                1335 acg gta aat ctc acg gtg ttg caa caa cca ttt gga cgt tat tgg    4118
Thr Val Asn Leu Thr Val Leu Gln Gln Pro Phe Gly Arg Tyr Trp
    1340                1345                1350 caa aaa gaa gtg gga tta aag gca gaa att tta cat ttc caa att    4163
Gln Lys Glu Val Gly Leu Lys Ala Glu Ile Leu His Phe Gln Ile
    1355                1360                1365 tcc gct ttt atc tca aaa tct caa ggt tca caa ctc ggc aaa cag    4208
Ser Ala Phe Ile Ser Lys Ser Gln Gly Ser Gln Leu Gly Lys Gln
    1370                1375                1380 caa aat gtg ggc gtg aaa ttg ggc tat cgt tgg taaaaatcaa         4251
Gln Asn Val Gly Val Lys Leu Gly Tyr Arg Trp
    1385                1390 cataatttta tcgtttattg ataaacaagg tgggtcagat cagatcccac ctttttttatt    4311 ccaataat                                                       4319

<210> SEQ ID NO 2
<211> LENGTH: 1394
<212> TYPE: PRT
<213> ORGANISM: Haemophilus influenzae

<400> SEQUENCE: 2

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Lys Gly Lys Phe Thr
        35                  40                  45

Val Gly Ala Gln Asn Ile Lys Val Tyr Asn Lys Gln Gly Gln Leu Val
    50                  55                  60

Gly Thr Ser Met Thr Lys Ala Pro Met Ile Asp Phe Ser Val Val Ser
65                  70                  75                  80

Arg Asn Gly Val Ala Ala Leu Val Glu Asn Gln Tyr Ile Val Ser Val
                85                  90                  95

Ala His Asn Val Gly Tyr Thr Asp Val Asp Phe Gly Ala Glu Gly Asn
            100                 105                 110

Asn Pro Asp Gln His Arg Phe Thr Tyr Lys Ile Val Lys Arg Asn Asn
        115                 120                 125

Tyr Lys Lys Asp Asn Leu His Pro Tyr Glu Asp Tyr His Asn Pro
    130                 135                 140

Arg Leu His Lys Phe Val Thr Glu Ala Ala Pro Ile Asp Met Thr Ser
145                 150                 155                 160

Asn Met Asn Gly Ser Thr Tyr Ser Asp Arg Thr Lys Tyr Pro Glu Arg
                165                 170                 175

Val Arg Ile Gly Ser Gly Arg Gln Phe Trp Arg Asn Asp Gln Asp Lys
            180                 185                 190

Gly Asp Gln Val Ala Gly Ala Tyr His Tyr Leu Thr Ala Gly Asn Thr
        195                 200                 205
```

-continued

```
His Asn Gln Arg Gly Ala Gly Asn Gly Tyr Ser Tyr Leu Gly Gly Asp
    210                 215                 220

Val Arg Lys Ala Gly Glu Tyr Gly Pro Leu Pro Ile Ala Gly Ser Lys
225                 230                 235                 240

Gly Asp Ser Gly Ser Pro Met Phe Ile Tyr Asp Ala Glu Lys Gln Lys
                245                 250                 255

Trp Leu Ile Asn Gly Ile Leu Arg Glu Gly Asn Pro Phe Glu Gly Lys
            260                 265                 270

Glu Asn Gly Phe Gln Leu Val Arg Lys Ser Tyr Phe Asp Glu Ile Phe
        275                 280                 285

Glu Arg Asp Leu His Thr Ser Leu Tyr Thr Arg Ala Gly Asn Gly Val
    290                 295                 300

Tyr Thr Ile Ser Gly Asn Asp Asn Gly Gln Gly Ser Ile Thr Gln Lys
305                 310                 315                 320

Ser Gly Ile Pro Ser Glu Ile Lys Ile Thr Leu Ala Asn Met Ser Leu
                325                 330                 335

Pro Leu Lys Glu Lys Asp Lys Val His Asn Pro Arg Tyr Asp Gly Pro
            340                 345                 350

Asn Ile Tyr Ser Pro Arg Leu Asn Asn Gly Glu Thr Leu Tyr Phe Met
        355                 360                 365

Asp Gln Lys Gln Gly Ser Leu Ile Phe Ala Ser Asp Ile Asn Gln Gly
    370                 375                 380

Ala Gly Gly Leu Tyr Phe Glu Gly Asn Phe Thr Val Ser Pro Asn Ser
385                 390                 395                 400

Asn Gln Thr Trp Gln Gly Ala Gly Ile His Val Ser Glu Asn Ser Thr
                405                 410                 415

Val Thr Trp Lys Val Asn Gly Val Glu His Asp Arg Leu Ser Lys Ile
            420                 425                 430

Gly Lys Gly Thr Leu His Val Gln Ala Lys Gly Glu Asn Lys Gly Ser
        435                 440                 445

Ile Ser Val Gly Asp Gly Lys Val Ile Leu Glu Gln Gln Ala Asp Asp
    450                 455                 460

Gln Gly Asn Lys Gln Ala Phe Ser Glu Ile Gly Leu Val Ser Gly Arg
465                 470                 475                 480

Gly Thr Val Gln Leu Asn Asp Asp Lys Gln Phe Asp Thr Asp Lys Phe
                485                 490                 495

Tyr Phe Gly Phe Arg Gly Gly Arg Leu Asp Leu Asn Gly His Ser Leu
            500                 505                 510

Thr Phe Lys Arg Ile Gln Asn Thr Asp Glu Gly Ala Met Ile Val Asn
        515                 520                 525

His Asn Thr Thr Gln Ala Ala Asn Val Thr Ile Thr Gly Asn Glu Ser
    530                 535                 540

Ile Val Leu Pro Asn Gly Asn Asn Ile Asn Lys Leu Asp Tyr Arg Lys
545                 550                 555                 560

Glu Ile Ala Tyr Asn Gly Trp Phe Gly Glu Thr Asp Lys Asn Lys His
                565                 570                 575

Asn Gly Arg Leu Asn Leu Ile Tyr Lys Pro Thr Thr Glu Asp Arg Thr
            580                 585                 590

Leu Leu Leu Ser Gly Gly Thr Asn Leu Lys Gly Asp Ile Thr Gln Thr
        595                 600                 605

Lys Gly Lys Leu Phe Phe Ser Gly Arg Pro Thr Pro His Ala Tyr Asn
    610                 615                 620
```

-continued

```
His Leu Asn Lys Arg Trp Ser Glu Met Glu Gly Ile Pro Gln Gly Glu
625                 630                 635                 640

Ile Val Trp Asp His Asp Trp Ile Asn Arg Thr Phe Lys Ala Glu Asn
            645                 650                 655

Phe Gln Ile Lys Gly Gly Ser Ala Val Val Ser Arg Asn Val Ser Ser
                660                 665                 670

Ile Glu Gly Asn Trp Thr Val Ser Asn Ala Asn Ala Thr Phe Gly
            675                 680                 685

Val Val Pro Asn Gln Gln Asn Thr Ile Cys Thr Arg Ser Asp Trp Thr
690                 695                 700

Gly Leu Thr Thr Cys Gln Lys Val Asp Leu Thr Asp Thr Lys Val Ile
705                 710                 715                 720

Asn Ser Ile Pro Lys Thr Gln Ile Asn Gly Ser Ile Asn Leu Thr Asp
                725                 730                 735

Asn Ala Thr Ala Asn Val Lys Gly Leu Ala Lys Leu Asn Gly Asn Val
            740                 745                 750

Thr Leu Thr Asn His Ser Gln Phe Thr Leu Ser Asn Asn Ala Thr Gln
        755                 760                 765

Ile Gly Asn Ile Arg Leu Ser Asp Asn Ser Thr Ala Thr Val Asp Asn
770                 775                 780

Ala Asn Leu Asn Gly Asn Val His Leu Thr Asp Ser Ala Gln Phe Ser
785                 790                 795                 800

Leu Lys Asn Ser His Phe Ser His Gln Ile Gln Gly Asp Lys Gly Thr
                805                 810                 815

Thr Val Thr Leu Glu Asn Ala Thr Trp Thr Met Pro Ser Asp Thr Thr
            820                 825                 830

Leu Gln Asn Leu Thr Leu Asn Asn Ser Thr Ile Thr Leu Asn Ser Ala
        835                 840                 845

Tyr Ser Ala Ser Ser Asn Asn Thr Pro Arg Arg Arg Ser Leu Glu Thr
850                 855                 860

Glu Thr Thr Pro Thr Ser Ala Glu His Arg Phe Asn Thr Leu Thr Val
865                 870                 875                 880

Asn Gly Lys Leu Ser Gly Gln Gly Thr Phe Gln Phe Thr Ser Ser Leu
                885                 890                 895

Phe Gly Tyr Lys Ser Asp Lys Leu Lys Leu Ser Asn Asp Ala Glu Gly
            900                 905                 910

Asp Tyr Ile Leu Ser Val Arg Asn Thr Gly Lys Glu Pro Glu Thr Leu
        915                 920                 925

Glu Gln Leu Thr Leu Val Glu Ser Lys Asp Asn Gln Pro Leu Ser Asp
930                 935                 940

Lys Leu Lys Phe Thr Leu Glu Asn Asp His Val Asp Ala Gly Ala Leu
945                 950                 955                 960

Arg Tyr Lys Leu Val Lys Asn Asp Gly Glu Phe Arg Leu His Asn Pro
                965                 970                 975

Ile Lys Glu Gln Glu Leu His Asn Asp Leu Val Arg Ala Glu Gln Ala
            980                 985                 990

Glu Arg Thr Leu Glu Ala Lys Gln Val Glu Pro Thr Ala Lys Thr Gln
        995                 1000                1005

Thr Gly Glu Pro Lys Val Arg Ser Arg Arg Ala Ala Arg Ala Ala
    1010                1015                1020

Phe Pro Asp Thr Leu Pro Asp Gln Ser Leu Leu Asn Ala Leu Glu
    1025                1030                1035
```

```
Ala Lys Gln Ala Glu Leu Thr Ala Glu Thr Gln Lys Ser Lys Ala
    1040                1045                1050

Lys Thr Lys Lys Val Arg Ser Lys Arg Ala Val Phe Ser Asp Pro
    1055                1060                1065

Leu Leu Asp Gln Ser Leu Phe Ala Leu Glu Ala Leu Glu Val
    1070                1075                1080

Ile Asp Ala Pro Gln Gln Ser Glu Lys Asp Arg Leu Ala Gln Glu
    1085                1090                1095

Glu Ala Glu Lys Gln Arg Lys Gln Lys Asp Leu Ile Ser Arg Tyr
    1100                1105                1110

Ser Asn Ser Ala Leu Ser Glu Leu Ser Ala Thr Val Asn Ser Met
    1115                1120                1125

Leu Ser Val Gln Asp Glu Leu Asp Arg Leu Phe Val Asp Gln Ala
    1130                1135                1140

Gln Ser Ala Val Trp Thr Asn Ile Ala Gln Asp Lys Arg Arg Tyr
    1145                1150                1155

Asp Ser Asp Ala Phe Arg Ala Tyr Gln Gln Gln Lys Thr Asn Leu
    1160                1165                1170

Arg Gln Ile Gly Val Gln Lys Ala Leu Ala Asn Gly Arg Ile Gly
    1175                1180                1185

Ala Val Phe Ser His Ser Arg Ser Asp Asn Thr Phe Asp Glu Gln
    1190                1195                1200

Val Lys Asn His Ala Thr Leu Thr Met Met Ser Gly Phe Ala Gln
    1205                1210                1215

Tyr Gln Trp Gly Asp Leu Gln Phe Gly Val Asn Val Gly Thr Gly
    1220                1225                1230

Ile Ser Ala Ser Lys Met Ala Glu Glu Gln Ser Arg Lys Ile His
    1235                1240                1245

Arg Lys Ala Ile Asn Tyr Gly Val Asn Ala Ser Tyr Gln Phe Arg
    1250                1255                1260

Leu Gly Gln Leu Gly Ile Gln Pro Tyr Phe Gly Val Asn Arg Tyr
    1265                1270                1275

Phe Ile Glu Arg Glu Asn Tyr Gln Ser Glu Glu Val Arg Val Lys
    1280                1285                1290

Thr Pro Ser Leu Ala Phe Asn Arg Tyr Asn Ala Gly Ile Arg Val
    1295                1300                1305

Asp Tyr Thr Phe Thr Pro Thr Asp Asn Ile Ser Val Lys Pro Tyr
    1310                1315                1320

Phe Phe Val Asn Tyr Val Asp Val Ser Asn Ala Asn Val Gln Thr
    1325                1330                1335

Thr Val Asn Leu Thr Val Leu Gln Gln Pro Phe Gly Arg Tyr Trp
    1340                1345                1350

Gln Lys Glu Val Gly Leu Lys Ala Glu Ile Leu His Phe Gln Ile
    1355                1360                1365

Ser Ala Phe Ile Ser Lys Ser Gln Gly Ser Gln Leu Gly Lys Gln
    1370                1375                1380

Gln Asn Val Gly Val Lys Leu Gly Tyr Arg Trp
    1385                1390

<210> SEQ ID NO 3
<211> LENGTH: 1541
<212> TYPE: PRT
<213> ORGANISM: Haemophilus influenzae
```

<400> SEQUENCE: 3

```
Met Leu Asn Lys Lys Phe Lys Leu Asn Phe Ile Ala Leu Thr Val Ala
 1               5                  10                  15
Tyr Ala Leu Thr Pro Tyr Thr Glu Ala Ala Leu Val Arg Asp Asp Val
            20                  25                  30
Asp Tyr Gln Ile Phe Arg Asp Phe Ala Glu Asn Lys Gly Lys Phe Ser
        35                  40                  45
Val Gly Ala Thr Asn Val Leu Val Lys Asp Lys Asn Lys Asp Leu
 50                  55                  60
Gly Thr Ala Leu Pro Asn Gly Ile Pro Met Ile Asp Phe Ser Val Val
 65                  70                  75                  80
Asp Val Asp Lys Arg Ile Ala Thr Leu Ile Asn Pro Gln Tyr Val Val
                85                  90                  95
Gly Val Lys His Val Ser Asn Gly Val Ser Glu Leu His Phe Gly Asn
            100                 105                 110
Leu Asn Gly Asn Met Asn Asn Gly Asn Ala Lys Ala His Arg Asp Val
        115                 120                 125
Ser Ser Glu Glu Asn Arg Tyr Phe Ser Val Glu Lys Asn Glu Tyr Pro
130                 135                 140
Thr Lys Leu Asn Gly Lys Thr Val Thr Thr Glu Asp Gln Thr Gln Lys
145                 150                 155                 160
Arg Arg Glu Asp Tyr Tyr Met Pro Arg Leu Asp Lys Phe Val Thr Glu
                165                 170                 175
Val Ala Pro Ile Glu Ala Ser Thr Ala Ser Ser Asp Ala Gly Thr Tyr
            180                 185                 190
Asn Asp Gln Asn Lys Tyr Pro Ala Phe Val Arg Leu Gly Ser Gly Ser
        195                 200                 205
Gln Phe Ile Tyr Lys Lys Gly Asp Asn Tyr Ser Leu Ile Leu Asn Asn
210                 215                 220
His Glu Val Gly Gly Asn Asn Leu Lys Leu Val Gly Asp Ala Tyr Thr
225                 230                 235                 240
Tyr Gly Ile Ala Gly Thr Pro Tyr Lys Val Asn His Glu Asn Asn Gly
                245                 250                 255
Leu Ile Gly Phe Gly Asn Ser Lys Glu Glu His Ser Asp Pro Lys Gly
            260                 265                 270
Ile Leu Ser Gln Asp Pro Leu Thr Asn Tyr Ala Val Leu Gly Asp Ser
        275                 280                 285
Gly Ser Pro Leu Phe Val Tyr Asp Arg Glu Lys Gly Lys Trp Leu Phe
290                 295                 300
Leu Gly Ser Tyr Asp Phe Trp Ala Gly Tyr Asn Lys Lys Ser Trp Gln
305                 310                 315                 320
Glu Trp Asn Ile Tyr Lys Ser Gln Phe Thr Lys Asp Val Leu Asn Lys
                325                 330                 335
Asp Ser Ala Gly Ser Leu Ile Gly Ser Lys Thr Asp Tyr Ser Trp Ser
            340                 345                 350
Ser Asn Gly Lys Thr Ser Thr Ile Thr Gly Gly Glu Lys Ser Leu Asn
        355                 360                 365
Val Asp Leu Ala Asp Gly Lys Asp Lys Pro Asn His Gly Lys Ser Val
370                 375                 380
Thr Phe Glu Gly Ser Gly Thr Leu Thr Leu Asn Asn Asn Ile Asp Gln
385                 390                 395                 400
Gly Ala Gly Gly Leu Phe Phe Glu Gly Asp Tyr Glu Val Lys Gly Thr
                405                 410                 415
```

-continued

```
Ser Asp Asn Thr Thr Trp Lys Gly Ala Gly Val Ser Val Ala Glu Gly
            420                 425                 430

Lys Thr Val Thr Trp Lys Val His Asn Pro Gln Tyr Asp Arg Leu Ala
            435                 440                 445

Lys Ile Gly Lys Gly Thr Leu Ile Val Glu Gly Thr Gly Asp Asn Lys
            450                 455                 460

Gly Ser Leu Lys Val Gly Asp Gly Thr Val Ile Leu Lys Gln Gln Thr
465                 470                 475                 480

Asn Gly Ser Gly Gln His Ala Phe Ala Ser Val Gly Ile Val Ser Gly
                485                 490                 495

Arg Ser Thr Leu Val Leu Asn Asp Asp Lys Gln Val Asp Pro Asn Ser
                500                 505                 510

Ile Tyr Phe Gly Phe Arg Gly Gly Arg Leu Asp Leu Asn Gly Asn Ser
            515                 520                 525

Leu Thr Phe Asp His Ile Arg Asn Ile Asp Asp Gly Ala Arg Leu Val
            530                 535                 540

Asn His Asn Met Thr Asn Ala Ser Asn Ile Thr Ile Thr Gly Glu Ser
545                 550                 555                 560

Leu Ile Thr Asp Pro Asn Thr Ile Thr Pro Tyr Asn Ile Asp Ala Pro
                565                 570                 575

Asp Glu Asp Asn Pro Tyr Ala Phe Arg Arg Ile Lys Asp Gly Gly Gln
                580                 585                 590

Leu Tyr Leu Asn Leu Glu Asn Tyr Thr Tyr Ala Leu Arg Lys Gly
            595                 600                 605

Ala Ser Thr Arg Ser Glu Leu Pro Lys Asn Ser Gly Glu Ser Asn Glu
            610                 615                 620

Asn Trp Leu Tyr Met Gly Lys Thr Ser Asp Glu Ala Lys Arg Asn Val
625                 630                 635                 640

Met Asn His Ile Asn Asn Glu Arg Met Asn Gly Phe Asn Gly Tyr Phe
                645                 650                 655

Gly Glu Glu Glu Gly Lys Asn Asn Gly Asn Leu Asn Val Thr Phe Lys
                660                 665                 670

Gly Lys Ser Glu Gln Asn Arg Phe Leu Leu Thr Gly Gly Thr Asn Leu
            675                 680                 685

Asn Gly Asp Leu Thr Val Glu Lys Gly Thr Leu Phe Leu Ser Gly Arg
690                 695                 700

Pro Thr Pro His Ala Arg Asp Ile Ala Gly Ile Ser Ser Thr Lys Lys
705                 710                 715                 720

Asp Pro His Phe Ala Glu Asn Asn Glu Val Val Val Glu Asp Asp Trp
                725                 730                 735

Ile Asn Arg Asn Phe Lys Ala Thr Thr Met Asn Val Thr Gly Asn Ala
            740                 745                 750

Ser Leu Tyr Ser Gly Arg Asn Val Ala Asn Ile Thr Ser Asn Ile Thr
            755                 760                 765

Ala Ser Asn Lys Ala Gln Val His Ile Gly Tyr Lys Thr Gly Asp Thr
            770                 775                 780

Val Cys Val Arg Ser Asp Tyr Thr Gly Tyr Val Thr Cys Thr Thr Asp
785                 790                 795                 800

Lys Leu Ser Asp Lys Ala Leu Asn Ser Phe Asn Pro Thr Asn Leu Arg
                805                 810                 815

Gly Asn Val Asn Leu Thr Glu Ser Ala Asn Phe Val Leu Gly Lys Ala
                820                 825                 830
```

```
Asn Leu Phe Gly Thr Ile Gln Ser Arg Gly Asn Ser Gln Val Arg Leu
            835                 840                 845

Thr Glu Asn Ser His Trp His Leu Thr Gly Asn Ser Asp Val His Gln
850                 855                 860

Leu Asp Leu Ala Asn Gly His Ile His Leu Asn Ser Ala Asp Asn Ser
865                 870                 875                 880

Asn Asn Val Thr Lys Tyr Asn Thr Leu Thr Val Asn Ser Leu Ser Gly
            885                 890                 895

Asn Gly Ser Phe Tyr Tyr Leu Thr Asp Leu Ser Asn Lys Gln Gly Asp
                900                 905                 910

Lys Val Val Thr Lys Ser Ala Thr Gly Asn Phe Thr Leu Gln Val
            915                 920                 925

Ala Asp Lys Thr Gly Glu Pro Asn His Asn Glu Leu Thr Leu Phe Asp
930                 935                 940

Ala Ser Lys Ala Gln Arg Asp His Leu Asn Val Ser Leu Val Gly Asn
945                 950                 955                 960

Thr Val Asp Leu Gly Ala Trp Lys Tyr Lys Leu Arg Asn Val Asn Gly
            965                 970                 975

Arg Tyr Asp Leu Tyr Asn Pro Glu Val Glu Lys Arg Asn Gln Thr Val
            980                 985                 990

Asp Thr Thr Asn Ile Thr Thr Pro  Asn Asn Ile Gln Ala  Asp Val Pro
            995                 1000                1005

Ser Val  Pro Ser Asn Glu  Glu Ile Ala Arg Val  Asp Glu Ala
     1010                1015                1020

Pro Val  Pro Pro Ala Pro  Ala Thr Pro Ser Glu  Thr Thr Glu
     1025                1030                1035

Thr Val  Ala Glu Asn Ser Lys  Gln Glu Ser Lys Thr  Val Glu Lys
     1040                1045                1050

Asn Glu  Gln Asp Ala Thr Glu  Thr Thr Ala Gln Asn  Arg Glu Val
     1055                1060                1065

Ala Lys  Glu Ala Lys Ser Asn  Val Lys Ala Asn Thr  Gln Thr Asn
     1070                1075                1080

Glu Val  Ala Gln Ser Gly Ser  Glu Thr Lys Glu Thr  Gln Thr Thr
     1085                1090                1095

Glu Thr  Lys Glu Thr Ala Thr  Val Glu Lys Glu Glu  Lys Ala Lys
     1100                1105                1110

Val Glu  Thr Glu Lys Thr Gln  Glu Val Pro Lys Val  Thr Ser Gln
     1115                1120                1125

Val Ser  Pro Lys Gln Glu Gln  Ser Glu Thr Val Gln  Pro Gln Ala
     1130                1135                1140

Glu Pro  Ala Arg Glu Asn Asp  Pro Thr Val Asn Ile  Lys Glu Pro
     1145                1150                1155

Gln Ser  Gln Thr Asn Thr Thr  Ala Asp Thr Glu Gln  Pro Ala Lys
     1160                1165                1170

Glu Thr  Ser Ser Asn Val Glu  Gln Pro Val Thr Glu  Ser Thr Thr
     1175                1180                1185

Val Asn  Thr Gly Asn Ser Val  Val Glu Asn Pro Glu  Asn Thr Thr
     1190                1195                1200

Pro Ala  Thr Thr Gln Pro Thr  Val Asn Ser Glu Ser  Ser Asn Lys
     1205                1210                1215

Pro Lys  Asn Arg His Arg Arg  Ser Val Arg Ser Val  Pro His Asn
     1220                1225                1230
```

-continued

```
Val Glu Pro Ala Thr Thr Ser Ser Asn Asp Arg Ser Thr Val Ala
    1235                1240                1245

Leu Cys Asp Leu Thr Ser Thr Asn Thr Asn Ala Val Leu Ser Asp
    1250                1255                1260

Ala Arg Ala Lys Ala Gln Phe Val Ala Leu Asn Val Gly Lys Ala
    1265                1270                1275

Val Ser Gln His Ile Ser Gln Leu Glu Met Asn Asn Glu Gly Gln
    1280                1285                1290

Tyr Asn Val Trp Val Ser Asn Thr Ser Met Asn Lys Asn Tyr Ser
    1295                1300                1305

Ser Ser Gln Tyr Arg Arg Phe Ser Ser Lys Ser Thr Gln Thr Gln
    1310                1315                1320

Leu Gly Trp Asp Gln Thr Ile Ser Asn Asn Val Gln Leu Gly Gly
    1325                1330                1335

Val Phe Thr Tyr Val Arg Asn Ser Asn Asn Phe Asp Lys Ala Thr
    1340                1345                1350

Ser Lys Asn Thr Leu Ala Gln Val Asn Phe Tyr Ser Lys Tyr Tyr
    1355                1360                1365

Ala Asp Asn His Trp Tyr Leu Gly Ile Asp Leu Gly Tyr Gly Lys
    1370                1375                1380

Phe Gln Ser Lys Leu Gln Thr Asn His Asn Ala Lys Phe Ala Arg
    1385                1390                1395

His Thr Ala Gln Phe Gly Leu Thr Ala Gly Lys Ala Phe Asn Leu
    1400                1405                1410

Gly Asn Phe Gly Ile Thr Pro Ile Val Gly Val Arg Tyr Ser Tyr
    1415                1420                1425

Leu Ser Asn Ala Asp Phe Ala Leu Asp Gln Ala Arg Ile Lys Val
    1430                1435                1440

Asn Pro Ile Ser Val Lys Thr Ala Phe Ala Gln Val Asp Leu Ser
    1445                1450                1455

Tyr Thr Tyr His Leu Gly Glu Phe Ser Val Thr Pro Ile Leu Ser
    1460                1465                1470

Ala Arg Tyr Asp Ala Asn Gln Gly Ser Gly Lys Ile Asn Val Asn
    1475                1480                1485

Gly Tyr Asp Phe Ala Tyr Asn Val Glu Asn Gln Gln Gln Tyr Asn
    1490                1495                1500

Ala Gly Leu Lys Leu Lys Tyr His Asn Val Lys Leu Ser Leu Ile
    1505                1510                1515

Gly Gly Leu Thr Lys Ala Lys Gln Ala Glu Lys Gln Lys Thr Ala
    1520                1525                1530

Glu Leu Lys Leu Ser Phe Ser Phe
    1535                1540
```

<210> SEQ ID NO 4
<211> LENGTH: 1545
<212> TYPE: PRT
<213> ORGANISM: Haemophilus influenzae

<400> SEQUENCE: 4

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45
```

-continued

```
Val Gly Ala Thr Asn Val Glu Val Arg Asp Lys Asn Asn Arg Pro Leu
 50                  55                  60
Gly Asn Val Leu Pro Asn Gly Ile Pro Met Ile Asp Phe Ser Val Val
 65                  70                  75                  80
Asp Val Asp Lys Arg Ile Ala Thr Leu Val Asn Pro Gln Tyr Val Val
                 85                  90                  95
Gly Val Lys His Val Ser Asn Gly Val Ser Glu Leu His Phe Gly Asn
                100                 105                 110
Leu Asn Gly Asn Met Asn Asn Gly Asn Ala Lys Ala His Arg Asp Val
                115                 120                 125
Ser Ser Glu Glu Asn Arg Tyr Tyr Thr Val Glu Lys Asn Glu Tyr Pro
130                 135                 140
Thr Lys Leu Asn Gly Lys Ala Val Thr Thr Glu Asp Gln Ala Gln Lys
145                 150                 155                 160
Arg Arg Glu Asp Tyr Tyr Met Pro Arg Leu Asp Lys Phe Val Thr Glu
                165                 170                 175
Val Ala Pro Ile Glu Ala Ser Thr Asp Ser Ser Thr Ala Gly Thr Tyr
                180                 185                 190
Asn Asn Lys Asp Lys Tyr Pro Tyr Phe Val Arg Leu Gly Ser Gly Thr
                195                 200                 205
Gln Phe Ile Tyr Glu Asn Gly Thr Arg Tyr Glu Leu Trp Leu Gly Lys
                210                 215                 220
Glu Gly Gln Lys Ser Asp Ala Gly Gly Tyr Asn Leu Lys Leu Val Gly
225                 230                 235                 240
Asn Ala Tyr Thr Tyr Gly Ile Ala Gly Thr Pro Tyr Glu Val Asn His
                245                 250                 255
Glu Asn Asp Gly Leu Ile Gly Phe Gly Asn Ser Asn Asn Glu Tyr Ile
                260                 265                 270
Asn Pro Lys Glu Ile Leu Ser Lys Lys Pro Leu Thr Asn Tyr Ala Val
                275                 280                 285
Leu Gly Asp Ser Gly Ser Pro Leu Phe Val Tyr Asp Arg Glu Lys Gly
                290                 295                 300
Lys Trp Leu Phe Leu Gly Ser Tyr Asp Tyr Trp Ala Gly Tyr Asn Lys
305                 310                 315                 320
Lys Ser Trp Gln Glu Trp Asn Ile Tyr Lys Pro Glu Phe Ala Glu Lys
                325                 330                 335
Ile Tyr Glu Gln Tyr Ser Ala Gly Ser Leu Ile Gly Ser Lys Thr Asp
                340                 345                 350
Tyr Ser Trp Ser Ser Asn Gly Lys Thr Ser Thr Ile Thr Gly Gly Glu
                355                 360                 365
Lys Ser Leu Asn Val Asp Leu Ala Asp Gly Lys Asp Lys Pro Asn His
                370                 375                 380
Gly Lys Ser Val Thr Phe Glu Gly Ser Gly Thr Leu Thr Leu Asn Asn
385                 390                 395                 400
Asn Ile Asp Gln Gly Ala Gly Gly Leu Phe Phe Glu Gly Asp Tyr Glu
                405                 410                 415
Val Lys Gly Thr Ser Asp Asn Thr Thr Trp Lys Gly Ala Gly Val Ser
                420                 425                 430
Val Ala Glu Gly Lys Thr Val Thr Trp Lys Val His Asn Pro Gln Tyr
                435                 440                 445
Asp Arg Leu Ala Lys Ile Gly Lys Gly Thr Leu Ile Val Glu Gly Thr
                450                 455                 460
```

-continued

Gly Asp Asn Lys Gly Ser Leu Lys Val Gly Asp Gly Thr Val Ile Leu
465                 470                 475                 480

Lys Gln Gln Thr Asn Gly Ser Gly Gln His Ala Phe Ala Ser Val Gly
            485                 490                 495

Ile Val Ser Gly Arg Ser Thr Leu Val Leu Asn Asp Asp Lys Gln Val
            500                 505                 510

Asp Pro Asn Ser Ile Tyr Phe Gly Phe Arg Gly Gly Arg Leu Asp Leu
            515                 520                 525

Asn Gly Asn Ser Leu Thr Phe Asp His Ile Arg Asn Ile Asp Glu Gly
            530                 535                 540

Ala Arg Leu Val Asn His Ser Thr Ser Lys His Ser Thr Val Thr Ile
545                 550                 555                 560

Thr Gly Asp Asn Leu Ile Thr Asp Pro Asn Val Ser Ile Tyr Tyr
                565                 570                 575

Val Lys Pro Leu Glu Asp Asp Asn Pro Tyr Ala Ile Arg Gln Ile Lys
            580                 585                 590

Tyr Gly Tyr Gln Leu Tyr Phe Asn Glu Glu Asn Arg Thr Tyr Tyr Ala
            595                 600                 605

Leu Lys Lys Asp Ala Ser Ile Arg Ser Glu Phe Pro Gln Asn Arg Gly
610                 615                 620

Glu Ser Asn Asn Ser Trp Leu Tyr Met Gly Thr Glu Lys Ala Asp Ala
625                 630                 635                 640

Gln Lys Asn Ala Met Asn His Ile Asn Asn Glu Arg Met Asn Gly Phe
                645                 650                 655

Asn Gly Tyr Phe Gly Glu Glu Glu Gly Lys Asn Asn Gly Asn Leu Asn
                660                 665                 670

Val Thr Phe Lys Gly Lys Ser Glu Gln Asn Arg Phe Leu Leu Thr Gly
            675                 680                 685

Gly Thr Asn Leu Asn Gly Asp Leu Asn Val Gln Gln Gly Thr Leu Phe
            690                 695                 700

Leu Ser Gly Arg Pro Thr Pro His Ala Arg Asp Ile Ala Gly Ile Ser
705                 710                 715                 720

Ser Thr Lys Lys Asp Ser His Phe Ser Glu Asn Glu Val Val Val
                725                 730                 735

Glu Asp Asp Trp Ile Asn Arg Asn Phe Lys Ala Thr Asn Ile Asn Val
            740                 745                 750

Thr Asn Asn Ala Thr Leu Tyr Ser Gly Arg Asn Val Glu Ser Ile Thr
            755                 760                 765

Ser Asn Ile Thr Ala Ser Asn Ala Lys Val His Ile Gly Tyr Lys
            770                 775                 780

Ala Gly Asp Thr Val Cys Val Arg Ser Asp Tyr Thr Gly Tyr Val Thr
785                 790                 795                 800

Cys Thr Thr Asp Lys Leu Ser Asp Lys Ala Leu Asn Ser Phe Asn Pro
            805                 810                 815

Thr Asn Leu Arg Gly Asn Val Asn Leu Thr Glu Ser Ala Asn Phe Val
            820                 825                 830

Leu Gly Lys Ala Asn Leu Phe Gly Thr Ile Gln Ser Arg Gly Asn Ser
            835                 840                 845

Gln Val Arg Leu Thr Glu Asn Ser His Trp His Leu Thr Gly Asn Ser
            850                 855                 860

Asp Val His Gln Leu Asp Leu Ala Asn Gly His Ile His Leu Asn Ser
865                 870                 875                 880

-continued

```
Ala Asp Asn Ser Asn Asn Val Thr Lys Tyr Asn Thr Leu Thr Val Asn
                885                 890                 895

Ser Leu Ser Gly Asn Gly Ser Phe Tyr Tyr Leu Thr Asp Leu Ser Asn
            900                 905                 910

Lys Gln Gly Asp Lys Val Val Thr Lys Ser Ala Thr Gly Asn Phe
        915                 920                 925

Thr Leu Gln Val Ala Asp Lys Thr Gly Glu Pro Asn His Asn Glu Leu
    930                 935                 940

Thr Leu Phe Asp Ala Ser Lys Ala Gln Arg Asp His Leu Asn Val Ser
945                 950                 955                 960

Leu Val Gly Asn Thr Val Asp Leu Gly Ala Trp Lys Tyr Lys Leu Arg
                965                 970                 975

Asn Val Asn Gly Arg Tyr Asp Leu Tyr Asn Pro Glu Val Glu Lys Arg
                980                 985                 990

Asn Gln Thr Val Asp Thr Thr Asn Ile Thr Thr Pro Asn Asn Ile Gln
            995                 1000                1005

Ala Asp Val Pro Ser Val Pro Ser Asn Asn Glu Glu Ile Ala Arg
    1010                1015                1020

Val Asp Glu Ala Pro Val Pro Pro Ala Pro Ala Thr Pro Ser
    1025                1030                1035

Glu Thr Thr Glu Thr Val Ala Glu Asn Ser Lys Gln Glu Ser Lys
    1040                1045                1050

Thr Val Glu Lys Asn Glu Gln Asp Ala Thr Glu Thr Thr Ala Gln
    1055                1060                1065

Asn Arg Glu Val Ala Lys Glu Ala Lys Ser Asn Val Lys Ala Asn
    1070                1075                1080

Thr Gln Thr Asn Glu Val Ala Gln Ser Gly Ser Glu Thr Lys Glu
    1085                1090                1095

Thr Gln Thr Thr Glu Thr Lys Glu Thr Ala Thr Val Glu Lys Glu
    1100                1105                1110

Glu Lys Ala Lys Val Glu Thr Glu Lys Thr Gln Glu Val Pro Lys
    1115                1120                1125

Val Thr Ser Gln Val Ser Pro Lys Gln Glu Gln Ser Glu Thr Val
    1130                1135                1140

Gln Pro Gln Ala Glu Pro Ala Arg Glu Asn Asp Pro Thr Val Asn
    1145                1150                1155

Ile Lys Glu Pro Gln Ser Gln Thr Asn Thr Thr Ala Asp Thr Glu
    1160                1165                1170

Gln Pro Ala Lys Glu Thr Ser Ser Asn Val Glu Gln Pro Val Thr
    1175                1180                1185

Glu Ser Thr Thr Val Asn Thr Gly Asn Ser Val Val Glu Asn Pro
    1190                1195                1200

Glu Asn Thr Thr Pro Ala Thr Thr Gln Pro Thr Val Asn Ser Glu
    1205                1210                1215

Ser Ser Asn Lys Pro Lys Asn Arg His Arg Ser Val Arg Ser
    1220                1225                1230

Val Pro His Asn Val Glu Pro Ala Thr Thr Ser Ser Asn Asp Arg
    1235                1240                1245

Ser Thr Val Ala Leu Cys Asp Leu Thr Ser Thr Asn Thr Asn Ala
    1250                1255                1260

Val Leu Ser Asp Ala Arg Ala Lys Ala Gln Phe Val Ala Leu Asn
    1265                1270                1275
```

-continued

Val Gly Lys Ala Val Ser Gln His Ile Ser Gln Leu Glu Met Asn
        1280            1285            1290

Asn Glu Gly Gln Tyr Asn Val Trp Val Ser Asn Thr Ser Met Asn
    1295            1300            1305

Lys Asn Tyr Ser Ser Ser Gln Tyr Arg Arg Phe Ser Ser Lys Ser
    1310            1315            1320

Thr Gln Thr Gln Leu Gly Trp Asp Gln Thr Ile Ser Asn Asn Val
    1325            1330            1335

Gln Leu Gly Gly Val Phe Thr Tyr Val Arg Asn Ser Asn Asn Phe
    1340            1345            1350

Asp Lys Ala Thr Ser Lys Asn Thr Leu Ala Gln Val Asn Phe Tyr
    1355            1360            1365

Ser Lys Tyr Tyr Ala Asp Asn His Trp Tyr Leu Gly Ile Asp Leu
    1370            1375            1380

Gly Tyr Gly Lys Phe Gln Ser Lys Leu Gln Thr Asn His Asn Ala
    1385            1390            1395

Lys Phe Ala Arg His Thr Ala Gln Phe Gly Leu Thr Ala Gly Lys
    1400            1405            1410

Ala Phe Asn Leu Gly Asn Phe Gly Ile Thr Pro Ile Val Gly Val
    1415            1420            1425

Arg Tyr Ser Tyr Leu Ser Asn Ala Asp Phe Ala Leu Asp Gln Ala
    1430            1435            1440

Arg Ile Lys Val Asn Pro Ile Ser Val Lys Thr Ala Phe Ala Gln
    1445            1450            1455

Val Asp Leu Ser Tyr Thr Tyr His Leu Gly Glu Phe Ser Val Thr
    1460            1465            1470

Pro Ile Leu Ser Ala Arg Tyr Asp Ala Asn Gln Gly Ser Gly Lys
    1475            1480            1485

Ile Asn Val Asn Gly Tyr Asp Phe Ala Tyr Asn Val Glu Asn Gln
    1490            1495            1500

Gln Gln Tyr Asn Ala Gly Leu Lys Leu Lys Tyr His Asn Val Lys
    1505            1510            1515

Leu Ser Leu Ile Gly Gly Leu Thr Lys Ala Lys Gln Ala Glu Lys
    1520            1525            1530

Gln Lys Thr Ala Glu Leu Lys Leu Ser Phe Ser Phe
    1535            1540            1545

<210> SEQ ID NO 5
<211> LENGTH: 1702
<212> TYPE: PRT
<213> ORGANISM: Haemophilus influenzae

<400> SEQUENCE: 5

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Arg Phe Ser
        35                  40                  45

Val Gly Ala Thr Asn Val Glu Val Arg Asp Lys Asn Asn His Ser Leu
    50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

-continued

```
Gly Val Lys His Val Ser Asn Gly Val Ser Glu Leu His Phe Gly Asn
            100                 105                 110

Leu Asn Gly Asn Met Asn Asn Gly Asn Asp Lys Ser His Arg Asp Val
        115                 120                 125

Ser Ser Glu Glu Asn Arg Tyr Phe Ser Val Glu Lys Asn Glu Tyr Pro
    130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Thr
        195                 200                 205

Gln Phe Ile Tyr Lys Lys Gly Asp Asn Tyr Ser Leu Ile Leu Asn Asn
    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
        275                 280                 285

Gly Ser Pro Leu Phe Val Tyr Asp Arg Glu Lys Gly Lys Trp Leu Phe
    290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Ile Gly Ser Asn Thr Gln Tyr Asn Trp Asn
            340                 345                 350

Pro Thr Gly Lys Thr Ser Val Ile Ser Asn Gly Ser Glu Ser Leu Asn
        355                 360                 365

Val Asp Leu Phe Asp Ser Ser Gln Asp Thr Asp Ser Lys Lys Asn Asn
    370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                405                 410                 415

Glu Val Lys Gly Thr Ser Asp Ser Thr Thr Trp Lys Gly Ala Gly Val
            420                 425                 430

Ser Val Ala Asp Gly Lys Thr Val Thr Trp Lys Val His Asn Pro Lys
        435                 440                 445

Ser Asp Arg Leu Ala Lys Ile Gly Lys Gly Thr Leu Ile Val Glu Gly
    450                 455                 460

Lys Gly Glu Asn Lys Gly Ser Leu Lys Val Gly Asp Gly Thr Val Ile
465                 470                 475                 480

Leu Lys Gln Gln Ala Asp Ala Asn Asn Lys Val Lys Ala Phe Ser Gln
                485                 490                 495

Val Gly Ile Val Ser Gly Arg Ser Thr Val Val Leu Asn Asp Asp Lys
            500                 505                 510
```

```
Gln Val Asp Pro Asn Ser Ile Tyr Phe Gly Phe Arg Gly Gly Arg Leu
    515                 520                 525

Asp Ala Asn Gly Asn Asn Leu Thr Phe Glu His Ile Arg Asn Ile Asp
530                 535                 540

Asp Gly Ala Arg Leu Val Asn His Asn Thr Ser Lys Thr Ser Thr Val
545                 550                 555                 560

Thr Ile Thr Gly Glu Ser Leu Ile Thr Asp Pro Asn Thr Ile Thr Pro
                565                 570                 575

Tyr Asn Ile Asp Ala Pro Asp Glu Asp Asn Pro Tyr Ala Phe Arg Arg
                580                 585                 590

Ile Lys Asp Gly Gly Gln Leu Tyr Leu Asn Leu Glu Asn Tyr Thr Tyr
            595                 600                 605

Tyr Ala Leu Arg Lys Gly Ala Ser Thr Arg Ser Glu Leu Pro Lys Asn
            610                 615                 620

Ser Gly Glu Ser Asn Glu Asn Trp Leu Tyr Met Gly Lys Thr Ser Asp
625                 630                 635                 640

Ala Ala Lys Arg Asn Val Met Asn His Ile Asn Asn Glu Arg Met Asn
                645                 650                 655

Gly Phe Asn Gly Tyr Phe Gly Glu Glu Gly Lys Asn Asn Gly Asn
                660                 665                 670

Leu Asn Val Thr Phe Lys Gly Lys Ser Glu Gln Asn Arg Phe Leu Leu
            675                 680                 685

Thr Gly Gly Thr Asn Leu Asn Gly Asp Leu Lys Val Glu Lys Gly Thr
690                 695                 700

Leu Phe Leu Ser Gly Arg Pro Thr Pro His Ala Arg Asp Ile Ala Gly
705                 710                 715                 720

Ile Ser Ser Thr Lys Lys Asp Gln His Phe Ala Glu Asn Asn Glu Val
                725                 730                 735

Val Val Glu Asp Asp Trp Ile Asn Arg Asn Phe Lys Ala Thr Asn Ile
                740                 745                 750

Asn Val Thr Asn Asn Ala Thr Leu Tyr Ser Gly Arg Asn Val Ala Asn
            755                 760                 765

Ile Thr Ser Asn Ile Thr Ala Ser Asp Asn Ala Lys Val His Ile Gly
    770                 775                 780

Tyr Lys Ala Gly Asp Thr Val Cys Val Arg Ser Asp Tyr Thr Gly Tyr
785                 790                 795                 800

Val Thr Cys Thr Thr Asp Lys Leu Ser Asp Lys Ala Leu Asn Ser Phe
                805                 810                 815

Asn Ala Thr Asn Val Ser Gly Ser Val Asn Leu Ser Gly Asn Ala Asn
                820                 825                 830

Phe Val Leu Gly Lys Ala Asn Leu Phe Gly Thr Ile Ser Gly Thr Gly
            835                 840                 845

Asn Ser Gln Val Arg Leu Thr Glu Asn Ser His Trp His Leu Thr Gly
    850                 855                 860

Asp Ser Asn Val Asn Gln Leu Asn Leu Asp Lys Gly His Ile His Leu
865                 870                 875                 880

Asn Ala Gln Asn Asp Ala Asn Lys Val Thr Thr Tyr Asn Thr Leu Thr
                885                 890                 895

Val Asn Ser Leu Ser Gly Asn Gly Ser Phe Tyr Tyr Leu Thr Asp Leu
            900                 905                 910

Ser Asn Lys Gln Gly Asp Lys Val Val Thr Lys Ser Ala Thr Gly
    915                 920                 925
```

-continued

```
Asn Phe Thr Leu Gln Val Ala Asp Lys Thr Gly Glu Pro Thr Lys Asn
            930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
                    965                 970                 975

Leu Arg Asn Val Asn Gly Arg Tyr Asp Leu Tyr Asn Pro Glu Val Glu
                980                 985                 990

Lys Arg Asn Gln Thr Val Asp Thr  Thr Asn Ile Thr Thr Pro Asn Asn
            995                 1000                1005

Ile Gln  Ala Asp Val Pro Ser  Val Pro Ser Asn  Glu Glu Ile
    1010                 1015                1020

Ala Arg  Val Glu Thr Pro Val  Pro Pro Ala Pro  Ala Thr Pro
    1025                 1030                1035

Ser Glu  Thr Thr Glu Thr Val  Ala Glu Asn Ser  Lys Gln Glu Ser
    1040                 1045                1050

Lys Thr  Val Glu Lys Asn Glu  Gln Asp Ala Thr  Glu Thr Thr Ala
    1055                 1060                1065

Gln Asn  Gly Glu Val Ala Glu  Glu Ala Lys Pro Ser  Val Lys Ala
    1070                 1075                1080

Asn Thr  Gln Thr Asn Glu Val  Ala Gln Ser Gly Ser  Glu Thr Glu
    1085                 1090                1095

Glu Thr  Gln Thr Thr Glu Ile  Lys Glu Thr Ala Lys  Val Glu Lys
    1100                 1105                1110

Glu Glu  Lys Ala Lys Val Glu  Lys Glu Lys Ala  Lys Val Glu
    1115                 1120                1125

Lys Asp  Glu Ile Gln Glu Ala  Pro Gln Met Ala Ser  Glu Thr Ser
    1130                 1135                1140

Pro Lys  Gln Ala Lys Pro Ala  Pro Lys Glu Val Ser  Thr Asp Thr
    1145                 1150                1155

Lys Val  Glu Glu Thr Gln Val  Gln Ala Gln Pro Gln  Thr Gln Ser
    1160                 1165                1170

Thr Thr  Val Ala Ala Ala Glu  Ala Thr Ser Pro Asn  Ser Lys Pro
    1175                 1180                1185

Ala Glu  Glu Thr Gln Pro Ser  Glu Lys Thr Asn Ala  Glu Pro Val
    1190                 1195                1200

Thr Pro  Val Val Ser Lys Asn  Gln Thr Glu Asn Thr  Thr Asp Gln
    1205                 1210                1215

Pro Thr  Glu Arg Glu Lys Thr  Ala Lys Val Glu Thr  Glu Lys Thr
    1220                 1225                1230

Gln Glu  Pro Pro Gln Val Ala  Ser Gln Ala Ser Pro  Lys Gln Glu
    1235                 1240                1245

Gln Ser  Glu Thr Val Gln Pro  Gln Ala Val Leu Glu  Ser Glu Asn
    1250                 1255                1260

Val Pro  Thr Val Asn Asn Ala  Glu Glu Val Gln Ala  Gln Leu Gln
    1265                 1270                1275

Thr Gln  Thr Ser Ala Thr Val  Ser Thr Lys Gln Pro  Ala Pro Glu
    1280                 1285                1290

Asn Ser  Ile Asn Thr Gly Ser  Ala Thr Ala Ile Thr  Glu Thr Ala
    1295                 1300                1305

Glu Lys  Ser Asp Lys Pro Gln  Thr Glu Thr Ala Ala  Ser Thr Glu
    1310                 1315                1320
```

-continued

```
Asp Ala Ser Gln His Lys Ala Asn Thr Val Ala Asp Asn Ser Val
1325                1330                1335

Ala Asn Asn Ser Glu Ser Ser Glu Pro Lys Ser Arg Arg Arg Arg
1340                1345                1350

Ser Ile Ser Gln Pro Gln Glu Thr Ser Ala Glu Glu Thr Thr Ala
1355                1360                1365

Ala Ser Thr Asp Glu Thr Thr Ile Ala Asp Asn Ser Lys Arg Ser
1370                1375                1380

Lys Pro Asn Arg Arg Ser Arg Arg Ser Val Arg Ser Glu Pro Thr
1385                1390                1395

Val Thr Asn Gly Ser Asp Arg Ser Thr Val Ala Leu Arg Asp Leu
1400                1405                1410

Thr Ser Thr Asn Thr Asn Ala Val Ile Ser Asp Ala Met Ala Lys
1415                1420                1425

Ala Gln Phe Val Ala Leu Asn Val Gly Lys Ala Val Ser Gln His
1430                1435                1440

Ile Ser Gln Leu Glu Met Asn Asn Glu Gly Gln Tyr Asn Val Trp
1445                1450                1455

Val Ser Asn Thr Ser Met Asn Glu Asn Tyr Ser Ser Ser Gln Tyr
1460                1465                1470

Arg Arg Phe Ser Ser Lys Ser Thr Gln Thr Gln Leu Gly Trp Asp
1475                1480                1485

Gln Thr Ile Ser Asn Asn Val Gln Leu Gly Gly Val Phe Thr Tyr
1490                1495                1500

Val Arg Asn Ser Asn Asn Phe Asp Lys Ala Ser Ser Lys Asn Thr
1505                1510                1515

Leu Ala Gln Val Asn Phe Tyr Ser Lys Tyr Tyr Ala Asp Asn His
1520                1525                1530

Trp Tyr Leu Gly Ile Asp Leu Gly Tyr Gly Lys Phe Gln Ser Asn
1535                1540                1545

Leu Lys Thr Asn His Asn Ala Lys Phe Ala Arg His Thr Ala Gln
1550                1555                1560

Phe Gly Leu Thr Ala Gly Lys Ala Phe Asn Leu Gly Asn Phe Gly
1565                1570                1575

Ile Thr Pro Ile Val Gly Val Arg Tyr Ser Tyr Leu Ser Asn Ala
1580                1585                1590

Asn Phe Ala Leu Ala Lys Asp Arg Ile Lys Val Asn Pro Ile Ser
1595                1600                1605

Val Lys Thr Ala Phe Ala Gln Val Asp Leu Ser Tyr Thr Tyr His
1610                1615                1620

Leu Gly Glu Phe Ser Val Thr Pro Ile Leu Ser Ala Arg Tyr Asp
1625                1630                1635

Thr Asn Gln Gly Ser Gly Lys Ile Asn Val Asn Gln Tyr Asp Phe
1640                1645                1650

Ala Tyr Asn Val Glu Asn Gln Gln Gln Tyr Asn Ala Gly Leu Lys
1655                1660                1665

Leu Lys Tyr His Asn Val Lys Leu Ser Leu Ile Gly Gly Leu Thr
1670                1675                1680

Lys Ala Lys Gln Ala Glu Lys Gln Lys Thr Ala Glu Leu Lys Leu
1685                1690                1695

Ser Phe Ser Phe
1700
```

-continued

```
<210> SEQ ID NO 6
<211> LENGTH: 1848
<212> TYPE: PRT
<213> ORGANISM: Haemophilus influenzae

<400> SEQUENCE: 6
```

| | | | | | | | | | | | | | | | |
|---|---|---|---|---|---|---|---|---|---|---|---|---|---|---|---|
| Met | Leu | Asn | Lys | Lys | Phe | Lys | Leu | Asn | Phe | Ile | Ala | Leu | Thr | Val | Ala |
| 1 | | | | 5 | | | | | 10 | | | | | 15 | |
| Tyr | Ala | Leu | Thr | Pro | Tyr | Thr | Glu | Ala | Ala | Leu | Val | Arg | Asp | Asp | Val |
| | | | 20 | | | | | 25 | | | | | 30 | | |
| Asp | Tyr | Gln | Ile | Phe | Arg | Asp | Phe | Ala | Glu | Asn | Lys | Gly | Lys | Phe | Ser |
| | | 35 | | | | | 40 | | | | | 45 | | | |
| Val | Gly | Ala | Thr | Asn | Val | Glu | Val | Arg | Asp | Lys | Lys | Asn | Gln | Ser | Leu |
| | 50 | | | | | 55 | | | | | 60 | | | | |
| Gly | Ser | Ala | Leu | Pro | Asn | Gly | Ile | Pro | Met | Ile | Asp | Phe | Ser | Val | Val |
| 65 | | | | | 70 | | | | | 75 | | | | | 80 |
| Asp | Val | Asp | Lys | Arg | Ile | Ala | Thr | Leu | Val | Asn | Pro | Gln | Tyr | Val | Val |
| | | | | 85 | | | | | 90 | | | | | 95 | |
| Gly | Val | Lys | His | Val | Ser | Asn | Gly | Val | Ser | Glu | Leu | His | Phe | Gly | Asn |
| | | | | 100 | | | | | 105 | | | | | 110 | |
| Leu | Asn | Gly | Asn | Met | Asn | Asn | Gly | Asn | Ala | Lys | Ser | His | Arg | Asp | Val |
| | | | 115 | | | | | 120 | | | | | 125 | | |
| Ser | Ser | Glu | Glu | Asn | Arg | Tyr | Tyr | Thr | Val | Glu | Lys | Asn | Asn | Phe | Pro |
| | 130 | | | | | 135 | | | | | 140 | | | | |
| Thr | Glu | Asn | Val | Thr | Ser | Phe | Thr | Lys | Glu | Gln | Asp | Ala | Gln | Lys |
| 145 | | | | | 150 | | | | | 155 | | | | | 160 |
| Arg | Arg | Glu | Asp | Tyr | Tyr | Met | Pro | Arg | Leu | Asp | Lys | Phe | Val | Thr | Glu |
| | | | | 165 | | | | | 170 | | | | | 175 | |
| Val | Ala | Pro | Ile | Glu | Ala | Ser | Thr | Ala | Asn | Asn | Asn | Lys | Gly | Glu | Tyr |
| | | | | 180 | | | | | 185 | | | | | 190 | |
| Asn | Asn | Ser | Asp | Lys | Tyr | Pro | Ala | Phe | Val | Arg | Leu | Gly | Ser | Gly | Thr |
| | | | 195 | | | | | 200 | | | | | 205 | | |
| Gln | Phe | Ile | Tyr | Lys | Lys | Gly | Ser | Arg | Tyr | Gln | Leu | Ile | Leu | Thr | Glu |
| | 210 | | | | | 215 | | | | | 220 | | | | |
| Lys | Asp | Lys | Gln | Gly | Asn | Leu | Leu | Arg | Asn | Trp | Asp | Val | Gly | Gly | Asp |
| 225 | | | | | 230 | | | | | 235 | | | | | 240 |
| Asn | Leu | Glu | Leu | Val | Gly | Asn | Ala | Tyr | Thr | Tyr | Gly | Ile | Ala | Gly | Thr |
| | | | | 245 | | | | | 250 | | | | | 255 | |
| Pro | Tyr | Lys | Val | Asn | His | Glu | Asn | Asn | Gly | Leu | Ile | Gly | Phe | Gly | Asn |
| | | | | 260 | | | | | 265 | | | | | 270 | |
| Ser | Lys | Glu | Glu | His | Ser | Asp | Pro | Lys | Gly | Ile | Leu | Ser | Gln | Asp | Pro |
| | | | 275 | | | | | 280 | | | | | 285 | | |
| Leu | Thr | Asn | Tyr | Ala | Val | Leu | Gly | Asp | Ser | Gly | Ser | Pro | Leu | Phe | Val |
| | 290 | | | | | 295 | | | | | 300 | | | | |
| Tyr | Asp | Arg | Glu | Lys | Gly | Lys | Trp | Leu | Phe | Leu | Gly | Ser | Tyr | Asp | Phe |
| 305 | | | | | 310 | | | | | 315 | | | | | 320 |
| Trp | Ala | Gly | Tyr | Asn | Lys | Lys | Ser | Trp | Gln | Glu | Trp | Asn | Ile | Tyr | Lys |
| | | | | 325 | | | | | 330 | | | | | 335 | |
| His | Glu | Phe | Ala | Glu | Lys | Ile | Tyr | Gln | Gln | Tyr | Ser | Ala | Gly | Ser | Leu |
| | | | 340 | | | | | 345 | | | | | 350 | | |
| Ile | Gly | Ser | Asn | Thr | Gln | Tyr | Thr | Trp | Gln | Ala | Thr | Gly | Ser | Thr | Ser |
| | | 355 | | | | | 360 | | | | | 365 | | | |
| Thr | Ile | Thr | Gly | Gly | Gly | Glu | Pro | Leu | Ser | Val | Asp | Leu | Thr | Asp | Gly |
| | 370 | | | | | 375 | | | | | 380 | | | | |

-continued

```
Lys Asp Lys Pro Asn His Gly Lys Ser Ile Thr Leu Lys Gly Ser Gly
385                 390                 395                 400

Thr Leu Thr Leu Asn Asn His Ile Asp Gln Gly Ala Gly Gly Leu Phe
            405                 410                 415

Phe Glu Gly Asp Tyr Glu Val Lys Gly Thr Ser Asp Ser Thr Thr Trp
        420                 425                 430

Lys Gly Ala Gly Val Ser Val Ala Asp Gly Lys Thr Val Thr Trp Lys
    435                 440                 445

Val His Asn Pro Lys Tyr Asp Arg Leu Ala Lys Ile Gly Lys Gly Thr
450                 455                 460

Leu Val Val Glu Gly Lys Gly Lys Asn Glu Gly Leu Leu Lys Val Gly
465                 470                 475                 480

Asp Gly Thr Val Ile Leu Lys Gln Lys Ala Asp Ala Asn Asn Lys Val
                485                 490                 495

Gln Ala Phe Ser Gln Val Gly Ile Val Ser Gly Arg Ser Thr Leu Val
            500                 505                 510

Leu Asn Asp Asp Lys Gln Val Asp Pro Asn Ser Ile Tyr Phe Gly Phe
        515                 520                 525

Arg Gly Gly Arg Leu Asp Leu Asn Gly Asn Ser Leu Thr Phe Asp His
    530                 535                 540

Ile Arg Asn Ile Asp Asp Gly Ala Arg Val Val Asn His Asn Met Thr
545                 550                 555                 560

Asn Thr Ser Asn Ile Thr Ile Thr Gly Glu Ser Leu Ile Thr Asn Pro
                565                 570                 575

Asn Thr Ile Thr Ser Tyr Asn Ile Glu Ala Gln Asp Asp His Pro
            580                 585                 590

Leu Arg Ile Arg Ser Ile Pro Tyr Arg Gln Leu Tyr Phe Asn Gln Asp
    595                 600                 605

Asn Arg Ser Tyr Tyr Thr Leu Lys Lys Gly Ala Ser Thr Arg Ser Glu
    610                 615                 620

Leu Pro Gln Asn Ser Gly Glu Ser Asn Glu Asn Trp Leu Tyr Met Gly
625                 630                 635                 640

Arg Thr Ser Asp Ala Ala Lys Arg Asn Val Met Asn His Ile Asn Asn
                645                 650                 655

Glu Arg Met Asn Gly Phe Asn Gly Tyr Phe Gly Glu Glu Thr Lys
            660                 665                 670

Ala Thr Gln Asn Gly Lys Leu Asn Val Thr Phe Asn Gly Lys Ser Asp
        675                 680                 685

Gln Asn Arg Phe Leu Leu Thr Gly Gly Thr Asn Leu Asn Gly Asp Leu
    690                 695                 700

Asn Val Glu Lys Gly Thr Leu Phe Leu Ser Gly Arg Pro Thr Pro His
705                 710                 715                 720

Ala Arg Asp Ile Ala Gly Ile Ser Ser Thr Lys Lys Asp Pro His Phe
                725                 730                 735

Thr Glu Asn Asn Glu Val Val Val Glu Asp Asp Trp Ile Asn Arg Asn
            740                 745                 750

Phe Lys Ala Thr Thr Met Asn Val Thr Gly Asn Ala Ser Leu Tyr Ser
        755                 760                 765

Gly Arg Asn Val Ala Asn Ile Thr Ser Asn Ile Thr Ala Ser Asn Asn
    770                 775                 780

Ala Gln Val His Ile Gly Tyr Lys Thr Gly Asp Thr Val Cys Val Arg
785                 790                 795                 800
```

-continued

```
Ser Asp Tyr Thr Gly Tyr Val Thr Cys His Asn Ser Asn Leu Ser Glu
            805                 810                 815

Lys Ala Leu Asn Ser Phe Asn Pro Thr Asn Leu Arg Gly Asn Val Asn
            820                 825                 830

Leu Thr Glu Asn Ala Ser Phe Thr Leu Gly Lys Ala Asn Leu Phe Gly
            835                 840                 845

Thr Ile Gln Ser Ile Gly Thr Ser Gln Val Asn Leu Lys Glu Asn Ser
    850                 855                 860

His Trp His Leu Thr Gly Asn Ser Asn Val Asn Gln Leu Asn Leu Thr
865             870                 875                 880

Asn Gly His Ile His Leu Asn Ala Gln Asn Asp Ala Asn Lys Val Thr
                885                 890                 895

Thr Tyr Asn Thr Leu Thr Val Asn Ser Leu Ser Gly Asn Gly Ser Phe
            900                 905                 910

Tyr Tyr Trp Val Asp Phe Thr Asn Asn Lys Ser Asn Lys Val Val Val
            915                 920                 925

Asn Lys Ser Ala Thr Gly Asn Phe Thr Leu Gln Val Ala Asp Lys Thr
    930                 935                 940

Gly Glu Pro Asn His Asn Glu Leu Thr Leu Phe Asp Ala Ser Asn Ala
945                 950                 955                 960

Thr Arg Asn Asn Leu Glu Val Thr Leu Ala Asn Gly Ser Val Asp Arg
                965                 970                 975

Gly Ala Trp Lys Tyr Lys Leu Arg Asn Val Asn Gly Arg Tyr Asp Leu
            980                 985                 990

Tyr Asn Pro Glu Val Glu Lys Arg  Asn Gln Thr Val Asp  Thr Thr Asn
            995                 1000                1005

Ile Thr  Thr Pro Asn Asp Ile  Gln Ala Asp Ala Pro  Ser Ala Gln
    1010                1015                1020

Ser Asn  Asn Glu Glu Ile Ala  Arg Val Glu Thr Pro  Val Pro Pro
    1025                1030                1035

Pro Ala  Pro Ala Thr Glu Ser  Ala Ile Ala Ser Glu  Gln Pro Glu
    1040                1045                1050

Thr Arg  Pro Ala Glu Thr Ala  Gln Pro Ala Met Glu  Glu Thr Asn
    1055                1060                1065

Thr Ala  Asn Ser Thr Glu Thr  Ala Pro Lys Ser Asp  Thr Ala Thr
    1070                1075                1080

Gln Thr  Glu Asn Pro Asn Ser  Glu Ser Val Pro Ser  Glu Thr Thr
    1085                1090                1095

Glu Lys  Val Ala Glu Asn Pro  Pro Gln Glu Asn Glu  Thr Val Ala
    1100                1105                1110

Lys Asn  Glu Gln Glu Ala Thr  Glu Pro Thr Pro Gln  Asn Gly Glu
    1115                1120                1125

Val Ala  Lys Glu Asp Gln Pro  Thr Val Glu Ala Asn  Thr Gln Thr
    1130                1135                1140

Asn Glu  Ala Thr Gln Ser Glu  Gly Lys Thr Glu Glu  Thr Gln Thr
    1145                1150                1155

Ala Glu  Thr Lys Ser Glu Pro  Thr Glu Ser Val Thr  Val Ser Glu
    1160                1165                1170

Asn Gln  Pro Glu Lys Thr Val  Ser Gln Ser Thr Glu  Asp Lys Val
    1175                1180                1185

Val Val  Glu Lys Glu Glu Lys  Ala Lys Val Glu Thr  Glu Glu Thr
    1190                1195                1200
```

```
Gln Lys Ala Pro Gln Val Thr Ser Lys Glu Pro Pro Lys Gln Ala
1205                1210                1215

Glu Pro Ala Pro Glu Glu Val Pro Thr Asp Thr Asn Ala Glu Glu
1220                1225                1230

Ala Gln Ala Leu Gln Gln Thr Gln Pro Thr Thr Val Ala Ala Ala
1235                1240                1245

Glu Thr Thr Ser Pro Asn Ser Lys Pro Ala Glu Glu Thr Gln Gln
1250                1255                1260

Pro Ser Glu Lys Thr Asn Ala Glu Pro Val Thr Pro Val Val Ser
1265                1270                1275

Glu Asn Thr Ala Thr Gln Pro Thr Glu Thr Glu Thr Ala Lys
1280                1285                1290

Val Glu Lys Glu Lys Thr Gln Glu Val Pro Gln Val Ala Ser Gln
1295                1300                1305

Glu Ser Pro Lys Gln Glu Gln Pro Ala Ala Lys Pro Gln Ala Gln
1310                1315                1320

Thr Lys Pro Gln Ala Glu Pro Ala Arg Glu Asn Val Leu Thr Thr
1325                1330                1335

Lys Asn Val Gly Glu Pro Gln Pro Gln Ala Gln Pro Gln Thr Gln
1340                1345                1350

Ser Thr Ala Val Pro Thr Thr Gly Glu Thr Ala Ala Asn Ser Lys
1355                1360                1365

Pro Ala Ala Lys Pro Gln Ala Gln Ala Lys Pro Gln Thr Glu Pro
1370                1375                1380

Ala Arg Glu Asn Val Ser Thr Val Asn Thr Lys Glu Pro Gln Ser
1385                1390                1395

Gln Thr Ser Ala Thr Val Ser Thr Glu Gln Pro Ala Lys Glu Thr
1400                1405                1410

Ser Ser Asn Val Glu Gln Pro Ala Pro Glu Asn Ser Ile Asn Thr
1415                1420                1425

Gly Ser Ala Thr Thr Met Thr Glu Thr Ala Glu Lys Ser Asp Lys
1430                1435                1440

Pro Gln Met Glu Thr Val Thr Glu Asn Asp Arg Gln Pro Glu Ala
1445                1450                1455

Asn Thr Val Ala Asp Asn Ser Val Ala Asn Asn Ser Glu Ser Ser
1460                1465                1470

Glu Ser Lys Ser Arg Arg Arg Arg Ser Val Ser Gln Pro Lys Glu
1475                1480                1485

Thr Ser Ala Glu Glu Thr Thr Val Ala Ser Thr Gln Glu Thr Thr
1490                1495                1500

Val Asp Asn Ser Val Ser Thr Pro Lys Pro Arg Ser Arg Arg Thr
1505                1510                1515

Arg Arg Ser Val Gln Thr Asn Ser Tyr Glu Pro Val Glu Leu Pro
1520                1525                1530

Thr Glu Asn Ala Glu Asn Ala Glu Asn Val Gln Ser Gly Asn Asn
1535                1540                1545

Val Ala Asn Ser Gln Pro Ala Leu Arg Asn Leu Thr Ser Lys Asn
1550                1555                1560

Thr Asn Ala Val Ile Ser Asn Ala Met Ala Lys Ala Gln Phe Val
1565                1570                1575

Ala Leu Asn Val Gly Lys Ala Val Ser Gln His Ile Ser Gln Leu
1580                1585                1590
```

-continued

```
Glu Met Asn Asn Glu Gly Gln Tyr Asn Val Trp Ile Ser Asn Thr
    1595                1600                1605

Ser Met Asn Lys Asn Tyr Ser Ser Glu Gln Tyr Arg Arg Phe Ser
    1610                1615                1620

Ser Lys Ser Thr Gln Thr Gln Leu Gly Trp Asp Gln Thr Ile Ser
    1625                1630                1635

Asn Asn Val Gln Leu Gly Gly Val Phe Thr Tyr Val Arg Asn Ser
    1640                1645                1650

Asn Asn Phe Asp Lys Ala Ser Ser Lys Asn Thr Leu Ala Gln Val
    1655                1660                1665

Asn Phe Tyr Ser Lys Tyr Tyr Ala Asp Asn His Trp Tyr Leu Gly
    1670                1675                1680

Ile Asp Leu Gly Tyr Gly Lys Phe Gln Ser Asn Leu Gln Thr Asn
    1685                1690                1695

Asn Asn Ala Lys Phe Ala Arg His Thr Ala Gln Ile Gly Leu Thr
    1700                1705                1710

Ala Gly Lys Ala Phe Asn Leu Gly Asn Phe Ala Val Lys Pro Thr
    1715                1720                1725

Val Gly Val Arg Tyr Ser Tyr Leu Ser Asn Ala Asp Phe Ala Leu
    1730                1735                1740

Ala Gln Asp Arg Ile Lys Val Asn Pro Ile Ser Val Lys Thr Ala
    1745                1750                1755

Phe Ala Gln Val Asp Leu Ser Tyr Thr Tyr His Leu Gly Glu Phe
    1760                1765                1770

Ser Ile Thr Pro Ile Leu Ser Ala Arg Tyr Asp Ala Asn Gln Gly
    1775                1780                1785

Asn Gly Lys Ile Asn Val Ser Val Tyr Asp Phe Ala Tyr Asn Val
    1790                1795                1800

Glu Asn Gln Gln Gln Tyr Asn Ala Gly Leu Lys Leu Lys Tyr His
    1805                1810                1815

Asn Val Lys Leu Ser Leu Ile Gly Gly Leu Thr Lys Ala Lys Gln
    1820                1825                1830

Ala Glu Lys Gln Lys Thr Ala Glu Val Lys Leu Ser Phe Ser Phe
    1835                1840                1845

<210> SEQ ID NO 7
<211> LENGTH: 1395
<212> TYPE: PRT
<213> ORGANISM: Haemophilus influenzae

<400> SEQUENCE: 7

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
                20                  25                  30

Asp Tyr Gln Tyr Tyr Arg Asp Phe Ala Glu Asn Lys Gly Lys Phe Thr
            35                  40                  45

Val Gly Ala Gln Asn Ile Lys Val Tyr Asn Lys Gln Gly Gln Leu Val
        50                  55                  60

Gly Thr Ser Met Thr Lys Ala Pro Met Ile Asp Phe Ser Val Val Ser
65                  70                  75                  80

Arg Asn Gly Val Ala Ala Leu Val Glu Asn Gln Tyr Ile Val Ser Val
                85                  90                  95

Ala His Asn Val Gly Tyr Thr Asp Val Asp Phe Gly Ala Glu Gly Asn
                100                 105                 110
```

```
Asn Pro Asp Gln His Arg Phe Thr Tyr Lys Ile Val Lys Arg Asn Asn
        115                 120                 125

Tyr Lys Lys Asp Asn Leu His Pro Tyr Glu Asp Tyr His Asn Pro
130                 135                 140

Arg Leu His Lys Phe Val Thr Glu Ala Ala Pro Ile Asp Met Thr Ser
145                 150                 155                 160

Asn Met Asn Gly Ser Thr Tyr Ser Asp Arg Thr Lys Tyr Pro Glu Arg
                165                 170                 175

Val Arg Ile Gly Ser Gly Arg Gln Phe Trp Arg Asn Asp Gln Asp Lys
            180                 185                 190

Gly Asp Gln Val Ala Gly Ala Tyr His Tyr Leu Thr Ala Gly Asn Thr
        195                 200                 205

His Asn Gln Arg Gly Ala Gly Asn Gly Tyr Ser Tyr Leu Gly Gly Asp
    210                 215                 220

Val Arg Lys Ala Gly Glu Tyr Gly Pro Leu Pro Ile Ala Gly Ser Lys
225                 230                 235                 240

Gly Asp Ser Gly Ser Pro Met Phe Ile Tyr Asp Ala Glu Lys Gln Lys
                245                 250                 255

Trp Leu Ile Asn Gly Ile Leu Arg Glu Gly Asn Pro Phe Glu Gly Lys
            260                 265                 270

Glu Asn Gly Phe Gln Leu Val Arg Lys Ser Tyr Phe Asp Glu Ile Phe
        275                 280                 285

Glu Arg Asp Leu His Thr Ser Leu Tyr Thr Arg Ala Gly Asn Gly Val
    290                 295                 300

Tyr Thr Ile Ser Gly Asn Asp Asn Gly Gln Gly Ser Ile Thr Gln Lys
305                 310                 315                 320

Ser Gly Ile Pro Ser Glu Ile Lys Ile Thr Leu Ala Asn Met Ser Leu
                325                 330                 335

Pro Leu Lys Glu Lys Asp Lys Val His Asn Pro Arg Tyr Asp Gly Pro
            340                 345                 350

Asn Ile Tyr Ser Pro Arg Leu Asn Asn Gly Glu Thr Leu Tyr Phe Met
        355                 360                 365

Asp Gln Lys Gln Gly Ser Leu Ile Phe Ala Ser Asp Ile Asn Gln Gly
    370                 375                 380

Ala Gly Gly Leu Tyr Phe Glu Gly Asn Phe Thr Val Ser Pro Asn Ser
385                 390                 395                 400

Asn Gln Thr Trp Gln Gly Ala Gly Ile His Val Ser Glu Asn Ser Thr
                405                 410                 415

Val Thr Trp Lys Val Asn Gly Val Glu His Asp Arg Leu Ser Lys Ile
            420                 425                 430

Gly Lys Gly Thr Leu His Val Gln Ala Lys Gly Glu Asn Lys Gly Ser
        435                 440                 445

Ile Ser Val Gly Asp Gly Lys Val Ile Leu Glu Gln Gln Ala Asp Asp
    450                 455                 460

Gln Gly Asn Lys Gln Ala Phe Ser Glu Ile Gly Leu Val Ser Gly Arg
465                 470                 475                 480

Gly Thr Val Gln Leu Asn Asp Asp Lys Gln Phe Asp Thr Asp Lys Phe
                485                 490                 495

Tyr Phe Gly Phe Arg Gly Gly Arg Leu Asp Leu Asn Gly His Ser Leu
            500                 505                 510

Thr Phe Lys Arg Ile Gln Asn Thr Asp Glu Gly Ala Met Ile Val Asn
        515                 520                 525
```

```
His Asn Thr Thr Gln Ala Ala Asn Val Thr Ile Thr Gly Asn Glu Ser
    530                 535                 540

Ile Val Leu Pro Asn Gly Asn Ile Asn Lys Leu Asp Tyr Arg Lys
545                 550                 555                 560

Glu Ile Ala Tyr Asn Gly Trp Phe Gly Glu Thr Asp Lys Asn Lys His
                565                 570                 575

Asn Gly Arg Leu Asn Leu Ile Tyr Lys Pro Thr Thr Glu Asp Arg Thr
                580                 585                 590

Leu Leu Leu Ser Gly Gly Thr Asn Leu Lys Gly Asp Ile Thr Gln Thr
            595                 600                 605

Lys Gly Lys Leu Phe Phe Ser Gly Arg Pro Thr Pro His Ala Tyr Asn
    610                 615                 620

His Leu Asn Lys Arg Trp Ser Glu Met Glu Gly Ile Pro Gln Gly Glu
625                 630                 635                 640

Ile Val Trp Asp His Asp Trp Ile Asn Arg Thr Phe Lys Ala Glu Asn
                645                 650                 655

Phe Gln Ile Lys Gly Gly Ser Ala Val Val Ser Arg Asn Val Ser Ser
                660                 665                 670

Ile Glu Gly Asn Trp Thr Val Ser Asn Asn Ala Asn Ala Thr Phe Gly
            675                 680                 685

Val Val Pro Asn Gln Gln Asn Thr Ile Cys Thr Arg Ser Asp Trp Thr
    690                 695                 700

Gly Leu Thr Thr Cys Gln Lys Val Asp Leu Thr Asp Thr Lys Val Ile
705                 710                 715                 720

Asn Ser Ile Pro Lys Thr Gln Ile Asn Gly Ser Ile Asn Leu Thr Asp
                725                 730                 735

Asn Ala Thr Ala Asn Val Lys Gly Leu Ala Lys Leu Asn Gly Asn Val
                740                 745                 750

Thr Leu Thr Asn His Ser Gln Phe Thr Leu Ser Asn Asn Ala Thr Gln
            755                 760                 765

Ile Gly Asn Ile Arg Leu Ser Asp Asn Ser Thr Ala Thr Val Asp Asn
    770                 775                 780

Ala Asn Leu Asn Gly Asn Val His Leu Thr Asp Ser Ala Gln Phe Ser
785                 790                 795                 800

Leu Lys Asn Ser His Phe Ser His Gln Ile Gln Gly Asp Lys Gly Thr
                805                 810                 815

Thr Val Thr Leu Glu Asn Ala Thr Trp Thr Met Pro Ser Asp Thr Thr
            820                 825                 830

Leu Gln Asn Leu Thr Leu Asn Asn Ser Thr Ile Thr Leu Asn Ser Ala
    835                 840                 845

Tyr Ser Ala Ser Ser Asn Asn Thr Pro Arg Arg Arg Arg Arg Ser Leu
850                 855                 860

Glu Thr Glu Thr Thr Pro Thr Ser Ala Glu His Arg Phe Asn Thr Leu
865                 870                 875                 880

Thr Val Asn Gly Lys Leu Ser Gly Gln Gly Thr Phe Gln Phe Thr Ser
                885                 890                 895

Ser Leu Phe Gly Tyr Lys Ser Asp Lys Leu Lys Leu Ser Asn Asp Ala
                900                 905                 910

Glu Gly Asp Tyr Ile Leu Ser Val Arg Asn Thr Gly Lys Glu Pro Glu
            915                 920                 925

Thr Leu Glu Gln Leu Thr Leu Val Glu Ser Lys Asp Asn Gln Pro Leu
    930                 935                 940
```

-continued

Ser Asp Lys Leu Lys Phe Thr Leu Glu Asn Asp His Val Asp Ala Gly
945                 950                 955                 960

Ala Leu Arg Tyr Lys Leu Val Lys Asn Asp Gly Glu Phe Arg Leu His
            965                 970                 975

Asn Pro Ile Lys Glu Gln Glu Leu His Asn Asp Leu Val Arg Ala Glu
        980                 985                 990

Gln Ala Glu Arg Thr Leu Glu Ala Lys Gln Val Glu Pro Thr Ala Lys
        995                 1000                1005

Thr Gln Thr Gly Glu Pro Lys Val Arg Ser Arg Arg Ala Ala Arg
    1010                1015                1020

Ala Ala Phe Pro Asp Thr Leu Pro Asp Gln Ser Leu Leu Asn Ala
    1025                1030                1035

Leu Glu Ala Lys Gln Ala Glu Leu Thr Ala Glu Thr Gln Lys Ser
    1040                1045                1050

Lys Ala Lys Thr Lys Lys Val Arg Ser Lys Arg Ala Val Phe Ser
    1055                1060                1065

Asp Pro Leu Leu Asp Gln Ser Leu Phe Ala Leu Glu Ala Ala Leu
    1070                1075                1080

Glu Val Ile Asp Ala Pro Gln Gln Ser Glu Lys Asp Arg Leu Ala
    1085                1090                1095

Gln Glu Glu Ala Glu Lys Gln Arg Lys Gln Lys Asp Leu Ile Ser
    1100                1105                1110

Arg Tyr Ser Asn Ser Ala Leu Ser Glu Leu Ser Ala Thr Val Asn
    1115                1120                1125

Ser Met Leu Ser Val Gln Asp Glu Leu Asp Arg Leu Phe Val Asp
    1130                1135                1140

Gln Ala Gln Ser Ala Val Trp Thr Asn Ile Ala Gln Asp Lys Arg
    1145                1150                1155

Arg Tyr Asp Ser Asp Ala Phe Arg Ala Tyr Gln Gln Lys Thr Asn
    1160                1165                1170

Leu Arg Gln Ile Gly Val Gln Lys Ala Leu Ala Asn Gly Arg Ile
    1175                1180                1185

Gly Ala Val Phe Ser His Ser Arg Ser Asp Asn Thr Phe Asp Glu
    1190                1195                1200

Gln Val Lys Asn His Ala Thr Leu Thr Met Met Ser Gly Phe Ala
    1205                1210                1215

Gln Tyr Gln Trp Gly Asp Leu Gln Phe Gly Val Asn Val Gly Thr
    1220                1225                1230

Gly Ile Ser Ala Ser Lys Met Ala Glu Glu Gln Ser Arg Lys Ile
    1235                1240                1245

His Arg Lys Ala Ile Asn Tyr Gly Val Asn Ala Ser Tyr Gln Phe
    1250                1255                1260

Arg Leu Gly Gln Leu Gly Ile Gln Pro Tyr Phe Gly Val Asn Arg
    1265                1270                1275

Tyr Phe Ile Glu Arg Glu Asn Tyr Gln Ser Glu Glu Val Arg Val
    1280                1285                1290

Lys Thr Pro Ser Leu Ala Phe Asn Arg Tyr Asn Ala Gly Ile Arg
    1295                1300                1305

Val Asp Tyr Thr Phe Thr Pro Thr Asp Asn Ile Ser Val Lys Pro
    1310                1315                1320

Tyr Phe Phe Val Asn Tyr Val Asp Val Ser Asn Ala Asn Val Gln
    1325                1330                1335

-continued

```
Thr Thr Val Asn Leu Thr Val Leu Gln Gln Pro Phe Gly Arg Tyr
    1340                1345                1350

Trp Gln Lys Glu Val Gly Leu Lys Ala Glu Ile Leu His Phe Gln
    1355                1360                1365

Ile Ser Ala Phe Ile Ser Lys Ser Gln Gly Ser Gln Leu Gly Lys
    1370                1375                1380

Gln Gln Asn Val Gly Val Lys Leu Gly Tyr Arg Trp
    1385                1390                1395

<210> SEQ ID NO 8
<211> LENGTH: 4305
<212> TYPE: DNA
<213> ORGANISM: Haemophilus influenzae
<220> FEATURE:
<221> NAME/KEY: misc_feature
<222> LOCATION: (1702)..(1702)
<223> OTHER INFORMATION: "n" at position 1702 can be any base.
<221> NAME/KEY: CDS
<222> LOCATION: (1)..(4305)
<223> OTHER INFORMATION:

<400> SEQUENCE: 8 atg aaa aaa act gta ttt cgt ctt aat ttt tta acc gct tgc att tca      48
Met Lys Lys Thr Val Phe Arg Leu Asn Phe Leu Thr Ala Cys Ile Ser
1               5                   10                  15 tta ggg ata gta tcg caa gcg tgg gca ggt cat act tat ttt ggg att      96
Leu Gly Ile Val Ser Gln Ala Trp Ala Gly His Thr Tyr Phe Gly Ile
            20                  25                  30 gac tac caa tat tat cgt gat ttt gcc gag aat gaa ggc aag ttt gca     144
Asp Tyr Gln Tyr Tyr Arg Asp Phe Ala Glu Asn Glu Gly Lys Phe Ala
        35                  40                  45 gtt ggg gct aaa aat att gat gtt tat aac aaa gaa ggg caa tta gtt     192
Val Gly Ala Lys Asn Ile Asp Val Tyr Asn Lys Glu Gly Gln Leu Val
    50                  55                  60 ggc aca tca atg aca aaa gcc ccg atg att gat ttc tca gtc gtt tcc     240
Gly Thr Ser Met Thr Lys Ala Pro Met Ile Asp Phe Ser Val Val Ser
65                  70                  75                  80 aga aat gga gtt gct gcc tta gta ggc gat cag tat att gtg agt gtg     288
Arg Asn Gly Val Ala Ala Leu Val Gly Asp Gln Tyr Ile Val Ser Val
                85                  90                  95 gca cat aat gta ggc tat acc aat gtg gat ttt ggt gct gaa gga caa     336
Ala His Asn Val Gly Tyr Thr Asn Val Asp Phe Gly Ala Glu Gly Gln
            100                 105                 110 aat cct gat caa cat cgt ttt act tat aaa att gtg aaa cgg aat aat     384
Asn Pro Asp Gln His Arg Phe Thr Tyr Lys Ile Val Lys Arg Asn Asn
        115                 120                 125 tat aat cac gat gcg aag cac cgc tat cta gat gac tac cat aat cca     432
Tyr Asn His Asp Ala Lys His Arg Tyr Leu Asp Asp Tyr His Asn Pro
    130                 135                 140 cgt tta cat aaa ttt gta acg gat gcg gca cca att gat atg act tca     480
Arg Leu His Lys Phe Val Thr Asp Ala Ala Pro Ile Asp Met Thr Ser
145                 150                 155                 160 cat atg gat ggc aat aag tat gca aat aag gaa aaa tat cct gaa cga     528
His Met Asp Gly Asn Lys Tyr Ala Asn Lys Glu Lys Tyr Pro Glu Arg
                165                 170                 175 gta cgc gtc gga tct gga gat cag tat tgg gat gac gat caa aac aac     576
Val Arg Val Gly Ser Gly Asp Gln Tyr Trp Asp Asp Asp Gln Asn Asn
            180                 185                 190 aga act tat tta tct gac gga tat aat tat tta aca ggt ggg aat aca     624
Arg Thr Tyr Leu Ser Asp Gly Tyr Asn Tyr Leu Thr Gly Gly Asn Thr
        195                 200                 205
```

```
                                         -continued tat aat caa agc ggt aga ggt gat gga tat tca tat gtg aga ggt gat         672
Tyr Asn Gln Ser Gly Arg Gly Asp Gly Tyr Ser Tyr Val Arg Gly Asp
    210                 215                 220 att cgc aaa gtt ggc gat tat ggt cca tta ccg att gca agt tca ttc         720
Ile Arg Lys Val Gly Asp Tyr Gly Pro Leu Pro Ile Ala Ser Ser Phe
225                 230                 235                 240 ggg gac agt gga tct cca atg ttt att tat gat gct gaa aca caa aaa         768
Gly Asp Ser Gly Ser Pro Met Phe Ile Tyr Asp Ala Glu Thr Gln Lys
                245                 250                 255 tgg cta att aat gga gta ttg cgg gag ggg caa cct tat aca ggc gaa         816
Trp Leu Ile Asn Gly Val Leu Arg Glu Gly Gln Pro Tyr Thr Gly Glu
    260                 265                 270 ttc gat gga ttt caa tta gcc cgt aaa tct ttc ctt gat gaa att ata         864
Phe Asp Gly Phe Gln Leu Ala Arg Lys Ser Phe Leu Asp Glu Ile Ile
            275                 280                 285 cgc aaa gat caa cca aat ggt ttt tta acc cct aag ggg aat ggc gtt         912
Arg Lys Asp Gln Pro Asn Gly Phe Leu Thr Pro Lys Gly Asn Gly Val
290                 295                 300 tat acc att tct aaa agt gac gat ggg ata gga gtt gtt act tcg aaa         960
Tyr Thr Ile Ser Lys Ser Asp Asp Gly Ile Gly Val Val Thr Ser Lys
305                 310                 315                 320 att gga aaa cct cgt gaa ata cct tta gcg aac aac aaa tta aaa ata        1008
Ile Gly Lys Pro Arg Glu Ile Pro Leu Ala Asn Asn Lys Leu Lys Ile
                325                 330                 335 gaa gat aaa gat act gtc tat aat aac aga tat aat ggt cct aat att        1056
Glu Asp Lys Asp Thr Val Tyr Asn Asn Arg Tyr Asn Gly Pro Asn Ile
            340                 345                 350 tat tct cct caa tta aac aat ggc aag aat att tat ttt gga gat gaa        1104
Tyr Ser Pro Gln Leu Asn Asn Gly Lys Asn Ile Tyr Phe Gly Asp Glu
        355                 360                 365 gaa tta gga tcc ata act tta acg act gat atc gat caa ggt gca ggc        1152
Glu Leu Gly Ser Ile Thr Leu Thr Thr Asp Ile Asp Gln Gly Ala Gly
370                 375                 380 ggt ttg tat ttt gag ggg gat ttt ata gtt tcg cct acc aaa aat gaa        1200
Gly Leu Tyr Phe Glu Gly Asp Phe Ile Val Ser Pro Thr Lys Asn Glu
385                 390                 395                 400 acg tgg aaa ggt gcg ggc att cat gtc agt gaa att agt acc gtt act        1248
Thr Trp Lys Gly Ala Gly Ile His Val Ser Glu Ile Ser Thr Val Thr
                405                 410                 415 tgg aaa gta aac ggc gtg gaa aat gat cga ctt tct aaa atc ggt aaa        1296
Trp Lys Val Asn Gly Val Glu Asn Asp Arg Leu Ser Lys Ile Gly Lys
            420                 425                 430 gga aca tta cac gtt aaa gcc aaa ggg gaa aat aaa ggt tcg atc agc        1344
Gly Thr Leu His Val Lys Ala Lys Gly Glu Asn Lys Gly Ser Ile Ser
        435                 440                 445 gta ggc gat ggt aaa gtc att ttg gag cag cag gca gac gat caa ggc        1392
Val Gly Asp Gly Lys Val Ile Leu Glu Gln Gln Ala Asp Asp Gln Gly
450                 455                 460 aac aaa caa gcc ttt agt gaa att ggc ttg gtt agc ggc aga ggg act        1440
Asn Lys Gln Ala Phe Ser Glu Ile Gly Leu Val Ser Gly Arg Gly Thr
465                 470                 475                 480 gtt caa tta aac gat gat aaa caa ttt gat acc gat aaa ttt tat ttc        1488
Val Gln Leu Asn Asp Asp Lys Gln Phe Asp Thr Asp Lys Phe Tyr Phe
                485                 490                 495 ggc ttt cgt ggt ggt cgc tta gat ctt aac gga cat tca tta acc ttt        1536
Gly Phe Arg Gly Gly Arg Leu Asp Leu Asn Gly His Ser Leu Thr Phe
            500                 505                 510 aaa cgt atc caa aat acg gac gag ggg gcg atg att gtg aac cat aat        1584
Lys Arg Ile Gln Asn Thr Asp Glu Gly Ala Met Ile Val Asn His Asn
        515                 520                 525
```

-continued

| | |
|---|---|
| aca act caa gtc gct aat att act att act ggg aac gaa agt att act<br>Thr Thr Gln Val Ala Asn Ile Thr Ile Thr Gly Asn Glu Ser Ile Thr<br>530                        535                      540 | 1632 |
| gct cca tct aat aaa aat aat att aat aaa ctt gat tac agc aaa gaa<br>Ala Pro Ser Asn Lys Asn Asn Ile Asn Lys Leu Asp Tyr Ser Lys Glu<br>545                        550                      555                      560 | 1680 |
| att gcc tac aac ggc tgg ttt ngc gaa aca gat aaa aat aaa cat aat<br>Ile Ala Tyr Asn Gly Trp Phe Xaa Glu Thr Asp Lys Asn Lys His Asn<br>                      565                      570                      575 | 1728 |
| gga cga tta aac ctt att tat aaa cca acc aca gaa gat cgt act ttg<br>Gly Arg Leu Asn Leu Ile Tyr Lys Pro Thr Thr Glu Asp Arg Thr Leu<br>580                        585                      590 | 1776 |
| cta ctt tca ggc ggc aca aac tta aaa ggc gat att act caa aca aaa<br>Leu Leu Ser Gly Gly Thr Asn Leu Lys Gly Asp Ile Thr Gln Thr Lys<br>                      595                      600                      605 | 1824 |
| ggt aaa cta ttt ttc agc ggt aga ccg aca ccc cac gcc tac aat cat<br>Gly Lys Leu Phe Phe Ser Gly Arg Pro Thr Pro His Ala Tyr Asn His<br>610                        615                      620 | 1872 |
| tta gac aaa cgt tgg tca gaa atg gaa ggt atc cca caa ggc gaa att<br>Leu Asp Lys Arg Trp Ser Glu Met Glu Gly Ile Pro Gln Gly Glu Ile<br>625                        630                      635                      640 | 1920 |
| gtg tgg gat tac gat tgg att aac cgc aca ttt aaa gct gaa aac ttc<br>Val Trp Asp Tyr Asp Trp Ile Asn Arg Thr Phe Lys Ala Glu Asn Phe<br>                      645                      650                      655 | 1968 |
| caa att aaa ggc gga agt gcg gtg gtt tct cgc aat gtt tct tca att<br>Gln Ile Lys Gly Gly Ser Ala Val Val Ser Arg Asn Val Ser Ser Ile<br>660                        665                      670 | 2016 |
| gag gga aat tgg aca gtc agc aat aat gca aat gcc aca ttt ggt gtt<br>Glu Gly Asn Trp Thr Val Ser Asn Asn Ala Asn Ala Thr Phe Gly Val<br>                      675                      680                      685 | 2064 |
| gtg cca aat cag caa aat acc att tgc acg cgt tca gat tgg aca gga<br>Val Pro Asn Gln Gln Asn Thr Ile Cys Thr Arg Ser Asp Trp Thr Gly<br>690                        695                      700 | 2112 |
| tta acg act tgt aaa aca gtt aat tta acc gat aaa aaa gtt att gat<br>Leu Thr Thr Cys Lys Thr Val Asn Leu Thr Asp Lys Lys Val Ile Asp<br>705                        710                      715                      720 | 2160 |
| tcc ata ccg aca aca caa att aat ggt tct att aat tta act gat aat<br>Ser Ile Pro Thr Thr Gln Ile Asn Gly Ser Ile Asn Leu Thr Asp Asn<br>                      725                      730                      735 | 2208 |
| gca aca gtg aat att aat ggt tta gca aaa ctt aat ggt aat gtc act<br>Ala Thr Val Asn Ile Asn Gly Leu Ala Lys Leu Asn Gly Asn Val Thr<br>740                        745                      750 | 2256 |
| tta ata aat cat agc caa ttt aca ttg agc aac aat gcc acc caa ata<br>Leu Ile Asn His Ser Gln Phe Thr Leu Ser Asn Asn Ala Thr Gln Ile<br>                      755                      760                      765 | 2304 |
| ggc aat atc aaa ctt tca aat cac gca aat gca agg gta aat aat gcc<br>Gly Asn Ile Lys Leu Ser Asn His Ala Asn Ala Arg Val Asn Asn Ala<br>770                        775                      780 | 2352 |
| act tta atg ggc gat gtg aat tta gcg gat act agc cgt ttt aca tta<br>Thr Leu Met Gly Asp Val Asn Leu Ala Asp Thr Ser Arg Phe Thr Leu<br>785                        790                      795                      800 | 2400 |
| agc aat caa gca aca cag att ggc aca atc agt ctt cat cag caa gct<br>Ser Asn Gln Ala Thr Gln Ile Gly Thr Ile Ser Leu His Gln Gln Ala<br>                      805                      810                      815 | 2448 |
| caa gca aca gtg gat aat gca aac ttg aac ggt aat gtg cat tta acg<br>Gln Ala Thr Val Asp Asn Ala Asn Leu Asn Gly Asn Val His Leu Thr<br>820                        825                      830 | 2496 |
| gat tct gcc aga ttt tct tta aaa aac agt cat ttt tcg cac caa att<br>Asp Ser Ala Arg Phe Ser Leu Lys Asn Ser His Phe Ser His Gln Ile<br>                      835                      840                      845 | 2544 |

```
cag ggc gac aaa gac aca aca gtg acg ttg gaa aat gcg act tgg aca      2592
Gln Gly Asp Lys Asp Thr Thr Val Thr Leu Glu Asn Ala Thr Trp Thr
850                 855                 860 atg cct agc gat act aca ttg cag aat tta acg cta aat aat agt act      2640
Met Pro Ser Asp Thr Thr Leu Gln Asn Leu Thr Leu Asn Asn Ser Thr
865                 870                 875                 880 gtt acg tta aat tca gct tat tca gct agc tca aat aat gcg cca cgt      2688
Val Thr Leu Asn Ser Ala Tyr Ser Ala Ser Ser Asn Asn Ala Pro Arg
                885                 890                 895 cgc cgc cgt tca tta gag acg gaa aca acg cca aca tcg gca gaa cat      2736
Arg Arg Arg Ser Leu Glu Thr Glu Thr Thr Pro Thr Ser Ala Glu His
900                 905                 910 cgt ttc aac aca ttg aca gta aat ggt aaa ttg agc ggg caa ggc aca      2784
Arg Phe Asn Thr Leu Thr Val Asn Gly Lys Leu Ser Gly Gln Gly Thr
        915                 920                 925 ttc caa ttt act cca tct tta ttt ggc tat gaa agc gat aaa tta aaa      2832
Phe Gln Phe Thr Pro Ser Leu Phe Gly Tyr Glu Ser Asp Lys Leu Lys
    930                 935                 940 tta tcc aat gac gct gag ggc gat tac aca tta tct gtt cgc aac aca      2880
Leu Ser Asn Asp Ala Glu Gly Asp Tyr Thr Leu Ser Val Arg Asn Thr
945                 950                 955                 960 ggc aaa gaa ccc gtg acc ctt gag caa tta act ttg gtt gaa agc aaa      2928
Gly Lys Glu Pro Val Thr Leu Glu Gln Leu Thr Leu Val Glu Ser Lys
                965                 970                 975 gat aat aaa ccg tta tca gac aaa ctc aaa ttt act tta gaa aat gac      2976
Asp Asn Lys Pro Leu Ser Asp Lys Leu Lys Phe Thr Leu Glu Asn Asp
            980                 985                 990 cac gtt gat gca ggt gca tta cgt  tat aaa tta gtg aag  aat aag ggc    3024
His Val Asp Ala Gly Ala Leu Arg  Tyr Lys Leu Val Lys  Asn Lys Gly
                995                      1000                1005 gaa ttc cgc ttg cat aac cca  ata aaa gag cag gaa  ttg cgc tct         3069
Glu Phe Arg Leu His Asn Pro  Ile Lys Glu Gln Glu  Leu Arg Ser
    1010                1015                     1020 gat tta gta aga gca gag caa  gca gaa cga aca tta  gaa gcc aaa         3114
Asp Leu Val Arg Ala Glu Gln  Ala Glu Arg Thr Leu  Glu Ala Lys
1025                1030                     1035 caa gtt gaa cag act gct gaa  aca caa aca agt aat  gca aga gtg         3159
Gln Val Glu Gln Thr Ala Glu  Thr Gln Thr Ser Asn  Ala Arg Val
    1040                1045                     1050 cgg tca aga aga gcg gtg ttg  tct gat acc ccg tct  gct caa agc         3204
Arg Ser Arg Arg Ala Val Leu  Ser Asp Thr Pro Ser  Ala Gln Ser
1055                1060                     1065 ctg tta aac gca tta gaa gtc  aaa caa gct gaa ccg  aat gct aaa         3249
Leu Leu Asn Ala Leu Glu Val  Lys Gln Ala Glu Pro  Asn Ala Lys
    1070                1075                     1080 aca caa aaa agt aag gca aaa  aca aaa aaa gcg cgg  tca aaa aga         3294
Thr Gln Lys Ser Lys Ala Lys  Thr Lys Lys Ala Arg  Ser Lys Arg
1085                1090                     1095 gca ttg aga gaa gcg ttt tct  gat acc ccg cct gat  cta agc cag         3339
Ala Leu Arg Glu Ala Phe Ser  Asp Thr Pro Pro Asp  Leu Ser Gln
    1100                1105                     1110 tta aac gta tta gaa gcc gca  ctt aag gtt att aat  gcc caa ccg         3384
Leu Asn Val Leu Glu Ala Ala  Leu Lys Val Ile Asn  Ala Gln Pro
1115                1120                     1125 caa aca gaa aaa gaa cgt caa  gct caa gag gaa gaa  gcg aaa aga         3429
Gln Thr Glu Lys Glu Arg Gln  Ala Gln Glu Glu Glu  Ala Lys Arg
    1130                1135                     1140 caa cgc aaa caa aaa gac ttg  atc agc cgt tac tca  aat agt gcg         3474
Gln Arg Lys Gln Lys Asp Leu  Ile Ser Arg Tyr Ser  Asn Ser Ala
1145                1150                     1155
```

```
tta tcg gag ttg tct gca aca gta aat agt atg ctt tcc gtt caa      3519
Leu Ser Glu Leu Ser Ala Thr Val Asn Ser Met Leu Ser Val Gln
    1160            1165                1170 gat gaa ttg gat cgt ctt ttt gta gat caa gca caa tct gcc ctg      3564
Asp Glu Leu Asp Arg Leu Phe Val Asp Gln Ala Gln Ser Ala Leu
1175            1180                1185 tgg aca aat atc gca cag gat aaa aga cgc tat gat tct gat gcg      3609
Trp Thr Asn Ile Ala Gln Asp Lys Arg Arg Tyr Asp Ser Asp Ala
    1190            1195                1200 ttc cgt gct tat cag cag aaa acg aac ttg cgt caa att ggg gtg      3654
Phe Arg Ala Tyr Gln Gln Lys Thr Asn Leu Arg Gln Ile Gly Val
1205            1210                1215 caa aaa gcc tta gat aat gga cga att ggg gcg gtt ttc tcg cat      3699
Gln Lys Ala Leu Asp Asn Gly Arg Ile Gly Ala Val Phe Ser His
    1220            1225                1230 agc cgt tca gat aat acc ttt gac gaa cag gtt aaa aat cac gcg      3744
Ser Arg Ser Asp Asn Thr Phe Asp Glu Gln Val Lys Asn His Ala
1235            1240                1245 aca tta acg atg atg tcg ggt ttt gcc caa tat caa tgg ggc gat      3789
Thr Leu Thr Met Met Ser Gly Phe Ala Gln Tyr Gln Trp Gly Asp
    1250            1255                1260 tta caa ttt ggt gta aac gtg ggc gcg gga att agt gcg agt aaa      3834
Leu Gln Phe Gly Val Asn Val Gly Ala Gly Ile Ser Ala Ser Lys
1265            1270                1275 atg gct gaa gaa caa agc cga aaa att cat cga aaa gcg ata aat      3879
Met Ala Glu Glu Gln Ser Arg Lys Ile His Arg Lys Ala Ile Asn
    1280            1285                1290 tat ggt gtg aat gca agt tat cag ttc cgt tta ggg caa ttg ggt      3924
Tyr Gly Val Asn Ala Ser Tyr Gln Phe Arg Leu Gly Gln Leu Gly
1295            1300                1305 att cag cct tat ttg ggt gtt aat cga tat ttt att gaa cgt gaa      3969
Ile Gln Pro Tyr Leu Gly Val Asn Arg Tyr Phe Ile Glu Arg Glu
    1310            1315                1320 aat tat caa tct gaa gaa gtg aaa gtg caa aca ccg agc ctt gca      4014
Asn Tyr Gln Ser Glu Glu Val Lys Val Gln Thr Pro Ser Leu Ala
1325            1330                1335 ttt aat cgc tat aat gct ggc att cga gtt gat tat aca ttt acc      4059
Phe Asn Arg Tyr Asn Ala Gly Ile Arg Val Asp Tyr Thr Phe Thr
    1340            1345                1350 ccg aca gat aat atc agc gtt aag cct tat ttc ttt gtc aat tat      4104
Pro Thr Asp Asn Ile Ser Val Lys Pro Tyr Phe Phe Val Asn Tyr
1355            1360                1365 gtt gat gtt tca aac gct aac gta caa acc act gta aat agc acg      4149
Val Asp Val Ser Asn Ala Asn Val Gln Thr Thr Val Asn Ser Thr
    1370            1375                1380 atg ttg caa caa tca ttt ggg cgt tat tgg caa aaa gaa gtg gga      4194
Met Leu Gln Gln Ser Phe Gly Arg Tyr Trp Gln Lys Glu Val Gly
1385            1390                1395 tta aag gca gaa att tta cat ttc caa ctt tcc gct ttt atc tca      4239
Leu Lys Ala Glu Ile Leu His Phe Gln Leu Ser Ala Phe Ile Ser
    1400            1405                1410 aaa tct caa ggt tca caa ctc ggt aaa cag caa aat gtg ggc gtg      4284
Lys Ser Gln Gly Ser Gln Leu Gly Lys Gln Gln Asn Val Gly Val
1415            1420                1425 aaa ttg ggc tat cgt tgg taa                                      4305
Lys Leu Gly Tyr Arg Trp
    1430
```

-continued

```
<210> SEQ ID NO 9
<211> LENGTH: 1434
<212> TYPE: PRT
<213> ORGANISM: Haemophilus influenzae
<220> FEATURE:
<221> NAME/KEY: misc_feature
<222> LOCATION: (568)..(568)
<223> OTHER INFORMATION: The 'Xaa' at location 568 stands for Ser, Gly,
      Arg, or Cys.
<221> NAME/KEY: misc_feature
<222> LOCATION: (1702)..(1702)
<223> OTHER INFORMATION: "n" at position 1702 can be any base.

<400> SEQUENCE: 9

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Glu Gly Lys Phe Ala
        35                  40                  45

Val Gly Ala Lys Asn Ile Asp Val Tyr Asn Lys Glu Gly Gln Leu Val
50                  55                  60

Gly Thr Ser Met Thr Lys Ala Pro Met Ile Asp Phe Ser Val Val Ser
65                  70                  75                  80

Arg Asn Gly Val Ala Ala Leu Val Gly Asp Gln Tyr Ile Val Ser Val
                85                  90                  95

Ala His Asn Val Gly Tyr Thr Asn Val Asp Phe Gly Ala Glu Gly Gln
            100                 105                 110

Asn Pro Asp Gln His Arg Phe Thr Tyr Lys Ile Val Lys Arg Asn Asn
        115                 120                 125

Tyr Asn His Asp Ala Lys His Arg Tyr Leu Asp Asp Tyr His Asn Pro
    130                 135                 140

Arg Leu His Lys Phe Val Thr Asp Ala Ala Pro Ile Asp Met Thr Ser
145                 150                 155                 160

His Met Asp Gly Asn Lys Tyr Ala Asn Lys Glu Lys Tyr Pro Glu Arg
                165                 170                 175

Val Arg Val Gly Ser Gly Asp Gln Tyr Trp Asp Asp Gln Asn Asn
            180                 185                 190

Arg Thr Tyr Leu Ser Asp Gly Tyr Asn Tyr Leu Thr Gly Gly Asn Thr
        195                 200                 205

Tyr Asn Gln Ser Gly Arg Gly Asp Gly Tyr Ser Tyr Val Arg Gly Asp
    210                 215                 220

Ile Arg Lys Val Gly Asp Tyr Gly Pro Leu Pro Ile Ala Ser Ser Phe
225                 230                 235                 240

Gly Asp Ser Gly Ser Pro Met Phe Ile Tyr Asp Ala Glu Thr Gln Lys
                245                 250                 255

Trp Leu Ile Asn Gly Val Leu Arg Glu Gly Gln Pro Tyr Thr Gly Glu
            260                 265                 270

Phe Asp Gly Phe Gln Leu Ala Arg Lys Ser Phe Leu Asp Glu Ile Ile
        275                 280                 285

Arg Lys Asp Gln Pro Asn Gly Phe Leu Thr Pro Lys Gly Asn Gly Val
    290                 295                 300

Tyr Thr Ile Ser Lys Ser Asp Asp Gly Ile Gly Val Val Thr Ser Lys
305                 310                 315                 320

Ile Gly Lys Pro Arg Glu Ile Pro Leu Ala Asn Asn Lys Leu Lys Ile
                325                 330                 335
```

-continued

```
Glu Asp Lys Asp Thr Val Tyr Asn Asn Arg Tyr Asn Gly Pro Asn Ile
            340                 345                 350

Tyr Ser Pro Gln Leu Asn Asn Gly Lys Asn Ile Tyr Phe Gly Asp Glu
            355                 360                 365

Glu Leu Gly Ser Ile Thr Leu Thr Thr Asp Ile Asp Gln Gly Ala Gly
            370                 375                 380

Gly Leu Tyr Phe Glu Gly Asp Phe Ile Val Ser Pro Thr Lys Asn Glu
385                 390                 395                 400

Thr Trp Lys Gly Ala Gly Ile His Val Ser Glu Ile Ser Thr Val Thr
                    405                 410                 415

Trp Lys Val Asn Gly Val Glu Asn Asp Arg Leu Ser Lys Ile Gly Lys
                    420                 425                 430

Gly Thr Leu His Val Lys Ala Lys Gly Glu Asn Lys Gly Ser Ile Ser
                    435                 440                 445

Val Gly Asp Gly Lys Val Ile Leu Glu Gln Gln Ala Asp Asp Gln Gly
            450                 455                 460

Asn Lys Gln Ala Phe Ser Glu Ile Gly Leu Val Ser Gly Arg Gly Thr
465                 470                 475                 480

Val Gln Leu Asn Asp Asp Lys Gln Phe Asp Thr Asp Lys Phe Tyr Phe
                    485                 490                 495

Gly Phe Arg Gly Gly Arg Leu Asp Leu Asn Gly His Ser Leu Thr Phe
                    500                 505                 510

Lys Arg Ile Gln Asn Thr Asp Glu Gly Ala Met Ile Val Asn His Asn
            515                 520                 525

Thr Thr Gln Val Ala Asn Ile Thr Ile Thr Gly Asn Glu Ser Ile Thr
            530                 535                 540

Ala Pro Ser Asn Lys Asn Asn Ile Asn Lys Leu Asp Tyr Ser Lys Glu
545                 550                 555                 560

Ile Ala Tyr Asn Gly Trp Phe Xaa Glu Thr Asp Lys Asn Lys His Asn
                    565                 570                 575

Gly Arg Leu Asn Leu Ile Tyr Lys Pro Thr Thr Glu Asp Arg Thr Leu
            580                 585                 590

Leu Leu Ser Gly Gly Thr Asn Leu Lys Gly Asp Ile Thr Gln Thr Lys
            595                 600                 605

Gly Lys Leu Phe Phe Ser Gly Arg Pro Thr Pro His Ala Tyr Asn His
            610                 615                 620

Leu Asp Lys Arg Trp Ser Glu Met Glu Gly Ile Pro Gln Gly Glu Ile
625                 630                 635                 640

Val Trp Asp Tyr Asp Trp Ile Asn Arg Thr Phe Lys Ala Glu Asn Phe
                    645                 650                 655

Gln Ile Lys Gly Gly Ser Ala Val Ser Arg Asn Val Ser Ser Ile
                    660                 665                 670

Glu Gly Asn Trp Thr Val Ser Asn Asn Ala Asn Ala Thr Phe Gly Val
            675                 680                 685

Val Pro Asn Gln Gln Asn Thr Ile Cys Thr Arg Ser Asp Trp Thr Gly
            690                 695                 700

Leu Thr Thr Cys Lys Thr Val Asn Leu Thr Asp Lys Lys Val Ile Asp
705                 710                 715                 720

Ser Ile Pro Thr Thr Gln Ile Asn Gly Ser Ile Asn Leu Thr Asp Asn
                    725                 730                 735

Ala Thr Val Asn Ile Asn Gly Leu Ala Lys Leu Asn Gly Asn Val Thr
                    740                 745                 750
```

-continued

```
Leu Ile Asn His Ser Gln Phe Thr Leu Ser Asn Asn Ala Thr Gln Ile
    755                 760                 765

Gly Asn Ile Lys Leu Ser Asn His Ala Asn Ala Arg Val Asn Asn Ala
    770                 775                 780

Thr Leu Met Gly Asp Val Asn Leu Ala Asp Thr Ser Arg Phe Thr Leu
785             790                 795                     800

Ser Asn Gln Ala Thr Gln Ile Gly Thr Ile Ser Leu His Gln Gln Ala
                805                 810                 815

Gln Ala Thr Val Asp Asn Ala Asn Leu Asn Gly Asn Val His Leu Thr
            820                 825                 830

Asp Ser Ala Arg Phe Ser Leu Lys Asn Ser His Phe Ser His Gln Ile
            835                 840                 845

Gln Gly Asp Lys Asp Thr Thr Val Thr Leu Glu Asn Ala Thr Trp Thr
    850                 855                 860

Met Pro Ser Asp Thr Thr Leu Gln Asn Leu Thr Leu Asn Asn Ser Thr
865             870                 875                     880

Val Thr Leu Asn Ser Ala Tyr Ser Ala Ser Asn Asn Ala Pro Arg
                885                 890                 895

Arg Arg Arg Ser Leu Glu Thr Glu Thr Thr Pro Thr Ser Ala Glu His
            900                 905                 910

Arg Phe Asn Thr Leu Thr Val Asn Gly Lys Leu Ser Gly Gln Gly Thr
    915                 920                 925

Phe Gln Phe Thr Pro Ser Leu Phe Gly Tyr Glu Ser Asp Lys Leu Lys
    930                 935                 940

Leu Ser Asn Asp Ala Glu Gly Asp Tyr Thr Leu Ser Val Arg Asn Thr
945             950                 955                     960

Gly Lys Glu Pro Val Thr Leu Glu Gln Leu Thr Leu Val Glu Ser Lys
                965                 970                 975

Asp Asn Lys Pro Leu Ser Asp Lys Leu Lys Phe Thr Leu Glu Asn Asp
            980                 985                 990

His Val Asp Ala Gly Ala Leu Arg Tyr Lys Leu Val Lys  Asn Lys Gly
    995                 1000                1005

Glu Phe Arg Leu His Asn Pro  Ile Lys Glu Gln Glu  Leu Arg Ser
    1010                1015                1020

Asp Leu Val Arg Ala Glu Gln  Ala Glu Arg Thr Leu  Glu Ala Lys
    1025                1030                1035

Gln Val Glu Gln Thr Ala Glu  Thr Gln Thr Ser Asn  Ala Arg Val
    1040                1045                1050

Arg Ser Arg Arg Ala Val Leu  Ser Asp Thr Pro Ser  Ala Gln Ser
    1055                1060                1065

Leu Leu Asn Ala Leu Glu Val  Lys Gln Ala Glu Pro  Asn Ala Lys
    1070                1075                1080

Thr Gln Lys Ser Lys Ala Lys  Thr Lys Lys Ala Arg  Ser Lys Arg
    1085                1090                1095

Ala Leu Arg Glu Ala Phe Ser  Asp Thr Pro Pro Asp  Leu Ser Gln
    1100                1105                1110

Leu Asn Val Leu Glu Ala Ala  Leu Lys Val Ile Asn  Ala Gln Pro
    1115                1120                1125

Gln Thr Glu Lys Glu Arg Gln  Ala Gln Glu Glu Glu  Ala Lys Arg
    1130                1135                1140

Gln Arg Lys Gln Lys Asp Leu  Ile Ser Arg Tyr Ser  Asn Ser Ala
    1145                1150                1155
```

-continued

Leu Ser Glu Leu Ser Ala Thr Val Asn Ser Met Leu Ser Val Gln
    1160            1165                1170

Asp Glu Leu Asp Arg Leu Phe Val Asp Gln Ala Gln Ser Ala Leu
    1175            1180                1185

Trp Thr Asn Ile Ala Gln Asp Lys Arg Arg Tyr Asp Ser Asp Ala
    1190            1195                1200

Phe Arg Ala Tyr Gln Gln Lys Thr Asn Leu Arg Gln Ile Gly Val
    1205            1210                1215

Gln Lys Ala Leu Asp Asn Gly Arg Ile Gly Ala Val Phe Ser His
    1220            1225                1230

Ser Arg Ser Asp Asn Thr Phe Asp Glu Gln Val Lys Asn His Ala
    1235            1240                1245

Thr Leu Thr Met Met Ser Gly Phe Ala Gln Tyr Gln Trp Gly Asp
    1250            1255                1260

Leu Gln Phe Gly Val Asn Val Gly Ala Gly Ile Ser Ala Ser Lys
    1265            1270                1275

Met Ala Glu Glu Gln Ser Arg Lys Ile His Arg Lys Ala Ile Asn
    1280            1285                1290

Tyr Gly Val Asn Ala Ser Tyr Gln Phe Arg Leu Gly Gln Leu Gly
    1295            1300                1305

Ile Gln Pro Tyr Leu Gly Val Asn Arg Tyr Phe Ile Glu Arg Glu
    1310            1315                1320

Asn Tyr Gln Ser Glu Glu Val Lys Val Gln Thr Pro Ser Leu Ala
    1325            1330                1335

Phe Asn Arg Tyr Asn Ala Gly Ile Arg Val Asp Tyr Thr Phe Thr
    1340            1345                1350

Pro Thr Asp Asn Ile Ser Val Lys Pro Tyr Phe Phe Val Asn Tyr
    1355            1360                1365

Val Asp Val Ser Asn Ala Asn Val Gln Thr Thr Val Asn Ser Thr
    1370            1375                1380

Met Leu Gln Gln Ser Phe Gly Arg Tyr Trp Gln Lys Glu Val Gly
    1385            1390                1395

Leu Lys Ala Glu Ile Leu His Phe Gln Leu Ser Ala Phe Ile Ser
    1400            1405                1410

Lys Ser Gln Gly Ser Gln Leu Gly Lys Gln Gln Asn Val Gly Val
    1415            1420                1425

Lys Leu Gly Tyr Arg Trp
    1430

<210> SEQ ID NO 10
<211> LENGTH: 4605
<212> TYPE: DNA
<213> ORGANISM: Haemophilus influenzae
<220> FEATURE:
<221> NAME/KEY: CDS
<222> LOCATION: (422)..(4597)
<223> OTHER INFORMATION:

<400> SEQUENCE: 10
tggcggcgga caaattattg cgacgggtac accagaacaa gttgctaaag taaaaagttc    60
ccacaccgct cgcttcctta aaccgatttt agaaaaacct tagaaaaaat gaccgcactt   120
tcagagaaaa ctcacataaa gtgcggttat tttattagtg atattgtttt aattttagtt   180
atctgtataa attacataca atattaatcc atcgcaagat tagattaccc actaagtatt   240
aagcaaaaac ctagaaattt tggcttaatt actatatagt tttactcatt tatttctttt   300

-continued

```
tgtgccttttt agttcattttt tttagctgaa atcccttaga aaatcaccgc acttttattg      360
ttcaatagtc gtttaaccac gtatttttta atacgaaaaa ttacttaatt aaataaacat      420 t atg aaa aaa act gta ttt cgt ctg aat ttt tta acc gct tgc att tca      469
  Met Lys Lys Thr Val Phe Arg Leu Asn Phe Leu Thr Ala Cys Ile Ser
  1               5                   10                  15 tta ggg ata gta tcg caa gcg tgg gca ggt cat act tat ttt ggg att       517
Leu Gly Ile Val Ser Gln Ala Trp Ala Gly His Thr Tyr Phe Gly Ile
            20                  25                  30 gac tac caa tat tat cgt gat ttt gcc gag aat aaa ggg aag ttt aca       565
Asp Tyr Gln Tyr Tyr Arg Asp Phe Ala Glu Asn Lys Gly Lys Phe Thr
        35                  40                  45 gtt ggg gct caa gat att gat atc tac aat aaa aaa ggg gaa atg ata       613
Val Gly Ala Gln Asp Ile Asp Ile Tyr Asn Lys Lys Gly Glu Met Ile
50                  55                  60 ggt acg atg atg aaa ggt gtg cct atg cct gat tta tct tcc atg gtt       661
Gly Thr Met Met Lys Gly Val Pro Met Pro Asp Leu Ser Ser Met Val
65                  70                  75                  80 cgt ggt ggt tat tca aca ttg ata agt gag cag cat tta att agc gtc       709
Arg Gly Gly Tyr Ser Thr Leu Ile Ser Glu Gln His Leu Ile Ser Val
                85                  90                  95 gca cat aat gta ggg tat gat gtc gtt gat ttt ggt atg gag ggg gaa       757
Ala His Asn Val Gly Tyr Asp Val Val Asp Phe Gly Met Glu Gly Glu
            100                 105                 110 aat cca gac caa cat cgt ttt aag tat aaa gtt gtt aaa cga tat aat       805
Asn Pro Asp Gln His Arg Phe Lys Tyr Lys Val Val Lys Arg Tyr Asn
        115                 120                 125 tat aag agc ggt gat aga caa tat aat gat tat caa cat cca aga tta       853
Tyr Lys Ser Gly Asp Arg Gln Tyr Asn Asp Tyr Gln His Pro Arg Leu
    130                 135                 140 gag aaa ttt gta acg gaa act gca cct att gaa atg gtt tca tat atg       901
Glu Lys Phe Val Thr Glu Thr Ala Pro Ile Glu Met Val Ser Tyr Met
145                 150                 155                 160 gat ggt aat cat tac aaa aat ttt aat caa tat cct ttg cga gtt aga       949
Asp Gly Asn His Tyr Lys Asn Phe Asn Gln Tyr Pro Leu Arg Val Arg
                165                 170                 175 gtt gga agt ggg cat caa tgg tgg aaa gac gat aat aat aaa acc att       997
Val Gly Ser Gly His Gln Trp Trp Lys Asp Asp Asn Asn Lys Thr Ile
            180                 185                 190 gga gac tta gcc tat gga ggt tca tgg tta ata ggt gga aat acc ttt      1045
Gly Asp Leu Ala Tyr Gly Gly Ser Trp Leu Ile Gly Gly Asn Thr Phe
        195                 200                 205 gaa gat gga cca gct ggt aac ggt aca tta gaa tta aat ggg cga gta      1093
Glu Asp Gly Pro Ala Gly Asn Gly Thr Leu Glu Leu Asn Gly Arg Val
    210                 215                 220 caa aat cct aat aaa tat ggt cca cta cct acg gca ggt tca ttc ggg      1141
Gln Asn Pro Asn Lys Tyr Gly Pro Leu Pro Thr Ala Gly Ser Phe Gly
225                 230                 235                 240 gat agt ggt tct cca atg ttt att tat gat aag gaa gtt aag aaa tgg      1189
Asp Ser Gly Ser Pro Met Phe Ile Tyr Asp Lys Glu Val Lys Lys Trp
                245                 250                 255 tta tta aat ggc gtg tta cgt gaa gga aat cct tat gct gca gta gga      1237
Leu Leu Asn Gly Val Leu Arg Glu Gly Asn Pro Tyr Ala Ala Val Gly
            260                 265                 270 aac agc tat caa att aca cga aaa gat tat ttt caa ggt att ctt aat      1285
Asn Ser Tyr Gln Ile Thr Arg Lys Asp Tyr Phe Gln Gly Ile Leu Asn
        275                 280                 285 caa gac att aca gct aat ttt tgg gat act aat gct gaa tat aga ttt      1333
Gln Asp Ile Thr Ala Asn Phe Trp Asp Thr Asn Ala Glu Tyr Arg Phe
    290                 295                 300
```

```
aat ata ggg agt gac cac aat gga aga gtg gca aca atc aaa agt aca    1381
Asn Ile Gly Ser Asp His Asn Gly Arg Val Ala Thr Ile Lys Ser Thr
305                 310                 315                 320 tta cct aaa aaa gct att cag cct gaa cga ata gtg ggt ctt tat gat    1429
Leu Pro Lys Lys Ala Ile Gln Pro Glu Arg Ile Val Gly Leu Tyr Asp
            325                 330                 335 aat agc caa ctt cat gat gct aga gat aaa aat ggc gat gaa tct ccc    1477
Asn Ser Gln Leu His Asp Ala Arg Asp Lys Asn Gly Asp Glu Ser Pro
        340                 345                 350 tct tat aaa ggt cct aat cca tgg tcg cca gca tta cat cat ggg aaa    1525
Ser Tyr Lys Gly Pro Asn Pro Trp Ser Pro Ala Leu His His Gly Lys
    355                 360                 365 agt att tac ttt ggc gat caa gga aca gga act tta aca att gaa aat    1573
Ser Ile Tyr Phe Gly Asp Gln Gly Thr Gly Thr Leu Thr Ile Glu Asn
370                 375                 380 aat ata aat caa ggt gca ggt gga ttg tat ttt gaa ggt aat ttt gtt    1621
Asn Ile Asn Gln Gly Ala Gly Gly Leu Tyr Phe Glu Gly Asn Phe Val
385                 390                 395                 400 gta aaa ggc aat caa aat aat ata act tgg caa ggt gca ggc gtt tct    1669
Val Lys Gly Asn Gln Asn Asn Ile Thr Trp Gln Gly Ala Gly Val Ser
            405                 410                 415 gtt gga gaa gaa agt act gtt gaa tgg cag gtg cat aat cca gaa ggc    1717
Val Gly Glu Glu Ser Thr Val Glu Trp Gln Val His Asn Pro Glu Gly
        420                 425                 430 gat cgc tta tcc aaa att ggg ctg gga acc tta ctt gtt aat ggt aaa    1765
Asp Arg Leu Ser Lys Ile Gly Leu Gly Thr Leu Leu Val Asn Gly Lys
    435                 440                 445 ggg aaa aac tta gga agc ctg agt gtc ggt aac ggt ttg gtt gtg tta    1813
Gly Lys Asn Leu Gly Ser Leu Ser Val Gly Asn Gly Leu Val Val Leu
450                 455                 460 gat caa caa gca gat gaa tca ggt caa aaa caa gcc ttt aaa gaa gtt    1861
Asp Gln Gln Ala Asp Glu Ser Gly Gln Lys Gln Ala Phe Lys Glu Val
465                 470                 475                 480 ggc att gta agt ggt aga gct acc gtt caa cta aat agt gca gat caa    1909
Gly Ile Val Ser Gly Arg Ala Thr Val Gln Leu Asn Ser Ala Asp Gln
            485                 490                 495 gtt gat cct aac aat att tat ttc ggc ttt cgt ggt ggt cgc tta gat    1957
Val Asp Pro Asn Asn Ile Tyr Phe Gly Phe Arg Gly Gly Arg Leu Asp
        500                 505                 510 ctt aat ggg cat tca tta acc ttt gaa cgt atc caa aat acg gat gaa    2005
Leu Asn Gly His Ser Leu Thr Phe Glu Arg Ile Gln Asn Thr Asp Glu
    515                 520                 525 ggc gcg atg att gtg aac cac aac gct tct caa acc gca aat att acg    2053
Gly Ala Met Ile Val Asn His Asn Ala Ser Gln Thr Ala Asn Ile Thr
530                 535                 540 att aca ggc aac gca act att aat tca gat agc aaa caa ctt act aat    2101
Ile Thr Gly Asn Ala Thr Ile Asn Ser Asp Ser Lys Gln Leu Thr Asn
545                 550                 555                 560 aaa aaa gat att gca ttt aac ggc tgg ttt ggt gag caa gat aaa gct    2149
Lys Lys Asp Ile Ala Phe Asn Gly Trp Phe Gly Glu Gln Asp Lys Ala
            565                 570                 575 aaa aca aat ggt cgt tta aat gtg aat tat caa cca gtt aat gca gaa    2197
Lys Thr Asn Gly Arg Leu Asn Val Asn Tyr Gln Pro Val Asn Ala Glu
        580                 585                 590 aat cat ttg ttg ctt tct ggg ggg aca aat tta aac ggc aat atc acg    2245
Asn His Leu Leu Leu Ser Gly Gly Thr Asn Leu Asn Gly Asn Ile Thr
    595                 600                 605 caa aat ggt ggt acg tta gtt ttt agt ggt cgt cca acg cct cat gct    2293
Gln Asn Gly Gly Thr Leu Val Phe Ser Gly Arg Pro Thr Pro His Ala
610                 615                 620
```

```
                            -continued tac aat cat tta aga aga gac ttg tct aac atg gaa ggt atc cca caa      2341
Tyr Asn His Leu Arg Arg Asp Leu Ser Asn Met Glu Gly Ile Pro Gln
625             630             635             640 ggc gaa att gtg tgg gat cac gat tgg atc aac cgc aca ttt aaa gct      2389
Gly Glu Ile Val Trp Asp His Asp Trp Ile Asn Arg Thr Phe Lys Ala
            645             650             655 gaa aac ttc caa att aaa ggc gga agt gcg gtg gtt tct cgc aat gtt      2437
Glu Asn Phe Gln Ile Lys Gly Gly Ser Ala Val Val Ser Arg Asn Val
        660             665             670 tct tca att gag gga aat tgg aca gtc agc aat aat gca aat gcc aca      2485
Ser Ser Ile Glu Gly Asn Trp Thr Val Ser Asn Asn Ala Asn Ala Thr
    675             680             685 ttt ggt gtt gtg cca aat cag caa aat acc att tgc acg cgt tca gat      2533
Phe Gly Val Val Pro Asn Gln Gln Asn Thr Ile Cys Thr Arg Ser Asp
690             695             700 tgg aca gga tta acg act tgt aaa aca gtt gat tta acc gat aaa aaa      2581
Trp Thr Gly Leu Thr Thr Cys Lys Thr Val Asp Leu Thr Asp Lys Lys
705             710             715             720 gtt att aat tcc ata ccg aca aca caa att aat ggt tct att aat tta      2629
Val Ile Asn Ser Ile Pro Thr Thr Gln Ile Asn Gly Ser Ile Asn Leu
            725             730             735 act gat aat gca aca gtg aat att cat ggt tta gca aaa ctt aat ggt      2677
Thr Asp Asn Ala Thr Val Asn Ile His Gly Leu Ala Lys Leu Asn Gly
        740             745             750 aat gtc act tta ata gat cac agc caa ttt aca ttg agc aac aat gcc      2725
Asn Val Thr Leu Ile Asp His Ser Gln Phe Thr Leu Ser Asn Asn Ala
    755             760             765 acc caa aca ggc aat atc aaa ctt tca aat cac gca aat gca acg gtg      2773
Thr Gln Thr Gly Asn Ile Lys Leu Ser Asn His Ala Asn Ala Thr Val
770             775             780 gac aat gca aat ttg aac ggt aat gtg aat tta atg gat tct gct caa      2821
Asp Asn Ala Asn Leu Asn Gly Asn Val Asn Leu Met Asp Ser Ala Gln
785             790             795             800 ttt tct tta aaa aac agc cat ttt tcg cac caa atc caa ggt ggg gaa      2869
Phe Ser Leu Lys Asn Ser His Phe Ser His Gln Ile Gln Gly Gly Glu
            805             810             815 gac aca aca gtg atg ttg gaa aat gcg act tgg aca atg cct agc gat      2917
Asp Thr Thr Val Met Leu Glu Asn Ala Thr Trp Thr Met Pro Ser Asp
        820             825             830 acc aca ttg cag aat tta acg cta aat aat agt act gtt acg tta aat      2965
Thr Thr Leu Gln Asn Leu Thr Leu Asn Asn Ser Thr Val Thr Leu Asn
    835             840             845 tca gct tat tca gct atc tca aat aat gcg cca cgc cgt cgc cgc cgt      3013
Ser Ala Tyr Ser Ala Ile Ser Asn Asn Ala Pro Arg Arg Arg Arg Arg
850             855             860 tca tta gag acg gaa aca acg cca aca tcg gca gaa cat cgt ttc aac      3061
Ser Leu Glu Thr Glu Thr Thr Pro Thr Ser Ala Glu His Arg Phe Asn
865             870             875             880 aca ttg aca gta aat ggt aaa ttg agc ggg caa ggc aca ttc caa ttt      3109
Thr Leu Thr Val Asn Gly Lys Leu Ser Gly Gln Gly Thr Phe Gln Phe
            885             890             895 act tca tct tta ttt ggc tat aaa agc gat aaa tta aaa tta tcc aat      3157
Thr Ser Ser Leu Phe Gly Tyr Lys Ser Asp Lys Leu Lys Leu Ser Asn
        900             905             910 gac gct gag ggc gat tac aca tta tct gtt cgc aac aca ggc aaa gaa      3205
Asp Ala Glu Gly Asp Tyr Thr Leu Ser Val Arg Asn Thr Gly Lys Glu
    915             920             925 ccc gtg acc ttt ggg caa tta act ttg gtt gaa agc aaa gat aat aaa      3253
Pro Val Thr Phe Gly Gln Leu Thr Leu Val Glu Ser Lys Asp Asn Lys
930             935             940
```

```
ccg tta tca gac aaa ctc aca ttc acg tta gaa aat gac cac gtt gat      3301
Pro Leu Ser Asp Lys Leu Thr Phe Thr Leu Glu Asn Asp His Val Asp
945                 950                 955                 960 gca ggt gca tta cgt tat aaa tta gtg aag aat gat ggc gaa ttc cgc      3349
Ala Gly Ala Leu Arg Tyr Lys Leu Val Lys Asn Asp Gly Glu Phe Arg
            965                 970                 975 tta cat aac cca ata aaa gag cag gaa ttg cgc tct gat tta gta aga      3397
Leu His Asn Pro Ile Lys Glu Gln Glu Leu Arg Ser Asp Leu Val Arg
                980                 985                 990 gca gag caa gca gaa cga aca tta gaa gcc aaa caa gtt gaa cag act      3445
Ala Glu Gln Ala Glu Arg Thr Leu Glu Ala Lys Gln Val Glu Gln Thr
            995                 1000                1005 gct aaa aca caa aca agt aag gca aga gtg cgg tca aga aga gcg          3490
Ala Lys Thr Gln Thr Ser Lys Ala Arg Val Arg Ser Arg Arg Ala
    1010                1015                1020 gtg ttt tct gat ccc ctg cct gct caa agc ctg tta aaa gca tta          3535
Val Phe Ser Asp Pro Leu Pro Ala Gln Ser Leu Leu Lys Ala Leu
    1025                1030                1035 gaa gcc aaa caa gct ctg act act gaa aca caa aca agt aag gca          3580
Glu Ala Lys Gln Ala Leu Thr Thr Glu Thr Gln Thr Ser Lys Ala
    1040                1045                1050 aaa aaa gtg cgg tca aaa aga gct gcg aga gag ttt tct gat acc          3625
Lys Lys Val Arg Ser Lys Arg Ala Ala Arg Glu Phe Ser Asp Thr
    1055                1060                1065 ctg cct gat caa ata tta caa gcc gca ctt gag gtt att gat gcc          3670
Leu Pro Asp Gln Ile Leu Gln Ala Ala Leu Glu Val Ile Asp Ala
    1070                1075                1080 caa cag caa gtg aaa aaa gaa cct caa act caa gag gaa gaa gag          3715
Gln Gln Gln Val Lys Lys Glu Pro Gln Thr Gln Glu Glu Glu Glu
    1085                1090                1095 aaa aga caa cgc aaa caa aaa gaa ttg atc agc cgt tac tca aat          3760
Lys Arg Gln Arg Lys Gln Lys Glu Leu Ile Ser Arg Tyr Ser Asn
    1100                1105                1110 agt gcg tta tcg gag ttg tct gcg aca gta aat agt atg ctt tcc          3805
Ser Ala Leu Ser Glu Leu Ser Ala Thr Val Asn Ser Met Leu Ser
    1115                1120                1125 gtt caa gat gaa ttg gat cgt ctt ttt gta gat caa gca caa tct          3850
Val Gln Asp Glu Leu Asp Arg Leu Phe Val Asp Gln Ala Gln Ser
    1130                1135                1140 gcc gtg tgg aca aat atc gca cag gat aaa aga cgc tat gat tct          3895
Ala Val Trp Thr Asn Ile Ala Gln Asp Lys Arg Arg Tyr Asp Ser
    1145                1150                1155 gat gcg ttc cgt gct tat cag cag aaa acg aac ttg cgt caa att          3940
Asp Ala Phe Arg Ala Tyr Gln Gln Lys Thr Asn Leu Arg Gln Ile
    1160                1165                1170 ggg gtg caa aaa gcc tta gat aat gga cga att ggg gcg gtt ttc          3985
Gly Val Gln Lys Ala Leu Asp Asn Gly Arg Ile Gly Ala Val Phe
    1175                1180                1185 tcg cat agc cgt tca gat aat acc ttt gac gaa cag gtt aaa aat          4030
Ser His Ser Arg Ser Asp Asn Thr Phe Asp Glu Gln Val Lys Asn
    1190                1195                1200 cac gcg aca tta gcg atg atg tcg ggt ttt gcc caa tat caa tgg          4075
His Ala Thr Leu Ala Met Met Ser Gly Phe Ala Gln Tyr Gln Trp
    1205                1210                1215 ggc gat tta caa ttt ggt gta aac gtg ggt gcg gga att agt gcg          4120
Gly Asp Leu Gln Phe Gly Val Asn Val Gly Ala Gly Ile Ser Ala
    1220                1225                1230 agt aaa atg gct gaa gaa caa agc cga aaa att cat cga aaa gcg          4165
Ser Lys Met Ala Glu Glu Gln Ser Arg Lys Ile His Arg Lys Ala
    1235                1240                1245
```

-continued

| | | | | | | | | | | |
|---|---|---|---|---|---|---|---|---|---|---|
| ata | aat | tat | ggt | gtg | aat | gca | agt | tat | cag | ttc | cgt | tta | ggg | caa | 4210 |
| Ile | Asn | Tyr | Gly | Val | Asn | Ala | Ser | Tyr | Gln | Phe | Arg | Leu | Gly | Gln | |
| | | 1250 | | | | 1255 | | | | 1260 | | | | | |

```
ata aat tat ggt gtg aat gca agt tat cag ttc cgt tta ggg caa      4210
Ile Asn Tyr Gly Val Asn Ala Ser Tyr Gln Phe Arg Leu Gly Gln
    1250                1255                1260 ttg ggt att cag cct tat ttg ggt gtt aat cga tat ttt att gaa      4255
Leu Gly Ile Gln Pro Tyr Leu Gly Val Asn Arg Tyr Phe Ile Glu
    1265                1270                1275 cgt gaa aat tat caa tct gaa gaa gtg aaa gtg caa aca ccg agc      4300
Arg Glu Asn Tyr Gln Ser Glu Glu Val Lys Val Gln Thr Pro Ser
    1280                1285                1290 ctt gta ttt aat cgc tat aat gct ggc att cga gtt gat tat aca      4345
Leu Val Phe Asn Arg Tyr Asn Ala Gly Ile Arg Val Asp Tyr Thr
    1295                1300                1305 ttt acc ccg aca gat aat atc agc att aag cct tat ttc ttc gtc      4390
Phe Thr Pro Thr Asp Asn Ile Ser Ile Lys Pro Tyr Phe Phe Val
    1310                1315                1320 aat tat gtt gat gtt tca aac gct aac gta caa acc act gta aat      4435
Asn Tyr Val Asp Val Ser Asn Ala Asn Val Gln Thr Thr Val Asn
    1325                1330                1335 cgc acg atg ttg caa caa tca ttt ggg cgt tat tgg caa aaa gaa      4480
Arg Thr Met Leu Gln Gln Ser Phe Gly Arg Tyr Trp Gln Lys Glu
    1340                1345                1350 gtg gga tta aag gca gaa att tta cat ttc caa ctt tcc gct ttt      4525
Val Gly Leu Lys Ala Glu Ile Leu His Phe Gln Leu Ser Ala Phe
    1355                1360                1365 atc tca aaa tct caa ggt caa caa ctc ggc aaa cag caa aat gtg      4570
Ile Ser Lys Ser Gln Gly Gln Gln Leu Gly Lys Gln Gln Asn Val
    1370                1375                1380 ggc gtg aaa ttg ggg tat cgt tgg taa aaatcaac                     4605
Gly Val Lys Leu Gly Tyr Arg Trp
    1385                1390
```

<210> SEQ ID NO 11
<211> LENGTH: 1391
<212> TYPE: PRT
<213> ORGANISM: Haemophilus influenzae

<400> SEQUENCE: 11

```
Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
                20                  25                  30

Asp Tyr Gln Tyr Tyr Arg Asp Phe Ala Glu Asn Lys Gly Lys Phe Thr
            35                  40                  45

Val Gly Ala Gln Asp Ile Asp Ile Tyr Asn Lys Lys Gly Glu Met Ile
        50                  55                  60

Gly Thr Met Met Lys Gly Val Pro Met Pro Asp Leu Ser Ser Met Val
65                  70                  75                  80

Arg Gly Gly Tyr Ser Thr Leu Ile Ser Glu Gln His Leu Ile Ser Val
                85                  90                  95

Ala His Asn Val Gly Tyr Asp Val Val Asp Phe Gly Met Glu Gly Glu
            100                 105                 110

Asn Pro Asp Gln His Arg Phe Lys Tyr Lys Val Val Lys Arg Tyr Asn
        115                 120                 125

Tyr Lys Ser Gly Asp Arg Gln Tyr Asn Asp Tyr Gln His Pro Arg Leu
    130                 135                 140

Glu Lys Phe Val Thr Glu Thr Ala Pro Ile Glu Met Val Ser Tyr Met
145                 150                 155                 160
```

-continued

```
Asp Gly Asn His Tyr Lys Asn Phe Asn Gln Tyr Pro Leu Arg Val Arg
            165                 170                 175

Val Gly Ser Gly His Gln Trp Trp Lys Asp Asn Asn Lys Thr Ile
        180                 185                 190

Gly Asp Leu Ala Tyr Gly Gly Ser Trp Leu Ile Gly Asn Thr Phe
        195                 200                 205

Glu Asp Gly Pro Ala Gly Asn Gly Thr Leu Glu Leu Asn Gly Arg Val
    210                 215                 220

Gln Asn Pro Asn Lys Tyr Gly Pro Leu Pro Thr Ala Gly Ser Phe Gly
225                 230                 235                 240

Asp Ser Gly Ser Pro Met Phe Ile Tyr Asp Lys Glu Val Lys Lys Trp
                245                 250                 255

Leu Leu Asn Gly Val Leu Arg Glu Gly Asn Pro Tyr Ala Ala Val Gly
            260                 265                 270

Asn Ser Tyr Gln Ile Thr Arg Lys Asp Tyr Phe Gln Gly Ile Leu Asn
        275                 280                 285

Gln Asp Ile Thr Ala Asn Phe Trp Asp Thr Asn Ala Glu Tyr Arg Phe
    290                 295                 300

Asn Ile Gly Ser Asp His Asn Gly Arg Val Ala Thr Ile Lys Ser Thr
305                 310                 315                 320

Leu Pro Lys Lys Ala Ile Gln Pro Glu Arg Ile Val Gly Leu Tyr Asp
                325                 330                 335

Asn Ser Gln Leu His Asp Ala Arg Asp Lys Asn Gly Asp Glu Ser Pro
            340                 345                 350

Ser Tyr Lys Gly Pro Asn Pro Trp Ser Pro Ala Leu His His Gly Lys
        355                 360                 365

Ser Ile Tyr Phe Gly Asp Gln Gly Thr Gly Thr Leu Thr Ile Glu Asn
    370                 375                 380

Asn Ile Asn Gln Gly Ala Gly Gly Leu Tyr Phe Glu Gly Asn Phe Val
385                 390                 395                 400

Val Lys Gly Asn Gln Asn Asn Ile Thr Trp Gln Gly Ala Gly Val Ser
                405                 410                 415

Val Gly Glu Glu Ser Thr Val Glu Trp Gln Val His Asn Pro Glu Gly
            420                 425                 430

Asp Arg Leu Ser Lys Ile Gly Leu Gly Thr Leu Leu Val Asn Gly Lys
        435                 440                 445

Gly Lys Asn Leu Gly Ser Leu Ser Val Gly Asn Gly Leu Val Val Leu
    450                 455                 460

Asp Gln Gln Ala Asp Glu Ser Gly Gln Lys Gln Ala Phe Lys Glu Val
465                 470                 475                 480

Gly Ile Val Ser Gly Arg Ala Thr Val Gln Leu Asn Ser Ala Asp Gln
                485                 490                 495

Val Asp Pro Asn Asn Ile Tyr Phe Gly Phe Arg Gly Gly Arg Leu Asp
            500                 505                 510

Leu Asn Gly His Ser Leu Thr Phe Glu Arg Ile Gln Asn Thr Asp Glu
        515                 520                 525

Gly Ala Met Ile Val Asn His Asn Ala Ser Gln Thr Ala Asn Ile Thr
    530                 535                 540

Ile Thr Gly Asn Ala Thr Ile Asn Ser Asp Ser Lys Gln Leu Thr Asn
545                 550                 555                 560

Lys Lys Asp Ile Ala Phe Asn Gly Trp Phe Gly Glu Gln Asp Lys Ala
                565                 570                 575
```

-continued

```
Lys Thr Asn Gly Arg Leu Asn Val Asn Tyr Gln Pro Val Asn Ala Glu
            580                 585                 590

Asn His Leu Leu Leu Ser Gly Gly Thr Asn Leu Asn Gly Asn Ile Thr
            595                 600                 605

Gln Asn Gly Gly Thr Leu Val Phe Ser Gly Arg Pro Thr Pro His Ala
            610                 615                 620

Tyr Asn His Leu Arg Arg Asp Leu Ser Asn Met Glu Gly Ile Pro Gln
625                 630                 635                 640

Gly Glu Ile Val Trp Asp His Asp Trp Ile Asn Arg Thr Phe Lys Ala
                    645                 650                 655

Glu Asn Phe Gln Ile Lys Gly Gly Ser Ala Val Val Ser Arg Asn Val
            660                 665                 670

Ser Ser Ile Glu Gly Asn Trp Thr Val Ser Asn Asn Ala Asn Ala Thr
            675                 680                 685

Phe Gly Val Val Pro Asn Gln Gln Asn Thr Ile Cys Thr Arg Ser Asp
            690                 695                 700

Trp Thr Gly Leu Thr Thr Cys Lys Thr Val Asp Leu Thr Asp Lys Lys
705                 710                 715                 720

Val Ile Asn Ser Ile Pro Thr Thr Gln Ile Asn Gly Ser Ile Asn Leu
                    725                 730                 735

Thr Asp Asn Ala Thr Val Asn Ile His Gly Leu Ala Lys Leu Asn Gly
            740                 745                 750

Asn Val Thr Leu Ile Asp His Ser Gln Phe Thr Leu Ser Asn Asn Ala
            755                 760                 765

Thr Gln Thr Gly Asn Ile Lys Leu Ser Asn His Ala Asn Ala Thr Val
            770                 775                 780

Asp Asn Ala Asn Leu Asn Gly Asn Val Asn Leu Met Asp Ser Ala Gln
785                 790                 795                 800

Phe Ser Leu Lys Asn Ser His Phe Ser His Gln Ile Gln Gly Gly Glu
                    805                 810                 815

Asp Thr Thr Val Met Leu Glu Asn Ala Thr Trp Thr Met Pro Ser Asp
            820                 825                 830

Thr Thr Leu Gln Asn Leu Thr Leu Asn Asn Ser Thr Val Thr Leu Asn
            835                 840                 845

Ser Ala Tyr Ser Ala Ile Ser Asn Asn Ala Pro Arg Arg Arg Arg Arg
850                 855                 860

Ser Leu Glu Thr Glu Thr Thr Pro Thr Ser Ala Glu His Arg Phe Asn
865                 870                 875                 880

Thr Leu Thr Val Asn Gly Lys Leu Ser Gly Gln Gly Thr Phe Gln Phe
                    885                 890                 895

Thr Ser Ser Leu Phe Gly Tyr Lys Ser Asp Lys Leu Lys Leu Ser Asn
            900                 905                 910

Asp Ala Glu Gly Asp Tyr Thr Leu Ser Val Arg Asn Thr Gly Lys Glu
            915                 920                 925

Pro Val Thr Phe Gly Gln Leu Thr Leu Val Glu Ser Lys Asp Asn Lys
            930                 935                 940

Pro Leu Ser Asp Lys Leu Thr Phe Thr Leu Glu Asn Asp His Val Asp
945                 950                 955                 960

Ala Gly Ala Leu Arg Tyr Lys Leu Val Lys Asn Asp Gly Glu Phe Arg
                    965                 970                 975

Leu His Asn Pro Ile Lys Glu Gln Glu Leu Arg Ser Asp Leu Val Arg
            980                 985                 990
```

-continued

Ala Glu Gln Ala Glu Arg Thr Leu Glu Ala Lys Gln Val Glu Gln Thr
        995                 1000                1005

Ala Lys Thr Gln Thr Ser Lys Ala Arg Val Arg Ser Arg Arg Ala
        1010                1015                1020

Val Phe Ser Asp Pro Leu Pro Ala Gln Ser Leu Leu Lys Ala Leu
        1025                1030                1035

Glu Ala Lys Gln Ala Leu Thr Thr Glu Thr Gln Thr Ser Lys Ala
        1040                1045                1050

Lys Lys Val Arg Ser Lys Arg Ala Ala Arg Glu Phe Ser Asp Thr
        1055                1060                1065

Leu Pro Asp Gln Ile Leu Gln Ala Ala Leu Glu Val Ile Asp Ala
        1070                1075                1080

Gln Gln Gln Val Lys Lys Glu Pro Gln Thr Gln Glu Glu Glu
        1085                1090                1095

Lys Arg Gln Arg Lys Gln Lys Glu Leu Ile Ser Arg Tyr Ser Asn
        1100                1105                1110

Ser Ala Leu Ser Glu Leu Ser Ala Thr Val Asn Ser Met Leu Ser
        1115                1120                1125

Val Gln Asp Glu Leu Asp Arg Leu Phe Val Asp Gln Ala Gln Ser
        1130                1135                1140

Ala Val Trp Thr Asn Ile Ala Gln Asp Lys Arg Arg Tyr Asp Ser
        1145                1150                1155

Asp Ala Phe Arg Ala Tyr Gln Lys Thr Asn Leu Arg Gln Ile
        1160                1165                1170

Gly Val Gln Lys Ala Leu Asp Asn Gly Arg Ile Gly Ala Val Phe
        1175                1180                1185

Ser His Ser Arg Ser Asp Asn Thr Phe Asp Glu Gln Val Lys Asn
        1190                1195                1200

His Ala Thr Leu Ala Met Met Ser Gly Phe Ala Gln Tyr Gln Trp
        1205                1210                1215

Gly Asp Leu Gln Phe Gly Val Asn Val Gly Ala Gly Ile Ser Ala
        1220                1225                1230

Ser Lys Met Ala Glu Glu Gln Ser Arg Lys Ile His Arg Lys Ala
        1235                1240                1245

Ile Asn Tyr Gly Val Asn Ala Ser Tyr Gln Phe Arg Leu Gly Gln
        1250                1255                1260

Leu Gly Ile Gln Pro Tyr Leu Gly Val Asn Arg Tyr Phe Ile Glu
        1265                1270                1275

Arg Glu Asn Tyr Gln Ser Glu Glu Val Lys Val Gln Thr Pro Ser
        1280                1285                1290

Leu Val Phe Asn Arg Tyr Asn Ala Gly Ile Arg Val Asp Tyr Thr
        1295                1300                1305

Phe Thr Pro Thr Asp Asn Ile Ser Ile Lys Pro Tyr Phe Phe Val
        1310                1315                1320

Asn Tyr Val Asp Val Ser Asn Ala Asn Val Gln Thr Thr Val Asn
        1325                1330                1335

Arg Thr Met Leu Gln Gln Ser Phe Gly Arg Tyr Trp Gln Lys Glu
        1340                1345                1350

Val Gly Leu Lys Ala Glu Ile Leu His Phe Gln Leu Ser Ala Phe
        1355                1360                1365

```
Ile Ser Lys Ser Gln Gly Ser  Gln Leu Gly Lys Gln  Gln Asn Val
    1370            1375              1380

Gly Val Lys Leu Gly Tyr Arg  Trp
    1385            1390

<210> SEQ ID NO 12
<211> LENGTH: 5245
<212> TYPE: DNA
<213> ORGANISM: Haemophilus influenzae
<220> FEATURE:
<221> NAME/KEY: CDS
<222> LOCATION: (430)..(4740)
<223> OTHER INFORMATION:

<400> SEQUENCE: 12
ggaggcagtg gtggcggaca aattattgcg acgggtacgc cagaacaagt tgccaaagta      60
gaaagttccc acaccgcccg cttccttaaa ccgattttag aaaaacctta gaaaaaatga     120
ccgcactttc agagaaaact cacataaagt gcggttattt tattagtgat attgttttaa     180
ttttagttat ctgtataaat tacatataat attaatccat cgcaagataa gattacccac     240
taagtattaa gcaaaaacct agaaattttg gcttaattac tatatagttt tactgcttta     300
ttttcttttg tgccttttag ttcgtttttt tagctgaaat cccttagaaa atcaccgcac     360
ttttattgtt caatagtcgt ttaaccacgt atttttttaat acgaaaaatt acttaattaa    420 ataaacatt atg aaa aaa act gta ttt cgt ctg aac ttt tta acc gct tgc    471
          Met Lys Lys Thr Val Phe Arg Leu Asn Phe Leu Thr Ala Cys
              1               5                   10 att tca tta ggg ata gta tcg caa gcg tgg gca ggt cac act tat ttt       519
Ile Ser Leu Gly Ile Val Ser Gln Ala Trp Ala Gly His Thr Tyr Phe
15                  20                  25                  30 ggg att gac tac caa tat tat cgt gat ttt gct gag aat aaa ggg aag       567
Gly Ile Asp Tyr Gln Tyr Tyr Arg Asp Phe Ala Glu Asn Lys Gly Lys
                35                  40                  45 ttt tca gtt ggg gct aaa aat att gag gtt tat aac aaa gag ggg act       615
Phe Ser Val Gly Ala Lys Asn Ile Glu Val Tyr Asn Lys Glu Gly Thr
            50                  55                  60 tta gtt ggc aca tca atg aca aaa gcc ccg atg att gat ttt tct gtg       663
Leu Val Gly Thr Ser Met Thr Lys Ala Pro Met Ile Asp Phe Ser Val
        65                  70                  75 gtg tcg cga aat ggg gtg gcg gca tta gta ggc gat cag tat att gtg       711
Val Ser Arg Asn Gly Val Ala Ala Leu Val Gly Asp Gln Tyr Ile Val
    80                  85                  90 agt gtg gca cat aac ggt gga tat aat agc gtt gat ttt gga gca gaa       759
Ser Val Ala His Asn Gly Gly Tyr Asn Ser Val Asp Phe Gly Ala Glu
95                  100                 105                 110 ggt cca aat ccc gat cag cat cgt ttt act tat caa att gta aaa aga       807
Gly Pro Asn Pro Asp Gln His Arg Phe Thr Tyr Gln Ile Val Lys Arg
                115                 120                 125 aat aat tat aag cca ggc aaa gat aac cct tat cat ggt gac tat cac       855
Asn Asn Tyr Lys Pro Gly Lys Asp Asn Pro Tyr His Gly Asp Tyr His
            130                 135                 140 atg cct cgt ttg cac aaa ttt gtc act gac gct gaa cca gca aag atg       903
Met Pro Arg Leu His Lys Phe Val Thr Asp Ala Glu Pro Ala Lys Met
        145                 150                 155 aca gac aat atg aat gga aag aac tac gct gat tta agt aaa tat cct       951
Thr Asp Asn Met Asn Gly Lys Asn Tyr Ala Asp Leu Ser Lys Tyr Pro
    160                 165                 170 gat cgt gtg cgt att ggt aca ggt gaa caa tgg tgg agg act gat gaa       999
Asp Arg Val Arg Ile Gly Thr Gly Glu Gln Trp Trp Arg Thr Asp Glu
175                 180                 185                 190
```

```
                                                                    -continued gaa caa aag caa gga agt aag agt tca tgg ctt gct gat gct tat ctg       1047
Glu Gln Lys Gln Gly Ser Lys Ser Ser Trp Leu Ala Asp Ala Tyr Leu
            195                 200                 205 tgg aga ata gca ggt aac aca cat tca caa agt gga gcg ggc aac ggc       1095
Trp Arg Ile Ala Gly Asn Thr His Ser Gln Ser Gly Ala Gly Asn Gly
            210                 215                 220 acg gta aac tta agt gga gat atc aca aaa cca aat aac tat gga cct       1143
Thr Val Asn Leu Ser Gly Asp Ile Thr Lys Pro Asn Asn Tyr Gly Pro
            225                 230                 235 ctt cct acg ggt gtt tcg ttt gga gat agt ggt tct cca atg ttt att       1191
Leu Pro Thr Gly Val Ser Phe Gly Asp Ser Gly Ser Pro Met Phe Ile
        240                 245                 250 tat gat gca ata aaa caa aaa tgg ctt att aat ggc gta ttg caa act       1239
Tyr Asp Ala Ile Lys Gln Lys Trp Leu Ile Asn Gly Val Leu Gln Thr
255                 260                 265                 270 ggt aac cct ttc tcg gga gct gga aat gga ttc caa tta att aga aaa       1287
Gly Asn Pro Phe Ser Gly Ala Gly Asn Gly Phe Gln Leu Ile Arg Lys
                275                 280                 285 aat tgg ttt tat gat aat gtc ttt gta gaa gat ttg cct ata aca ttt       1335
Asn Trp Phe Tyr Asp Asn Val Phe Val Glu Asp Leu Pro Ile Thr Phe
            290                 295                 300 tta gag cca aga agt aac ggt cat tat tca ttt act tca aat aat aat       1383
Leu Glu Pro Arg Ser Asn Gly His Tyr Ser Phe Thr Ser Asn Asn Asn
        305                 310                 315 gga act ggt acg gtt act caa acg aat gaa aaa gtg agt atg cct caa       1431
Gly Thr Gly Thr Val Thr Gln Thr Asn Glu Lys Val Ser Met Pro Gln
    320                 325                 330 ttt aaa gtc aga acg gtt cag tta ttt aat gaa gca tta aaa gaa aaa       1479
Phe Lys Val Arg Thr Val Gln Leu Phe Asn Glu Ala Leu Lys Glu Lys
335                 340                 345                 350 gat aaa gaa cct gtt tat gct gca ggt ggt gta aat gct tat aaa cca       1527
Asp Lys Glu Pro Val Tyr Ala Ala Gly Gly Val Asn Ala Tyr Lys Pro
                355                 360                 365 aga cta aat aat ggt aaa aat att tac ttt ggc gat cga gga aca gga       1575
Arg Leu Asn Asn Gly Lys Asn Ile Tyr Phe Gly Asp Arg Gly Thr Gly
            370                 375                 380 act tta aca att gaa aat aat ata aat caa ggt gct ggt ggt ttg tat       1623
Thr Leu Thr Ile Glu Asn Asn Ile Asn Gln Gly Ala Gly Gly Leu Tyr
        385                 390                 395 ttt gag ggt aac ttt acg gta tct tca gaa aat aat gca act tgg caa       1671
Phe Glu Gly Asn Phe Thr Val Ser Ser Glu Asn Asn Ala Thr Trp Gln
    400                 405                 410 ggt gct gga gtg cat gta ggt gaa gac agt act gtt act tgg aaa gta       1719
Gly Ala Gly Val His Val Gly Glu Asp Ser Thr Val Thr Trp Lys Val
415                 420                 425                 430 aac ggc gtg gaa cat gat cgc ctt tct aaa att ggt aaa gga acg ttg       1767
Asn Gly Val Glu His Asp Arg Leu Ser Lys Ile Gly Lys Gly Thr Leu
                435                 440                 445 cat att caa gca aaa ggt gaa aac tta ggc tca att agc gta ggt gac       1815
His Ile Gln Ala Lys Gly Glu Asn Leu Gly Ser Ile Ser Val Gly Asp
            450                 455                 460 ggc aaa gtc att tta gat caa caa gcc gat gag aac aac caa aaa caa       1863
Gly Lys Val Ile Leu Asp Gln Gln Ala Asp Glu Asn Asn Gln Lys Gln
        465                 470                 475 gcc ttt aaa gaa gtt ggc att gta agt ggt aga gct acc gtt caa cta       1911
Ala Phe Lys Glu Val Gly Ile Val Ser Gly Arg Ala Thr Val Gln Leu
    480                 485                 490 aat agt gca gat caa gtt gat cct aac aat att tat ttc gga ttt cgt       1959
Asn Ser Ala Asp Gln Val Asp Pro Asn Asn Ile Tyr Phe Gly Phe Arg
495                 500                 505                 510
```

-continued

| | | |
|---|---|---|
| ggt ggt cgc tta gat ctt aac gga cat tca tta acc ttt aaa cgt atc<br>Gly Gly Arg Leu Asp Leu Asn Gly His Ser Leu Thr Phe Lys Arg Ile<br>              515                  520                  525 | 2007 |
| caa aat acg gac gag ggc gcg atg att gtg aac cat aat aca act caa<br>Gln Asn Thr Asp Glu Gly Ala Met Ile Val Asn His Asn Thr Thr Gln<br>     530                  535                  540 | 2055 |
| gtc gct aat att act att act ggg aac gaa agt att act gct cca tct<br>Val Ala Asn Ile Thr Ile Thr Gly Asn Glu Ser Ile Thr Ala Pro Ser<br>         545                  550                 555 | 2103 |
| aat aaa aat aat att aat aaa ctt gat tac agc aaa gaa att gct tac<br>Asn Lys Asn Asn Ile Asn Lys Leu Asp Tyr Ser Lys Glu Ile Ala Tyr<br>560                  565                  570 | 2151 |
| aac ggt tgg ttt ggc gaa aca gat gaa aat aaa cac aat gga aga tta<br>Asn Gly Trp Phe Gly Glu Thr Asp Glu Asn Lys His Asn Gly Arg Leu<br>575                  580                  585               590 | 2199 |
| aac ctt att tat aaa cca acc aca gaa gat cgt act ttg cta ctt tca<br>Asn Leu Ile Tyr Lys Pro Thr Thr Glu Asp Arg Thr Leu Leu Leu Ser<br>                  595                  600               605 | 2247 |
| ggt gga aca aat tta aaa ggc aat att act cag gaa ggc ggc act tta<br>Gly Gly Thr Asn Leu Lys Gly Asn Ile Thr Gln Glu Gly Gly Thr Leu<br>     610                  615                  620 | 2295 |
| gtg ttt agt ggt cgc cca act cca cac gct tac aat cat tta aat cgc<br>Val Phe Ser Gly Arg Pro Thr Pro His Ala Tyr Asn His Leu Asn Arg<br>         625                  630                 635 | 2343 |
| cca aac gag ctt ggg cga cct caa ggc gaa gtg gtt att gat gac gat<br>Pro Asn Glu Leu Gly Arg Pro Gln Gly Glu Val Val Ile Asp Asp Asp<br>640                  645                  650 | 2391 |
| tgg atc acc cgc aca ttt aaa gct gaa aac ttc caa att aaa ggc gga<br>Trp Ile Thr Arg Thr Phe Lys Ala Glu Asn Phe Gln Ile Lys Gly Gly<br>655                  660                  665               670 | 2439 |
| agt gcg gtg gtt tct cgc aat gtt tct tca att gag gga aat tgg aca<br>Ser Ala Val Val Ser Arg Asn Val Ser Ser Ile Glu Gly Asn Trp Thr<br>                  675                  680               685 | 2487 |
| gtc agc aat aat gca aat gcc gca ttt ggt gtt gtg cca aat cag caa<br>Val Ser Asn Asn Ala Asn Ala Ala Phe Gly Val Val Pro Asn Gln Gln<br>     690                  695                  700 | 2535 |
| aat acc att tgc acg cgt tca gat tgg aca gga tta acg act tgt aaa<br>Asn Thr Ile Cys Thr Arg Ser Asp Trp Thr Gly Leu Thr Thr Cys Lys<br>         705                  710                 715 | 2583 |
| act gtg gat tta acc gat aca aaa gtt att aat tcc ata ccg aca aca<br>Thr Val Asp Leu Thr Asp Thr Lys Val Ile Asn Ser Ile Pro Thr Thr<br>720                  725                  730 | 2631 |
| caa att aat ggc tct att aat tta act gat aat gca aca gtg aat att<br>Gln Ile Asn Gly Ser Ile Asn Leu Thr Asp Asn Ala Thr Val Asn Ile<br>735                  740                  745               750 | 2679 |
| cat ggt tta gca aaa ctt aat ggt aat gtc act tta ata aat cat agc<br>His Gly Leu Ala Lys Leu Asn Gly Asn Val Thr Leu Ile Asn His Ser<br>                  755                  760               765 | 2727 |
| caa ttt aca ttg agc aac aat gcc acc caa aca ggc aat atc caa ctt<br>Gln Phe Thr Leu Ser Asn Asn Ala Thr Gln Thr Gly Asn Ile Gln Leu<br>     770                  775                  780 | 2775 |
| tca aat cac gca aat gca acg gtg gac aat gca aat ttg aac ggt aat<br>Ser Asn His Ala Asn Ala Thr Val Asp Asn Ala Asn Leu Asn Gly Asn<br>         785                  790                 795 | 2823 |
| gtg cat tta acg gat tct gct caa ttt tct tta aaa aac agc cat ttt<br>Val His Leu Thr Asp Ser Ala Gln Phe Ser Leu Lys Asn Ser His Phe<br>800                  805                  810 | 2871 |
| tcg cac caa att cag ggc gac aaa gac aca aca gtg acg ttg gaa aat<br>Ser His Gln Ile Gln Gly Asp Lys Asp Thr Thr Val Thr Leu Glu Asn<br>815                  820                  825               830 | 2919 |

-continued

```
gcg act tgg aca atg cct agc gat gcc aca ttg cag aat tta acg cta        2967
Ala Thr Trp Thr Met Pro Ser Asp Ala Thr Leu Gln Asn Leu Thr Leu
            835                 840                 845 aat aat agt act gtt acg tta aat tca gct tat tca gct agc tca aat        3015
Asn Asn Ser Thr Val Thr Leu Asn Ser Ala Tyr Ser Ala Ser Ser Asn
        850                 855                 860 aat gcg cca cgt cac cgc cgt tca tta gag acg gaa aca acg cca aca        3063
Asn Ala Pro Arg His Arg Arg Ser Leu Glu Thr Glu Thr Thr Pro Thr
    865                 870                 875 tcg gca gaa cat cgt ttc aac aca ttg aca gta aat ggt aaa ttg agc        3111
Ser Ala Glu His Arg Phe Asn Thr Leu Thr Val Asn Gly Lys Leu Ser
880                 885                 890 ggg caa ggc aca ttc caa ttt act tca tct tta ttt ggc tat aaa agc        3159
Gly Gln Gly Thr Phe Gln Phe Thr Ser Ser Leu Phe Gly Tyr Lys Ser
895                 900                 905                 910 gat aaa tta aaa tta tcc aat gac gct gag ggc gat tac aca tta tct        3207
Asp Lys Leu Lys Leu Ser Asn Asp Ala Glu Gly Asp Tyr Thr Leu Ser
            915                 920                 925 gtt cgc aac aca ggc aaa gaa ccc gaa gcc ctt gag caa tta act ttg        3255
Val Arg Asn Thr Gly Lys Glu Pro Glu Ala Leu Glu Gln Leu Thr Leu
        930                 935                 940 gtt gaa agc aaa gat aat aaa ccg tta tca gac aaa ctc aaa ttt act        3303
Val Glu Ser Lys Asp Asn Lys Pro Leu Ser Asp Lys Leu Lys Phe Thr
    945                 950                 955 tta gaa aat gac cac gtt gat gca ggt gca tta cgt tat aaa tta gtg        3351
Leu Glu Asn Asp His Val Asp Ala Gly Ala Leu Arg Tyr Lys Leu Val
960                 965                 970 aag aat aat ggc gaa ttc cgc ttg cat aac cca ata aaa gag cag gaa        3399
Lys Asn Asn Gly Glu Phe Arg Leu His Asn Pro Ile Lys Glu Gln Glu
975                 980                 985                 990 ttg cgc aat gat tta gta aga gca gag caa gca gaa cga aca tta gaa        3447
Leu Arg Asn Asp Leu Val Arg Ala Glu Gln Ala Glu Arg Thr Leu Glu
            995                 1000                1005 gcc aaa caa gtt gaa cag act gct gaa aca caa aca agt aat gca            3492
Ala Lys Gln Val Glu Gln Thr Ala Glu Thr Gln Thr Ser Asn Ala
        1010                1015                1020 aga gtg cgg tca aaa aga gcg gtg ttt tct gat acc ctg cct gat            3537
Arg Val Arg Ser Lys Arg Ala Val Phe Ser Asp Thr Leu Pro Asp
    1025                1030                1035 caa agc cag tta gac gta tta caa gcc gaa caa gtt gaa ccg act            3582
Gln Ser Gln Leu Asp Val Leu Gln Ala Glu Gln Val Glu Pro Thr
1040                1045                1050 gct gaa aaa caa aaa aat aag gca aaa aaa gtg cgg tca aaa aga            3627
Ala Glu Lys Gln Lys Asn Lys Ala Lys Lys Val Arg Ser Lys Arg
        1055                1060                1065 gcg gtg ttt tct gat acc ctg cct gat caa agc cag tta gac gta            3672
Ala Val Phe Ser Asp Thr Leu Pro Asp Gln Ser Gln Leu Asp Val
    1070                1075                1080 tta caa gcc gaa caa gtt gaa ccg act gct gaa aaa caa aaa aat            3717
Leu Gln Ala Glu Gln Val Glu Pro Thr Ala Glu Lys Gln Lys Asn
1085                1090                1095 aag gca aaa aaa gtg cgg tca aaa aga gcc gcg aga gag ttt tct            3762
Lys Ala Lys Lys Val Arg Ser Lys Arg Ala Ala Arg Glu Phe Ser
        1100                1105                1110 gat acc ccg ctt gat cta agc cgg tta aag gta tta gaa gtc aaa            3807
Asp Thr Pro Leu Asp Leu Ser Arg Leu Lys Val Leu Glu Val Lys
    1115                1120                1125 ctt gag gtt att aat gcc caa cag caa gtg aaa aaa gaa cct caa            3852
Leu Glu Val Ile Asn Ala Gln Gln Gln Val Lys Lys Glu Pro Gln
1130                1135                1140
```

```
                                                  -continued gat caa gag aaa  caa cgc aaa caa  aaa gac ttg atc  agc cgt tat         3897
Asp Gln Glu Lys  Gln Arg Lys Gln  Lys Asp Leu Ile  Ser Arg Tyr
            1145              1150              1155 tca aat agt gcg  tta tca gaa tta  tct gca aca gta  aat agt atg         3942
Ser Asn Ser Ala  Leu Ser Glu Leu  Ser Ala Thr Val  Asn Ser Met
            1160              1165              1170 ctt tct gtt caa  gat gaa tta gat  cgt ctt ttt gta  gat caa gca         3987
Leu Ser Val Gln  Asp Glu Leu Asp  Arg Leu Phe Val  Asp Gln Ala
            1175              1180              1185 caa tct gcc gtg  tgg aca aat atc  gca cag gat aaa  aga cgc tat         4032
Gln Ser Ala Val  Trp Thr Asn Ile  Ala Gln Asp Lys  Arg Arg Tyr
            1190              1195              1200 gat tct gat gcg  ttc cgt gct tat  cag cag aaa acg  aac tta cgt         4077
Asp Ser Asp Ala  Phe Arg Ala Tyr  Gln Gln Lys Thr  Asn Leu Arg
            1205              1210              1215 caa att ggg gtg  caa aaa gcc tta  gct aat gga cga  att ggg gca         4122
Gln Ile Gly Val  Gln Lys Ala Leu  Ala Asn Gly Arg  Ile Gly Ala
            1220              1225              1230 gtt ttc tcg cat  agc cgt tca gat  aat act ttt gat  gaa cag gtt         4167
Val Phe Ser His  Ser Arg Ser Asp  Asn Thr Phe Asp  Glu Gln Val
            1235              1240              1245 aaa aat cac gcg  aca tta acg atg  atg tcg ggt ttt  gcc caa tat         4212
Lys Asn His Ala  Thr Leu Thr Met  Met Ser Gly Phe  Ala Gln Tyr
            1250              1255              1260 caa tgg ggc gat  tta caa ttt ggt  gta aac gtg gga  acg gga atc         4257
Gln Trp Gly Asp  Leu Gln Phe Gly  Val Asn Val Gly  Thr Gly Ile
            1265              1270              1275 agt gcg agt aaa  atg gct gaa gaa  caa agc cga aaa  att cat cga         4302
Ser Ala Ser Lys  Met Ala Glu Glu  Gln Ser Arg Lys  Ile His Arg
            1280              1285              1290 aaa gcg ata aat  tat ggc gtg aat  gca agt tat cag  ttc cgt tta         4347
Lys Ala Ile Asn  Tyr Gly Val Asn  Ala Ser Tyr Gln  Phe Arg Leu
            1295              1300              1305 ggg caa ttg ggc  att cag cct tat  ttt gga gtt aat  cgc tat ttt         4392
Gly Gln Leu Gly  Ile Gln Pro Tyr  Phe Gly Val Asn  Arg Tyr Phe
            1310              1315              1320 att gaa cgt gaa  aat tat caa tct  gag gaa gtg aaa  gtg aaa acg         4437
Ile Glu Arg Glu  Asn Tyr Gln Ser  Glu Glu Val Lys  Val Lys Thr
            1325              1330              1335 cct agc ctt gca  ttt aat cgc tat  aat gct ggc att  cga gtt gat         4482
Pro Ser Leu Ala  Phe Asn Arg Tyr  Asn Ala Gly Ile  Arg Val Asp
            1340              1345              1350 tat aca ttt act  ccg aca gat aat  atc agc gtt aag  cct tat ttc         4527
Tyr Thr Phe Thr  Pro Thr Asp Asn  Ile Ser Val Lys  Pro Tyr Phe
            1355              1360              1365 ttc gtc aat tat  gtt gat gtt tca  aac gct aac gta  caa acc acg         4572
Phe Val Asn Tyr  Val Asp Val Ser  Asn Ala Asn Val  Gln Thr Thr
            1370              1375              1380 gta aat agc acg  gtg ttg caa caa  cca ttt gga cgt  tat tgg caa         4617
Val Asn Ser Thr  Val Leu Gln Gln  Pro Phe Gly Arg  Tyr Trp Gln
            1385              1390              1395 aaa gaa gtg gga  tta aaa gcg gaa  att tta cat ttc  caa ctt tct         4662
Lys Glu Val Gly  Leu Lys Ala Glu  Ile Leu His Phe  Gln Leu Ser
            1400              1405              1410 gct ttt att tct  aaa tct caa ggt  tcg caa ctc ggc  aaa cag caa         4707
Ala Phe Ile Ser  Lys Ser Gln Gly  Ser Gln Leu Gly  Lys Gln Gln
            1415              1420              1425 aat gtg ggc gtg  aaa ttg ggg tat  cgt tgg taa aaatcaacat              4750
Asn Val Gly Val  Lys Leu Gly Tyr  Arg Trp
            1430              1435
```

-continued

```
aattgtatcg tttattgata acaaggtgg ggcagatccc acctttttta tttcaataat    4810
ggaactttat ttaattaaga gcatctaagt agcaccccat atagggggatt aattaagagg    4870 atttaataat gaatttaact aaactttttac cagcatttgc tgctgcagtc gtattatctg    4930
cttgtgcaaa ggatgcacct gaaatgacaa aatcatctgc gcaaatagct gaaatgcaaa    4990
cacttccaac aatcactgat aaacagttg tatattcctg caataaacaa actgtaactg    5050
ccgtgtatca atttgaaaac caagaaccag ttgctgcaat ggtaagtgtg ggcgatggca    5110
ttattgcgaa agatttact cgtgataaat cacaaaatga ctttacaagt ttcgtttctg    5170
gggattatgt ttggaatgta gatagtggct taacgttaga taaatttgat tctgttgtgc    5230
ctgtcaattt aattc                                                    5245
```

<210> SEQ ID NO 13
<211> LENGTH: 1436
<212> TYPE: PRT
<213> ORGANISM: Haemophilus influenzae

<400> SEQUENCE: 13

```
Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
                20                  25                  30

Asp Tyr Gln Tyr Tyr Arg Asp Phe Ala Glu Asn Lys Gly Lys Phe Ser
            35                  40                  45

Val Gly Ala Lys Asn Ile Glu Val Tyr Asn Lys Glu Gly Thr Leu Val
        50                  55                  60

Gly Thr Ser Met Thr Lys Ala Pro Met Ile Asp Phe Ser Val Val Ser
65                  70                  75                  80

Arg Asn Gly Val Ala Ala Leu Val Gly Asp Gln Tyr Ile Val Ser Val
                85                  90                  95

Ala His Asn Gly Gly Tyr Asn Ser Val Asp Phe Gly Ala Glu Gly Pro
            100                 105                 110

Asn Pro Asp Gln His Arg Phe Thr Tyr Gln Ile Val Lys Arg Asn Asn
        115                 120                 125

Tyr Lys Pro Gly Lys Asp Asn Pro Tyr His Gly Asp Tyr His Met Pro
    130                 135                 140

Arg Leu His Lys Phe Val Thr Asp Ala Glu Pro Ala Lys Met Thr Asp
145                 150                 155                 160

Asn Met Asn Gly Lys Asn Tyr Ala Asp Leu Ser Lys Tyr Pro Asp Arg
                165                 170                 175

Val Arg Ile Gly Thr Gly Glu Gln Trp Trp Arg Thr Asp Glu Glu Gln
            180                 185                 190

Lys Gln Gly Ser Lys Ser Ser Trp Leu Ala Asp Ala Tyr Leu Trp Arg
        195                 200                 205

Ile Ala Gly Asn Thr His Ser Gln Ser Gly Ala Gly Asn Gly Thr Val
    210                 215                 220

Asn Leu Ser Gly Asp Ile Thr Lys Pro Asn Asn Tyr Gly Pro Leu Pro
225                 230                 235                 240

Thr Gly Val Ser Phe Gly Asp Ser Gly Ser Pro Met Phe Ile Tyr Asp
                245                 250                 255

Ala Ile Lys Gln Lys Trp Leu Ile Asn Gly Val Leu Gln Thr Gly Asn
            260                 265                 270

Pro Phe Ser Gly Ala Gly Asn Gly Phe Gln Leu Ile Arg Lys Asn Trp
        275                 280                 285
```

-continued

```
Phe Tyr Asp Asn Val Phe Val Glu Asp Leu Pro Ile Thr Phe Leu Glu
    290                 295                 300
Pro Arg Ser Asn Gly His Tyr Ser Phe Thr Ser Asn Asn Gly Thr
305                 310                 315                 320
Gly Thr Val Thr Gln Thr Asn Glu Lys Val Ser Met Pro Gln Phe Lys
                325                 330                 335
Val Arg Thr Val Gln Leu Phe Asn Glu Ala Leu Lys Glu Lys Asp Lys
                340                 345                 350
Glu Pro Val Tyr Ala Ala Gly Gly Val Asn Ala Tyr Lys Pro Arg Leu
            355                 360                 365
Asn Asn Gly Lys Asn Ile Tyr Phe Gly Asp Arg Gly Thr Gly Thr Leu
370                 375                 380
Thr Ile Glu Asn Asn Ile Asn Gln Gly Ala Gly Leu Tyr Phe Glu
385                 390                 395                 400
Gly Asn Phe Thr Val Ser Ser Glu Asn Asn Ala Thr Trp Gln Gly Ala
                405                 410                 415
Gly Val His Val Gly Glu Asp Ser Thr Val Thr Trp Lys Val Asn Gly
            420                 425                 430
Val Glu His Asp Arg Leu Ser Lys Ile Gly Lys Gly Thr Leu His Ile
            435                 440                 445
Gln Ala Lys Gly Glu Asn Leu Gly Ser Ile Ser Val Gly Asp Gly Lys
        450                 455                 460
Val Ile Leu Asp Gln Gln Ala Asp Glu Asn Asn Gln Lys Gln Ala Phe
465                 470                 475                 480
Lys Glu Val Gly Ile Val Ser Gly Arg Ala Thr Val Gln Leu Asn Ser
                485                 490                 495
Ala Asp Gln Val Asp Pro Asn Asn Ile Tyr Phe Gly Phe Arg Gly Gly
            500                 505                 510
Arg Leu Asp Leu Asn Gly His Ser Leu Thr Phe Lys Arg Ile Gln Asn
        515                 520                 525
Thr Asp Glu Gly Ala Met Ile Val Asn His Asn Thr Thr Gln Val Ala
        530                 535                 540
Asn Ile Thr Ile Thr Gly Asn Glu Ser Ile Thr Ala Pro Ser Asn Lys
545                 550                 555                 560
Asn Asn Ile Asn Lys Leu Asp Tyr Ser Lys Glu Ile Ala Tyr Asn Gly
                565                 570                 575
Trp Phe Gly Glu Thr Asp Glu Asn Lys His Asn Gly Arg Leu Asn Leu
            580                 585                 590
Ile Tyr Lys Pro Thr Thr Glu Asp Arg Thr Leu Leu Ser Gly Gly
        595                 600                 605
Thr Asn Leu Lys Gly Asn Ile Thr Gln Glu Gly Gly Thr Leu Val Phe
610                 615                 620
Ser Gly Arg Pro Thr Pro His Ala Tyr Asn His Leu Asn Arg Pro Asn
625                 630                 635                 640
Glu Leu Gly Arg Pro Gln Gly Glu Val Val Ile Asp Asp Trp Ile
                645                 650                 655
Thr Arg Thr Phe Lys Ala Glu Asn Phe Gln Ile Lys Gly Gly Ser Ala
            660                 665                 670
Val Val Ser Arg Asn Val Ser Ser Ile Glu Gly Asn Trp Thr Val Ser
            675                 680                 685
Asn Asn Ala Asn Ala Ala Phe Gly Val Val Pro Asn Gln Gln Asn Thr
690                 695                 700
```

```
Ile Cys Thr Arg Ser Asp Trp Thr Gly Leu Thr Thr Cys Lys Thr Val
705                 710                 715                 720

Asp Leu Thr Asp Thr Lys Val Ile Asn Ser Ile Pro Thr Thr Gln Ile
            725                 730                 735

Asn Gly Ser Ile Asn Leu Thr Asp Asn Ala Thr Val Asn Ile His Gly
            740                 745                 750

Leu Ala Lys Leu Asn Gly Asn Val Thr Leu Ile Asn His Ser Gln Phe
            755                 760                 765

Thr Leu Ser Asn Asn Ala Thr Gln Thr Gly Asn Ile Gln Leu Ser Asn
770                 775                 780

His Ala Asn Ala Thr Val Asp Asn Ala Asn Leu Asn Gly Asn Val His
785                 790                 795                 800

Leu Thr Asp Ser Ala Gln Phe Ser Leu Lys Asn Ser His Phe Ser His
                805                 810                 815

Gln Ile Gln Gly Asp Lys Asp Thr Thr Val Thr Leu Glu Asn Ala Thr
                820                 825                 830

Trp Thr Met Pro Ser Asp Ala Thr Leu Gln Asn Leu Thr Leu Asn Asn
                835                 840                 845

Ser Thr Val Thr Leu Asn Ser Ala Tyr Ser Ala Ser Ser Asn Asn Ala
850                 855                 860

Pro Arg His Arg Arg Ser Leu Glu Thr Glu Thr Thr Pro Thr Ser Ala
865                 870                 875                 880

Glu His Arg Phe Asn Thr Leu Thr Val Asn Gly Lys Leu Ser Gly Gln
                885                 890                 895

Gly Thr Phe Gln Phe Thr Ser Ser Leu Phe Gly Tyr Lys Ser Asp Lys
                900                 905                 910

Leu Lys Leu Ser Asn Asp Ala Glu Gly Asp Tyr Thr Leu Ser Val Arg
            915                 920                 925

Asn Thr Gly Lys Glu Pro Glu Ala Leu Glu Gln Leu Thr Leu Val Glu
            930                 935                 940

Ser Lys Asp Asn Lys Pro Leu Ser Asp Lys Leu Lys Phe Thr Leu Glu
945                 950                 955                 960

Asn Asp His Val Asp Ala Gly Ala Leu Arg Tyr Lys Leu Val Lys Asn
                965                 970                 975

Asn Gly Glu Phe Arg Leu His Asn Pro Ile Lys Glu Gln Glu Leu Arg
            980                 985                 990

Asn Asp Leu Val Arg Ala Glu Gln Ala Glu Arg Thr Leu Glu Ala Lys
            995                 1000                1005

Gln Val Glu Gln Thr Ala Glu Thr Gln Thr Ser Asn Ala Arg Val
    1010                1015                1020

Arg Ser Lys Arg Ala Val Phe Ser Asp Thr Leu Pro Asp Gln Ser
    1025                1030                1035

Gln Leu Asp Val Leu Gln Ala Glu Gln Val Glu Pro Thr Ala Glu
    1040                1045                1050

Lys Gln Lys Asn Lys Ala Lys Lys Val Arg Ser Lys Arg Ala Val
    1055                1060                1065

Phe Ser Asp Thr Leu Pro Asp Gln Ser Gln Leu Asp Val Leu Gln
    1070                1075                1080

Ala Glu Gln Val Glu Pro Thr Ala Glu Lys Gln Lys Asn Lys Ala
    1085                1090                1095

Lys Lys Val Arg Ser Lys Arg Ala Ala Arg Glu Phe Ser Asp Thr
    1100                1105                1110
```

```
Pro Leu Asp Leu Ser Arg Leu Lys Val Leu Glu Val Lys Leu Glu
    1115                1120                1125

Val Ile Asn Ala Gln Gln Val Lys Lys Glu Pro Gln Asp Gln
    1130                1135                1140

Glu Lys Gln Arg Lys Gln Lys Asp Leu Ile Ser Arg Tyr Ser Asn
    1145                1150                1155

Ser Ala Leu Ser Glu Leu Ser Ala Thr Val Asn Ser Met Leu Ser
    1160                1165                1170

Val Gln Asp Glu Leu Asp Arg Leu Phe Val Asp Gln Ala Gln Ser
    1175                1180                1185

Ala Val Trp Thr Asn Ile Ala Gln Asp Lys Arg Arg Tyr Asp Ser
    1190                1195                1200

Asp Ala Phe Arg Ala Tyr Gln Gln Lys Thr Asn Leu Arg Gln Ile
    1205                1210                1215

Gly Val Gln Lys Ala Leu Ala Asn Gly Arg Ile Gly Ala Val Phe
    1220                1225                1230

Ser His Ser Arg Ser Asp Asn Thr Phe Asp Glu Gln Val Lys Asn
    1235                1240                1245

His Ala Thr Leu Thr Met Met Ser Gly Phe Ala Gln Tyr Gln Trp
    1250                1255                1260

Gly Asp Leu Gln Phe Gly Val Asn Val Gly Thr Gly Ile Ser Ala
    1265                1270                1275

Ser Lys Met Ala Glu Glu Gln Ser Arg Lys Ile His Arg Lys Ala
    1280                1285                1290

Ile Asn Tyr Gly Val Asn Ala Ser Tyr Gln Phe Arg Leu Gly Gln
    1295                1300                1305

Leu Gly Ile Gln Pro Tyr Phe Gly Val Asn Arg Tyr Phe Ile Glu
    1310                1315                1320

Arg Glu Asn Tyr Gln Ser Glu Glu Val Lys Val Lys Thr Pro Ser
    1325                1330                1335

Leu Ala Phe Asn Arg Tyr Asn Ala Gly Ile Arg Val Asp Tyr Thr
    1340                1345                1350

Phe Thr Pro Thr Asp Asn Ile Ser Val Lys Pro Tyr Phe Phe Val
    1355                1360                1365

Asn Tyr Val Asp Val Ser Asn Ala Asn Val Gln Thr Thr Val Asn
    1370                1375                1380

Ser Thr Val Leu Gln Gln Pro Phe Gly Arg Tyr Trp Gln Lys Glu
    1385                1390                1395

Val Gly Leu Lys Ala Glu Ile Leu His Phe Gln Leu Ser Ala Phe
    1400                1405                1410

Ile Ser Lys Ser Gln Gly Ser Gln Leu Gly Lys Gln Gln Asn Val
    1415                1420                1425

Gly Val Lys Leu Gly Tyr Arg Trp
    1430                1435

<210> SEQ ID NO 14
<211> LENGTH: 4822
<212> TYPE: DNA
<213> ORGANISM: Haemophilus influenzae
<220> FEATURE:
<221> NAME/KEY: CDS
<222> LOCATION: (388)..(4563)
<223> OTHER INFORMATION:
```

```
<400> SEQUENCE: 14
cctgaagacg ttgctcaagt taaaggctct cacacagccc gattccttaa accgatttta      60
gaaaaacctt agaaaaaatg accgcacttt cagagaaaac tcacataaag tgcggttatt     120
ttattagtga tattgtttta attatttgta taaattacat acaatattaa tccatcgaaa     180
aataagatta cccactaagt attaagccaa aacctagaaa ttttggctta attactatat     240
aattttactc ctttattttc ttttgtgcct tttagttagt tcgttttta gctgaaatcc      300 ctcagaaaat caccgcactt ttattgttca atagtcgttt aaccacgtat tttttaatac     360
gaaaaattac ttaattaaat aaacatt atg aaa aaa act gta ttt cgt ctt aat     414
                                Met Lys Lys Thr Val Phe Arg Leu Asn
                                  1               5 ttt cta acc gct tgt att tca tta ggg ata gta tcg caa gcg tgg gca       462
Phe Leu Thr Ala Cys Ile Ser Leu Gly Ile Val Ser Gln Ala Trp Ala
 10              15                  20                  25 ggt cac act tat ttt ggg att gac tac caa tat tat cgt gat ttt gcc       510
Gly His Thr Tyr Phe Gly Ile Asp Tyr Gln Tyr Tyr Arg Asp Phe Ala
                 30                  35                  40 gag aat aaa ggg aag ttt aca gtt ggg gct caa gat att gat atc tac       558
Glu Asn Lys Gly Lys Phe Thr Val Gly Ala Gln Asp Ile Asp Ile Tyr
             45                  50                  55 aat aaa aaa ggg gaa atg ata ggt acg atg atg aaa ggt gtg cct atg       606
Asn Lys Lys Gly Glu Met Ile Gly Thr Met Met Lys Gly Val Pro Met
         60                  65                  70 cct gat tta tct tcc atg gtt cgt ggt ggt tat tca aca ttg ata agt       654
Pro Asp Leu Ser Ser Met Val Arg Gly Gly Tyr Ser Thr Leu Ile Ser
     75                  80                  85 gag cag cat tta att agc gtc gca cat aat gta ggg tat gat gtc gtt       702
Glu Gln His Leu Ile Ser Val Ala His Asn Val Gly Tyr Asp Val Val
 90                  95                 100                 105 gat ttt ggt atg gag ggg gaa aat cca gac caa cat cgt ttt aag tat       750
Asp Phe Gly Met Glu Gly Glu Asn Pro Asp Gln His Arg Phe Lys Tyr
                110                 115                 120 aaa gtt gtt aaa cga tat aat tat aag agc ggt gat aga caa tat aat       798
Lys Val Val Lys Arg Tyr Asn Tyr Lys Ser Gly Asp Arg Gln Tyr Asn
            125                 130                 135 gat tat caa cat cca aga tta gag aaa ttt gta acg gaa act gca cct       846
Asp Tyr Gln His Pro Arg Leu Glu Lys Phe Val Thr Glu Thr Ala Pro
        140                 145                 150 att gaa atg gtt tca tat atg gat ggt aat cat tac aaa aat ttt aat       894
Ile Glu Met Val Ser Tyr Met Asp Gly Asn His Tyr Lys Asn Phe Asn
    155                 160                 165 caa tat cct ttg cga gtt aga gtt gga agt ggg cat caa tgg tgg aaa       942
Gln Tyr Pro Leu Arg Val Arg Val Gly Ser Gly His Gln Trp Trp Lys
170                 175                 180                 185 gac gat aat aat aaa acc att gga gac tta gcc tat gga ggt tca tgg       990
Asp Asp Asn Asn Lys Thr Ile Gly Asp Leu Ala Tyr Gly Gly Ser Trp
                190                 195                 200 tta ata ggt gga aat acc ttt gaa gat gga cca gct ggt aac ggt aca      1038
Leu Ile Gly Gly Asn Thr Phe Glu Asp Gly Pro Ala Gly Asn Gly Thr
            205                 210                 215 tta gaa tta aat ggg cga gta caa aat cct aat aaa tat ggt cca cta      1086
Leu Glu Leu Asn Gly Arg Val Gln Asn Pro Asn Lys Tyr Gly Pro Leu
        220                 225                 230 cct acg gca ggt tca ttc ggg gat agt ggt tct cca atg ttt att tat      1134
Pro Thr Ala Gly Ser Phe Gly Asp Ser Gly Ser Pro Met Phe Ile Tyr
    235                 240                 245
```

```
gat aag gaa gtt aag aaa tgg tta tta aat ggc gtg tta cgt gaa gga      1182
Asp Lys Glu Val Lys Lys Trp Leu Leu Asn Gly Val Leu Arg Glu Gly
250                 255                 260                 265 aat cct tat gct gca gta gga aac agc tat caa att aca cga aaa gat      1230
Asn Pro Tyr Ala Ala Val Gly Asn Ser Tyr Gln Ile Thr Arg Lys Asp
                270                 275                 280 tat ttt caa ggt att ctt aat caa gac att aca gct aat ttt tgg gat      1278
Tyr Phe Gln Gly Ile Leu Asn Gln Asp Ile Thr Ala Asn Phe Trp Asp
            285                 290                 295 act aat gct gaa tat aga ttt aat ata ggg agt gac cac aat gga aga      1326
Thr Asn Ala Glu Tyr Arg Phe Asn Ile Gly Ser Asp His Asn Gly Arg
        300                 305                 310 gtg gca aca atc aaa agt aca tta cct aaa aaa gct att cag cct gaa      1374
Val Ala Thr Ile Lys Ser Thr Leu Pro Lys Lys Ala Ile Gln Pro Glu
    315                 320                 325 cga ata gtg ggt ctt tat gat aat agc caa ctt cat gat gct aga gat      1422
Arg Ile Val Gly Leu Tyr Asp Asn Ser Gln Leu His Asp Ala Arg Asp
330                 335                 340                 345 aaa aat ggc gat gaa tct ccc tct tat aaa ggt cct aat cca tgg tcg      1470
Lys Asn Gly Asp Glu Ser Pro Ser Tyr Lys Gly Pro Asn Pro Trp Ser
                350                 355                 360 cca gca tta cat cat ggg aaa agt att tac ttt ggc gat caa gga aca      1518
Pro Ala Leu His His Gly Lys Ser Ile Tyr Phe Gly Asp Gln Gly Thr
            365                 370                 375 gga act tta aca att gaa aat aat ata aat caa ggt gca ggt gga ttg      1566
Gly Thr Leu Thr Ile Glu Asn Asn Ile Asn Gln Gly Ala Gly Gly Leu
        380                 385                 390 tat ttt gaa ggt aat ttt gtt gta aaa ggc aat caa aat aat ata act      1614
Tyr Phe Glu Gly Asn Phe Val Val Lys Gly Asn Gln Asn Asn Ile Thr
    395                 400                 405 tgg caa ggt gca ggc gtt tct gtt gga gaa gaa agt act gtt gaa tgg      1662
Trp Gln Gly Ala Gly Val Ser Val Gly Glu Glu Ser Thr Val Glu Trp
410                 415                 420                 425 cag gtg cat aat cca gaa ggc gat cgc tta tcc aaa att ggg ctg gga      1710
Gln Val His Asn Pro Glu Gly Asp Arg Leu Ser Lys Ile Gly Leu Gly
                430                 435                 440 acc tta ctt gtt aat ggt aaa ggg aaa aac tta gga agc ctg agt gtc      1758
Thr Leu Leu Val Asn Gly Lys Gly Lys Asn Leu Gly Ser Leu Ser Val
            445                 450                 455 ggt aac ggt ttg gtt gtg tta gat caa caa gca gat gaa tca ggt caa      1806
Gly Asn Gly Leu Val Val Leu Asp Gln Gln Ala Asp Glu Ser Gly Gln
        460                 465                 470 aaa caa gcc ttt aaa gaa gtt ggc att gta agt ggt aga gct acc gtt      1854
Lys Gln Ala Phe Lys Glu Val Gly Ile Val Ser Gly Arg Ala Thr Val
    475                 480                 485 caa cta aat agt gca gat caa gtt gat cct aac aat att tat ttc ggc      1902
Gln Leu Asn Ser Ala Asp Gln Val Asp Pro Asn Asn Ile Tyr Phe Gly
490                 495                 500                 505 ttt cgt ggt ggt cgc tta gat ctt aat ggg cat tca tta acc ttt gaa      1950
Phe Arg Gly Gly Arg Leu Asp Leu Asn Gly His Ser Leu Thr Phe Glu
                510                 515                 520 cgt atc caa aat acg gat gaa ggc gcg atg att gtg aac cac aac gct      1998
Arg Ile Gln Asn Thr Asp Glu Gly Ala Met Ile Val Asn His Asn Ala
            525                 530                 535 tct caa acc gca aat att acg att aca ggc aac gca act att aat tca      2046
Ser Gln Thr Ala Asn Ile Thr Ile Thr Gly Asn Ala Thr Ile Asn Ser
        540                 545                 550 gat agc aaa caa ctt act aat aaa aaa gat att gca ttt aac ggc tgg      2094
Asp Ser Lys Gln Leu Thr Asn Lys Lys Asp Ile Ala Phe Asn Gly Trp
    555                 560                 565
```

```
                                        -continued ttt ggt gag caa gat aaa gct aaa aca aat ggt cgt tta aat gtg aat    2142
Phe Gly Glu Gln Asp Lys Ala Lys Thr Asn Gly Arg Leu Asn Val Asn
570                 575                 580                 585 tat caa cca gtt aat gca gaa aat cat ttg ttg ctt tct ggg ggg aca    2190
Tyr Gln Pro Val Asn Ala Glu Asn His Leu Leu Leu Ser Gly Gly Thr
                590                 595                 600 aat tta aac ggc aat atc acg caa aat ggt ggt acg tta gtt ttt agt    2238
Asn Leu Asn Gly Asn Ile Thr Gln Asn Gly Gly Thr Leu Val Phe Ser
        605                 610                 615 ggt cgt cca acg cct cat gct tac aat cat tta aga aga gac ttg tct    2286
Gly Arg Pro Thr Pro His Ala Tyr Asn His Leu Arg Arg Asp Leu Ser
    620                 625                 630 aac atg gaa ggt atc cca caa ggc gaa att gtg tgg gat cac gat tgg    2334
Asn Met Glu Gly Ile Pro Gln Gly Glu Ile Val Trp Asp His Asp Trp
635                 640                 645 atc aac cgc aca ttt aaa gct gaa aac ttc caa att aaa ggc gga agt    2382
Ile Asn Arg Thr Phe Lys Ala Glu Asn Phe Gln Ile Lys Gly Gly Ser
650                 655                 660                 665 gcg gtg gtt tct cgc aat gtt tct tca att gag gga aat tgg aca gtc    2430
Ala Val Val Ser Arg Asn Val Ser Ser Ile Glu Gly Asn Trp Thr Val
                670                 675                 680 agc aat aat gca aat gcc aca ttt ggt gtt gtg cca aat cag caa aat    2478
Ser Asn Asn Ala Asn Ala Thr Phe Gly Val Val Pro Asn Gln Gln Asn
        685                 690                 695 acc att tgc acg cgt tca gat tgg aca gga tta acg act tgt aaa aca    2526
Thr Ile Cys Thr Arg Ser Asp Trp Thr Gly Leu Thr Thr Cys Lys Thr
    700                 705                 710 gtt gat tta acc gat aaa aaa gtt att aat tcc ata ccg aca aca caa    2574
Val Asp Leu Thr Asp Lys Lys Val Ile Asn Ser Ile Pro Thr Thr Gln
715                 720                 725 att aat ggt tct att aat tta act gat aat gca aca gtg aat att cat    2622
Ile Asn Gly Ser Ile Asn Leu Thr Asp Asn Ala Thr Val Asn Ile His
730                 735                 740                 745 ggt tta gca aaa ctt aat ggt aat gtc act tta ata gat cac agc caa    2670
Gly Leu Ala Lys Leu Asn Gly Asn Val Thr Leu Ile Asp His Ser Gln
                750                 755                 760 ttt aca ttg agc aac aat gcc acc caa gca ggc aat atc aaa ctt tca    2718
Phe Thr Leu Ser Asn Asn Ala Thr Gln Ala Gly Asn Ile Lys Leu Ser
        765                 770                 775 aat cac gca aat gca acg gtg gac aat gca aat ttg aac ggt aat gtg    2766
Asn His Ala Asn Ala Thr Val Asp Asn Ala Asn Leu Asn Gly Asn Val
    780                 785                 790 aat tta atg gat tct gct caa ttt tct tta aaa aac agc cat ttt tcg    2814
Asn Leu Met Asp Ser Ala Gln Phe Ser Leu Lys Asn Ser His Phe Ser
795                 800                 805 cac caa atc caa ggt ggg gaa gac aca aca gtg atg ttg gaa aat gcg    2862
His Gln Ile Gln Gly Gly Glu Asp Thr Thr Val Met Leu Glu Asn Ala
810                 815                 820                 825 act tgg aca atg cct agc gat acc aca ttg cag aat tta acg cta aat    2910
Thr Trp Thr Met Pro Ser Asp Thr Thr Leu Gln Asn Leu Thr Leu Asn
                830                 835                 840 aat agt act gtt acg tta aat tca gct tat tca gct atc tca aat aat    2958
Asn Ser Thr Val Thr Leu Asn Ser Ala Tyr Ser Ala Ile Ser Asn Asn
        845                 850                 855 gcg cca cgc cgt cgc cgc cgt tca tta gag acg gaa aca acg cca aca    3006
Ala Pro Arg Arg Arg Arg Arg Ser Leu Glu Thr Glu Thr Thr Pro Thr
    860                 865                 870 tcg gca gaa cat cgt ttc aac aca ttg aca gta aat ggt aaa ttg agc    3054
Ser Ala Glu His Arg Phe Asn Thr Leu Thr Val Asn Gly Lys Leu Ser
875                 880                 885
```

```
                                                              -continued ggg caa ggc aca ttc caa ttt act tca tct tta ttt ggc tat aaa agc      3102
Gly Gln Gly Thr Phe Gln Phe Thr Ser Ser Leu Phe Gly Tyr Lys Ser
890                 895                 900                 905 gat aaa tta aaa tta tcc aat gac gct gag ggc gat tac aca tta tct      3150
Asp Lys Leu Lys Leu Ser Asn Asp Ala Glu Gly Asp Tyr Thr Leu Ser
                910                 915                 920 gtt cgc aac aca ggc aaa gaa ccc gtg acc ttt ggg caa tta act ttg      3198
Val Arg Asn Thr Gly Lys Glu Pro Val Thr Phe Gly Gln Leu Thr Leu
            925                 930                 935 gtt gaa agc aaa gat aat aaa ccg tta tca gac aaa ctc aca ttc acg      3246
Val Glu Ser Lys Asp Asn Lys Pro Leu Ser Asp Lys Leu Thr Phe Thr
        940                 945                 950 tta gaa aat gac cac gtt gat gca ggt gca tta cgt tat aaa tta gtg      3294
Leu Glu Asn Asp His Val Asp Ala Gly Ala Leu Arg Tyr Lys Leu Val
    955                 960                 965 aag aat gat ggc gaa ttc cgc tta cat aac cca ata aaa gag cag gaa      3342
Lys Asn Asp Gly Glu Phe Arg Leu His Asn Pro Ile Lys Glu Gln Glu
970                 975                 980                 985 ttg cgc tct gat tta gta aga gca gag caa gca gaa cga aca tta  gaa     3390
Leu Arg Ser Asp Leu Val Arg Ala Glu Gln Ala Glu Arg Thr Leu  Glu
                990                 995                 1000 gcc aaa caa gtt  gaa cag act gct aaa  aca caa aca agt aag  gca       3435
Ala Lys Gln Val  Glu Gln Thr Ala Lys  Thr Gln Thr Ser Lys  Ala
                 1005                 1010                 1015 aga gtg cgg tca aga aga gcg gtg ttt  tct gat ccc ctg cct gct         3480
Arg Val Arg Ser Arg Arg Ala Val Phe  Ser Asp Pro Leu Pro Ala
                1020                 1025                 1030 caa agc ctg tta  aac gca tta gaa gcc  aaa caa gct ctg act  act       3525
Gln Ser Leu Leu  Asn Ala Leu Glu Ala  Lys Gln Ala Leu Thr  Thr
                 1035                 1040                 1045 gaa aca caa aca  agt aag gca aaa aaa  gtg cgg tca aaa aga  gct       3570
Glu Thr Gln Thr  Ser Lys Ala Lys Lys  Val Arg Ser Lys Arg  Ala
                 1050                 1055                 1060 gcg aga gag ttt  tct gat acc ctg cct  gat caa ata tta caa  gcc       3615
Ala Arg Glu Phe  Ser Asp Thr Leu Pro  Asp Gln Ile Leu Gln  Ala
                 1065                 1070                 1075 gca ctt gag gtt  att gat gcc caa cag  caa gtg aaa aaa gaa  cct       3660
Ala Leu Glu Val  Ile Asp Ala Gln Gln  Gln Val Lys Lys Glu  Pro
                 1080                 1085                 1090 caa act caa gag  gaa gaa gag aaa aga  caa cgc aaa caa aaa  gaa       3705
Gln Thr Gln Glu  Glu Glu Glu Lys Arg  Gln Arg Lys Gln Lys  Glu
                 1095                 1100                 1105 ttg atc agc cgt  tac tca aat agt gcg  tta tcg gag ttg tct  gcg       3750
Leu Ile Ser Arg  Tyr Ser Asn Ser Ala  Leu Ser Glu Leu Ser  Ala
                 1110                 1115                 1120 aca gta aat agt  atg ctt tcc gtt caa  gat gaa ttg gat cgt  ctt       3795
Thr Val Asn Ser  Met Leu Ser Val Gln  Asp Glu Leu Asp Arg  Leu
                 1125                 1130                 1135 ttt gta gat caa  gca caa tct gcc gtg  tgg aca aat atc gca  cag       3840
Phe Val Asp Gln  Ala Gln Ser Ala Val  Trp Thr Asn Ile Ala  Gln
                 1140                 1145                 1150 gat aaa aga cgc  tat gat tct gat gcg  ttc cgt gct tat cag  cag       3885
Asp Lys Arg Arg  Tyr Asp Ser Asp Ala  Phe Arg Ala Tyr Gln  Gln
                 1155                 1160                 1165 aaa acg aac ttg  cgt caa att ggg gtg  caa aaa gcc tta gat  aat       3930
Lys Thr Asn Leu  Arg Gln Ile Gly Val  Gln Lys Ala Leu Asp  Asn
                 1170                 1175                 1180 gga cga att ggg  gcg gtt ttc tcg cat  agc cgt tca gat aat  acc       3975
Gly Arg Ile Gly  Ala Val Phe Ser His  Ser Arg Ser Asp Asn  Thr
                 1185                 1190                 1195
```

-continued

| | | |
|---|---|---|
| ttt gac gaa cag gtt aaa aat cac gcg aca tta gcg atg atg tct<br>Phe Asp Glu Gln Val Lys Asn His Ala Thr Leu Ala Met Met Ser<br>1200              1205              1210 | 4020 |
| ggt ttt gcc caa tat caa tgg ggc gat tta caa ttt ggt gta aac<br>Gly Phe Ala Gln Tyr Gln Trp Gly Asp Leu Gln Phe Gly Val Asn<br>    1215              1220              1225 | 4065 |
| gtg ggt gcg gga att agt gcg agt aaa atg gct gaa gaa caa agc<br>Val Gly Ala Gly Ile Ser Ala Ser Lys Met Ala Glu Glu Gln Ser<br>1230              1235              1240 | 4110 |
| cga aaa att cat cga aaa gcg ata aat tat ggt gtg aat gca agt<br>Arg Lys Ile His Arg Lys Ala Ile Asn Tyr Gly Val Asn Ala Ser<br>    1245              1250              1255 | 4155 |
| tat cag ttc cgt tta ggg caa ttg ggt att cag cct tat ttg ggt<br>Tyr Gln Phe Arg Leu Gly Gln Leu Gly Ile Gln Pro Tyr Leu Gly<br>1260              1265              1270 | 4200 |
| gtt aat cga tat ttt att gaa cgt gaa aat tat caa tct gaa gaa<br>Val Asn Arg Tyr Phe Ile Glu Arg Glu Asn Tyr Gln Ser Glu Glu<br>    1275              1280              1285 | 4245 |
| gtg aaa gtg caa aca ccg agc ctt gta ttt aat cgc tat aat gct<br>Val Lys Val Gln Thr Pro Ser Leu Val Phe Asn Arg Tyr Asn Ala<br>1290              1295              1300 | 4290 |
| ggc att cga gtt gat tat aca ttt acc ccg aca gat aat atc agc<br>Gly Ile Arg Val Asp Tyr Thr Phe Thr Pro Thr Asp Asn Ile Ser<br>    1305              1310              1315 | 4335 |
| att aag cct tat ttc ttc gtc aat tat gtt gat gtt tca aac gct<br>Ile Lys Pro Tyr Phe Phe Val Asn Tyr Val Asp Val Ser Asn Ala<br>1320              1325              1330 | 4380 |
| aac gta caa acc act gta aat cgc acg atg ttg caa caa tca ttt<br>Asn Val Gln Thr Thr Val Asn Arg Thr Met Leu Gln Gln Ser Phe<br>    1335              1340              1345 | 4425 |
| ggg cgt tat tgg caa aaa gaa gtg gga tta aag gca gaa att tta<br>Gly Arg Tyr Trp Gln Lys Glu Val Gly Leu Lys Ala Glu Ile Leu<br>1350              1355              1360 | 4470 |
| cat ttc caa ctt tcc gct ttt atc tca aaa tct caa ggt tca caa<br>His Phe Gln Leu Ser Ala Phe Ile Ser Lys Ser Gln Gly Ser Gln<br>    1365              1370              1375 | 4515 |
| ctc ggc aaa cag caa aat gtg ggc gtg aaa ttg ggg tat cgt tgg<br>Leu Gly Lys Gln Gln Asn Val Gly Val Lys Leu Gly Tyr Arg Trp<br>1380              1385              1390 | 4560 |
| taa aaatcaacat aattttatcg tttattgata aacaaggtgg ggcagatcaa | 4613 |
| atcctacctt ttttattcca ataatggaac tttattttat taaaggtatc taagtagcac | 4673 |
| cctatatagg gattaattaa gaggatttaa taatgaattt aactaaaatt ttacccacat | 4733 |
| ttgctgctgt agtcgtatta tctgcttgtg caaaggatgc acctgaaatg acaaaatcat | 4793 |
| ctgcgcaaat agctgaaatg caaacactt | 4822 |

<210> SEQ ID NO 15
<211> LENGTH: 1391
<212> TYPE: PRT
<213> ORGANISM: Haemophilus influenzae

<400> SEQUENCE: 15

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Lys Gly Lys Phe Thr
        35                  40                  45

-continued

Val Gly Ala Gln Asp Ile Asp Ile Tyr Asn Lys Lys Gly Glu Met Ile
 50                  55                  60

Gly Thr Met Met Lys Gly Val Pro Met Pro Asp Leu Ser Ser Met Val
 65                  70                  75                  80

Arg Gly Gly Tyr Ser Thr Leu Ile Ser Glu Gln His Leu Ile Ser Val
                 85                  90                  95

Ala His Asn Val Gly Tyr Asp Val Val Asp Phe Gly Met Glu Gly Glu
             100                 105                 110

Asn Pro Asp Gln His Arg Phe Lys Tyr Lys Val Val Lys Arg Tyr Asn
         115                 120                 125

Tyr Lys Ser Gly Asp Arg Gln Tyr Asn Asp Tyr Gln His Pro Arg Leu
     130                 135                 140

Glu Lys Phe Val Thr Glu Thr Ala Pro Ile Glu Met Val Ser Tyr Met
 145                 150                 155                 160

Asp Gly Asn His Tyr Lys Asn Phe Asn Gln Tyr Pro Leu Arg Val Arg
                 165                 170                 175

Val Gly Ser Gly His Gln Trp Trp Lys Asp Asn Asn Lys Thr Ile
             180                 185                 190

Gly Asp Leu Ala Tyr Gly Gly Ser Trp Leu Ile Gly Gly Asn Thr Phe
         195                 200                 205

Glu Asp Gly Pro Ala Gly Asn Gly Thr Leu Glu Leu Asn Gly Arg Val
 210                 215                 220

Gln Asn Pro Asn Lys Tyr Gly Pro Leu Pro Thr Ala Gly Ser Phe Gly
 225                 230                 235                 240

Asp Ser Gly Ser Pro Met Phe Ile Tyr Asp Lys Glu Val Lys Lys Trp
                 245                 250                 255

Leu Leu Asn Gly Val Leu Arg Glu Gly Asn Pro Tyr Ala Ala Val Gly
         260                 265                 270

Asn Ser Tyr Gln Ile Thr Arg Lys Asp Tyr Phe Gln Gly Ile Leu Asn
     275                 280                 285

Gln Asp Ile Thr Ala Asn Phe Trp Asp Thr Asn Ala Glu Tyr Arg Phe
 290                 295                 300

Asn Ile Gly Ser Asp His Asn Gly Arg Val Ala Thr Ile Lys Ser Thr
 305                 310                 315                 320

Leu Pro Lys Lys Ala Ile Gln Pro Glu Arg Ile Val Gly Leu Tyr Asp
                 325                 330                 335

Asn Ser Gln Leu His Asp Ala Arg Asp Lys Asn Gly Asp Glu Ser Pro
         340                 345                 350

Ser Tyr Lys Gly Pro Asn Pro Trp Ser Pro Ala Leu His His Gly Lys
     355                 360                 365

Ser Ile Tyr Phe Gly Asp Gln Gly Thr Gly Thr Leu Thr Ile Glu Asn
 370                 375                 380

Asn Ile Asn Gln Gly Ala Gly Gly Leu Tyr Phe Glu Gly Asn Phe Val
 385                 390                 395                 400

Val Lys Gly Asn Gln Asn Asn Ile Thr Trp Gln Gly Ala Gly Val Ser
                 405                 410                 415

Val Gly Glu Glu Ser Thr Val Glu Trp Gln Val His Asn Pro Glu Gly
         420                 425                 430

Asp Arg Leu Ser Lys Ile Gly Leu Gly Thr Leu Leu Val Asn Gly Lys
     435                 440                 445

Gly Lys Asn Leu Gly Ser Leu Ser Val Gly Asn Gly Leu Val Val Leu
 450                 455                 460

```
Asp Gln Gln Ala Asp Glu Ser Gly Gln Lys Gln Ala Phe Lys Glu Val
465                 470                 475                 480

Gly Ile Val Ser Gly Arg Ala Thr Val Gln Leu Asn Ser Ala Asp Gln
                485                 490                 495

Val Asp Pro Asn Asn Ile Tyr Phe Gly Phe Arg Gly Gly Arg Leu Asp
            500                 505                 510

Leu Asn Gly His Ser Leu Thr Phe Glu Arg Ile Gln Asn Thr Asp Glu
            515                 520                 525

Gly Ala Met Ile Val Asn His Asn Ala Ser Gln Thr Ala Asn Ile Thr
530                 535                 540

Ile Thr Gly Asn Ala Thr Ile Asn Ser Asp Ser Lys Gln Leu Thr Asn
545                 550                 555                 560

Lys Lys Asp Ile Ala Phe Asn Gly Trp Phe Gly Glu Gln Asp Lys Ala
                565                 570                 575

Lys Thr Asn Gly Arg Leu Asn Val Asn Tyr Gln Pro Val Asn Ala Glu
            580                 585                 590

Asn His Leu Leu Leu Ser Gly Gly Thr Asn Leu Asn Gly Asn Ile Thr
            595                 600                 605

Gln Asn Gly Gly Thr Leu Val Phe Ser Gly Arg Pro Thr Pro His Ala
610                 615                 620

Tyr Asn His Leu Arg Arg Asp Leu Ser Asn Met Glu Gly Ile Pro Gln
625                 630                 635                 640

Gly Glu Ile Val Trp Asp His Asp Trp Ile Asn Arg Thr Phe Lys Ala
                645                 650                 655

Glu Asn Phe Gln Ile Lys Gly Gly Ser Ala Val Val Ser Arg Asn Val
            660                 665                 670

Ser Ser Ile Glu Gly Asn Trp Thr Val Ser Asn Asn Ala Asn Ala Thr
            675                 680                 685

Phe Gly Val Val Pro Asn Gln Gln Asn Thr Ile Cys Thr Arg Ser Asp
690                 695                 700

Trp Thr Gly Leu Thr Thr Cys Lys Thr Val Asp Leu Thr Asp Lys Lys
705                 710                 715                 720

Val Ile Asn Ser Ile Pro Thr Thr Gln Ile Asn Gly Ser Ile Asn Leu
                725                 730                 735

Thr Asp Asn Ala Thr Val Asn Ile His Gly Leu Ala Lys Leu Asn Gly
            740                 745                 750

Asn Val Thr Leu Ile Asp His Ser Gln Phe Thr Leu Ser Asn Asn Ala
            755                 760                 765

Thr Gln Ala Gly Asn Ile Lys Leu Ser Asn His Ala Asn Ala Thr Val
770                 775                 780

Asp Asn Ala Asn Leu Asn Gly Asn Val Asn Leu Met Asp Ser Ala Gln
785                 790                 795                 800

Phe Ser Leu Lys Asn Ser His Phe Ser His Gln Ile Gln Gly Gly Glu
                805                 810                 815

Asp Thr Thr Val Met Leu Glu Asn Ala Thr Trp Thr Met Pro Ser Asp
            820                 825                 830

Thr Thr Leu Gln Asn Leu Thr Leu Asn Asn Ser Thr Val Thr Leu Asn
            835                 840                 845

Ser Ala Tyr Ser Ala Ile Ser Asn Asn Ala Pro Arg Arg Arg Arg Arg
850                 855                 860

Ser Leu Glu Thr Glu Thr Thr Pro Thr Ser Ala Glu His Arg Phe Asn
865                 870                 875                 880
```

```
Thr Leu Thr Val Asn Gly Lys Leu Ser Gly Gln Gly Thr Phe Gln Phe
                885                 890                 895

Thr Ser Ser Leu Phe Gly Tyr Lys Ser Asp Lys Leu Lys Leu Ser Asn
            900                 905                 910

Asp Ala Glu Gly Asp Tyr Thr Leu Ser Val Arg Asn Thr Gly Lys Glu
        915                 920                 925

Pro Val Thr Phe Gly Gln Leu Thr Leu Val Glu Ser Lys Asp Asn Lys
    930                 935                 940

Pro Leu Ser Asp Lys Leu Thr Phe Thr Leu Glu Asn Asp His Val Asp
945                 950                 955                 960

Ala Gly Ala Leu Arg Tyr Lys Leu Val Lys Asn Asp Gly Glu Phe Arg
                965                 970                 975

Leu His Asn Pro Ile Lys Glu Gln Glu Leu Arg Ser Asp Leu Val Arg
            980                 985                 990

Ala Glu Gln Ala Glu Arg Thr Leu  Glu Ala Lys Gln Val  Glu Gln Thr
            995                1000                1005

Ala Lys  Thr Gln Thr Ser Lys  Ala Arg Val Arg Ser  Arg Arg Ala
    1010                1015                1020

Val Phe  Ser Asp Pro Leu Pro  Ala Gln Ser Leu Leu  Asn Ala Leu
    1025                1030                1035

Glu Ala  Lys Gln Ala Leu Thr  Thr Glu Thr Gln Thr  Ser Lys Ala
    1040                1045                1050

Lys Lys  Val Arg Ser Lys Arg  Ala Ala Arg Glu Phe  Ser Asp Thr
    1055                1060                1065

Leu Pro  Asp Gln Ile Leu Gln  Ala Ala Leu Glu Val  Ile Asp Ala
    1070                1075                1080

Gln Gln  Gln Val Lys Lys Glu  Pro Gln Thr Gln Glu  Glu Glu Glu
    1085                1090                1095

Lys Arg  Gln Arg Lys Gln Lys  Glu Leu Ile Ser Arg  Tyr Ser Asn
    1100                1105                1110

Ser Ala  Leu Ser Glu Leu Ser  Ala Thr Val Asn Ser  Met Leu Ser
    1115                1120                1125

Val Gln  Asp Glu Leu Asp Arg  Leu Phe Val Asp Gln  Ala Gln Ser
    1130                1135                1140

Ala Val  Trp Thr Asn Ile Ala  Gln Asp Lys Arg Arg  Tyr Asp Ser
    1145                1150                1155

Asp Ala  Phe Arg Ala Tyr Gln  Gln Lys Thr Asn Leu  Arg Gln Ile
    1160                1165                1170

Gly Val  Gln Lys Ala Leu Asp  Asn Gly Arg Ile Gly  Ala Val Phe
    1175                1180                1185

Ser His  Ser Arg Ser Asp Asn  Thr Phe Asp Glu Gln  Val Lys Asn
    1190                1195                1200

His Ala  Thr Leu Ala Met Met  Ser Gly Phe Ala Gln  Tyr Gln Trp
    1205                1210                1215

Gly Asp  Leu Gln Phe Gly Val  Asn Val Gly Ala Gly  Ile Ser Ala
    1220                1225                1230

Ser Lys  Met Ala Glu Glu Gln  Ser Arg Lys Ile His  Arg Lys Ala
    1235                1240                1245

Ile Asn  Tyr Gly Val Asn Ala  Ser Tyr Gln Phe Arg  Leu Gly Gln
    1250                1255                1260

Leu Gly  Ile Gln Pro Tyr Leu  Gly Val Asn Arg Tyr  Phe Ile Glu
    1265                1270                1275
```

| Arg | Glu | Asn | Tyr | Gln | Ser | Glu | Val | Lys | Val | Gln | Thr | Pro | Ser |
| | 1280 | | | | 1285 | | | | | 1290 | | | |

Leu Val Phe Asn Arg Tyr Asn Ala Gly Ile Arg Val Asp Tyr Thr
    1295                    1300                    1305

Phe Thr Pro Thr Asp Asn Ile Ser Ile Lys Pro Tyr Phe Phe Val
    1310                    1315                    1320

Asn Tyr Val Asp Val Ser Asn Ala Asn Val Gln Thr Thr Val Asn
    1325                    1330                    1335

Arg Thr Met Leu Gln Gln Ser Phe Gly Arg Tyr Trp Gln Lys Glu
    1340                    1345                    1350

Val Gly Leu Lys Ala Glu Ile Leu His Phe Gln Leu Ser Ala Phe
    1355                    1360                    1365

Ile Ser Lys Ser Gln Gly Ser Gln Leu Gly Lys Gln Gln Asn Val
    1370                    1375                    1380

Gly Val Lys Leu Gly Tyr Arg Trp
    1385                    1390

<210> SEQ ID NO 16
<211> LENGTH: 4828
<212> TYPE: DNA
<213> ORGANISM: Haemophilus influenzae
<220> FEATURE:
<221> NAME/KEY: CDS
<222> LOCATION: (313)..(4548)
<223> OTHER INFORMATION:

<400> SEQUENCE: 16

```
tgaccgcact ttcagagaaa actcacataa agtgcggtta ttttattagt gatattgttt      60
taattttagt tatctgtata aattacatac aatattaatc catcgcaaga taagattacc     120
cactaagtat taagcaaaaa cctagaaatt ttggcttaat tactatatag ttttactcat     180
ttattttctt ttgtgccttt tagttcgttt ttttagctga aatcccttag aaaatcaccg     240
cacttttatt gttcaatagt cgtttaacca cgtattttt aatacgaaaa attacttaat      300
taaataaaca tt atg aaa aaa act gta ttt cgt ctg aat ttt tta acc gct    351
              Met Lys Lys Thr Val Phe Arg Leu Asn Phe Leu Thr Ala
                1               5                  10 tgc att tca tta ggg ata gta tcg caa gcg tgg gca ggt cat act tat    399
Cys Ile Ser Leu Gly Ile Val Ser Gln Ala Trp Ala Gly His Thr Tyr
 15                  20                  25 ttt ggg att gac tac caa tat tat cgt gat ttt gcc gag aat aaa ggg    447
Phe Gly Ile Asp Tyr Gln Tyr Tyr Arg Asp Phe Ala Glu Asn Lys Gly
 30                  35                  40                  45 aag ttc aca gtt ggg gct aaa aat att gag gtt tac aat aaa aat gga    495
Lys Phe Thr Val Gly Ala Lys Asn Ile Glu Val Tyr Asn Lys Asn Gly
                 50                  55                  60 aat tta gtt ggc aca tca atg aca aaa gcc cca atg att gat ttt tcc    543
Asn Leu Val Gly Thr Ser Met Thr Lys Ala Pro Met Ile Asp Phe Ser
             65                  70                  75 gtg gtg tcg cga aat ggg gtg gcg gca ttg gtg ggc gat cag tat att    591
Val Val Ser Arg Asn Gly Val Ala Ala Leu Val Gly Asp Gln Tyr Ile
         80                  85                  90 gtg agt gtg gca cat aat gta ggc tat acc aat gtg gat ttt ggt gct    639
Val Ser Val Ala His Asn Val Gly Tyr Thr Asn Val Asp Phe Gly Ala
     95                 100                 105 gaa gga caa aat cct gat caa cat cgt ttt act tat aaa att gtg aaa    687
Glu Gly Gln Asn Pro Asp Gln His Arg Phe Thr Tyr Lys Ile Val Lys
110                 115                 120                 125
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cgg | aat | aat | tat | aaa | aac | gat | caa | acg | cat | cct | tat | gag | aaa | gac | tac | 735  |
| Arg | Asn | Asn | Tyr | Lys | Asn | Asp | Gln | Thr | His | Pro | Tyr | Glu | Lys | Asp | Tyr |      |
|     |     |     |     | 130 |     |     |     |     | 135 |     |     |     |     | 140 |     |      |

| cac | aac | cca | cgc | tta | cat | aaa | ttt | gtt | acg | gaa | gcc | acc | cca | atc | gat | 783 |
|-----|-----|-----|-----|-----|-----|-----|-----|-----|-----|-----|-----|-----|-----|-----|-----|-----|
| His | Asn | Pro | Arg | Leu | His | Lys | Phe | Val | Thr | Glu | Ala | Thr | Pro | Ile | Asp |     |
|     |     |     | 145 |     |     |     |     | 150 |     |     |     |     | 155 |     |     |     |

| atg | act | tct | gat | atg | aac | ggc | aac | aaa | tat | aca | gat | agg | acg | aaa | tat | 831 |
|-----|-----|-----|-----|-----|-----|-----|-----|-----|-----|-----|-----|-----|-----|-----|-----|-----|
| Met | Thr | Ser | Asp | Met | Asn | Gly | Asn | Lys | Tyr | Thr | Asp | Arg | Thr | Lys | Tyr |     |
|     | 160 |     |     |     |     | 165 |     |     |     |     | 170 |     |     |     |     |     |

| ccc | gaa | cgc | gtg | cgt | atc | ggc | tcc | ggg | tgg | cag | ttt | tgg | cga | aac | gat | 879 |
|-----|-----|-----|-----|-----|-----|-----|-----|-----|-----|-----|-----|-----|-----|-----|-----|-----|
| Pro | Glu | Arg | Val | Arg | Ile | Gly | Ser | Gly | Trp | Gln | Phe | Trp | Arg | Asn | Asp |     |
|     | 175 |     |     |     |     | 180 |     |     |     |     | 185 |     |     |     |     |     |

| caa | aac | aac | ggc | gac | caa | gtt | gcc | ggc | gca | tat | cat | tac | ctg | aca | gca | 927 |
|-----|-----|-----|-----|-----|-----|-----|-----|-----|-----|-----|-----|-----|-----|-----|-----|-----|
| Gln | Asn | Asn | Gly | Asp | Gln | Val | Ala | Gly | Ala | Tyr | His | Tyr | Leu | Thr | Ala |     |
| 190 |     |     |     |     | 195 |     |     |     |     | 200 |     |     |     |     | 205 |     |

| ggc | aat | aca | cac | aac | caa | ggc | gga | gca | ggg | ggc | ggc | tgg | tca | agt | ctg | 975 |
|-----|-----|-----|-----|-----|-----|-----|-----|-----|-----|-----|-----|-----|-----|-----|-----|-----|
| Gly | Asn | Thr | His | Asn | Gln | Gly | Gly | Ala | Gly | Gly | Gly | Trp | Ser | Ser | Leu |     |
|     |     |     | 210 |     |     |     |     | 215 |     |     |     |     | 220 |     |     |     |

| agc | ggc | gat | gtg | cgc | caa | gcg | ggc | aat | tac | ggc | ccc | att | cct | att | gca | 1023 |
|-----|-----|-----|-----|-----|-----|-----|-----|-----|-----|-----|-----|-----|-----|-----|-----|------|
| Ser | Gly | Asp | Val | Arg | Gln | Ala | Gly | Asn | Tyr | Gly | Pro | Ile | Pro | Ile | Ala |      |
|     |     |     |     | 225 |     |     |     |     | 230 |     |     |     |     | 235 |     |      |

| ggc | tca | agc | ggc | gac | agc | ggt | tcg | cct | atg | ttt | att | tat | gat | gcg | gaa | 1071 |
|-----|-----|-----|-----|-----|-----|-----|-----|-----|-----|-----|-----|-----|-----|-----|-----|------|
| Gly | Ser | Ser | Gly | Asp | Ser | Gly | Ser | Pro | Met | Phe | Ile | Tyr | Asp | Ala | Glu |      |
|     |     | 240 |     |     |     |     | 245 |     |     |     |     | 250 |     |     |     |      |

| aaa | caa | aaa | tgg | ttg | att | aac | ggc | gta | ttg | agg | acc | ggc | aac | cct | tgg | 1119 |
|-----|-----|-----|-----|-----|-----|-----|-----|-----|-----|-----|-----|-----|-----|-----|-----|------|
| Lys | Gln | Lys | Trp | Leu | Ile | Asn | Gly | Val | Leu | Arg | Thr | Gly | Asn | Pro | Trp |      |
|     | 255 |     |     |     |     | 260 |     |     |     |     | 265 |     |     |     |     |      |

| gcg | ggg | aca | gag | aat | aca | ttc | caa | ctg | gta | cgc | aag | tct | ttt | ttt | gat | 1167 |
|-----|-----|-----|-----|-----|-----|-----|-----|-----|-----|-----|-----|-----|-----|-----|-----|------|
| Ala | Gly | Thr | Glu | Asn | Thr | Phe | Gln | Leu | Val | Arg | Lys | Ser | Phe | Phe | Asp |      |
| 270 |     |     |     |     | 275 |     |     |     |     | 280 |     |     |     |     | 285 |      |

| gaa | atc | ctt | gaa | aaa | gat | ttg | cgt | aca | tcg | ttt | tat | agc | cca | tcg | ggc | 1215 |
|-----|-----|-----|-----|-----|-----|-----|-----|-----|-----|-----|-----|-----|-----|-----|-----|------|
| Glu | Ile | Leu | Glu | Lys | Asp | Leu | Arg | Thr | Ser | Phe | Tyr | Ser | Pro | Ser | Gly |      |
|     |     |     |     | 290 |     |     |     |     | 295 |     |     |     |     | 300 |     |      |

| aat | ggt | gca | tac | acc | att | aca | gac | aaa | ggc | gac | ggc | agc | ggc | att | gtc | 1263 |
|-----|-----|-----|-----|-----|-----|-----|-----|-----|-----|-----|-----|-----|-----|-----|-----|------|
| Asn | Gly | Ala | Tyr | Thr | Ile | Thr | Asp | Lys | Gly | Asp | Gly | Ser | Gly | Ile | Val |      |
|     |     |     | 305 |     |     |     |     | 310 |     |     |     |     | 315 |     |     |      |

| aaa | caa | caa | aca | gga | aga | cca | tct | gaa | gtc | cgc | atc | ggt | tta | aaa | gac | 1311 |
|-----|-----|-----|-----|-----|-----|-----|-----|-----|-----|-----|-----|-----|-----|-----|-----|------|
| Lys | Gln | Gln | Thr | Gly | Arg | Pro | Ser | Glu | Val | Arg | Ile | Gly | Leu | Lys | Asp |      |
|     |     | 320 |     |     |     |     | 325 |     |     |     |     | 330 |     |     |     |      |

| gac | aaa | tta | cct | gcc | gaa | ggt | aaa | gac | gat | gtt | tac | caa | tac | caa | ggt | 1359 |
|-----|-----|-----|-----|-----|-----|-----|-----|-----|-----|-----|-----|-----|-----|-----|-----|------|
| Asp | Lys | Leu | Pro | Ala | Glu | Gly | Lys | Asp | Asp | Val | Tyr | Gln | Tyr | Gln | Gly |      |
|     | 335 |     |     |     |     | 340 |     |     |     |     | 345 |     |     |     |     |      |

| cca | aat | ata | tac | ctg | cct | cgt | ttg | aat | aac | ggt | gga | aac | ctg | tat | ttc | 1407 |
|-----|-----|-----|-----|-----|-----|-----|-----|-----|-----|-----|-----|-----|-----|-----|-----|------|
| Pro | Asn | Ile | Tyr | Leu | Pro | Arg | Leu | Asn | Asn | Gly | Gly | Asn | Leu | Tyr | Phe |      |
| 350 |     |     |     |     | 355 |     |     |     |     | 360 |     |     |     |     | 365 |      |

| gga | gat | caa | aaa | aac | ggc | act | gtt | acc | tta | tca | acc | aac | atc | aac | caa | 1455 |
|-----|-----|-----|-----|-----|-----|-----|-----|-----|-----|-----|-----|-----|-----|-----|-----|------|
| Gly | Asp | Gln | Lys | Asn | Gly | Thr | Val | Thr | Leu | Ser | Thr | Asn | Ile | Asn | Gln |      |
|     |     |     | 370 |     |     |     |     | 375 |     |     |     |     | 380 |     |     |      |

| ggt | gcg | ggc | ggt | ttg | tat | ttt | gag | ggt | aac | ttt | acg | gta | tct | tca | gaa | 1503 |
|-----|-----|-----|-----|-----|-----|-----|-----|-----|-----|-----|-----|-----|-----|-----|-----|------|
| Gly | Ala | Gly | Gly | Leu | Tyr | Phe | Glu | Gly | Asn | Phe | Thr | Val | Ser | Ser | Glu |      |
|     |     |     | 385 |     |     |     |     | 390 |     |     |     |     | 395 |     |     |      |

| aat | aat | gca | act | tgg | caa | ggt | gct | gga | gtg | cat | gta | ggt | gaa | gac | agt | 1551 |
|-----|-----|-----|-----|-----|-----|-----|-----|-----|-----|-----|-----|-----|-----|-----|-----|------|
| Asn | Asn | Ala | Thr | Trp | Gln | Gly | Ala | Gly | Val | His | Val | Gly | Glu | Asp | Ser |      |
|     |     | 400 |     |     |     |     | 405 |     |     |     |     | 410 |     |     |     |      |

| act | gtt | act | tgg | aaa | gta | aat | ggt | gtt | gaa | aat | gat | cgc | ctt | tct | aaa | 1599 |
|-----|-----|-----|-----|-----|-----|-----|-----|-----|-----|-----|-----|-----|-----|-----|-----|------|
| Thr | Val | Thr | Trp | Lys | Val | Asn | Gly | Val | Glu | Asn | Asp | Arg | Leu | Ser | Lys |      |
|     | 415 |     |     |     |     | 420 |     |     |     |     | 425 |     |     |     |     |      |

| atc | ggc | aaa | ggc | aca | ttg | cac | gtt | aaa | gcc | aaa | ggg | gaa | aat | aaa | ggt | 1647 |
|-----|-----|-----|-----|-----|-----|-----|-----|-----|-----|-----|-----|-----|-----|-----|-----|------|
| Ile | Gly | Lys | Gly | Thr | Leu | His | Val | Lys | Ala | Lys | Gly | Glu | Asn | Lys | Gly |      |
| 430 |     |     |     |     | 435 |     |     |     |     | 440 |     |     |     |     | 445 |      |

-continued

```
tcg atc agc gta ggc gat ggt aaa gtc att ttg gag cag cag gca gac    1695
Ser Ile Ser Val Gly Asp Gly Lys Val Ile Leu Glu Gln Gln Ala Asp
            450                 455                 460 gat caa ggc aac aaa caa gcc ttt agt gaa att ggc ttg gtt agt ggc    1743
Asp Gln Gly Asn Lys Gln Ala Phe Ser Glu Ile Gly Leu Val Ser Gly
        465                 470                 475 aga ggt acg gtt cag tta aac gat gac aag caa ttt aat act gat aaa    1791
Arg Gly Thr Val Gln Leu Asn Asp Asp Lys Gln Phe Asn Thr Asp Lys
    480                 485                 490 ttt tat ttc ggc ttc cgt ggt ggt cgc tta gat ctt aat ggg cat tca    1839
Phe Tyr Phe Gly Phe Arg Gly Gly Arg Leu Asp Leu Asn Gly His Ser
495                 500                 505 tta acc ttt aaa cgt atc caa aat acg gat gag gga gca acg att gtt    1887
Leu Thr Phe Lys Arg Ile Gln Asn Thr Asp Glu Gly Ala Thr Ile Val
510                 515                 520                 525 aat cac aat gcc aca aca gaa tct aca gtg acc att act ggc agc gat    1935
Asn His Asn Ala Thr Thr Glu Ser Thr Val Thr Ile Thr Gly Ser Asp
                530                 535                 540 acc att aat gac aac act ggc gat tta acc aat aaa cgt gat att gct    1983
Thr Ile Asn Asp Asn Thr Gly Asp Leu Thr Asn Lys Arg Asp Ile Ala
            545                 550                 555 ttt aat ggt tgg ttt ggt gat aaa gat gat act aaa aat act gga cgt    2031
Phe Asn Gly Trp Phe Gly Asp Lys Asp Asp Thr Lys Asn Thr Gly Arg
        560                 565                 570 ttg aat gtt act tac aat ccg ctt aac aaa gat aat cac ttc ctt cta    2079
Leu Asn Val Thr Tyr Asn Pro Leu Asn Lys Asp Asn His Phe Leu Leu
    575                 580                 585 tca ggt gga aca aat tta aaa ggc aat att act caa gac ggt ggc act    2127
Ser Gly Gly Thr Asn Leu Lys Gly Asn Ile Thr Gln Asp Gly Gly Thr
590                 595                 600                 605 tta gtg ttt agt ggt cgc cca aca cca cac gca tac aat cat tta aat    2175
Leu Val Phe Ser Gly Arg Pro Thr Pro His Ala Tyr Asn His Leu Asn
                610                 615                 620 cgc cta aac gag ctt ggg cga cct aag ggc gaa gtg gtt att gat gac    2223
Arg Leu Asn Glu Leu Gly Arg Pro Lys Gly Glu Val Val Ile Asp Asp
            625                 630                 635 gat tgg atc aac cgt aca ttt aaa gct gaa aac ttc caa att aaa ggc    2271
Asp Trp Ile Asn Arg Thr Phe Lys Ala Glu Asn Phe Gln Ile Lys Gly
        640                 645                 650 gga agt acg gtg gtt tct cgc aat gtt tct tca att gaa gga aat tgg    2319
Gly Ser Thr Val Val Ser Arg Asn Val Ser Ser Ile Glu Gly Asn Trp
    655                 660                 665 aca atc agc aat aac gcc aac gcg aca ttt ggt gtt gtg cca aat caa    2367
Thr Ile Ser Asn Asn Ala Asn Ala Thr Phe Gly Val Val Pro Asn Gln
670                 675                 680                 685 caa aat acc att tgc acg cgt tca gat tgg aca gga tta acg act tgt    2415
Gln Asn Thr Ile Cys Thr Arg Ser Asp Trp Thr Gly Leu Thr Thr Cys
                690                 695                 700 aaa aca gtt aat tta acc gat aaa aaa gtt att gat tcc ata ccg aca    2463
Lys Thr Val Asn Leu Thr Asp Lys Lys Val Ile Asp Ser Ile Pro Thr
            705                 710                 715 aca caa att aat ggc tct att aat tta act aat aat gca aca gtg aat    2511
Thr Gln Ile Asn Gly Ser Ile Asn Leu Thr Asn Asn Ala Thr Val Asn
        720                 725                 730 att cat ggt tta gca aaa ctt aat ggt aat gtc act tta ata aat cat    2559
Ile His Gly Leu Ala Lys Leu Asn Gly Asn Val Thr Leu Ile Asn His
    735                 740                 745 agc caa ttt aca ttg agc aac aat gcc acc caa aca ggc aat atc caa    2607
Ser Gln Phe Thr Leu Ser Asn Asn Ala Thr Gln Thr Gly Asn Ile Gln
750                 755                 760                 765
```

```
                                                                 -continued ctt tca aat cac gca aat gca acg gtg gat aat gca aac ttg aac ggt      2655
Leu Ser Asn His Ala Asn Ala Thr Val Asp Asn Ala Asn Leu Asn Gly
                770                 775                 780 aat gtg cat tta acg gat tct gct caa ttt tct tta aaa aac agc cat      2703
Asn Val His Leu Thr Asp Ser Ala Gln Phe Ser Leu Lys Asn Ser His
            785                 790                 795 ttt tcg cac caa att cag ggc gac aaa gac aca aca gtg acg ttg gaa      2751
Phe Ser His Gln Ile Gln Gly Asp Lys Asp Thr Thr Val Thr Leu Glu
        800                 805                 810 aat gcg act tgg aca atg cct agc gat act aca ttg cag aat tta acg      2799
Asn Ala Thr Trp Thr Met Pro Ser Asp Thr Thr Leu Gln Asn Leu Thr
    815                 820                 825 cta aat aat agt act gtt acg tta aat tca gct tat tca gct agc tca      2847
Leu Asn Asn Ser Thr Val Thr Leu Asn Ser Ala Tyr Ser Ala Ser Ser
830                 835                 840                 845 aat aat gcg cca cgt cac cgc cgt tca tta gag acg gaa aca acg cca      2895
Asn Asn Ala Pro Arg His Arg Arg Ser Leu Glu Thr Glu Thr Thr Pro
                850                 855                 860 aca tcg gaa gaa cat cgt ttc aac aca ttg aca gta aat ggt aaa ttg      2943
Thr Ser Glu Glu His Arg Phe Asn Thr Leu Thr Val Asn Gly Lys Leu
            865                 870                 875 agc ggg caa ggc aca ttc caa ttt act tca tct tta ttt ggc tat aaa      2991
Ser Gly Gln Gly Thr Phe Gln Phe Thr Ser Ser Leu Phe Gly Tyr Lys
        880                 885                 890 agc gat aaa ata aaa tta tct aat gac gct gaa ggc gat tac aca tta      3039
Ser Asp Lys Ile Lys Leu Ser Asn Asp Ala Glu Gly Asp Tyr Thr Leu
    895                 900                 905 gct gtt cgc gac aca ggc aaa gaa cct gtg acc ctt gag caa tta act      3087
Ala Val Arg Asp Thr Gly Lys Glu Pro Val Thr Leu Glu Gln Leu Thr
910                 915                 920                 925 tta att gaa ggc ttg gat aat caa ccc ttg cca gat aag cta aaa att      3135
Leu Ile Glu Gly Leu Asp Asn Gln Pro Leu Pro Asp Lys Leu Lys Ile
                930                 935                 940 act tta aaa aat aaa cac gtt gat gcg ggt gca tgg cgt tat gaa tta      3183
Thr Leu Lys Asn Lys His Val Asp Ala Gly Ala Trp Arg Tyr Glu Leu
            945                 950                 955 gtg aag aaa aac ggc gaa ttc cgc ttg cat aat cca ata aaa gag cag      3231
Val Lys Lys Asn Gly Glu Phe Arg Leu His Asn Pro Ile Lys Glu Gln
        960                 965                 970 gaa ttg cgc aat gat tta gta aaa gca gag caa gta gaa cga gca tta      3279
Glu Leu Arg Asn Asp Leu Val Lys Ala Glu Gln Val Glu Arg Ala Leu
    975                 980                 985 gaa gca aaa caa gct gaa ctg act act aaa aaa  caa aaa act gag gct     3327
Glu Ala Lys Gln Ala Glu Leu Thr Thr Lys Lys  Gln Lys Thr Glu Ala
990                 995                 1000                1005 aaa gtg cgg tca aaa  aga gcg gcg ttt tct  gat acc ccg cct gat        3372
Lys Val Arg Ser Lys  Arg Ala Ala Phe Ser  Asp Thr Pro Pro Asp
                1010                 1015                1020 caa agc cag tta aac  gca tta caa gcc gaa  ctc gag acg att aat        3417
Gln Ser Gln Leu Asn  Ala Leu Gln Ala Glu  Leu Glu Thr Ile Asn
            1025                 1030                 1035 gcc caa cag caa gtg  gca caa gcg gtg caa  aat cag aaa gta act        3462
Ala Gln Gln Gln Val  Ala Gln Ala Val Gln  Asn Gln Lys Val Thr
        1040                 1045                 1050 gca ctt aac caa aag  aac gag caa gtt aaa  acc act caa gat aaa        3507
Ala Leu Asn Gln Lys  Asn Glu Gln Val Lys  Thr Thr Gln Asp Lys
    1055                 1060                 1065 gca aat tta gtc ttg  gca act gca ttg gtg  gaa aaa gaa acc gct        3552
Ala Asn Leu Val Leu  Ala Thr Ala Leu Val  Glu Lys Glu Thr Ala
                1070                 1075                 1080
```

```
cag att gat ttt gct  aat gca aaa tta gct  cag ttg aat tta aca       3597
Gln Ile Asp Phe Ala  Asn Ala Lys Leu Ala  Gln Leu Asn Leu Thr
            1085                1090                     1095 caa caa cta gaa aaa  gcc tta gca gtg gct  gag caa gca gaa aaa       3642
Gln Gln Leu Glu Lys  Ala Leu Ala Val Ala  Glu Gln Ala Glu Lys
            1100                1105                     1110 gag cgt aaa gct caa  gag caa gcg aaa aga  caa cgc aaa caa aaa       3687
Glu Arg Lys Ala Gln  Glu Gln Ala Lys Arg  Gln Arg Lys Gln Lys
            1115                1120                     1125 gac ttg atc agc cgt  tat tca aat agt gcg  tta tca gaa tta tct       3732
Asp Leu Ile Ser Arg  Tyr Ser Asn Ser Ala  Leu Ser Glu Leu Ser
            1130                1135                     1140 gca aca gta aat agt  atg ctt tcc gtt caa  gat gaa tta gat cgt       3777
Ala Thr Val Asn Ser  Met Leu Ser Val Gln  Asp Glu Leu Asp Arg
            1145                1150                     1155 ctt ttt gta gat caa  gct caa tct gcg gtg  tgg aca aat atc tca       3822
Leu Phe Val Asp Gln  Ala Gln Ser Ala Val  Trp Thr Asn Ile Ser
            1160                1165                     1170 cag gat aaa aga cgt  tat gat tct gat gcg  ttc cgt gct tat cag       3867
Gln Asp Lys Arg Arg  Tyr Asp Ser Asp Ala  Phe Arg Ala Tyr Gln
            1175                1180                     1185 cag aaa acg aac ttg  cgt caa att ggg gtg  caa aaa gcc tta gct       3912
Gln Lys Thr Asn Leu  Arg Gln Ile Gly Val  Gln Lys Ala Leu Ala
            1190                1195                     1200 aac gga cga att ggg  gca gtt ttc tcg cat  agc cgt tca gat aat       3957
Asn Gly Arg Ile Gly  Ala Val Phe Ser His  Ser Arg Ser Asp Asn
            1205                1210                     1215 act ttt gat gaa cag  gtt aaa aat cac gca  aca tta acg atg atg       4002
Thr Phe Asp Glu Gln  Val Lys Asn His Ala  Thr Leu Thr Met Met
            1220                1225                     1230 tcg ggt ttt gcc caa  tat caa tgg ggt gat  tta caa ttt ggt gta       4047
Ser Gly Phe Ala Gln  Tyr Gln Trp Gly Asp  Leu Gln Phe Gly Val
            1235                1240                     1245 aac gtg gga acg gga  att agt gcg agt aaa  atg gct gaa gaa caa       4092
Asn Val Gly Thr Gly  Ile Ser Ala Ser Lys  Met Ala Glu Glu Gln
            1250                1255                     1260 agc cga aaa att cat  cga aaa gcg ata aat  tat ggc gtg aat gca       4137
Ser Arg Lys Ile His  Arg Lys Ala Ile Asn  Tyr Gly Val Asn Ala
            1265                1270                     1275 agt tat tcg ttc cat  tta ggg caa ttg ggt  att cag cct tat ttt       4182
Ser Tyr Ser Phe His  Leu Gly Gln Leu Gly  Ile Gln Pro Tyr Phe
            1280                1285                     1290 gga gtt aat cgc tat  ttt att gaa cgt aaa  aat tat caa tct gag       4227
Gly Val Asn Arg Tyr  Phe Ile Glu Arg Lys  Asn Tyr Gln Ser Glu
            1295                1300                     1305 gaa gtg aaa gtg caa  aca ccg agc ctt gca  ttt aat cgc tat aat       4272
Glu Val Lys Val Gln  Thr Pro Ser Leu Ala  Phe Asn Arg Tyr Asn
            1310                1315                     1320 gct gga gta cgg gtc  gat tat acg ttt acc  ccg aca gag aat atc       4317
Ala Gly Val Arg Val  Asp Tyr Thr Phe Thr  Pro Thr Glu Asn Ile
            1325                1330                     1335 agc gtt aag cct tat  ttc ttc gtc aat tat  gtt gat gtt tca aac       4362
Ser Val Lys Pro Tyr  Phe Phe Val Asn Tyr  Val Asp Val Ser Asn
            1340                1345                     1350 gct aac gta caa acc  act gta aat cgc gcg  gtg ttg caa caa cca       4407
Ala Asn Val Gln Thr  Thr Val Asn Arg Ala  Val Leu Gln Gln Pro
            1355                1360                     1365 ttt gga cgt tat tgg  caa aaa gaa gtg gga  tta aaa gcg gaa att       4452
Phe Gly Arg Tyr Trp  Gln Lys Glu Val Gly  Leu Lys Ala Glu Ile
            1370                1375                     1380
```

| | | |
|---|---|---|
| tta cat ttc caa ctt tct gct ttt att tct aaa tct caa ggt tcg<br>Leu His Phe Gln Leu Ser Ala Phe Ile Ser Lys Ser Gln Gly Ser<br>                   1385                          1390                       1395 | 4497 |
| caa ctc ggt aaa cag cga aat atg ggc gtg aaa tta gga tat cgt<br>Gln Leu Gly Lys Gln Arg Asn Met Gly Val Lys Leu Gly Tyr Arg<br>                   1400                          1405                       1410 | 4542 |
| tgg taa aaatcaacat aatttattc taataatgga actttattta attaaaagta<br>Trp | 4598 |
| tctaagtagc accctatagg ggattaatta agaggattta ataatgaatt taactaaaat | 4658 |
| tttacccgca tttgctgctg cagtcgtatt atctgcttgt gcaaggatg cacctgaaat | 4718 |
| gacaaaatca tctgcgcaaa tagctgaaat gcaaacactt ccaacaatca ctgataaaac | 4778 |
| agttgtatat tcttgcaata aacaaactgt gactgcagtg tatcaatttg | 4828 |

<210> SEQ ID NO 17
<211> LENGTH: 1411
<212> TYPE: PRT
<213> ORGANISM: Haemophilus influenzae

<400> SEQUENCE: 17

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Lys Gly Lys Phe Thr
        35                  40                  45

Val Gly Ala Lys Asn Ile Glu Val Tyr Asn Lys Asn Gly Asn Leu Val
    50                  55                  60

Gly Thr Ser Met Thr Lys Ala Pro Met Ile Asp Phe Ser Val Val Ser
65                  70                  75                  80

Arg Asn Gly Val Ala Ala Leu Val Gly Asp Gln Tyr Ile Val Ser Val
                85                  90                  95

Ala His Asn Val Gly Tyr Thr Asn Val Asp Phe Gly Ala Glu Gly Gln
            100                 105                 110

Asn Pro Asp Gln His Arg Phe Thr Tyr Lys Ile Val Lys Arg Asn Asn
        115                 120                 125

Tyr Lys Asn Asp Gln Thr His Pro Tyr Glu Lys Asp Tyr His Asn Pro
    130                 135                 140

Arg Leu His Lys Phe Val Thr Glu Ala Thr Pro Ile Asp Met Thr Ser
145                 150                 155                 160

Asp Met Asn Gly Asn Lys Tyr Thr Asp Arg Thr Lys Tyr Pro Glu Arg
                165                 170                 175

Val Arg Ile Gly Ser Gly Trp Gln Phe Trp Arg Asn Asp Gln Asn Asn
            180                 185                 190

Gly Asp Gln Val Ala Gly Ala Tyr His Tyr Leu Thr Ala Gly Asn Thr
        195                 200                 205

His Asn Gln Gly Gly Ala Gly Gly Trp Ser Ser Leu Ser Gly Asp
    210                 215                 220

Val Arg Gln Ala Gly Asn Tyr Gly Pro Ile Pro Ile Ala Gly Ser Ser
225                 230                 235                 240

Gly Asp Ser Gly Ser Pro Met Phe Ile Tyr Asp Ala Glu Lys Gln Lys
                245                 250                 255

Trp Leu Ile Asn Gly Val Leu Arg Thr Gly Asn Pro Trp Ala Gly Thr
            260                 265                 270

-continued

```
Glu Asn Thr Phe Gln Leu Val Arg Lys Ser Phe Phe Asp Glu Ile Leu
        275                 280                 285

Glu Lys Asp Leu Arg Thr Ser Phe Tyr Ser Pro Ser Gly Asn Gly Ala
        290                 295                 300

Tyr Thr Ile Thr Asp Lys Gly Asp Gly Ser Gly Ile Val Lys Gln Gln
305                 310                 315                 320

Thr Gly Arg Pro Ser Glu Val Arg Ile Gly Leu Lys Asp Asp Lys Leu
                325                 330                 335

Pro Ala Glu Gly Lys Asp Asp Val Tyr Gln Tyr Gln Gly Pro Asn Ile
                340                 345                 350

Tyr Leu Pro Arg Leu Asn Asn Gly Asn Leu Tyr Phe Gly Asp Gln
        355                 360                 365

Lys Asn Gly Thr Val Thr Leu Ser Thr Asn Ile Asn Gln Gly Ala Gly
        370                 375                 380

Gly Leu Tyr Phe Glu Gly Asn Phe Thr Val Ser Ser Glu Asn Asn Ala
385                 390                 395                 400

Thr Trp Gln Gly Ala Gly Val His Val Gly Glu Asp Ser Thr Val Thr
                405                 410                 415

Trp Lys Val Asn Gly Val Glu Asn Asp Arg Leu Ser Lys Ile Gly Lys
                420                 425                 430

Gly Thr Leu His Val Lys Ala Lys Gly Glu Asn Lys Gly Ser Ile Ser
        435                 440                 445

Val Gly Asp Gly Lys Val Ile Leu Glu Gln Gln Ala Asp Asp Gln Gly
450                 455                 460

Asn Lys Gln Ala Phe Ser Glu Ile Gly Leu Val Ser Gly Arg Gly Thr
465                 470                 475                 480

Val Gln Leu Asn Asp Asp Lys Gln Phe Asn Thr Asp Lys Phe Tyr Phe
                485                 490                 495

Gly Phe Arg Gly Gly Arg Leu Asp Leu Asn Gly His Ser Leu Thr Phe
                500                 505                 510

Lys Arg Ile Gln Asn Thr Asp Glu Gly Ala Thr Ile Val Asn His Asn
        515                 520                 525

Ala Thr Thr Glu Ser Thr Val Thr Ile Thr Gly Ser Asp Thr Ile Asn
        530                 535                 540

Asp Asn Thr Gly Asp Leu Thr Asn Lys Arg Asp Ile Ala Phe Asn Gly
545                 550                 555                 560

Trp Phe Gly Asp Lys Asp Asp Thr Lys Asn Thr Gly Arg Leu Asn Val
                565                 570                 575

Thr Tyr Asn Pro Leu Asn Lys Asp Asn His Phe Leu Leu Ser Gly Gly
                580                 585                 590

Thr Asn Leu Lys Gly Asn Ile Thr Gln Asp Gly Gly Thr Leu Val Phe
        595                 600                 605

Ser Gly Arg Pro Thr Pro His Ala Tyr Asn His Leu Asn Arg Leu Asn
        610                 615                 620

Glu Leu Gly Arg Pro Lys Gly Glu Val Val Ile Asp Asp Trp Ile
625                 630                 635                 640

Asn Arg Thr Phe Lys Ala Glu Asn Phe Gln Ile Lys Gly Gly Ser Thr
                645                 650                 655

Val Val Ser Arg Asn Val Ser Ser Ile Glu Gly Asn Trp Thr Ile Ser
                660                 665                 670

Asn Asn Ala Asn Ala Thr Phe Gly Val Val Pro Asn Gln Gln Asn Thr
        675                 680                 685
```

```
Ile Cys Thr Arg Ser Asp Trp Thr Gly Leu Thr Thr Cys Lys Thr Val
690                 695                 700

Asn Leu Thr Asp Lys Lys Val Ile Asp Ser Ile Pro Thr Thr Gln Ile
705                 710                 715                 720

Asn Gly Ser Ile Asn Leu Thr Asn Asn Ala Thr Val Asn Ile His Gly
                725                 730                 735

Leu Ala Lys Leu Asn Gly Asn Val Thr Leu Ile Asn His Ser Gln Phe
            740                 745                 750

Thr Leu Ser Asn Asn Ala Thr Gln Thr Gly Asn Ile Gln Leu Ser Asn
        755                 760                 765

His Ala Asn Ala Thr Val Asp Asn Ala Asn Leu Asn Gly Asn Val His
770                 775                 780

Leu Thr Asp Ser Ala Gln Phe Ser Leu Lys Asn Ser His Phe Ser His
785                 790                 795                 800

Gln Ile Gln Gly Asp Lys Asp Thr Thr Val Thr Leu Glu Asn Ala Thr
                805                 810                 815

Trp Thr Met Pro Ser Asp Thr Thr Leu Gln Asn Leu Thr Leu Asn Asn
            820                 825                 830

Ser Thr Val Thr Leu Asn Ser Ala Tyr Ser Ala Ser Ser Asn Asn Ala
        835                 840                 845

Pro Arg His Arg Ser Leu Glu Thr Glu Thr Pro Thr Ser Glu
850                 855                 860

Glu His Arg Phe Asn Thr Leu Thr Val Asn Gly Lys Leu Ser Gly Gln
865                 870                 875                 880

Gly Thr Phe Gln Phe Thr Ser Ser Leu Phe Gly Tyr Lys Ser Asp Lys
                885                 890                 895

Ile Lys Leu Ser Asn Asp Ala Glu Gly Asp Tyr Thr Leu Ala Val Arg
            900                 905                 910

Asp Thr Gly Lys Glu Pro Val Thr Leu Glu Gln Leu Thr Leu Ile Glu
        915                 920                 925

Gly Leu Asp Asn Gln Pro Leu Pro Asp Lys Leu Lys Ile Thr Leu Lys
930                 935                 940

Asn Lys His Val Asp Ala Gly Ala Trp Arg Tyr Glu Leu Val Lys Lys
945                 950                 955                 960

Asn Gly Glu Phe Arg Leu His Asn Pro Ile Lys Glu Gln Glu Leu Arg
                965                 970                 975

Asn Asp Leu Val Lys Ala Glu Gln Val Glu Arg Ala Leu Glu Ala Lys
            980                 985                 990

Gln Ala Glu Leu Thr Thr Lys Lys  Gln Lys Thr Glu Ala  Lys Val Arg
        995                 1000                 1005

Ser Lys  Arg Ala Ala Phe Ser  Asp Thr Pro Pro Asp  Gln Ser Gln
    1010                 1015                 1020

Leu Asn  Ala Leu Gln Ala Glu  Leu Glu Thr Ile Asn  Ala Gln Gln
    1025                 1030                 1035

Gln Val  Ala Gln Ala Val Gln  Asn Gln Lys Val Thr  Ala Leu Asn
    1040                 1045                 1050

Gln Lys  Asn Glu Gln Val Lys  Thr Thr Gln Asp Lys  Ala Asn Leu
    1055                 1060                 1065

Val Leu  Ala Thr Ala Leu Val  Glu Lys Glu Thr Ala  Gln Ile Asp
    1070                 1075                 1080

Phe Ala  Asn Ala Lys Leu Ala  Gln Leu Asn Leu Thr  Gln Gln Leu
    1085                 1090                 1095
```

-continued

```
Glu Lys Ala Leu Ala Val Ala Glu Gln Ala Glu Lys Glu Arg Lys
    1100                1105                1110
Ala Gln Glu Gln Ala Lys Arg Gln Arg Lys Gln Lys Asp Leu Ile
    1115                1120                1125
Ser Arg Tyr Ser Asn Ser Ala Leu Ser Glu Leu Ser Ala Thr Val
    1130                1135                1140
Asn Ser Met Leu Ser Val Gln Asp Glu Leu Asp Arg Leu Phe Val
    1145                1150                1155
Asp Gln Ala Gln Ser Ala Val Trp Thr Asn Ile Ser Gln Asp Lys
    1160                1165                1170
Arg Arg Tyr Asp Ser Asp Ala Phe Arg Ala Tyr Gln Gln Lys Thr
    1175                1180                1185
Asn Leu Arg Gln Ile Gly Val Gln Lys Ala Leu Ala Asn Gly Arg
    1190                1195                1200
Ile Gly Ala Val Phe Ser His Ser Arg Ser Asp Asn Thr Phe Asp
    1205                1210                1215
Glu Gln Val Lys Asn His Ala Thr Leu Thr Met Met Ser Gly Phe
    1220                1225                1230
Ala Gln Tyr Gln Trp Gly Asp Leu Gln Phe Gly Val Asn Val Gly
    1235                1240                1245
Thr Gly Ile Ser Ala Ser Lys Met Ala Glu Glu Gln Ser Arg Lys
    1250                1255                1260
Ile His Arg Lys Ala Ile Asn Tyr Gly Val Asn Ala Ser Tyr Ser
    1265                1270                1275
Phe His Leu Gly Gln Leu Gly Ile Gln Pro Tyr Phe Gly Val Asn
    1280                1285                1290
Arg Tyr Phe Ile Glu Arg Lys Asn Tyr Gln Ser Glu Glu Val Lys
    1295                1300                1305
Val Gln Thr Pro Ser Leu Ala Phe Asn Arg Tyr Asn Ala Gly Val
    1310                1315                1320
Arg Val Asp Tyr Thr Phe Thr Pro Thr Glu Asn Ile Ser Val Lys
    1325                1330                1335
Pro Tyr Phe Phe Val Asn Tyr Val Asp Val Ser Asn Ala Asn Val
    1340                1345                1350
Gln Thr Thr Val Asn Arg Ala Val Leu Gln Gln Pro Phe Gly Arg
    1355                1360                1365
Tyr Trp Gln Lys Glu Val Gly Leu Lys Ala Glu Ile Leu His Phe
    1370                1375                1380
Gln Leu Ser Ala Phe Ile Ser Lys Ser Gln Gly Ser Gln Leu Gly
    1385                1390                1395
Lys Gln Arg Asn Met Gly Val Lys Leu Gly Tyr Arg Trp
    1400                1405                1410
```

<210> SEQ ID NO 18
<211> LENGTH: 47
<212> TYPE: PRT
<213> ORGANISM: Haemophilus influenzae

<400> SEQUENCE: 18

```
Met Lys Lys Thr Val Phe Arg Leu Asn Phe Leu Thr Ala Cys Ile Ser
1               5                   10                  15
Leu Gly Ile Val Ser Gln Ala Trp Ala Gly His Thr Tyr Phe Gly Ile
                20                  25                  30
Asp Tyr Gln Tyr Tyr Arg Asp Phe Ala Glu Asn Lys Gly Lys Phe
            35                  40                  45
```

```
<210> SEQ ID NO 19
<211> LENGTH: 7
<212> TYPE: PRT
<213> ORGANISM: Haemophilus influenzae

<400> SEQUENCE: 19

Asn Pro Asp Gln His Arg Phe
1               5

<210> SEQ ID NO 20
<211> LENGTH: 11
<212> TYPE: PRT
<213> ORGANISM: Haemophilus influenzae

<400> SEQUENCE: 20

Gly Asp Ser Gly Ser Pro Met Phe Ile Tyr Asp
1               5                   10

<210> SEQ ID NO 21
<211> LENGTH: 14
<212> TYPE: PRT
<213> ORGANISM: Haemophilus influenzae

<400> SEQUENCE: 21

Ile Asn Gln Gly Ala Gly Gly Leu Tyr Phe Glu Gly Asn Gly
1               5                   10

<210> SEQ ID NO 22
<211> LENGTH: 7
<212> TYPE: PRT
<213> ORGANISM: Haemophilus influenzae

<400> SEQUENCE: 22

Asp Arg Leu Ser Lys Ile Gly
1               5

<210> SEQ ID NO 23
<211> LENGTH: 18
<212> TYPE: PRT
<213> ORGANISM: Haemophilus influenzae

<400> SEQUENCE: 23

Tyr Phe Gly Phe Arg Gly Gly Arg Leu Asp Leu Asn Gly His Ser Leu
1               5                   10                  15

Thr Phe

<210> SEQ ID NO 24
<211> LENGTH: 15
<212> TYPE: PRT
<213> ORGANISM: Haemophilus influenzae

<400> SEQUENCE: 24

Arg Ile Gln Asn Thr Asp Glu Gly Ala Met Ile Val Asn His Asn
1               5                   10                  15

<210> SEQ ID NO 25
<211> LENGTH: 9
<212> TYPE: PRT
<213> ORGANISM: Haemophilus influenzae

<400> SEQUENCE: 25

Leu Leu Leu Ser Gly Gly Thr Asn Leu
1               5
```

```
<210> SEQ ID NO 26
<211> LENGTH: 13
<212> TYPE: PRT
<213> ORGANISM: Haemophilus influenzae

<400> SEQUENCE: 26

Phe Ser Gly Arg Pro Thr Pro His Ala Tyr Asn His Leu
1               5                   10

<210> SEQ ID NO 27
<211> LENGTH: 36
<212> TYPE: PRT
<213> ORGANISM: Haemophilus influenzae

<400> SEQUENCE: 27

Arg Thr Phe Lys Ala Glu Asn Phe Gln Ile Lys Gly Gly Ser Ala Val
1               5                   10                  15

Val Ser Arg Asn Val Ser Ser Ile Glu Gly Asn Trp Thr Val Ser Asn
            20                  25                  30

Asn Ala Asn Ala
        35

<210> SEQ ID NO 28
<211> LENGTH: 23
<212> TYPE: PRT
<213> ORGANISM: Haemophilus influenzae

<400> SEQUENCE: 28

Phe Gly Val Val Pro Asn Gln Gln Asn Thr Ile Cys Thr Arg Ser Asp
1               5                   10                  15

Trp Thr Gly Leu Thr Thr Cys
            20

<210> SEQ ID NO 29
<211> LENGTH: 7
<212> TYPE: PRT
<213> ORGANISM: Haemophilus influenzae

<400> SEQUENCE: 29

Lys Val Ile Asn Ser Ile Pro
1               5

<210> SEQ ID NO 30
<211> LENGTH: 14
<212> TYPE: PRT
<213> ORGANISM: Haemophilus influenzae

<400> SEQUENCE: 30

Thr Gln Ile Asn Gly Ser Ile Asn Leu Thr Asp Asn Ala Thr
1               5                   10

<210> SEQ ID NO 31
<211> LENGTH: 11
<212> TYPE: PRT
<213> ORGANISM: Haemophilus influenzae

<400> SEQUENCE: 31

Gly Leu Ala Lys Leu Asn Gly Asn Val Thr Leu
1               5                   10

<210> SEQ ID NO 32
<211> LENGTH: 12
<212> TYPE: PRT
<213> ORGANISM: Haemophilus influenzae
```

```
<400> SEQUENCE: 32

His Ser Gln Phe Thr Leu Ser Asn Asn Ala Thr Gln
1               5                   10

<210> SEQ ID NO 33
<211> LENGTH: 12
<212> TYPE: PRT
<213> ORGANISM: Haemophilus influenzae

<400> SEQUENCE: 33

Ala Thr Val Asp Asn Ala Asn Leu Asn Gly Asn Val
1               5                   10

<210> SEQ ID NO 34
<211> LENGTH: 18
<212> TYPE: PRT
<213> ORGANISM: Haemophilus influenzae

<400> SEQUENCE: 34

Asp Ser Ala Gln Phe Ser Leu Lys Asn Ser His Phe Ser His Gln Ile
1               5                   10                  15

Gln Gly

<210> SEQ ID NO 35
<211> LENGTH: 11
<212> TYPE: PRT
<213> ORGANISM: Haemophilus influenzae

<400> SEQUENCE: 35

Leu Glu Asn Ala Thr Trp Thr Met Pro Ser Asp
1               5                   10

<210> SEQ ID NO 36
<211> LENGTH: 11
<212> TYPE: PRT
<213> ORGANISM: Haemophilus influenzae

<400> SEQUENCE: 36

Thr Leu Gln Asn Leu Thr Leu Asn Asn Ser Thr
1               5                   10

<210> SEQ ID NO 37
<211> LENGTH: 8
<212> TYPE: PRT
<213> ORGANISM: Haemophilus influenzae

<400> SEQUENCE: 37

Thr Leu Asn Ser Ala Tyr Ser Ala
1               5

<210> SEQ ID NO 38
<211> LENGTH: 54
<212> TYPE: PRT
<213> ORGANISM: Haemophilus influenzae

<400> SEQUENCE: 38

Arg Arg Ser Leu Glu Thr Glu Thr Thr Pro Thr Ser Ala Glu His Arg
1               5                   10                  15

Phe Asn Thr Leu Thr Val Asn Gly Lys Leu Ser Gly Gln Gly Thr Phe
                20                  25                  30

Gln Phe Thr Ser Ser Leu Phe Gly Tyr Lys Ser Asp Lys Leu Ser Asn
            35                  40                  45
```

-continued

Asp Ala Glu Gly Asp Tyr
    50

<210> SEQ ID NO 39
<211> LENGTH: 10
<212> TYPE: PRT
<213> ORGANISM: Haemophilus influenzae

<400> SEQUENCE: 39

Leu Ser Val Arg Asn Thr Gly Lys Glu Pro
1               5                   10

<210> SEQ ID NO 40
<211> LENGTH: 10
<212> TYPE: PRT
<213> ORGANISM: Haemophilus influenzae

<400> SEQUENCE: 40

Gln Leu Thr Leu Val Glu Ser Lys Asp Asn
1               5                   10

<210> SEQ ID NO 41
<211> LENGTH: 20
<212> TYPE: PRT
<213> ORGANISM: Haemophilus influenzae

<400> SEQUENCE: 41

Phe Thr Leu Glu Asn Asp His Val Asp Ala Gly Ala Leu Arg Tyr Lys
1               5                   10                  15

Leu Val Lys Asn
            20

<210> SEQ ID NO 42
<211> LENGTH: 14
<212> TYPE: PRT
<213> ORGANISM: Haemophilus influenzae

<400> SEQUENCE: 42

Gly Glu Phe Arg Leu His Asn Pro Ile Lys Glu Gln Glu Leu
1               5                   10

<210> SEQ ID NO 43
<211> LENGTH: 18
<212> TYPE: PRT
<213> ORGANISM: Haemophilus influenzae

<400> SEQUENCE: 43

Asp Leu Val Arg Ala Glu Gln Ala Glu Arg Thr Leu Glu Ala Lys Gln
1               5                   10                  15

Val Glu

<210> SEQ ID NO 44
<211> LENGTH: 73
<212> TYPE: PRT
<213> ORGANISM: Haemophilus influenzae

<400> SEQUENCE: 44

Leu Ile Ser Arg Tyr Ser Asn Ser Ala Leu Ser Glu Leu Ser Ala Thr
1               5                   10                  15

Val Asn Ser Met Leu Ser Val Gln Asp Glu Leu Asp Arg Leu Phe Val
                20                  25                  30

Asp Gln Ala Gln Ser Ala Val Trp Thr Asn Ile Ala Gln Asp Lys Arg
            35                  40                  45

```
Arg Tyr Asp Ser Asp Ala Phe Arg Ala Tyr Gln Gln Lys Thr Asn Leu
    50                  55                  60

Arg Gln Ile Gly Val Gln Lys Ala Leu
65                  70

<210> SEQ ID NO 45
<211> LENGTH: 27
<212> TYPE: PRT
<213> ORGANISM: Haemophilus influenzae

<400> SEQUENCE: 45

Asn Gly Arg Ile Gly Ala Val Phe Ser His Ser Arg Ser Asp Asn Thr
1               5                   10                  15

Phe Asp Glu Gln Val Lys Asn His Ala Thr Leu
            20                  25

<210> SEQ ID NO 46
<211> LENGTH: 20
<212> TYPE: PRT
<213> ORGANISM: Haemophilus influenzae

<400> SEQUENCE: 46

Met Met Ser Gly Phe Ala Gln Tyr Gln Trp Gly Asp Leu Gln Phe Gly
1               5                   10                  15

Val Asn Val Gly
            20

<210> SEQ ID NO 47
<211> LENGTH: 40
<212> TYPE: PRT
<213> ORGANISM: Haemophilus influenzae

<400> SEQUENCE: 47

Gly Ile Ser Ala Ser Lys Met Ala Glu Glu Ser Arg Lys Ile His
1               5                   10                  15

Arg Lys Ala Ile Asn Tyr Gly Val Asn Ala Ser Tyr Gln Phe Arg Lys
            20                  25                  30

Gly Gln Leu Gly Ile Gln Pro Tyr
            35                  40

<210> SEQ ID NO 48
<211> LENGTH: 17
<212> TYPE: PRT
<213> ORGANISM: Haemophilus influenzae

<400> SEQUENCE: 48

Gly Val Asn Arg Tyr Phe Ile Glu Arg Glu Asn Tyr Gln Ser Glu Glu
1               5                   10                  15

Val

<210> SEQ ID NO 49
<211> LENGTH: 20
<212> TYPE: PRT
<213> ORGANISM: Haemophilus influenzae

<400> SEQUENCE: 49

Phe Asn Arg Asn Ala Gly Ile Arg Val Asp Tyr Thr Phe Thr Pro Thr
1               5                   10                  15

Asp Asn Ile Ser
            20
```

```
<210> SEQ ID NO 50
<211> LENGTH: 21
<212> TYPE: PRT
<213> ORGANISM: Haemophilus influenzae

<400> SEQUENCE: 50

Lys Pro Tyr Phe Phe Val Asn Tyr Val Asp Val Ser Asn Ala Asn Val
1               5                   10                  15

Gln Thr Thr Val Asn
            20

<210> SEQ ID NO 51
<211> LENGTH: 19
<212> TYPE: PRT
<213> ORGANISM: Haemophilus influenzae

<400> SEQUENCE: 51

Phe Gly Arg Tyr Trp Gln Lys Glu Val Gly Leu Lys Ala Glu Ile Leu
1               5                   10                  15

His Phe Gln

<210> SEQ ID NO 52
<211> LENGTH: 26
<212> TYPE: PRT
<213> ORGANISM: Haemophilus influenzae

<400> SEQUENCE: 52

Ser Ala Phe Ile Ser Lys Ser Gln Gly Ser Gln Leu Gly Lys Gln Gln
1               5                   10                  15

Asn Val Gly Val Lys Leu Gly Tyr Arg Trp
            20                  25

<210> SEQ ID NO 53
<211> LENGTH: 8
<212> TYPE: PRT
<213> ORGANISM: Haemophilus influenzae

<400> SEQUENCE: 53

Gly Asp Ser Gly Ser Pro Met Phe
1               5

<210> SEQ ID NO 54
<211> LENGTH: 8
<212> TYPE: PRT
<213> ORGANISM: Neisseria gonorrhoeae

<400> SEQUENCE: 54

Gly Asp Ser Gly Ser Pro Leu Phe
1               5

<210> SEQ ID NO 55
<211> LENGTH: 7
<212> TYPE: PRT
<213> ORGANISM: Haemophilus influenzae

<400> SEQUENCE: 55

His Thr Tyr Phe Gly Ile Asp
1               5

<210> SEQ ID NO 56
<211> LENGTH: 28
<212> TYPE: DNA
<213> ORGANISM: Haemophilus influenzae
```

```
-continued

<400> SEQUENCE: 56
tgcaggatcc ccgcagactg gattgttg                                    28

<210> SEQ ID NO 57
<211> LENGTH: 28
<212> TYPE: DNA
<213> ORGANISM: Haemophilus influenzae

<400> SEQUENCE: 57
tgcaggatcc gatctgcccc accttgtt                                    28

<210> SEQ ID NO 58
<211> LENGTH: 7
<212> TYPE: PRT
<213> ORGANISM: Haemophilus influenzae

<400> SEQUENCE: 58

Gly Asp Ser Gly Ser Pro Met
1               5
```

HAEMOPHILUS ADHERENCE AND PENETRATION PROTEINS

This is a continuation-in-part application of application Ser. No. 08/296,791 filed Aug. 25, 1994, now U.S. Pat. No. 6,245,337 and application Ser. No. 09/839,996, filed Apr. 20, 2001, pending.

FIELD OF THE INVENTION

The invention relates to Haemophilus adhesion and penetration proteins, nucleic acids, and vaccines.

BACKGROUND OF THE INVENTION

Most bacterial diseases begin with colonization of a particular mucosal surface (Beachey et al., 1981, J. Infect. Dis. 143:325–345). Successful colonization requires that an organism overcome mechanical cleansing of the mucosal surface and evade the local immune response. The process of colonization is dependent upon specialized microbial factors that promote binding to host cells (Hultgren et a., 1993 Cell, 73:887–901). In some cases the colonizing organism will subsequently enter (invade) these cells and survive intracellularly (Falkow, 1991, Cell 65:1099–1102).

Haemophilus influenzae is a common commensal organism of the human respiratory tract (Kuklinska and Kilian, 1984, Eur. J. Clin. Microbiol. 3:249–252). It is a human-specific organism that normally resides in the human nasopharynx and must colonize this site in order to avoid extinction. This microbe has a number of surface structures capable of promoting attachment to host cells (Guerina et al., 1982, J. Infect. Dis. 146:564; Pichichero et al., 1982, Lancet ii:960–962; St. Geme et al., 1993, Proc. Natl. Acad. Sci. U.S.A. 90:2875–2879). In addition, H. influenzae has acquired the capacity to enter and survive within these cells (Forsgren et al., 1994, Infect. Immun. 62:673–679; St. Geme and Falkow, 1990, Infect. Immun. 58:4036–4044; St. Geme and Falkow, 1991, Infect. Immun. 59:1325–1333, Infect. Immun. 59:3366–3371). As a result, this bacterium is an important cause of both localized respiratory tract and systemic disease (Turk, 1984, J. Med. Microbiol. 18:1–16). Nonencapsulated, non-typable (NT) strains account for the majority of local disease (Turk, 1984, supra); in contrast, serotype b strains, which express a capsule composed of a polymer of ribose and ribitol-5-phosphate (PRP), are responsible for over 95% of cases of H. influenzae systemic disease (Turk, 1982, Clinical importance of Haemophilus influenzae, p. 3–9. In S. H. Sell and P. F. Wright (ed.), Haemophilus influenzae epidemiology, immunology, and prevention of disease. Elsevier/North-Holland Publishing Co., New York).

The initial step in the pathogenesis of disease due to H. influenzae involves colonization of the upper respiratory mucosa (Murphy et a., 1987, J. Infect. Dis. 5:723–731). Colonization with a particular strain may persist for weeks to months, and most individuals remain asymptomatic throughout this period (Spinosa et al., 1986, 1. Infect. Dis. 154:100–109). However, in certain circumstances colonization will be followed by contiguous spread within the respiratory tract, resulting in local disease in the middle ear, the sinuses, the conjunctiva, or the lungs.

Alternatively, on occasion bacteria will penetrate the nasopharyngeal epithelial barrier and enter the bloodstream.

In vitro observations and animal studies suggest that bacterial surface appendages called pili (or fimbriae) play an important role in H. influenzae colonization. In 1982 two groups reported a correlation between piliation and increased attachment to human oropharyngeal epithelial cells and erythrocytes (Guerina et a., supra; Pichichero et al., supra). Other investigators have demonstrated that anti-pilus antibodies block in vitro attachment by piliated H. influenzae (Forney et a., 1992, J. Infect. Dis. 165:464–470; van Alphen et al., 1988, Infect. Immun. 56:1800–1806). Recently Weber et al. insertionally inactivated the pilus structural gene in an H. influenzae type b strain and thereby eliminated expression of pili; the resulting mutant exhibited a reduced capacity for colonization of year-old monkeys (Weber et al., 1991, Infect. Immun. 59:4724–4728).

A number of reports suggest that nonpilus factors also facilitate Haemophilus colonization. Using the human nasopharyngeal organ culture model, Farley et al. (1986, J. Infect. Dis. 161:274–280) and Loeb et al. (1988, Infect. Immun. 49:484–489) noted that nonpiliated type b strains were capable of mucosal attachment. Read and coworkers made similar observations upon examining nontypable strains in a model that employs nasal turbinate tissue in organ culture (1991, J. Infect. Dis. 163:549–558). In the monkey colonization study by Weber et al. (1991, supra), nonpiliated organisms retained a capacity for colonization, though at reduced densities; moreover, among monkeys originally infected with the piliated strain, virtually all organisms recovered from the nasopharynx were nonpiliated. All of these observations are consistent with the finding that nasopharyngeal isolates from children colonized with H. influenzae are frequently nonpiliated (Mason et al., 1985, Infect. Immun. 49:98–103; Brinton et al., 1989, Pediatr. Infect. Dis. J. 8:554–561).

Previous studies have shown that H. influenzae are capable of entering (invading) cultured human epithelial cells via a pili-independent mechanism (St. Geme and Falkow, 1990, supra; St. Geme and Falkow, 1991, supra). Although H. influenzae is not generally considered an intracellular parasite, a recent report suggests that these in vitro findings may have an in vivo correlate (Forsgren et al., 1994, supra). Forsgren and coworkers examined adenoids from 10 children who had their adenoids removed because of long-standing secretory otitis media or adenoidal hypertrophy. In all 10 cases there were viable intracellular H. influenzae. Electron microscopy demonstrated that these organisms were concentrated in the reticular crypt epithelium and in macrophage-like cells in the subepithelial layer of tissue. One possibility is that bacterial entry into host cells provides a mechanism for evasion of the local immune response, thereby allowing persistence in the respiratory tract.

Thus, a vaccine for the therapeutic and prophylactic treatment of Haemophilus infection is desirable. Accordingly, it is an object of the present invention to provide for recombinant Haemophilus Adherence and Penetration (HAP) proteins and variants thereof, and to produce useful quantities of these HAP proteins using recombinant DNA techniques.

It is a further object of the invention to provide recombinant nucleic acids encoding HAP proteins, and expression vectors and host cells containing the nucleic acid encoding the HAP protein.

An additional object of the invention is to provide monoclonal antibodies for the diagnosis of Haemophilus infection.

A further object of the invention is to provide methods for producing the HAP proteins, and a vaccine comprising the HAP proteins of the present invention. Methods for the therapeutic and prophylactic treatment of Haemophilus infection are also provided.

SUMMARY OF THE INVENTION

In accordance with the foregoing objects, the present invention provides recombinant HAP proteins, and isolated or recombinant nucleic acids which encode the HAP proteins of the present invention. Also provided are expression vectors which comprise DNA encoding a HAP protein operably linked to transcriptional and translational regulatory DNA, and host cells which contain the expression vectors.

The invention also provides methods for producing HAP proteins which comprises culturing a host cell transformed with an expression vector and causing expression of the nucleic acid encoding the HAP protein to produce a recombinant HAP protein.

The invention also includes vaccines for *Haemophilus influenzae* infection comprising an HAP protein for prophylactic or therapeutic use in generating an immune response in a patient. Methods of treating or preventing *Haemophilus influenzae* infection comprise administering a vaccine.

BRIEF DESCRIPTION OF THE DRAWINGS

FIGS. 1A and 1B depict light micrographs of *H. influenzae* strains DB117(pGJB103) and DB117(pN187) incubated with Chang epithelial cells. Bacteria were incubated with an epithelial monolayer for 30 minutes before rinsing and straining with Giemsa stain. FIG. 1A: *H. influenzae* strain DB117 carrying cloning vector alone (pGJB103); FIG. 1B: *H. influenzae* strain DB117 harboring recombinant plasmid pN187. Bar represents 3.5 μm.

FIGS. 2A, 2B, 2C and 2D depict thin section transmission electron micrographs demonstrating interaction between *H. influenzae* strains N187 and DB117 (pN187) with Chang epithelial cells. Bacteria were incubated with epithelial monolayers for four hours before rinsing and processing for examination by transmission electron microscopy. FIG. 2A: strain N187 associated with the epithelial cell surface and present in an intracellular location; FIG. 2B: *H. influenzae* DB117 (pN187) in intimate contact with the epithelial cell surface; FIG. 2C: strain DB117 (pN187) in the process of entering an epithelial cell; FIG. 2D: strain DB117(pN187) present in an intracellular location. Bar represents 1 μm.

FIG. 3 depicts outer membrane protein profiles of various strains. Outer membrane proteins were isolated on the basis of sarcosyl insolubility and resolved on a 10% SDS-polyacrylamide gel. Proteins were visualized by staining with Coomassie blue. Lane 1, *H. influenzae* strain DB117 (pGJB103); lane 2, strain DB117(pN187); lane 3, DB117(pJS106); lane 4, *E. coli* HB101(pGJB103); lane 5, HB101(pN187). Note novel proteins at ~160 kD and 45 kD marked by asterisks in lanes 2 and 3.

FIG. 4 depicts a restriction map of pN187 and derivatives and locations of mini-Tn10 kan insertions. pN187 is a derivative of pGJB103 that contains an 8.5-kb Sau3AI fragment of chromosomal DNA from *H. influenzae* strain N187. Vector sequences are represented by hatched boxes. Letters above top horizontal line indicate restriction enzyme sites: Bg, Bg/II; C, ClaI; E, EcoRI; P, PstI. Numbers and lollipops above top horizontal line show positions of mini-Tn10 kan insertions; open lollipops represent insertions that have no effect on adherence and invasion, while closed lollipops indicate insertions that eliminate the capacity of pN187 to promote association with epithelial monolayers. Heavy horizontal line with arrow represents location of hap locus within pN187 and direction of transcription. (+): recombinant plasmids that promote adherence and invasion; (−): recombinant plasmids that fail to promote adherence and invasion.

FIG. 5 depicts the identification of plasmid-encoded proteins using the bacteriophage T7 expression system. Bacteria were radiolabeled with [$^{35}$S] methionine, and whole cell lysates were resolved on a 10% SDS-polyacrylamide gel. Proteins were visualized by autoradiography. Lane 1, *E. coli*XL-1Blue(pT7-7) uninduced; lane 2, XL-1Blue(pT7-7) induced with IPTG; lane 3, XL-1Blue(pJS103) uninduced; lane 4, XL-1Blue(pJS103) induced with IPTG; lane 5, XL-1Blue(pJS104) uninduced; lane 6, XL-1Blue(pJS104) induced with IPTG. The plasmids pJS103 and pJS104 are derivatives of pT7-7 that contain the 6.7-kb PstI fragment from pN187 in opposite orientations. Asterisk indicates overexpressed protein in XL-1 Blue(pJS104).

FIGS. 6A–6F depict the nucleotide sequence (SEQ ID NO: 1) and predicted amino acid sequence (SEQ ID NO: 2) of hap gene. Putative −10 and −35 sequences 5' to the hap coding sequence are underlined; a putative rho-independent terminator 3' to the hap stop codon is indicated with inverted arrows. The first 25 amino acids of the protein, which are boxed, represent the signal sequence.

FIGS. 7A–7F depict a sequence comparison of the hap product (SEQ ID NO: 2) and the cloned *H. influenzae* IgA1 proteases (SEQ ID NO: 3–6). Amino acid homologies between the deduced hap gene product and the iga gene products from *H. influenzae* HK368 (SEQ ID NO: 3), HK61 (SEQ ID NO: 6), HK393 (SEQ ID NO: 4), and HK715 (SEQ ID NO: 5) are shown. Dashes indicate gaps introduced in the sequences in order to obtain maximal homology. A consensus sequence for the five proteins is shown on the lower line. The conserved serine-type protease catalytic domain is underlined, and the common active site serine is denoted by an asterisk. The conserved cysteines are also indicated by asterisks.

FIG. 8 depicts the IgA1 protease activity assay. Culture supernatants were assayed for the ability to cleave IgA1. Reaction mixtures were resolved on a 10% SDS-polyacrylamide gel and then transferred to a nitrocellulose membrane. The membrane was probed with antibody against human IgA1 heavy chain. Lane 1, *H. influenzae* strain N187; lane 2, strain DB117(pGJB103); lane 3, strain DB117(pN187). The cleavage product patterns suggest that strain N187 contains a type 2 IgA1 protease while strains DB117(pGJB103) and DB117(pN187) contain a type 1 enzyme. The upper band of ~70-kD seen with the DB117 derivatives represents intact IgA1 heavy chain.

FIGS. 9A and 9B depict southern analysis of chromosomal DNA from strain *H. influenzae* N187, probing with hap versus iga. DNA fragments were separated on a 0.7% agarose gel and transferred bidirectionally to nitrocellulose membranes prior to probing with either hap or iga. Lane 1, N187 chromosomal DNA digested with EcoRI; lane 2, N187 chromosomal DNA digested with Bg/II; lane 3, N187 chromosomal DNA digested with BamHI; lane 4, the 4.8-kb ClaI-PstI fragment from pN187 that contains the intact hap gene. FIG. 9A: Hybridization with the 4.8-kb ClaI-PstI fragment containing the hap gene; FIG. 9B: hybridization with the iga gene from *H. influenzae* strain Rd, carried as a 4.8-kb ClaI-EcoRI fragment in pVD116.

FIG. 10 depicts a SDS-polyacrylamide gel of secreted proteins. Bacteria were grown to late log phase, and culture supernatants were precipitated with trichloroacetic acid and then resolved on a 10% SDS-polyacrylamide gel. Proteins were visualized by staining with Coomassie blue. Lane 1, *H. influenzae* strain DB117(pGJB103); lane 2, DB117(pN187); lane 3, DB117(pJS106); lane 4, DB117(pJS102); lane 5, DB117(pJS105); lane 6, DB117(Tn10-18); lane 7, DB117

Figure 12:
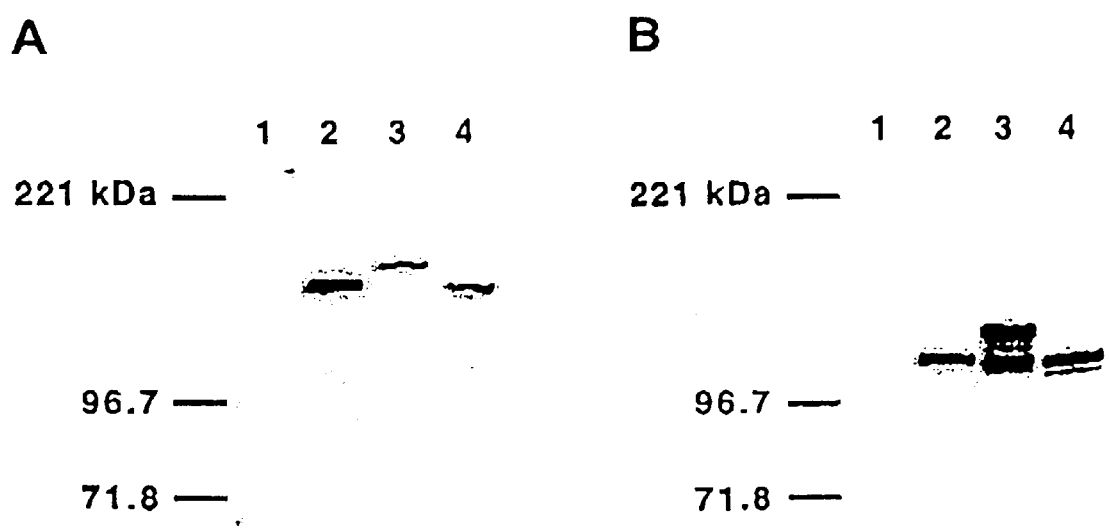

(Tn10-4'); lane 8, DB117(Tn10-30); lane 9, DB117(Tn10-16); lane 10, DB117(Tn10-10); lane II, DB117(Tn10-8); lane 12, N187. Asterisk indicates 110-kD secreted protein encoded by hap.

FIGS. 11A–11D depicts an alignment of the deduced amino acid sequence of HAP proteins obtained from various *H. influenzae* strains. The strains include N187 (SEQ ID NO: 7), TN106 (SEQ ID NO: 11) and 860295 (SEQ ID NO: 13).

FIGS. 12A–12B depicts Western blot of Hap proteins. Panel A shows outer membrane proteins, and panel B shows culture supernatants after precipitation with trichloroacetic acid. In each panel, lane 1 contains DB117/pGJB103 (vector), lane 2 contains DB117/pJS106 (encoding HapN187), lane 3 contains DB117/pHapP860295, and lane 4 contains DB117/pHapTN106. Immunoblotting was performed with guinea pig antiserum GP74, which was raised against purified $Hap_S$ from strain N187 and recognizes full-length Hap in outer membranes and $Hap_S$ in culture supernatants. Without being bound by theory, it is thought that the lower band in lane 3 of panel B presumably reflects autoproteolysis of multiple sites in Hap from strain P860925 (Fink et al; 2001).

Figure 13:
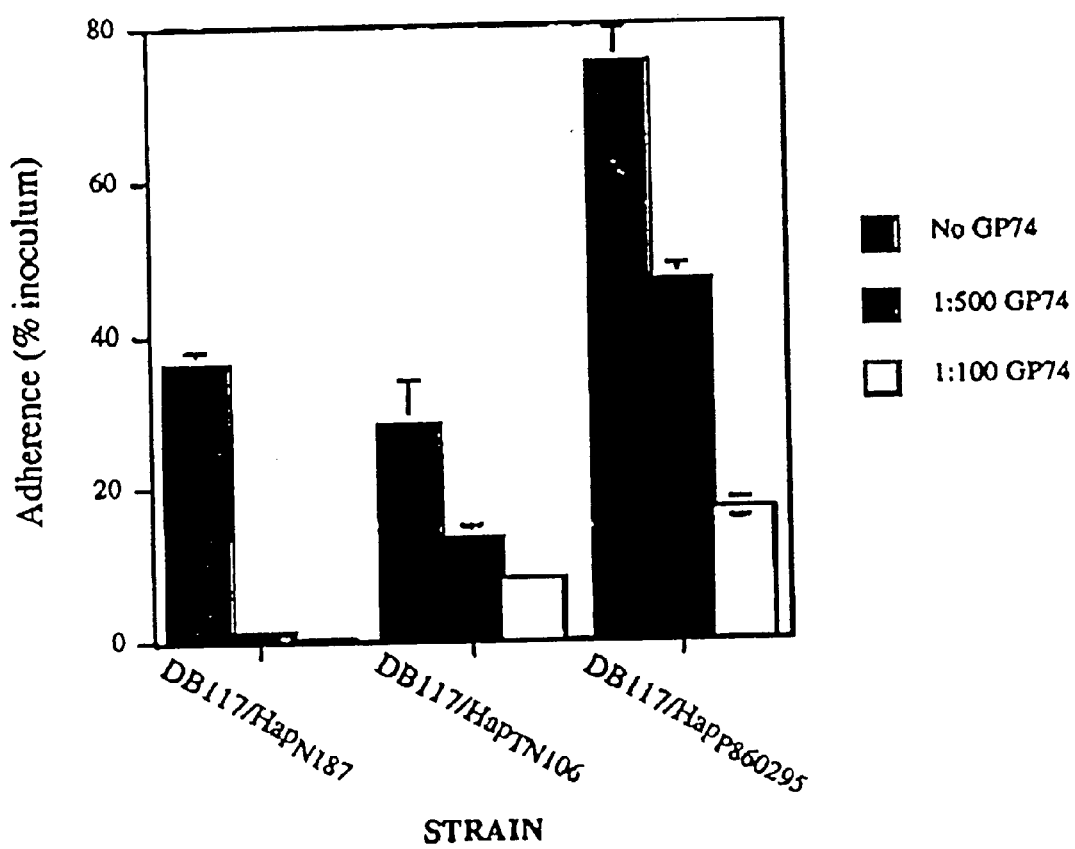

FIG. 13 Adherence to Chang epithelial cells by *H. influenzae* strain DB117 expressing HapN187, HapTN 106, or HapP860295 and the inhibitory effect of preincubation with anti-HapS antiserum. Adherence was determined in 30 minute assays and was calculated by dividing the number of adherent bacteria by the number of inoculated bacteria. For all strains, inocula were approximately $2 \times 10^7$ CFU/ml. Bars represent the mean+standard error of the mean.

Figure 14:
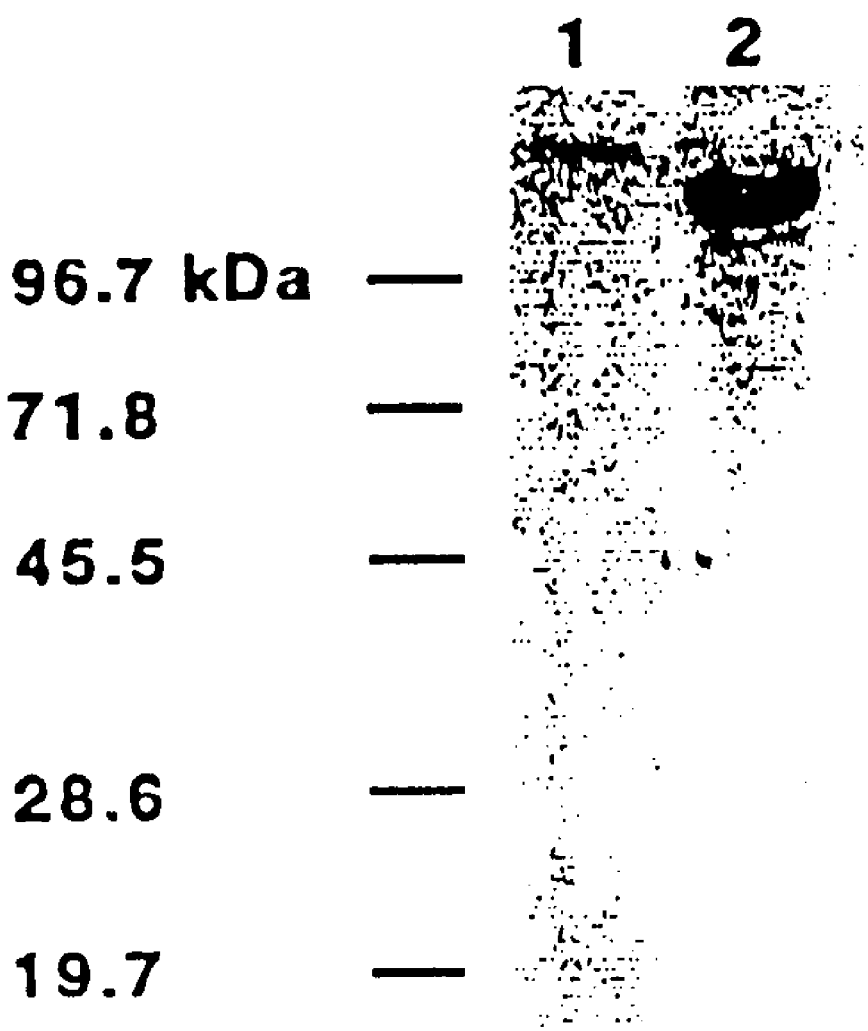

FIG. 14 depicts SDS-PAGE of purified HAPs proteins from both strain P860295 and strain N187. Amino terminal amino acid sequencing confirmed that purified protein was Haps.

Figure 15:
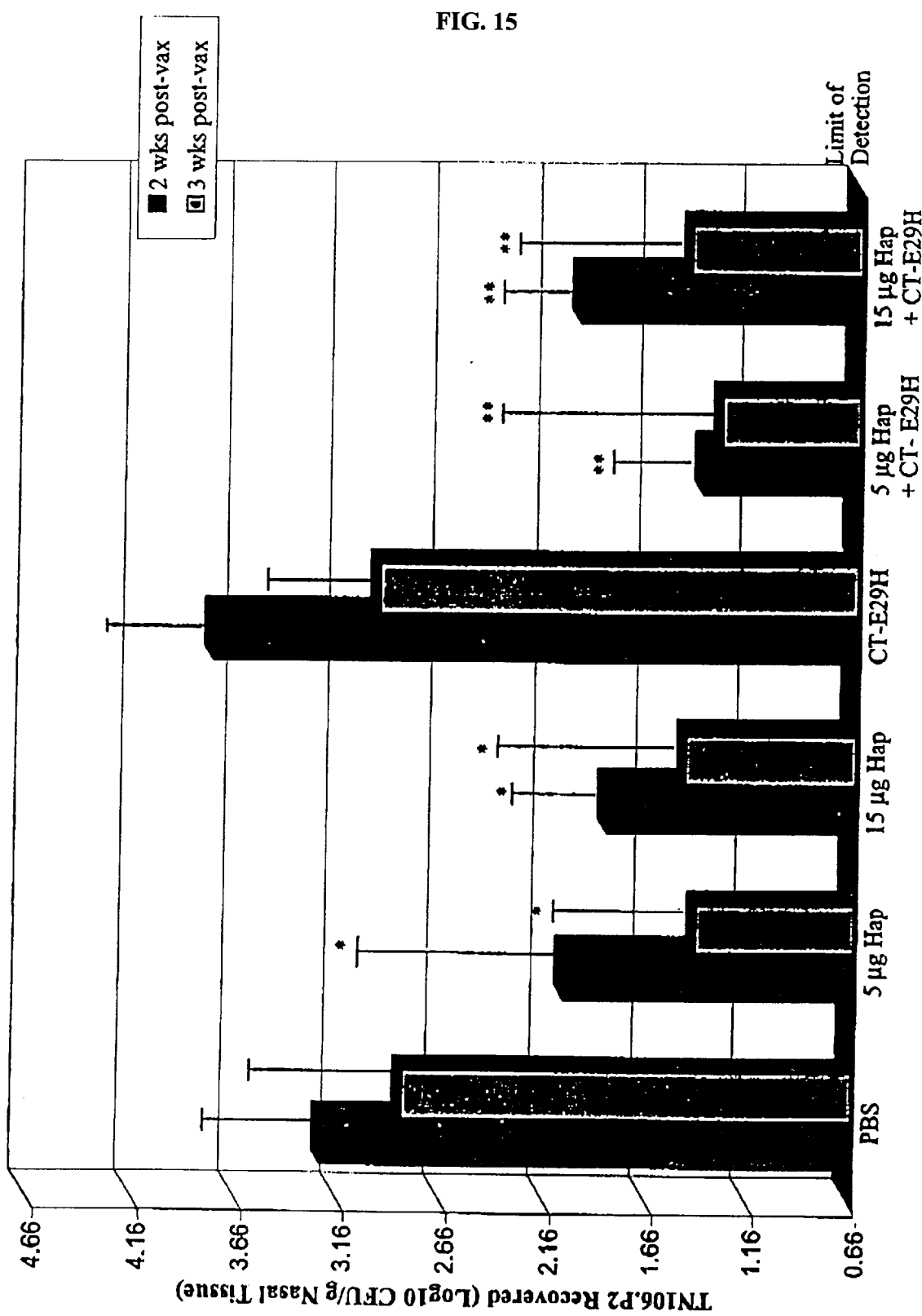

FIG. 15 depicts clearance of NTHi TN106.P2 in Balb/c mice vaccinated with $Hap_S$ P860295 with and without CT-E29H. Six week old female Balb/c mice were vaccinated intranasally with $Hap_S$ from P860295, HAP+CT-E29H, or Formalin Fixed TN106.P2 in a 40 µl volume at weeks 0, 1, 3, & 5. Five animals from each group were IN challenged with ~$1 \times 10^6$ CFU/;mouse in 10 µl, 2 and 3 weeks post vaccination. Nasal tissue were harvested 3 days after challenge. (*=Statistically different from 0.1 µg E29H control/ Student's T test; @=Statistically different from PBS control/ Student's T test.

FIGS. 16A–16C depicts the nucleotide sequence for NTHi strain 11 hap gene (SEQ ID NO: 8) (start codon to stop codon).

FIG. 17 depicts the amino acid sequence for NTHi strain 11 Hap protein (SEQ ID NO: 9) (first amino acid to last amino acid).

FIGS. 18A–18C depicts the nucleotide sequence for NTHi strain TN106 hap gene (SEQ ID NO: 10) (start codon begins at position 422, stop codon begins at position 4595).

FIG. 19 depicts the amino acid sequence for NTHi strain TN106 Hap protein (SEQ ID NO: 11) (first amino acid to last amino acid).

FIGS. 20A–20C depicts the nucleotide sequence for NTHi strain 860295 hap gene (SEQ ID NO: 12) (start codon begins at position 430, stop codon begins at position 4738).

FIG. 21 depicts the amino acid sequence for NTHi strain 860295 Hap protein (SEQ ID NO: 13) (first amino acid to last amino acid).

FIGS. 22A–22C depicts the nucleotide sequence for NTHi strain 3219B hap gene (SEQ ID NO: 14) (start codon begins at position 388, stop codon begins at position 4561).

FIG. 23 depicts the amino acid sequence for NTHi strain 3219B Hap protein (SEQ ID NO: 15) (first amino acid to last amino acid).

FIGS. 24A–24C depicts the nucleotide sequence for NTHi strain 1396B hap gene (SEQ ID NO: 16)(start codon begins at position 313, stop codon begins at position 4546).

FIG. 25 depicts the amino acid sequence for NTHi strain 1396B Hap protein (SEQ ID NO: 17) (first amino acid to last amino acid).

DETAILED DESCRIPTION OF THE INVENTION

The present invention provides novel Haemophilus Adhesion and Penetration (HAP) proteins. In a preferred embodiment, the HAP proteins are from Haemophilus strains, and in the preferred embodiment, from *Haemophilus influenzae*. However, using the techniques outlined below, HAP proteins from other *Haemophilus influenzae* strains, including but not limited to NTHI TN 106, TN106.P2, N187, P860295, 11, 3219B, 1396B or from other bacterial species such as Neisseria spp. or Bordetella spp. may also be obtained.

A HAP protein may be identified in several ways. A HAP nucleic acid or HAP protein is initially identified by substantial nucleic acid and/or amino acid sequence homology to the sequences shown in FIG. 6. Such homology can be based upon the overall nucleic acid or amino acid sequence. In addition a HAP protein is identifiable by substantial amino acid sequence homology or identity to the sequences shown in FIGS. 11 (SEQ ID NOS 7, 11, 13), 17 (SEQ ID NO 9), 19 (SEQ ID NO 11), 21 (SEQ ID NO 13), 23 (SEQ ID NO 15) or 25 (SEQ ID NO 17). In addition a HAP nucleic acid is identified by substantial nucleic acid sequence indentity to the sequences set forth in FIGS. 16 (SEQ ID NO 8), 18 (SEQ ID NO 10), 20 (SEQ ID NO 12), 22 (SEQ ID NO 14), or 24 (SEQ ID NO 16).

The HAP proteins of the present invention have limited homology to *Haemophilus influenzae* and *N. gonorrhoeae* serine-type IgA1 proteases. This homology, shown in FIG. 7, is approximately 30–35% at the amino acid level, with several stretches showing 55–60% identity, including amino acids 457–549, 399–466, 572–622, and 233–261. However, the homology between the HAP protein and the IgA1 protease is considerably lower than the similarity among the IgA1 proteases themselves.

In addition, the full length HAP protein has homology to Tsh, a hemagglutinin expressed by an avian *E. coli* strain (Provence and Curtiss 1994, Infect. Immun. 62:1369–1380). The homology is greatest in the N-terminal half of the proteins, and the overall homology is 30.5% homologous. The full length HAP protein also has homology with pertactin, a 69 kD outer membrane protein expressed by *B. pertussis*, with the middle portion of the proteins showing 39% homology. HAP also has 34–52% homology with six regions of HpmA, a calcium-independent hemolysin expressed by *Proteus mirabilis* (Uphoff and Welch, 1990, J. Bacteriol. 172:1206–1216).

As used herein, a protein is a "HAP protein" if the overall homology of the protein sequence to one of the amino acid sequences shown in FIGS. 6, 11, 17, 19, 21, 23, or 25, is preferably greater than about 40–50%, more preferably greater than about 60% and most preferably greater than 80%. In some embodiments the homology will be as high as about 90 to 95 or 98%. This homology will be determined using standard techniques known in the art, such as the Best Fit sequence program described by Devereux et al., *Nucl.*

Acid Res. 12:387–395 (1984). The alignment may include the introduction of gaps in the sequences to be aligned. In addition, for sequences which contain either more or fewer amino acids than the proteins shown in FIG. 6 or FIG. 11, it is understood that the percentage of homology will be determined based on the number of homologous amino acids in relation to the total number of amino acids. Thus, for example, homology of sequences shorter than that shown in FIG. 6 or 11, as discussed below, will be determined using the number of amino acids in the shorter sequence.

HAP proteins of the present invention may be shorter than the amino acid sequence shown in FIG. 6 or 11. As shown in the Examples, the HAP protein may undergo post-translational processing similar to that seen for the serine-type IgA1 proteases expressed by *Haemophilus influenzae* and *N. gonorrhoeae*. These proteases are synthesized as preproteins with three functional domains: the N-terminal signal peptide, the protease, and a C-terminal helper domain. Following movement of these proteins into the periplasmic space, the carboxy terminal β-domain of the proenzyme is inserted into the outer membrane, possibly forming a pore (Poulsen et al., 1989, Infect. Immun. 57:3097–3105; Pohlner et al., 1987, Nature (London). 325:458–462; Klauser et al., 1992, EMBO J. 11:2327–2335; Klauser et al., 1993, J. Mol. Biol. 234:579–593). Subsequently the amino end of the protein is exported through the outer membrane, and auto-proteolytic cleavage occurs to result in secretion of the mature 100 to 106-kD protease. The 45 to 56-kD C-terminal β-domain remains associated with the outer membrane following the cleavage event. As shown in the Examples, the HAP nucleic acid is associated with expression of a 155 kD outer membrane protein. The secreted gene product is an approximately 110 kD protein, with the simultaneous appearance of a 45 kD outer membrane protein. The 45 kD protein corresponds to amino acids from about 1037 to about 1395 of FIG. 6. Any one of these proteins is considered a HAP protein for the purposes of this invention.

Thus, in a preferred embodiment, included within the defintion of HAP proteins are portions or fragments of the sequence shown in FIG. 6 or 11. The fragments may be fragments of the entire sequence, the 110 kD sequence, or the 45 kD sequence. Generally, the HAP protein fragments may range in size from about 10 amino acids to about 1900 amino acids, with from about 50 to about 1000 amino acids being preferred, and from about 100 to about 500 amino acids also preferred. Particularly preferred fragments are sequences unique to HAP; these sequences have particular use in cloning HAP proteins from other organisms or to generate antibodies specific to HAP proteins. Unique sequences are easily identified by those skilled in the art after examination of the HAP protein sequence and comparison to other proteins; for example, by examination of the sequence alignment shown in FIG. 7. For instance, as compared to the IgA proteases, unique sequences include, but are not limited to, amino acids 11–14, 16–22, 108–120, 155–164, 257–265, 281–288, 318–336, 345–353, 398–416, 684–693, 712–718, 753–761, 871–913, 935–953, 985–1008, 1023–1034, 1067–1076, 1440–1048, 1585–1592, 1631–1639, 1637–1648, 1735–1743, 1863–1871, 1882–1891, 1929–1941, and 1958–1966 (using the numbering of FIG. 7). HAP protein fragments which are included within the definition of a HAP protein include N- or C-terminal truncations and deletions which still allow the protein to be biologically active; for example, which still exhibit proteolytic activity in the case of the 110 kD putative protease sequence. In addition, when the HAP protein is to be used to generate antibodies, for example as a vaccine, the HAP protein must share at least one epitope or determinant with either the full length protein, the 110 kD protein or the 45 kD protein, shown in FIG. 6. In a preferred embodiment, the epitope is unique to the HAP protein; that is, antibodies generated to a unique epitope exhibit little or no cross-reactivity with other proteins. By "epitope" or "determinant" herein is meant a portion of a protein which will generate and/or bind an antibody. Thus, in most instances, antibodies made to a smaller HAP protein will be able to bind to the full length protein.

In a preferred embodiment the HAP protein contains sequences conserved among HAP proteins from different species or strains. As shown in FIG. 11, alignment of the amino acid sequences of Hap TN106, HapP860295, and HapN187 revealed absolute identity through the first 47 amino acids, divergence over the next 350 amino acids, and then marked similarity over the final 1000–1050 amino acids. Accordingly, in a preferred embodiment the HAP protein of the invention includes amino acids 1–47 of the proteins shown in FIG. 11. In another embodiment the HAP protein of the invention includes amino acids that are invariant among the sequences set forth in FIG. 11 and contiguous for at least about 3, preferably at least about 5 and most preferably at least about 8 amino acids in length. Preferred peptides are included in the following Table 1.

TABLE 1

| SEQ. ID NO. | PEPTIDE SEQUENCE |
|---|---|
| 18 | MKKTVFRLNFLTACISLGIVSQAWAGHTYFGIDYQYYRD FAENKGKF |
| 19 | NPDQHRF |
| 20 | GDSGSPMFIYD |
| 21 | INQGAGGLYFEGNG |
| 22 | DRLSKIG |
| 23 | YFGFRGGRLDLNGHSLTF |
| 24 | RIQNTDEGAMIVNHN |
| 25 | LLLSGGTNL |
| 26 | FSGRPTPHAYNHL |
| 27 | RTFKAENFQIKGGSAVVSRNVSSIEGNWTVSNNANA |
| 28 | FGVVPNQQNTICTRSDWTGLTTC |
| 29 | KVINSIP |
| 30 | TQINGSINLTDNAT |
| 31 | GLAKLNGNVTL |
| 32 | HSQFTLSNNATQ |
| 33 | ATVDNANLNGNV |
| 34 | DSAQFSLKNSHFSHQIQG |
| 35 | LENATWTMPSD |
| 36 | TLQNLTLNNST |
| 37 | TLNSAYSA |
| 38 | RRSLETETTPTSAEHRFNTLTVNGKLSGQGTFQFTSSLFGY KSDKLSNDAEGDY |
| 39 | LSVRNTGKEP |
| 40 | QLTLVESKDN |
| 41 | FTLENDHVDAGALRYKLVKN |
| 42 | GEFRLHNPIKEQEL |
| 43 | DLVRAEQAERTLEAKQVE |
| 44 | LISRYSNSALSELSATVNSMLSVQDELDRLFVDQAQSA VWTNIAQDKRRYDSDAFRAYQQKTNLRQIGVQKAL |
| 45 | NGRIGAVFSHSRSDNTFDEQVKNHATL |
| 46 | MMSGFAQYQWGDLQFGVNVG |
| 47 | GISASKMAEEQSRKIHRKAINYGVNASYQFRKGQLGIQPY |
| 48 | GVNRYFIERENYQSEEV |
| 49 | FNRNAGIRVDYTFTPTDNIS |
| 50 | KPYFFVNYVDVSNANVQTTVN |
| 51 | FGRYWQKEVGLKAEILHFQ |
| 52 | SAFISKSQGSQLGKQQNVGVKLGYRW |

In some embodiments, the fragment of the HAP protein used to generate antibodies are small; thus, they may be used as haptens and coupled to protein carriers to generate antibodies, as is known in the art. In one embodiment the fragment of the HAP protein is a fragment of one of the peptides listed above. In this embodiment the fragment need only comprise a single epitope.

Accordingly in one embodiment the invention provides a composition comprising at least one of the peptides as shown in Table I. In addition the invention provides a polypeptide comprising at least one of the peptides as shown in Table I.

Preferably, the antibodies are generated to a portion of the HAP protein which remains attached to the *Haemophilus influenzae* organism. For example, the HAP protein can be used to vaccinate a patient to produce antibodies which upon exposure to the *Haemophilus influenzae* organism (e.g. during a subsequent infection) bind to the organism and allow an immune response. Thus, in one embodiment, the antibodies are generated to the roughly 45 kD fragment of the full length HAP protein. Preferably, the antibodies are generated to the portion of the 45 kD fragment which is exposed at the outer membrane.

In an alternative embodiment, the antibodies bind to the mature secreted 110 kD fragment. For example, as explained in detail below, the HAP proteins of the present invention may be administered therapeutically to generate neutralizing antibodies to the 110 kD putative protease, to decrease the undesirable effects and/or binding activity of the 100 kD fragment.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIGS. 6, 16, 18, 20, 22 or 24, is preferably greater than 40%, more preferably greater than about 60% and most preferably greater than 80%. In some embodiments the homology will be as high as about 90 to 95 or 98%.

In one embodiment, the nucleic acid homology is determined through hybridization studies. Thus, for example, nucleic acids which hybridize under high stringency to all or part of the nucleic acid sequence shown in FIG. 6 are considered HAP protein genes. High stringency conditions include washes with 0.1XSSC at 65° C. for 2 hours.

In one embodiment the nucleic acid of the invention are preferably greater than 40%, more preferably greater than about 60% and most preferably greater than 80% identical to the nucleic acids as set forth in FIGS. 6, 16, 18, 20, 22 or 24. In some embodiments the identity will be as high as about 90 to 95 or 98% up to 100%.

The HAP proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequence shown in FIG. 6, but may contain ribonucleotides as well as deoxyribonucleotides. Generally, anti-sense nucleic acids function to prevent expression of mRNA, such that a HAP protein is not made, or made at reduced levels. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated HAP protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host, or found in the absence of the host cells themselves. Thus, the protein may be partially or substantially purified. The definition includes the production of a HAP protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of HAP protein are HAP proteins from other organisms, including, but not limited to various *H. influenza* strains, which are cloned and expressed as outlined below.

In the case of anti-sense nucleic acids, an anti-sense nucleic acid is defined as one which will hybridize to all or part of the corresponding non-coding sequence of the sequence shown in FIG. 6. Generally, the hybridization conditions used for the determination of anti-sense hybridization will be high stringency conditions, such as 0.1XSSC at 65° C.

Once the HAP protein nucleic acid is identified, it can be cloned and, if necessary, its constituent parts recombined to form the entire HAP protein nucleic acid. Once isolated from its natural source, e.g., contained within a plasmid or other vector or excised therefrom as a linear nucleic acid segment, the recombinant HAP protein nucleic acid can be further used as a probe to identify and isolate other HAP protein nucleic acids. It can also be used as a "precursor" nucleic acid to make modified or variant HAP protein nucleic acids and proteins.

Using the nucleic acids of the present invention which encode HAP protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the HAP protein. "Operably linked" in this context means that the transcriptional and translational regulatory DNA is positioned relative to the coding sequence of the HAP protein in such a manner that transcription is initiated. Generally, this will mean that the promoter and transcriptional initiation or start sequences are positioned 5' to the HAP protein coding region. The transcriptional and translational regulatory nucleic acid will generally be appropriate to the host cell used to express the HAP protein; for example, transcriptional and translational regulatory nucleic acid sequences from Bacillus will be used to express the HAP protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The HAP proteins of the present invention are produced by culturing a host cell transformed with an expression vector containing nucleic acid encoding a HAP protein, under the appropriate conditions to induce or cause expression of the HAP protein. The conditions appropriate for HAP protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, immortalized mammalian myeloid and lymphoid cell lines.

In a preferred embodiment, HAP proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of HAP protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the HAP protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, HAP proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the HAP protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for HAP protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, HAP protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia quillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant HAP protein may be expressed intracellularly or secreted. The HAP protein may also be made as a fusion protein, using techniques well known in the art. Thus, for example, if the desired epitope is small, the HAP protein may be fused to a carrier protein to form an immunogen. Alternatively, the HAP protein may be made as a fusion protein to increase expression.

Also included within the definition of HAP proteins of the present invention are amino acid sequence variants. These variants fall into one or more of three classes: substitutional, insertional or deletional variants. These variants ordinarily are prepared by site specific mutagenesis of nucleotides in the DNA encoding the HAP protein, using cassette mutagenesis or other techniques well known in the art, to produce DNA encoding the variant, and thereafter expressing the DNA in recombinant cell culture as outlined above. However, variant HAP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the HAP protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed HAP protein variants screened for the optimal combination of desired activity. Techniques for making substitution mutations at predetermined sites in DNA having a known sequence are well known, for example, PCR primer mutagenesis. Screening of the mutants is done using assays of HAP protein activities; for example, mutated HAP genes are placed in HAP deletion strains and tested for HAP activity, as disclosed herein. The creation of deletion strains, given a gene sequence, is known in the art. For example, nucleic acid encoding the variants may be expressed in a *Haemophilus influenzae* strain deficient in the HAP protein, and the adhesion and infectivity of the variant *Haemophilus influenzae* evaluated. Alternatively, the variant HAP protein may be expressed and its biological characteristics evaluated, for example its proteolytic activity.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when one of the domains of the HAP protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the HAP protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |

CHART I-continued

| Original Residue | Exemplary Substitutions |
| --- | --- |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the HAP protein is altered. For example, the proteolytic activity of the larger 110 kD domain of the HAP protein may be altered, through the substitution of the amino acids of the active site. The putative catalytic domain of this protein was considered to be GDSGSPMF (SEQ ID NO: 53). The residues of the active site may be individually or simultaneously altered to decrease or eliminate proteolytic activity. This may be done to decrease the toxicity or side effects of the vaccine. Similarly, the cleavage site between the 45 kD domain and the 100 kD domain may be altered, for example to eliminate proteolytic processing to form the two domains. Indeed, the catalytic triad has been defined as His98, Asp 140 and Ser 243. Each of these amino acids has been mutated; the mutations eliminated proteolytic activity. In addition, four sites have been identified at which autoproteolytic cleavage occurs (Hendrixson et al., 1997; Hendrixson and St. Geme, 1998; Fink et al., 2001).

In a preferred embodiment, the HAP protein is purified or isolated after expression. HAP proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the HAP protein may be purified using a standard anti-HAP antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the HAP protein. In some instances no purification will be necessary.

Once expressed and purified if necessary, the HAP proteins are useful in a number of applications.

For example, the HAP proteins can be coupled, using standard technology, to affinity chromatography columns. These columns may then be used to purify antibodies from samples obtained from animals or patients exposed to the *Haemophilus influenzae* organism. The purified antibodies may then be used as outlined below.

Additionally, the HAP proteins are useful to make antibodies to HAP proteins. These antibodies find use in a number of applications. In a preferred embodiment, the antibodies are used to diagnose the presence of an *Haemophilus influenzae* infection in a sample or patient. This will be done using techniques well known in the art; for example, samples such as blood or tissue samples may be obtained from a patient and tested for reactivity with the antibodies, for example using standard techniques such as ELISA. In a preferred embodiment, monoclonal antibodies are generated to the HAP protein, using techniques well known in the art. As outlined above, the antibodies may be generated to the full length HAP protein, or a portion of the HAP protein.

Antibodies generated to HAP proteins may also be used in passive immunization treatments, as is known in the art.

Antibodies generated to unique sequences of HAP proteins may also be used to screen expression libraries from other organisms to find, and subsequently clone, HAP nucleic acids from other organisms.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the HAP protein antibody may be labelled for detection, or a secondary antibody to the HAP protein antibody may be created and labelled.

In one embodiment, the antibodies generated to the HAP proteins of the present invention are used to purify or separate HAP proteins or the *Haemophilus influenzae* organism from a sample. Thus for example, antibodies generated to HAP proteins which will bind to the *Haemophilus influenzae* organism may be coupled, using standard technology, to affinity chromatography columns. These columns can be used to pull out the Haemophilus organism from environmental or tissue samples. Alternatively, antibodies generated to the soluble 110 kD portion of the full-length portion of the protein shown in FIG. 7 may be used to purify the 110 kD protein from samples.

In a preferred embodiment, the HAP proteins of the present invention are used as vaccines for the prophylactic or therapeutic treatment of a *Haemophilus influenzae* infection in a patient. By "vaccine" herein is meant an antigen or compound which elicits an immune response in an animal or patient. The vaccine may be administered prophylactically, for example to a patient never previously exposed to the antigen, such that subsequent infection by the *Haemophilus influenzae* organism is prevented. Alternatively, the vaccine may be administered therapeutically to a patient previously exposed or infected by the *Haemophilus influenzae* organism. While infection cannot be prevented, in this case an immune response is generated which allows the patient's immune system to more effectively combat the infection. Thus, for example, there may be a decrease or lessening of the symptoms associated with infection.

In a preferred embodiment the HAP proteins of the invention protect against infection by *H. influenza*. That is, administration of at least one of the HAP proteins of the invention to a patient results in protection against *H. influenza* infection. In another embodiment administration of at least one HAP protein of the invention results in reduced colonization by *H. influenza*. In a particularly preferred embodiment administration of at least one of the HAP proteins of the invention results in protection against infection or colonization by a heterologous strain of *Haemophilus influenzae* By "heterologous" is meant a strain that is not the same strain from which the HAP protein is obtained. Accordingly, the present invention provides a method of vaccinating against infection by a heterologous strain of *H. influenza*.

A "patient" for the purposes of the present invention includes both humans and other animals and organisms. Thus the methods are applicable to both human therapy and veterinary applications.

The administration of the HAP protein as a vaccine is done in a variety of ways, including but not limited to intramuscular or subcutaneous injection, intranasal delivery, oral delivery, intravenous delivery and intradermal delivery as is known in the art. Generally, the HAP proteins can be formulated according to known methods to prepare pharmaceutically useful compositions, whereby therapeutically effective amounts of the HAP protein are combined in admixture with a pharmaceutically acceptable carrier vehicle. Suitable vehicles and their formulation are well known in the art. Such compositions will contain an effective amount of the HAP protein together with a suitable amount of vehicle in order to prepare pharmaceutically acceptable compositions for effective administration to the host. The composition may include salts, buffers, carrier proteins such as serum albumin, targeting molecules to localize the HAP protein at the appropriate site or tissue within the organism, and other molecules. The composition may include adjuvants as well. In a preferred embodiment the HAP protein is administered combined with an adjuvant as is known in the art, such as aluminum hydroxide. In a preferred embodiment the adjuvant is a modified cholera toxin adjuvant.

Cholera toxin (CT) is well known as a potent mucosal adjuvant but is highly toxic to humans (Snider, D. P., 1995, Crit. Rev. Immunol 15:317–48). CT-E29H is a mutant form of CT that contains a histidine in place of a glutamic acid at residue 29 in the enzymatic A subunit. This mutant lacks enzymatic activity and has <1% of the cellular toxicity of native cholera toxin but remains fully active as an adjuvant, suggesting considerable utility in humans (Tebbey et al., 2000, Vaccine 18:2723–34). Accordingly, in a preferred embodiment the invention provides a composition comprising a HAP protein of the invention and cholera toxin CT-E29H. In addition the invention provides a method of improving immunization by administering an immunogenic protein of the invention and an adjuvant. In a preferred embodiment the adjuvant is CT-E29H.

In one embodiment, the vaccine is administered as a single dose; that is, one dose is adequate to induce a sufficient immune response to prophylactically or therapeutically treat a *Haemophilus influenzae* infection. In alternate embodiments, the vaccine is administered as several doses over a period of time, as a primary vaccination and "booster" vaccinations.

By "therapeutically effective amounts" herein is meant an amount of the HAP protein which is sufficient to induce an immune response. This amount may be different depending on whether prophylactic or therapeutic treatment is desired. Generally, this ranges from about 0.001 mg to about 1 gm, with a preferred range of about 0.05 mg to about 0.5 g, and the preferred dose being 0.1 mg to about 0.1 g These amounts may be adjusted if adjuvants are used.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Cloning of the HAP Protein

Bacterial Strains, plasmids, and phage. *H. influenzae* strain N187 is a clinical isolate that was originally cultivated from the middle ear fluid of a child with acute otitis media. This strain was classified as nontypable based on the absence of agglutination with typing antisera for *H. influenzae* types a–f (Burroughs Wellcome) and the failure to hybridize with pU038, a plasmid that contains the entire cap b locus (Kroll and Moxon, 1988, J. Bacteriol. 170:859–864).

*H. influenzae* strain DB117 is a rec-1 mutant of Rd, a capsule-deficient serotype d strain that has been in the laboratory for over 40 years (Alexander and Leidy, 1951, J. Exp. Med. 83:345–359); DB117 was obtained from G. Barcak (University of Maryland, Baltimore, Md.) (Sellow et al., 1968). DB117 is deficient for in vitro adherence and invasion, as assayed below.

*H. influenzae* strain 12 is the nontypable strain from which the genes encoding the HMW1 and HMW2 proteins were cloned (Barenkamp and Leininger, 1992, Infect. Immun. 60:1302–1313); HMW1 and HMW2 are the prototypic members of a family of nontypable Haemophilus antigenically-related high-molecular-weight adhesive proteins (St. Geme et al., 1993).

*E. coli* HB101, which is nonadherent and noninvasive, has been previously described (Sambrook et al., 1989, Molecular cloning: a laboratory manual, 2nd ed. Cold Spring Harbor Laboratory, Cold Spring Harbor, N.Y.). *E. coli* DH5α was obtained from Bethesda Research Laboratories. *E. coli* MC1061 was obtained from H. Kimsey (Tufts University, Boston, Mass.). *E. coli* XL-1Blue and the plasmid pBluescript KS- were obtained from Stratagene. Plasmid pT7-7 and phage mGP1-2 were provided by S. Tabor (Harvard Medical School, Boston, Mass.) (Tabor and Richardson, 1985, Proc. Nati. Acad. Sci. USA. 82:1074–1078). The *E. coli*-Haemophilus shuttle vector pGJB103 (Tomb et al, 1989, Rd. J. Bacteriol. 171:3796–3802) and phage λ1105 (Way et al., 1984, Gene. 32:3 69–379) were provided by G. Barcak (University of Maryland, Baltimore, Md.). Plasmid pVD116 harbors the IgA1 protease gene from *H. influenzae* strain Rd (Koomey and Falkow, 1984, Infect. Immun. 43:101–107) and was obtained from M. Koomey (University of Michigan, Ann Arbor, Mich.).

Growth conditions. *H. influenzae* strains were grown as described (Anderson et al., 1972, J. Clin. Invest. 51:31–38). They were stored at −80° C. in brain heart infusion broth with 25% glycerol. *E. coli* strains were grown on LB agar or in LB broth. They were stored at −80° C. in LB broth with 50% glycerol.

For *H. influenzae*, tetracycline was used in a concentration of 5 μg/ml and kanamycin was used in a concentration of 25 μg/ml. For *E. coli*, antibiotics were used in the following concentrations: tetracycline, 12.5 μg/ml; kanamycin, 50 μg/ml; ampicillin, 100 μg/ml.

Recombinant DNA methods. DNA ligations, restriction endonuclease digestions, and gel electrophoresis were performed according to standard techniques (Sambrook et al., 1989, supra). Plasmids were introduced into *E. coli* strains by either chemical transformation or electroporation, as described (Sambrook et al, 1989, supra; Dower et a., 1988, Nucleic Acids Res. 16:6127–6145). In *H. influenzae* transformation was performed using the MIV method of Herriott et al. (1970, J. Bacteriol. 101:517–524), and electroporation was carried out using the protocol developed for *E. coli* (Dower et al., 1988, supra).

Construction of genomic library from *H. influenzae* strain N187. High-molecular-weight chromosomal DNA was prepared from 3 ml of an overnight broth culture of *H. influenzae* N187 as previously described (Mekalanos, 1983, Cell. 35:253–263). Following partial digestion with Sau3AI, 8 to 12 kb fragments were eluted into DEAE paper (Schleicher & Schuell, Keene, H. H.) and then ligated to Bg/II-digested calf intestine phosphatase-treated pGJB103. The ligation mixture was electroporated into *H. influenzae* DB117, and transformants were selected on media containing tetracycline.

Transposon mutagenesis. Mutagenesis of plasmid DNA was performed using the mini-Tn10 kan element described by Way et al. (1984, supra). Initially, the appropriate plasmid was introduced into *E. coli* MC1061. The resulting strain was infected with λ1105, which carries the mini-Tn 10 kan transposon. Transductants were grown overnight in the presence of kanamycin and an antibiotic to select for the plasmid, and plasmid DNA was isolated using the alkaline lysis method. In order to recover plasmids containing a transposon insertion, plasmid DNA was electroporated into *E. coli* DH5α, plating on media containing kanamycin and the appropriate second antibiotic.

In order to establish more precisely the region of pN187 involved in promoting interaction with host cells, initially this plasmid was subjected to restriction endonuclease analysis. Subsequently, several subclones were constructed in the vector pGJB103 and were reintroduced into *H. influenzae* strain DB117. The resulting strains were then examined for adherence and invasion. As summarized in FIG. 4, subclones containing either a 3.9-kb PstI-Bg/II fragment (pJS105) or the adjoining 4.2-kb Bg/II fragment (pJS102) failed to confer the capacity to associate with Chang cells. In contrast, a subclone containing an insert that included portions of both of these fragments (pJS106) did promote interaction with epithelial monolayers. Transposon mutagenesis performed on pN187 confirmed that the flanking portions of the insert in this plasmid were not required for the adherent/invasive phenotype. On the other hand, a transposon insertion located adjacent to the Bg/II site in pJS106 eliminated adherence and invasion. An insertion between the second EcoRI and PstI sites in this plasmid had a similar effect (FIG. 4).

Examination of plasmid-encoded proteins. In order to examine plasmid encoded proteins, relevant DNA was ligated into the bacteriophage T7 expression vector pT7-7, and the resulting construct was transformed into *E. coli* XL-1Blue. Plasmid pT7-7 contains the T7 phage φ10 promoter and ribosomal binding site upstream of a multiple cloning site (Tabor and Richardson, 1985, supra). The T7 promoter was induced by infection with the recombinant M13 phage mGP1-2 and addition of isopropyl-β-D-thiogalactopyranoside (final concentration, 1 mM). Phage mGP1-2 contains the gene encoding T7 RNA polymerase, which activates the (φ10 promoter in pT7-7 (Tabor and Richardson, 1985, supra).

Like DB117 (pN187), strain DB117 carrying pJS106 expressed new outer membrane proteins 160-kD and 45-kD in size (FIG. 3, lane 3). In order to examine whether the 6.5-kb insert in pJS106 actually encodes these proteins, this fragment of DNA was ligated into the bacteriophage T7 expression vector pT7-7. The resulting plasmid containing the insert in the same orientation as in pN187 was designated pJS104, and the plasmid with the insert in the opposite orientation was designated pJS103. Both pJS104, and pJS103 were introduced into *E. coli* XL-1 Blue, producing XL-1 Blue(pJS104) and XL-1 Blue(pJS103), respectively. As a negative control, pT7-7 was also transformed into XL-1 Blue. The T7 promoter was induced in these three strains by infection with the recombinant M13 phage mGP1-2 and addition of isopropyl-β-D-thiogalactopyranoside (final concentration, 1 mM), and induced proteins were detected using [$^{35}$S] methionine. As shown in FIG. 5, induction of XL-1 Blue(pJS104) resulted in expression of a 160-kD protein and several smaller proteins which presumably represent degradation products. In contrast, when XL-1 Blue (pJS103) and XL-1 Blue(pT7-7) were induced, there was no expression of these proteins. There was no 45-kD protein induced in any of the three strains. This experiment suggested that the 6.5-kb insert present in pJS106 contains the structural gene for the 160-kD outer membrane protein identified in DB117(pJS106). On the other hand, this analysis failed to establish the origin of the 45-kD membrane protein expressed by DB117(pJS106).

Adherence and invasion assays. Adherence and invasion assays were performed with Chang epithelial cells [Wong-Kilbourne derivative, clone 1-5c-4 (human conjunctiva)], which were seeded into wells of 24-well tissue culture plates as previously described (St. Geme and Falkow, 1990). Adherence was measured after incubating bacteria with epithelial monolayers for 30 minutes as described (St. Geme et al, 1993). Invasion assays were carried out according to our original protocol and involved incubating bacteria with epithelial cells for four hours followed by treatment with gentamicin for two hours (100 μg/ml) (St. Geme and Falkow, 1990).

Nucleotide sequence determination and analysis. Nucleotide sequence was determined using a Sequenase kit and double stranded plasmid template. DNA fragments were subcloned into pBluescript KS⁻ and sequenced along both strands by primer walking. DNA sequence analysis was performed using the Genetics Computer Group (GCG) software package from the University of Wisconsin (Devereux et al., 1984). Sequence similarity searches were carried out using the BLAST program of the National Center for Biotechnology Information (Altschul et al., 1990, J. Mol. Biol. 215:403–410). The DNA sequence described here will be deposited in the EMBL/GenBank/DDBJ Nucleotide Sequence Data Libraries.

Based on the our subcloning results, we reasoned that the central Bg/II site in pN187 was positioned within an open reading frame. Examination of a series of mini-Tn10 kan mutants supported this conclusion (FIG. 4). Consequently, we sequenced DHA on either side of this Bg/II site and identified a 4182 bp gene, which we have designated hap for Haemophilus adherence and penetration (FIG. 6). This gene encodes a 1394 amino acid polypeptide, which we have called Hap, with a calculated molecular mass of 155.4-kD, in good agreement with the molecular mass of the larger of the two novel outer membrane proteins expressed by DB117 (pN187) and the protein expressed after induction of XL-1 Blue/pJS104. The hap gene has a G+C content of 39.1%, similar to the published estimate of 38.7% for the whole genome (Kilian, 1976, J. Gen. Microbiol. 93:9–62). Putative −10 and −35 promoter sequences are present upstream of the initiation codon. A consensus ribosomal binding site is lacking. A sequence similar to a rho-independent transcription terminator is present beginning 39 nucleotides beyond the stop codon and contains interrupted inverted repeats with the potential for forming a hairpin structure containing a loop of three bases and a stem of eight bases. Similar to the situation with typical *E. coli* terminators, this structure is followed by a stretch rich in T residues. Analysis of the predicted amino acid sequence suggested the presence of a 25 amino acid signal peptide at the amino terminus. This region has characteristics typical of procaryotic signal peptides, with three positive H-terminal charges, a central hydrophobic region, and alanine residues at positions 23 and 25 (−3 and −1 relative to the putative cleavage site) (von Heijne, 1984, J. Mol. Biol. 173:243–251).

Comparison of the deduced amino acid sequence of Hap with other proteins. A protein sequence similarity search was performed with the predicted amino acid sequence using the BLAST network service of the National Center for Biotechnology Information (Altschul et al., 1990, supra). This search revealed homology with the IgA1 proteases of *H. influenzae* and *Neisseria gonorrhoeae*. Alignment of the derived amino acid sequences for the hap gene product and the IgA1 proteases from four different *H. influenzae* strains revealed homology across the extent of the proteins (FIG. 7), with several stretches showing 55–60% identity and 70–80% similarity. Similar levels of homology were noted between the hap product and the IgA1 protease from *N. gonorrhoeae* strain MS11. This homology includes the region identified as the catalytic site of the IgA1 proteases, which is comprised of the sequence GDSGSPLF (SEQ ID NO: 54), where 2 is the active site serine characteristic of serine proteases (Brenner, 1988, Nature (London). 334:528–530; Poulsen et al., 1992, J. Bacteriol. 174:2913–2921). In the case of Hap, the corresponding sequence is GDSGSPMF (SEQ ID NO: 53). The hap product also contains two cysteines corresponding to the cysteines proposed to be important in forming the catalytic domain of the IgA proteases (Pohlner et a., 1987, supra). Overall there is 30–35% identity and 51–55% similarity between the hap gene product and the *H. influenzae* and *N. gonorrhoeae* IgA proteases.

The deduced amino acid sequence encoded by hap was also found to contain significant homology to Tsh, a hemagglutinin expressed by an avian *E. coli* strain (Provence and Curtiss, 1994, supra). This homology extends throughout both proteins but is greatest in the H-terminal half of each. Overall the two proteins are 30.5% identical and 51.6% similar. Tsh is also synthesized as a preprotein and is secreted as a smaller form; like the IgA1 proteases and perhaps Hap, a carboxy terminal peptide remains associated with the outer membrane (D. Provence, personal communication). While this protein is presumed to have proteolytic activity, its substrate has not yet been determined. Interestingly, Tsh was first identified on the basis of its capacity to promote agglutination of erythrocytes. Thus Hap and Tsh are possibly the first members of a novel class of adhesive proteins that are processed analogously to the IgA1 proteases.

Homology was also noted with pertactin, a 69-kD outer membrane protein expressed by *B. pertussis* (Charles et al., 1989, Proc. Nati. Acad. Sci. USA. 86:3554–3558). The middle portions of these two molecules are 39% identical and nearly 60% similar. This protein contains the amino acid triplet arginine-glycine-aspartic acid (RGD) and has been shown to promote attachment to cultured mammalian cells via this sequence (Leininger et al., 1991, Proc. Natl. Acad. Sci. USA. 88:345–349). Although Bordetella species are not generally considered intracellular parasites, work by Ewanowich and coworkers indicates that these respiratory pathogens are capable of in vitro entry into human epithelial cells (Ewanowich et al., 1989, Infect. Immun. 57:2698–2704; Ewanowich et. al., 1989, Infect. Immun. 57:1240–1247). Recently Leininger et al. reported that pre-incubation of epithelial monolayers with an RGD-containing peptide derived from the pertactin sequence specifically inhibited B. pertussis entry (Leininger et al., 1992, Infect. Immun. 60:2380–2385). In addition, these investigators found that coating of *Staphylococcus aureus* with purified pertactin resulted in more efficient *S. aureus* entry; the RGD-containing peptide from pertactin inhibited this pertactin-enhanced entry by 75%. Although the hap product lacks an RGD motif, it is possible that Hap and pertactin serve similar biologic functions for *H. influenzae* and Bordetella species, respectively.

Additional analysis revealed significant homology (34 to 52% identity, 42 to 70% similarity) with six regions of HpmA, a calcium-independent hemolysin expressed by *Proteus mirabilis* (Uphoff and Welch, 1990, supra).

The hap locus is distinct from the *H. influenzae* IgA1 protease gene. Given the degree of similarity between the hap gene product and *H. influenzae* IgA1 protease, we wondered whether we had isolated the IgA1 protease gene of strain N187. To examine this possibility, we performed IgA1 protease activity assays. Among *H. influenzae* strains, two enzymatically distinct types of IgA1 protease have been found (Mulks et al., 1982, J. Infect. Dis. 146:266–274). Type 1 enzymes cleave the Pro-Ser peptide bond between residues 231 and 232 in the hinge region of human IgA1 heavy chain and generate fragments of roughly 28-kD and 31-kD; type 2 enzymes cleave the Pro-Thr bond between residues 235 and 236 in the hinge region and generate 26.5-kD and 32.5-kD fragments. Previous studies of the parent strain from which DB117 was derived have demonstrated that this strain produces a type 1 IgA1 protease (Koomey and Falkow, 1984, supra). As shown in FIG. 8, comparison of the proteolytic activities of strain DB117 and strain N187 suggested that N187 produces a type 2 IgA1 protease. We reasoned that DB117(pN187) might generate a total of four fragments from IgA1 protease, consistent with two distinct cleavage specificities. Examination of DB117(pN187) revealed instead that this transformant produces the same two fragments of the IgA1 heavy chain as does DB117, arguing that this strain produces only a type 1 enzyme.

In an effort to obtain additional evidence against the possibility that plasmid pN187 contains the N187 IgA1 protease gene, we performed a series of Southern blots. As shown in FIG. 9, when genomic DNA from strain N187 was digested with EcoRI, Bg/II, or BamHI and then probed with the hap gene, one set of hybridizing fragments was detected. Probing of the same DNA with the iga gene from *H. influenzae* strain Rd resulted in a different set of hybridizing bands. Moreover, the iga gene failed to hybridize with a purified 4.8-kb fragment that contained the intact hap gene.

The recombinant plasmid associated with adherence and invasion encodes a secreted protein. The striking homology between the hap gene product and the Haemophilus and Neisseria IgA1 proteases suggested the possibility that these proteins might be processed in a similar manner. The IgA1 proteases are synthesized as preproteins with three functional domains: the N-terminal signal peptide, the protease, and a C-terminal helper domain, which is postulated to form a pore in the outer membrane for secretion of the protease (Poulsen et al., 1989, supra; Pohlner et al., 1987, supra). The C-terminal peptide remains associated with the outer membrane following an autoproteolytic cleavage event that results in release of the mature enzyme. Consistent with the possibility that the hap gene product follows a similar fate, we found that DB117(pN187) produced a secreted protein approximately 110-kD in size that was absent from DB117 (pGJB103) (FIG. 10). This protein was also produced by DB117(pJS106), but not by DB117(pJ5102) or DB117 (pJS105). Furthermore, the two mutants with transposon insertions within the hap coding region were deficient in this protein. In order to determine the relationship between hap and the secreted protein, this protein was transferred to a PVDF membrane and N-terminal amino acid sequencing was performed. Excessive background on the first cycle precluded identification of the first amino acid residue of the free amino terminus. The sequence of the subsequent seven residues was found to be HTYFGID (SEQ ID NO: 55), which corresponds to amino acids 27 through 33 of the hap product.

The introduction of hap into laboratory strains of E. coli strains was unable to endow these organisms with the capacity for adherence or invasion. In considering these results, it is noteworthy that the E. coli transformants failed to express either the 160-kD or the 45-kD outer membrane protein. Accordingly, they also failed to express the 110-kD secreted protein. The explanation for this lack of expression is unclear. One possibility is that the H. influenzae promoter or ribosomal binding site was poorly recognized in E. coli. Indeed the putative −35 sequence upstream of the hap initiation codon is fairly divergent from the σ70 consensus sequence, and the ribosomal binding site is unrecognizable. Alternatively, an accessory gene may be required for proper export of the Hap protein, although the striking homology with the IgA proteases, which are normally expressed and secreted in E. coli, argues against this hypothesis.

In considering the possibility that the hap gene product promotes adherence and invasion by directly binding to a host cell surface structure, it seems curious that the mature protein is secreted from the organism. However, there are examples of other adherence factors that are also secreted. Filamentous hemagglutinin is a 220-kD protein expressed by B. pertussis that mediates in vitro adherence and facilitates natural colonization (Relman et al., 1989, Proc. Natl. Acad. Sci. U.S.A. 86:2637–2641; Kimura et al., 1990, Infect. Immun. 58:7–16).

This protein remains surface-associated to some extent but is also released from the cell.

The process of Filamentous hemagglutinin secretion involves an accessory protein designated FhaC, which appears to be localized to the outer membrane (Willems et al., 1994, Molec. Microbiol. 11:337–347). Similarly, the Ipa proteins implicated in Shigella invasion are also secreted. Secretion of these proteins requires the products of multiple genes within the mxi and spa loci (Allaoui et al., 1993, Molec. Microbiol. 7:59–68; Andrews et al., 1991, Infect. Immun. 59:1997–2005; Venkatsan et al., 1992, J. Bacteriol. 174:1990–2001).

It is conceivable that secretion is simply a consequence of the mechanism for export of the hap gene product to the surface of the organism. However, it is noteworthy that the secreted protein contains a serine-type protease catalytic domain and shows homology with the P. mirobilis hemolysin. These findings suggest that the mature Hap protein may possess proteolytic activity and raise the possibility that Hap promotes interaction with the host cell at a distance by modifying the host cell surface. Alternatively, Hap may modify the bacterial surface in order to facilitate interaction with a host cell receptor. It is possible that hap encodes a molecule with dual functions, serving as both adhesin and protease.

Analysis of outer membrane and secreted proteins. Outer membrane proteins were isolated on the basis of sarcosyl insolubility according to the method of Carlone et al. (1986, J. Clin. Microbiol. 24:330–332). Secreted proteins were isolated by centrifuging bacterial cultures at 16,000 g for 10 minutes, recovering the supernatant, and precipitating with trichloroacetic acid in a final concentration of 10%. SDS-polyacrylamide gel electrophoresis was performed as previously described (Laemmli, 1970, Nature (London). 227:680–685).

To identify proteins that might be involved in the interaction with the host cell surface, outer membrane protein profiles for DB117(pN187) and DB117(pGJB103) were compared. As shown in FIG. 3, DB117(pN187) expressed two new outer membrane proteins: a high-molecular-weight protein approximately 160-kD in size and a 45-kD protein. E. coli HB101 harboring pN187 failed to express these proteins, suggesting an explanation for the observation that HB101(pN187) is incapable of adherence or invasion.

Previous studies have demonstrated that a family of antigenically-related high-molecular-weight proteins with similarity to filamentous hemagglutinin of Bordetella pertussis mediate attachment by nontypable H. influenzae to cultured epithelial cells (St. Geme et al., 1993). To explore the possibility that the gene encoding the strain H187 member of this family was cloned, whole cell lysates of N187, DB117(pN187), and DB117(pGJB103) were examined by Western immunoblot. Our control strain for this experiment was H. influenzae strain 12. Using a polyclonal antiserum directed against HMW1 and HMW2, the prototypic proteins in this family, we identified a 140-kD protein in strain H187 (not shown). In contrast, this antiserum failed to react with either DB 117(pN 187) or DB 117(pGJB103) (not shown), indicating that pN187 has no relationship to HMW protein expression.

Determination of amino terminal sequence. Secreted proteins were precipitated with trichloroacetic acid, separated on a 10% SDS-polyacrylamide gel, and electrotransferred to a polyvinylidene difluoride (PVDF) membrane (Matsudaira, 1987, J. Biol. Chem. 262:10035–10038). Following staining with Coomassie Brilliant Blue R-250, the 110-kD protein was cut from the PVDF membrane and submitted to the Protein Chemistry Laboratory at Washington University School of Medicine for amino terminal sequence determination. Sequence analysis was performed by automated Edman degradation using an Applied Biosystems Model 470A protein sequencer.

Examination of IgA1 protease activity. In order to assess IgA1 protease activity, bacteria were inoculated into broth and grown aerobically overnight. Samples were then centrifuged in a microphage for two minutes, and supernatants were collected. A 10 μl volume of supernatant was mixed with 16 μl of 0.5 μg/ml human IgA1 (Calbiochem), and chloramphenicol was added to a final concentration of 2 μg/ml. After overnight incubation at 37° C., reaction mixtures were electrophoresed on a 10% SDS-polyacrylamide gel, transferred to a nitrocellulose membrane, and probed with goat anti-human IgA1 heavy chain conjugated to alkaline phosphatase (Kirkegaard & Perry). The membrane was developed by immersion in phosphatase substrate solution (5-bromo-4-chloro-3-indolylphosphate toluidinium-nitro blue tetrazolium substrate system; Kirkegaard & Perry).

Immunoblot analysis. Immunoblot analysis of bacterial whole cell lysates was carried out as described (St. Geme et al., 1991).

Southern hybridization. Southern blotting was performed using high stringency conditions as previously described (St. Geme and Falkow, 1991).

Microscopy.

i. Light microscopy. Samples of epithelial cells with associated bacteria were stained with Giemsa stain and examined by light microscopy as described (St. Geme and Falkow, 1990).

ii. Transmission electron microscopy. For transmission electron microscopy, bacteria were incubated with epithelial cell monolayers for four hours and were then rinsed four times with PBS, fixed with 2% glutaraldehyde/1% osmium tetroxide in 0.1 M sodium phosphate buffer pH 6.4 for two hours on ice, and stained with 0.25% aqueous uranyl acetate overnight. Samples were then dehydrated in graded ethanol solutions and embedded in polybed. Ultrathin sections (0.4 $\mu$m) were examined in a Phillips 201c electron microscope.

As shown in FIG. 2, DB117(pN187) incubated with monolayers for four hours demonstrated intimate interaction with the epithelial cell surface and was occasionally found to be intracellular. In a given thin section, invaded cells generally contained one or two intracellular organisms. Of note, intracellular bacteria were more common in sections prepared with strain N187, an observation consistent with results using the gentamicin assay. In contrast, examination of samples prepared with strain DB117 carrying cloning vector alone (pGJB103) failed to reveal internalized bacteria (not shown).

Example 2

HAP Immunization

Bacterial Strains. NTHi strains N187 and P860295 were isolated from middle ear fluid of children with acute otitis media, while NTHi strain TN106 was isolated from a patient with pneumonia. Strain N187 is the strain from which the hap gene was originally cloned (Sanders et al., 1993, Infect. Immun. 61:3966–3975; St. Geme et al., 1994, Mol. Microbiol. 14:217–233). Strain P860295 was obtained from Dr. Charles Brinton (University of Pittsburgh), and strain TN106 was obtained from Dr. Eric Hansen (University of Texas, Southwestern School of Medicine). Strain TN106.P2 is a derivative of TN106 that was recovered after plating on medium containing 100 $\mu$g/ml of streptomycin, then inoculating into the nasopharynx of a Balb/c mouse. Strains TN106.P2 and TN106 are indistinguishable in terms of morphology and growth characteristics. H. influenzae strain DB117 is a rec1 mutant of Rd, a capsule-deficient serotype d strain (Setlow et al., 1968, J. Bacteriol. 95:546–558). DB117 contains a nonfunctional hap gene because of a spontaneous nonsense mutation at codon 710 and is nonadherent in assays with cultured epithelial cells (Fleischmann et a., 1995. Rd. Science 269:496–512.).

H. influenzae strains were grown on chocolate agar supplemented with 1% IsoVitaleX, on brain heart infusion agar supplemented with hemin and NAD (BHI-XV agar), or in brain-heart infusion broth supplemented with hemin and NAD (BHIs), as described previously (St. Geme and Falkow, 1990, supra). These strains were stored at −80° C. in BHI broth with 20% glycerol. E. coli strains were grown on Luria-Bertani (LB) agar or in LB broth and were stored at −80° C. in LB broth with 50% glycerol. Antibiotic concentrations used to select for plasmids included 5 $\mu$g/ml tetracycline in H. influenzae and 100 $\mu$g/ml ampicillin and 12.5 $\mu$g/ml tetracycline in E. coli. DNA ligations, restriction endonuclease digestions and gel electrophoresis were performed according to standard techniques (Sambrook et al., 1989, supra). Plasmids were introduced into E. coli by electroporation (Dower et al., 1988, supra). In H. influenzae, transformation was performed using the MIV method of Herriott et al. (Herriott e a., 1970, supra).

Cloning and Sequencing of hap from Strains P860295 and TN106

The hap gene was cloned from strains P860295 and TN106 using the polymerase chain reaction (PCR) and primers corresponding to sequence flanking hap in strain N187. Reactions were performed with Expand polymerase (Roche Molecular Biochemicals) to enhance long range amplification and to minimize PCR-related errors. The 5' primer was based on sequence beginning approximately 500 base pairs upstream of hap (5'-TGCAGGATCCCCGCAGACTGGATTGTTG-3') (SEQ ID NO: 56), and the 3' primer corresponded to sequence beginning roughly 50 base pairs downstream of hap (5'-TGCAGGATCCGATCTGCCCCACCTTGTT-3')(SEQ ID NO: 57). To facilitate initial cloning, both the 5' and the 3' primers included a BamHI site. The amplified genes were cloned into BamHI-digested pUC19 and BglII-digested pGJB103.

Nucleotide sequencing was performed using an Applied Biosystems automated sequencer and the Big Dye Terminator Premix-20 kit (Applied Biosystems/Perkins Elmer). Double-stranded plasmid DNA was used as template, and sequencing was carried out along both strands. With strain TN106, clones from two separate PCR assays were sequenced, and the two sequences were identical. With strain P860295, a single clone was sequenced. The sequences for hapTN106 and hapP860295 have been submitted to GeneBank and are awaiting accession numbers.

The hapTN106 gene encodes a protein with 1392 amino acids, and the hapP860295 gene encodes a slightly larger protein with a total of 1436 amino acids. HapTN106 is 80% similar and 77% identical to HapN187, while HapP860295 is 85% similar and 83% identical to HapN187. Overall, the predicted amino acid sequences of Hap TN106 and Hap P860295 are 82% similar and 79% identical to each other.

As shown in FIG. 11, alignment of the amino acid sequences of Hap TN106, HapP860295, and HapN187 revealed absolute identity through the first 47 amino acids, then significant divergence over the next 350 amino acids, and then marked similarity over the final 1000–1050 amino acids. Of note, the signal peptide and the sequence containing the active site serine residue (GDSGSPM) (SEQ ID NO: 58) are completely conserved in all three proteins. Similarly, the amino acids in the P1 (leucine), P3 (serine), and P4 (glutamine) positions of the primary autoproteolytic cleavage site between HapS and HapB are invariant.

Protein Analysis and Western Immunoblotting

Outer membrane proteins were isolated from H. influenzae on the basis of sarcosyl insolubility, as described previously (Carlone et al., 1986, supra). Proteins released into the culture supernatant were precipitated using trichloroacetic acid, as described previously (St. Geme et al., 1994, Mol. Microbiol. 14:217–233). Proteins were resolved by sodium dodecyl sulfate-polyacrylamide gel electrophoresis (SDS-PAGE) on 7–10% polyacrylamide gels, and Western blots were performed as detailed elsewhere (Laemmli, 1970, supra; Towbin, et al., 1979, Proc. Natl. Acad. Sci. USA 76:4350–4354). Hap was detected using guinea pig antiserum GP74, which was raised against purified HapS and reacts with full-length Hap and $Hap_s$.

As shown in FIG. 12, Western analysis of outer membrane proteins and secreted proteins from strain DB117/pHap (TN106) revealed full-length protein at ~155 kDa and $Hap_S$ at ~110 kDa, virtually identical to control samples from strain DB117/pJS106 (HapN187). Examination of protein samples from strain DB 117/pHap(P860295) revealed that full-length Hap migrated at ~160 kDa and that HapS migrated at ~115 kDa.

Adherence Assays

Adherence assays were performed with Chang conjunctival epithelial cells (Wong-Kilbourne derivative, clone 1-5c-4 [human conjunctiva], as previously described (St. Geme, et al., 1993, supra). Percent adherence was calculated by dividing the number of adherent colony-forming units per monolayer by the number of inoculated colony-forming units.

To assess adhesive activity, DB117/pHap(TN106) and DB117/pHap(P860295) were compared with DB117/pJS106 in adherence assays with Chang conjunctival epithelial cells. As shown in FIG. 13, both Hap TN106 and HapP860295 promoted appreciable levels of adherence to these cells, similar to levels associated with HapN187. To extend this result, we examined whether antiserum raised against HapS purified from strain N187 could block adherence mediated by either HapP860295 or Hap TN106. As shown in FIG. 13, in experiments with DB117/pHap (TN106), preincubation with a 1:500 dilution of guinea pig antiserum GP74 resulted in a nearly 50% decrease in adherence, and preincubation with a 1:100 dilution of GP74 resulted in a 70% decrease in adherence. Similarly, with DB117/pHap(P860295), a 1:500 dilution of GP74 blocked adherence by 40%, and a 1:100 dilution of GP74 blocked adherence by almost 80%.

Purification of NTHi P860295 $Hap_S$ protein. To purify $Hap_S$ from strain P860295, bacteria were grown in BHIs broth for 18 hours at 35° C. with aeration, i.e. to stationary phase. The bacterial cells were pelleted by centrifuging at 10,000 x g at 4° C. and were discarded. Without being bound by theory, it is thought that the autoproteolysis of HAP results in secretion of $Hap_S$. As such, the supernatant was collected and concentrated 20-fold using an Amicon stirred cell, then adjusted to 60% saturation with ammonium sulfate powder, incubated overnight at 4° C., and centrifuged at 17,000 x g for 1 hour at 4° C. The resulting precipitate was dissolved in 50 mM sodium phosphate buffer, pH 5.8, 1 mM EDTA, 50 mM NaCl and was dialyzed at 4° C. against the same buffer (Buffer 1), then centrifuged at 100,000 x g for 1 hour at 4° C. to remove insoluble material. A 10 ml bed volume CM sepharose (Pharmacia) column was equilibrated with Buffer 1, and 70 ml of the above soluble material was loaded onto the column at a flow rate of 5 ml/min. The column was washed with Buffer 1 until the OD280 reached baseline, and the flow through material was discarded. Next the column was washed with 3 column volumes of 50 mM sodium phosphate buffer, pH7.0, 1 mM EDTA, 50 mM NaCl. $Hap_S$ was eluted with 50 mM sodium phosphate buffer, pH 8.0, 1 mM EDTA, 0.5 M NaCl. Fractions were examined by SDS-PAGE analysis, and fractions containing $Hap_S$ were pooled. Hap, from NTHi strain N187 was purified as previously described (Hendrixson, et al., 1997, Mol. Microbiol. 26:505–518; Hendrixson and St. Geme, 1998, Mol. Cell 2:841–850). Strain P860295 $Hap_S$ was purified from the native strain, while strain N187 $Hap_S$ was purified from DB117 harboring pJS106 (encoding HapN187). Using this purification scheme, highly pure protein from both strain P860295 and strain N187 (FIG. 14) was recovered. Amino terminal amino acid sequencing (described below) confirmed that purified protein was $Hap_S$.

Determination of N-terminal amino acid sequence To confirm the identity of purified $Hap_S$, protein was resolved by SDS-PAGE, then electrotransferred to a polyvinylidene membrane. After staining with Coomassie brilliant blue R-250, protein was excised from the membrane and submitted to Midwest Analytical, Inc. (St. Louis, Mo.). Amino-terminal sequence determination was performed by automated Edman degradation using a Perkin-Elmer Biosystems model 477A sequencing system.

Intranasal immunization of mice. Groups of ten, 6-week old, female Balb/c mice were immunized intranasally with $Hap_S$ purified from either strain P860295 or strain N187. $Hap_S$ was diluted in Dulbecco's PBS (D-PBS) to a final concentration of 5 or 15 µg/40 µl, with or without 0.1 µg CT-E29H (a mutant cholera toxin used as an adjuvant) (Tebbey, et al., 2000, Vaccine 18:2723–34). Control mice received D-PBS alone or D-PBS with 0.1 µg CT-E29H, again in 40 µl volumes.

Prior to intranasal immunization, mice were anesthetized with an injectable mixture of ketamine (0.008 mls x body weight)/xylazene (0.007 mls x body weight), a mixture that maintains a state of anesthesia for 15–20 minutes. Immunizing preparations were delivered by pipette in a volume of 20 µl/nostril. The pipette was positioned so that the tip touched the opening of the nostril and liquid was drawn into the nasopharynx during breathing. Immediately following immunization, mice were placed in a supine position for a 3 to 5 minutes. Mice were immunized at weeks 0, 1, 3, and 5.

Intranasal challenge of mice. Either two or three weeks after the final immunization, animals were challenged intranasally with approximately 1×10⁶ CFU of strain TN106.P2. The TN106.P2 challenge strain was prepared for challenge by first inoculating three BBL Chocolate II agar plates from frozen stocks. Plates were incubated overnight at 37° C. in 5% $CO_2$. Five ml of D-PBS was added to each plate and bacteria were resuspended with a curved glass rod. Bacteria from all three plates were combined with an additional 10 ml of D-PBS and the suspension was poured over a D-PBS pre-wetted nylon wool column to remove clumps of bacteria and debris. The suspension was diluted with D-PBS to an OD490=0.33, which was shown to equal ~1.0×10⁸ CFU/ml. This suspension was used for challenge. Mice were anesthetized as described for immunization, and 5 µl of bacteria were administered in each nostril. Twenty minutes after the challenge began, an aliquot of the bacterial suspension was diluted in D-PBS and plated onto BHI-XV agar to determine the actual inoculum. Three days after challenge, nasal tissue was harvested, weighed, homogenized and plated on BHI-XV plates containing 100 µg/ml streptomycin. Following incubation of plates overnight, colonies were counted, and CFU/g of nasal tissue were determined. Statistical differences among groups were analyzed using the Student t-test (JMP Software v3.2.1)

Measurement of serum antibody responses by ELISA To quantitate serum antibody responses against $Hap_S$, purified Hap$_S$ was diluted and then blocked with 1% bovine serum albumin (BSA)/PBS at 37° C. for 2 hours. Mouse sera were diluted in 1% BSA/PBS/0.05% Tween 20 (diluent buffer) and were transferred to coated and blocked plates. After incubation at 37° C. overnight, plates were washed and then incubated with a 1:15,000 dilution of biotinylated rabbit anti-mouse IgG at 37° C. for 2 hours. Next plates were washed again and then incubated with a 1:10,000 dilution of streptavidin-HRP (Zymed) at room temperature for 30 minutes. Finally, plates were washed and incubated with ABTS peroxidase substrate (Kirkegaard and Perry Laboratories) at room temperature for 20 minutes. Reactions were stopped with 1% SDS, and absorbance of ABTS was measured at 405 nm. ELISA endpoints were defined as the highest dilution of sera giving an OD405 of >0.1. Control wells containing all reagents except for mouse sera had baseline OD405 values of <0.05.

Serum antibody responses. Animals immunized IN will primarily produce a secretory immune response. Addition of CT-E29H increases the secretory immune response and also helps induce a serum antibody response. The volumes of the immunogens used in this experiment (40 μl) probably resulted in some of the material being aspirated into the mice's lungs, further increasing the immune response in the serum. The anti-Hap$_S$ ELISA titers of the sera obtained from immunized mice are shown in Table 2. The titers are somewhat lower than those usually seen with parenteral immunization since animals were immunized via the IN route. Significant increases in anti-Hap$_S$ titers were seen in the sera. The responses increase in a dose dependent manner and are augmented approximately 3-fold by addition of 0.1 μg of CT-E29H. This augmentation occurs at both dosage levels. No anti-Hap$_S$ titers are seen in any of the control groups. Secretory IgA titers were not obtained from nasopharyngeal secretions.

TABLE 2

Systemic hmoral immune response in Balb/c mice after intranasal vaccination with Hap$_S$ admixed with or without CT-E29H

| Vaccine | Route (40 μl) | Dose (μg) | Adjuvant | Anti-Hap$_S$ ELISA (IgG) |
|---|---|---|---|---|
| HAP | IN | 5 | — | 1,604 |
| HAP | IN | 15 | — | 5,204 |
| HAP | IN | 5 | CT-E29H | 4,653 |
| HAP | IN | 15 | CT-E29H | 15,111 |
| — | IN | — | CT-E29H | <500 |
| 1xPBS | IN | — | — | <500 |
| Formalin Fixed TN106.P2 | IN | — | — | <500 |

6-week old female Balb/c mice were vaccinated week 0, 1, 3, & 5.
Week 7 Sera - no antibody titers were detected in earlier bleeds.

Effect of Hap$_S$ immunization on nasopharyngeal colonization. IN immunization with purified native Hap$_S$ protein from NTHi strain P860295 significantly reduced the nasal colonization of NGHi strain TN106.P2 as shown in FIG. 15. The reductions in recovered NTHi per gram of nasal tissue ranged from 1.5 to 2.5 logs when animals were challenged 2 weeks after the last immunization to approximately 1.5 logs when the animals were challenged 3 weeks after the last immunization. all of the differences observed in groups immunized with Hap$_s$, whether with or without CT-E29H, were significant as measured by the Student's T-test. The lowest level of colonization for all groups was in the 5 μg Hap$_S$ dose mixed with 0.1 μg CT-E29H. These results indicate that IN immunization with Hap$_S$ mixed CT-E29H given enhanced immune responses as comapred to IN immunization with Hap$_S$ alone, and that the antibodies elicited by Hap$_S$ are biologically active against a heterologous NTHi challenge.

Having described the preferred embodiments of the present invention it will appear to those of ordinary skill in the art that various modifications may be made to the disclosed embodiments, and that such modifications are intended to be within the scope of the present invention.

What is claimed is:

1. A recombinant Haemoplilus adhesion and penetration protein encoded by a nucleic acid selected from the group consisting of SEQ ID NOS:8, 10, 12, 14 and 16.

2. A recombinant Haemophilus adhesion and penetration protein which has a sequence selected from the group consisting of the sequence shown in SEQ ID NOS:7, 9, 11 and 13.

3. A composition comprising a pharmaceutically acceptable carrier and an Haemophilus adhesion and penetration protein according to claim 1 or 2.

4. A composition according to claim 3 further comprising an adjuvant.

5. A method of inducing an immune response in a patient comprising administering to said patient the composition of claim 3, wherein said composition is in an amount effective to induce an immune response.

6. The method according to claim 5, wherein said immune response is generated against a strain of Haemophilus that is heterologous to the strain from which the Haemophilus adhesion and penetration protein is obtained.

* * * * *